US012292447B2

(12) United States Patent
MacIntosh et al.

(10) Patent No.: US 12,292,447 B2
(45) Date of Patent: May 6, 2025

(54) LC-MS/MS-BASED METHODS FOR CHARACTERIZING PROTEINS

(71) Applicants: Nuseed Pty Ltd., Laverton North (AU); COMMONWEALTH SCIENTIFIC & INDUSTRIAL RESEARCH ORG., Act (AU)

(72) Inventors: Susan MacIntosh, Saint Paul, MN (US); Michelle Colgrave, Brisbane (AU); Keren Byrne, St. Lucia (AU); Jo Caine, Parkville (AU); Xue-Rong Zhou, Canberra (AU)

(73) Assignees: Nuseed Nutritional Australia Pty Ltd, Victoria (AU); Commonwealth Scientific and Industrial Research Organisation, Act (AU)

( * ) Notice: Subject to any disclaimer, the term of this patent is extended or adjusted under 35 U.S.C. 154(b) by 722 days.

(21) Appl. No.: 16/492,089

(22) PCT Filed: Mar. 8, 2018

(86) PCT No.: PCT/US2018/021423
§ 371 (c)(1),
(2) Date: Sep. 6, 2019

(87) PCT Pub. No.: WO2018/165350
PCT Pub. Date: Sep. 13, 2018

(65) Prior Publication Data
US 2021/0263041 A1      Aug. 26, 2021

Related U.S. Application Data

(60) Provisional application No. 62/468,331, filed on Mar. 7, 2017.

(51) Int. Cl.
*G01N 33/68* (2006.01)
*G01N 30/72* (2006.01)
(Continued)

(52) U.S. Cl.
CPC ..... *G01N 33/6848* (2013.01); *G01N 30/7233* (2013.01); *H01J 49/0036* (2013.01);
(Continued)

(58) Field of Classification Search
None
See application file for complete search history.

(56) References Cited

U.S. PATENT DOCUMENTS

2010/0331200 A1   12/2010   Gordon et al.

FOREIGN PATENT DOCUMENTS

CN      106442683 A    2/2017
EP        3593133 A1    1/2020
(Continued)

OTHER PUBLICATIONS

Bronsema, K.J., et al. High-Sensitivity LC-MS/MS Quantification of Peptides and Proteins in Complex Biological Samples: The Impact of Enzymatic Digestion and Internal Standard Selection on Method Performance, Analytical Chemistry, 85, 9528-9535 (Year: 2013).*

(Continued)

*Primary Examiner* — Xiaoyun R Xu
(74) *Attorney, Agent, or Firm* — Wiley Rein LLP

(57) ABSTRACT

The embodiments herein provide methods to analyze the in vitro stability of recalcitrant or membrane-bound proteins in simulated gastric fluid (SGF) comprising the proteolytic enzyme, pepsin, and in combination with a novel pepsin-trypsin assay employing state-of-the-art mass spectrometric approaches, such as LC-MS/MS, to monitor the precise degradation products. The extent of protein digestion can be evaluated by the appearance of peptic products and the disappearance of tryptic peptide products (as a proxy for intact protein). The embodiments herein also provide methods for protein quantitation using high-sensitivity (Continued)

LC-MRM-MS quantification. The methods embodied herein are particularly useful in charactering proteins produced in transgenic plants, such as canola genetically engineered to produce long chain omega-3 polyunsaturated fatty acids.

7 Claims, 80 Drawing Sheets

Specification includes a Sequence Listing.

(51) Int. Cl.
  *H01J 49/00* (2006.01)
  *G01N 30/02* (2006.01)
(52) U.S. Cl.
  CPC .............. *G01N 2030/027* (2013.01); *G01N 2333/96433* (2013.01); *G01N 2333/96477* (2013.01)

(56) References Cited

FOREIGN PATENT DOCUMENTS

| JP | 2009508118 A | 2/2009 |
|---|---|---|
| WO | 2018/165350 A1 | 9/2018 |

OTHER PUBLICATIONS

"Extended European Search Report received for European Patent Application No. 18764619.5, mailed on Jul. 23, 2021", 14 pages.

Office Action received for Japanese Patent Application No. Tokugan2019-548596, mailed on Feb. 21, 2022, 5 pages (Official Copy only).

Mao, "Mass Spectrometry—Based Analysis of Digestive Stability of Target Protein in Genetically Modified Organism", Shipin Kexue/Food Science, vol. 37, No. 19, 2016, pp. 64-69.

Liu, "A proteomic analysis of seeds from Bt-transgenic *Brassica napus* and hybrids with wild *B. juncea*", Scientific Reports, vol. 5, Article No. 15480, 2015, 13 pages.

International Search issued in WO 2018/165350 A1, filed Sep. 13, 2018, which claims priority from PCT/US18/021423, filed Mar. 8, 2018.

Written Opinion issued in WO 2018/165350 A1, filed Sep. 13, 2018, hich claims priority from PCT/US18/021423, filed Mar. 8, 2018.

Colangelo, CM et al."Review of software tools for design and analysis of large scale MRM proteomic datasets" Methods, Jun. 15, 2013, Epub May 21, 2013, vol. 61, No. 3, pp. 287-298; abstract, p. 289, 1st col. 3rd paragraph; p. 291, 1st col. 3rd paragraph, p. 292, 1st col. 2nd paragraph, p. 293, 2nd col. 1st paragraph, p. 296, 1st col. 2nd paragraph; DOI: 10.1016/j.ymeth.2013.05.0004.

Golizeh, M. et al., "Optimized proteomic analysis of rat liver microsomoes using dual enzyme digestion with 2D-LC-MS/MS", Journal of Proteomics, Apr. 26, 2013, Epub Feb. 20, 2013, vol. 82, pp. 166-178; DOI: 1016/j.jprot. 2013.02.01.

McShane, E. et al., "Kinetic Analysis of Protein Stability Reveals Age-Dependent Degradiation", Oct. 20, 2016, Epub. Oct. 6, 2016, vol. 167, No. 3: pp. 803-815, DOI: 10.106/j.cell Sep. 15, 2016.

Cox HD, et al. "Efficient Digestion and Mass Spectral Analysis of Vesicular Glutamate Transporter 1: A Recombinant Membrane Protein Expressed in Yeast.", Journal of Proteome Research, Feb. 2008, Epub: Jan. 8, 2008, vol. 7, No. 2; pp. 570-578; abstract: DOI: 10.1021/pr070452b.

Office Action received for Chinese Patent Application No. 2018800298765, mailed on Dec. 9, 2020, 6 pages. (Official Copy Only).

Partial Supplementary European Search Report received for European Patent Application No. 18764619.5, mailed on Apr. 23, 2021, 16 pages.

Wijesinha-Bettoni, et al. "The Structural Characteristics of Non-specific Lipid Transfer Proteins Explain Their Resistance to Gastroduodenal Proteolysis", Biochemistry, vol. 49, No. 10, Feb. 2, 2010, pp. 2130-2139.

Yum, et al. "Interaction of the Protease Resistant Proteins with the Intestinal Mucosa Membrane Proteins (1036.3)", The FASEB Journal, vol. 28, Issue S1, XP00952692, Apr. 1, 2014, 2 pages.

\* cited by examiner

FIG. 2

(A) Picpa-ω3D: Score = 49.7, 43.9% coverage, 39 peptides
MSKVTVSGSEILEGSTKTVPRRSGNVASFKQQKTAIDTFGNVFKVPDYTIKDILDAIPKHCYERSLVKSMSYVVRDIVAISAI
AYVGLTYIPLLPNEFLRR*FAAWSAYVFS*I*SCFGFGIWI*LGHECGHSAFSNYG*WVNDTVGW*VLHSLVMVPYFSWKFSHAKHHKA
TGHMTRDMVFVPYTAEEFKEKHQVTSLHDIAEEETPIYSVFALLFQQLGGLSLYLATNATGQPYPGVSKFFKSHYWPSSPVFD
KKDYWYIVLSDLGILATLTSVYTAYK*VFGFWPTFITWFCPWI*LVNHWLVFVTFLQHTDSSMPHYDAQEWTFAKGAAATIDRE
FGILGIIFHDIIETHVLHHYVSRIPFYHAREATECIKKVMGEHYRHTDENMWVSLWKTWRSCQFVENHDGVYMFRNCNNVGV
KPKDT  (SEQ ID NO:1)

(B) Lackl-Δ12D: Score 16.5, 28.6% coverage, 13 peptides
MS*AVTVTGSDPKNRGSSSNTEQEVPKVAIDTNGNVFSVPDFTIKDILGAIPHECYERP*LATSLYYVFRDIFCMLTTGYLTHK
ILYPLLISYTSNSIIKF*TFWALYTYVQGLFGTGIWV*LAHECGHQAFSDYGIVNDFVGWTLHSYLMVPYFSWKYSHGKHHKAT
GHMTRDMVFVPATKEEFKKSRNFFGNLAEYSEDSPLRTLYELLVQQLGGWIAYLFVNVTGQPYPDVPSWKWNHFWLTSPLFE
QRDALYIFLSDLGILTQGIVLTLWYKK*FGGWSLFINWFVPYIW*VNHWLVFITFLQHTDPTMPHYNAEEWTFAKGAAATIDRK
FGFIGPHIFHDIIETHVLHHYCSRIPFYNARPASEAIKKVMGKHYRSSDENMWKSLWKSFRSCQYVDGDNGVLMFRNINNCG
VGAAEK  (SEQ ID NO:2)

(C) Micpu-Δ6D: Score = 67.6, Coverage = 66.7%, 48 peptides
MCPPKTDGR*SSPRSPLTRSKSSAEALDAKDASTAPVDLKTLEPHELAATFETRWVRVEDVEYDVTNFKHPGGSVIFYMLANT*
GADATEAFKEFHMRSLKAWKMLRALPSRPAEIKRSESEDAPMLEDFARWRAELERDGFFKPSITHVAYR*LLELLATFALGTA*
*LMYAGYPIIASVVYGAFFGAR*CGWVQHEGGHNSLTGSVYVDKRLQAMTCGFGLSTSGEMWNQMHNKHHATPQKVRHDMDLDT
TPAVAFFNTAVEDNRPRGFSRAWARLQAWTFVPVTSGLLVQAFWIYVLHPRQVLRKKNYEEASWMLVSHVVRTAVIKLATGY
*SWPVAYWWFTFGNWIAYMYLFAHFSTSHTHLPVVPSDK*HLSWVNYAVDHTVDIDPSRGYVNWLMGYLNCQVIHHLFPDMPQF
RQPEVSRRFVPFAKKWGLNYKVLSYYGAWKATFSNLDKVGQHYYVNGKAEKAH  (SEQ ID NO:3)

(D) Pyrco-Δ6E: Score 8.3, 22.9% coverage, 6 peptides
MEFAQPLVAMAQEQYAAIDAVVAPAIFSATDSIGWGLKPISSATKDLPLVESPTPLILSLLAYFAIVGSGLVYRKVFPRTVK
GQDPFLLKALMLAHNVFLIGLSLYMCLKLVYEAYVNKYSFWGNAYNPAQTEMAKVIWIFYVSKIYEFMDTFIMLLKGNVNQV
SFLHVYHHGSISGIWWMITYAAPGGDAYFSAALNSWVHVCMYTYYFMAAVLFK DEKTKRKYLWWGRYLTQMQMFQFFMNLLQ
AVYLLYSSSPYPKFIAQLLVVYMVTLLMLFGNFYYMKHHASK  (SEQ ID NO:4)

(E) Pavsa-Δ5D: Score 27.3, 34.6% coverage, 17 peptides
MPPRDSYSYAAPPSAQLHEVDTPQEHDKKELVIGDRAYDVTNFYKRHPGGK*IIAYQVGTDATDAYKQFHVRSAKADKMLKSL*
*PSRPVHKGYSPRRADLIADFQEFTKQLEAEGMFEPSLPHVAYRLAEVIAMHVAGAALIWHGYTFAGIAMLGVVQGRCGWLMH
EGGHYSLTGNIAFDRAIQVACYGLGCGMSGAWWRNQRNKHHATPQKLQHDVDLDTLPLVAFHERIAAKVKSPAMKAWLSMQA
KLFAPVTTLLVALGWQLYLHPRHMLRTKHYDELAMLGIRYGLVGYLAANYGAGYVLACYLLYVQLGAMYIFCNFAVSHTHLP
VVEPNEHATWVEYAANHTTNCSPSWWCDWWMSYLNYQIEHHLYPSMPQFRHPKIAPRVKQLFEKHGLHYDVRGYFEAMADTF
ANLDNVAHAPEKKMQ  (SEQ ID NO:5)

(F) Pyrco-Δ5E: Score 25.6, 51.3% coverage, 28 peptides
MASIAIPAALAGTLGYVTYNVANPDIPASEKVPAYFMQVEYWGPTIGTIGYLLFIYFGKRIMQNRSQPFGLKNAMLVYNFYQ
TFFNSYCIYLFVTSHRAQGLK VWGNIPDMTANSWGISQVIWLHYNNKYVELLDTFFMVRRK FDQLSFLHIYHHTLLIWSNF
VVMK LEPVGDCYFGSSVNTFVHVIMYSYYGLAALGVNCFWKKYITQIQMLQFCICASHSIYTAYVQNTAFWLPYLQLWVMVN
*MFVLFANFYRKRYKSKGAKKQ*  (SEQ ID NO:6)

(G) Pavsa-Δ4D: Score = 61.4, 82.1% coverage, 51 peptides
MPPSAAKQMGASTGVHAGVTDSSAFTRKDVADRPDLTIVGDSVYDAK*AFRSEHPGGAHFVSLFGGRDATEAFMEYHRRAWPK*
SRMSP*FHVGSLASTEEPVAADEGYLQLCARIAKMVPSVSSGFAPASYWVKAGLILGSAIALEAYMLYAGKRLLPSIVLGWLF
ALIGLNIQHDANHGALSKSASVNLALGLCQDWIGGSMILWLQEHVVMHHLHTNDVDKDPDQK*AHGALRLKPTDAWSPMHWLQ
HLYLLPGETMYAFKLLFLDISELVMWRWEGEPISKLAGYLFMPSLLLKLTFWAR*FVALPLYLAPSVHTAVCIAATVMTGSFY
LAFFFFISHNFEGVASVGPDGSITSMTRGASFLKRQAETSSNVGGPLLATLNGGLNYQIEHHLFPRVHHGFYPRLAPLVKAE
LEARGIEYKHYPTIWSNLASTLRHMYALGRRPRSKAE  (SEQ ID NO:7)

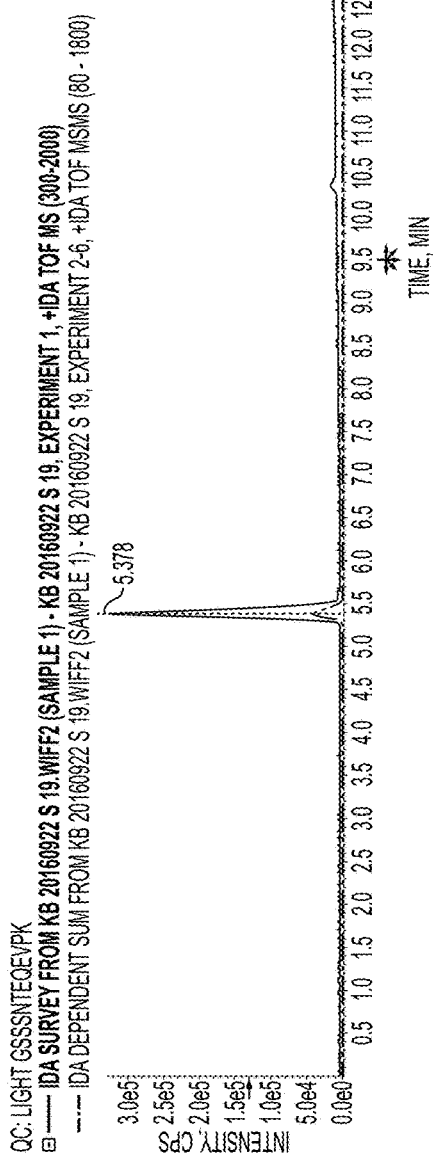
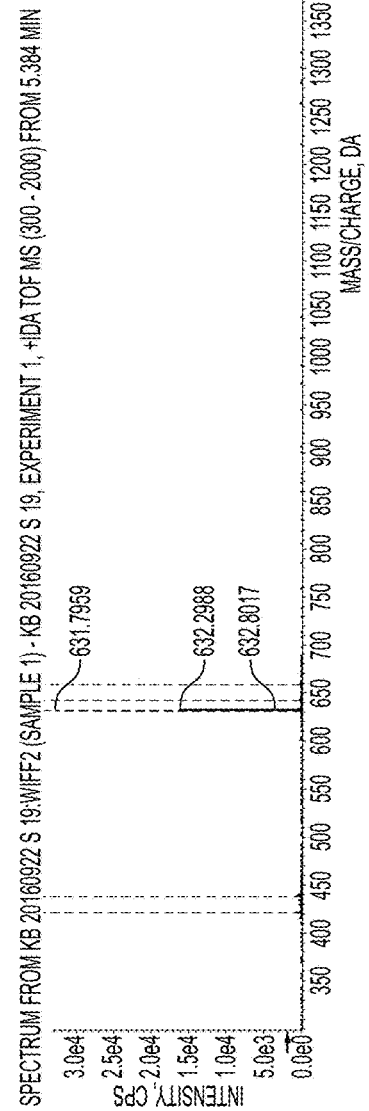
FIG. 3A

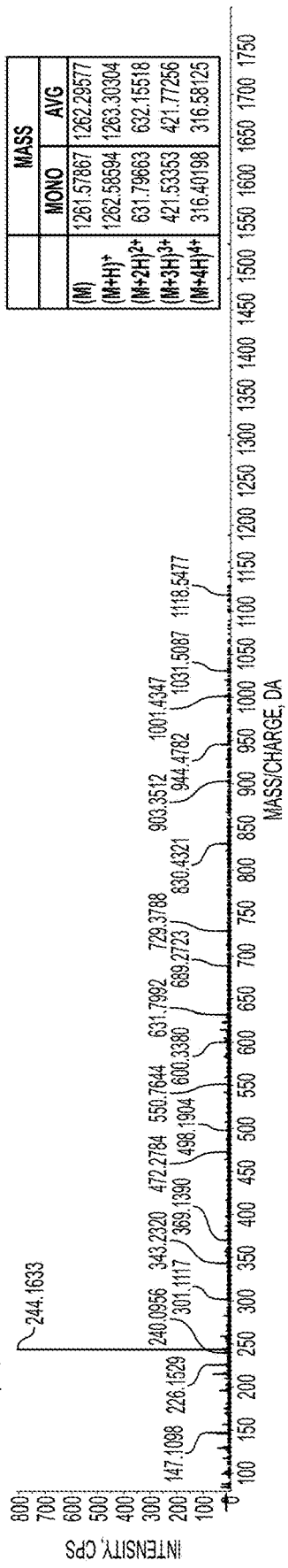
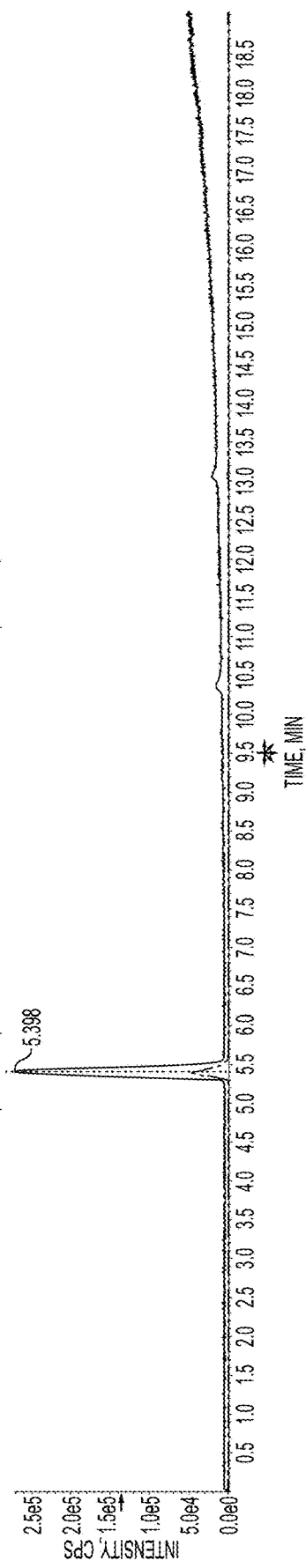
FIG. 3A (CONT.)
FIG. 3B

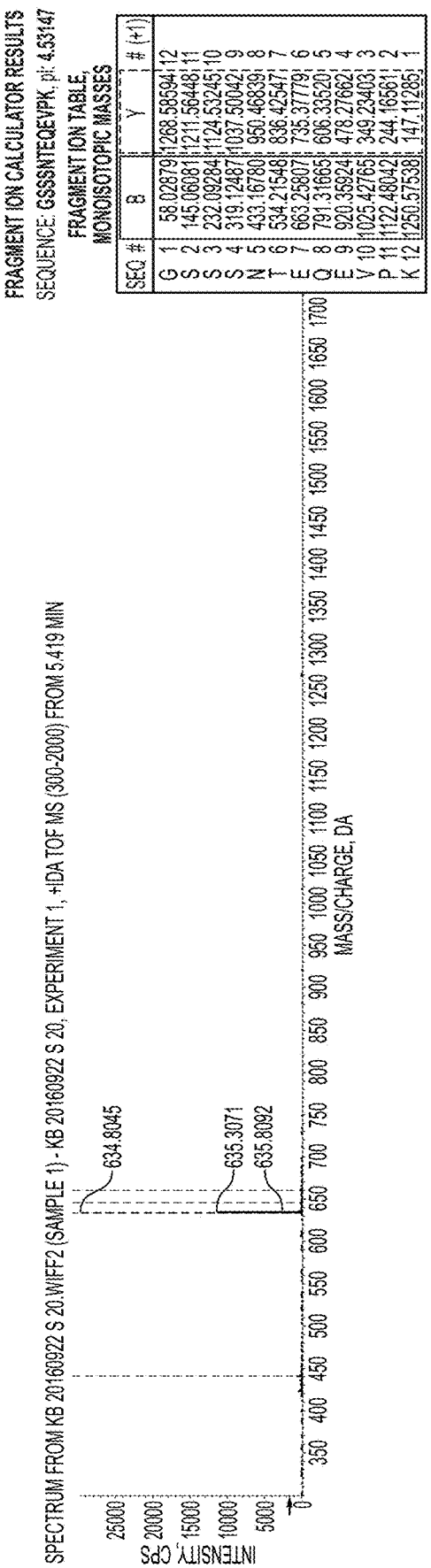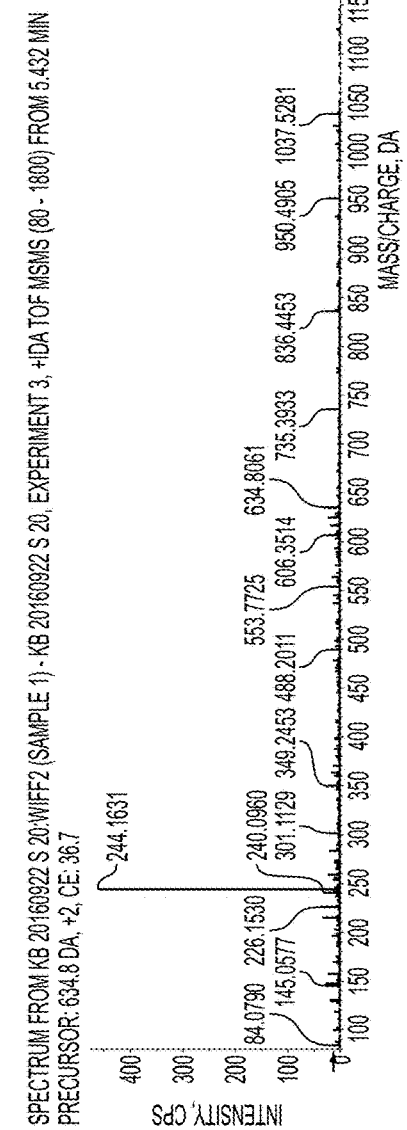
FIG. 3B (CONT.)

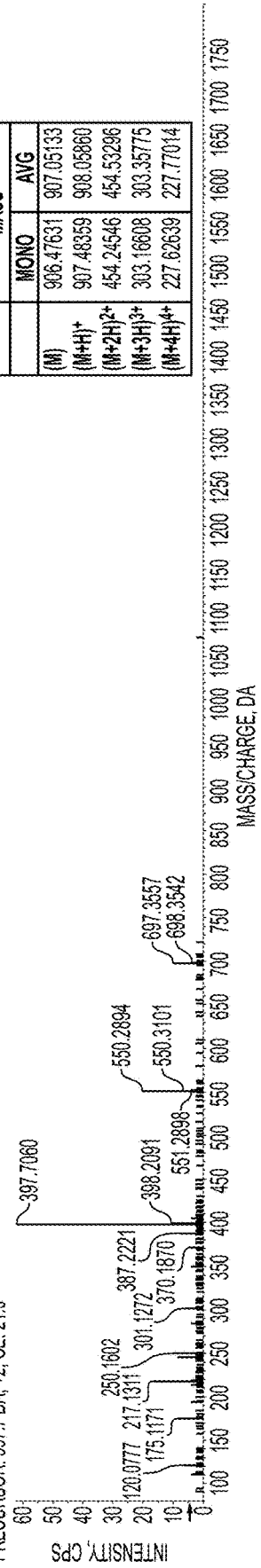
FIG. 4B (CONT.)

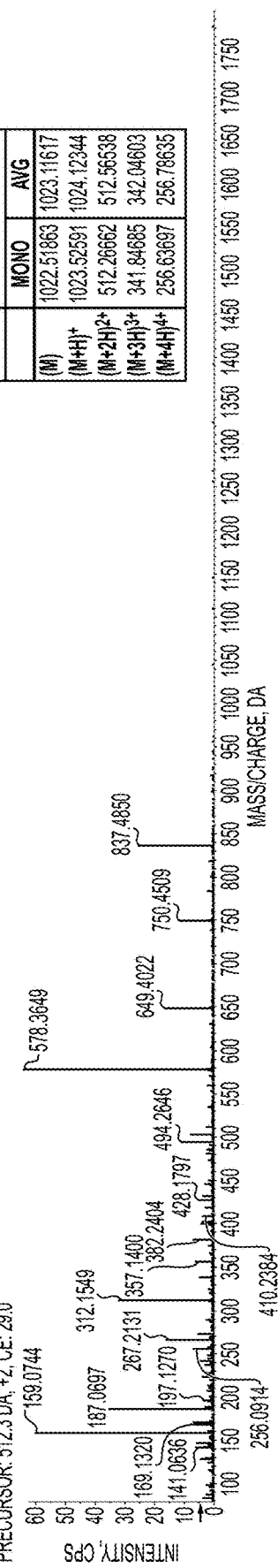
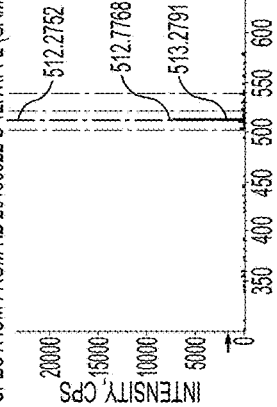
FIG. 5B (CONT.)

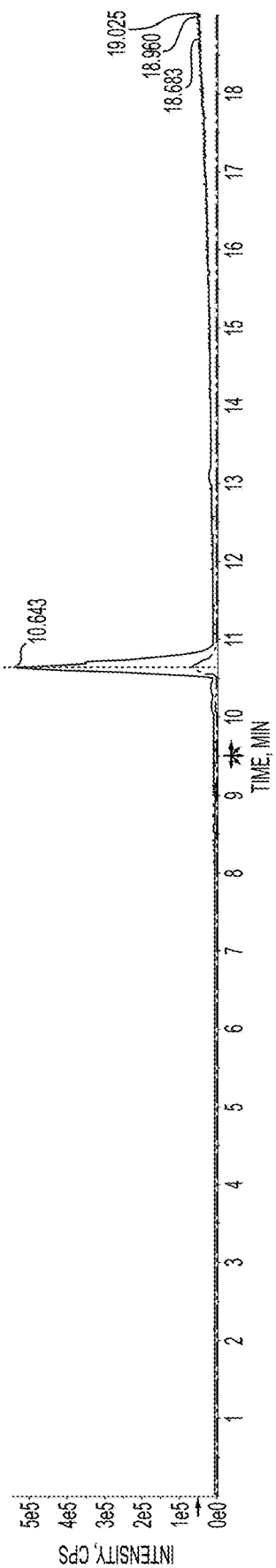
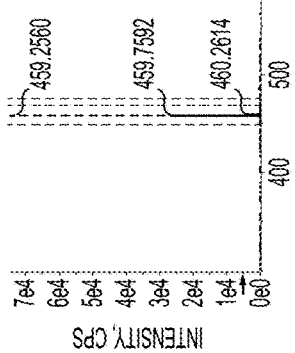
FIG. 6A

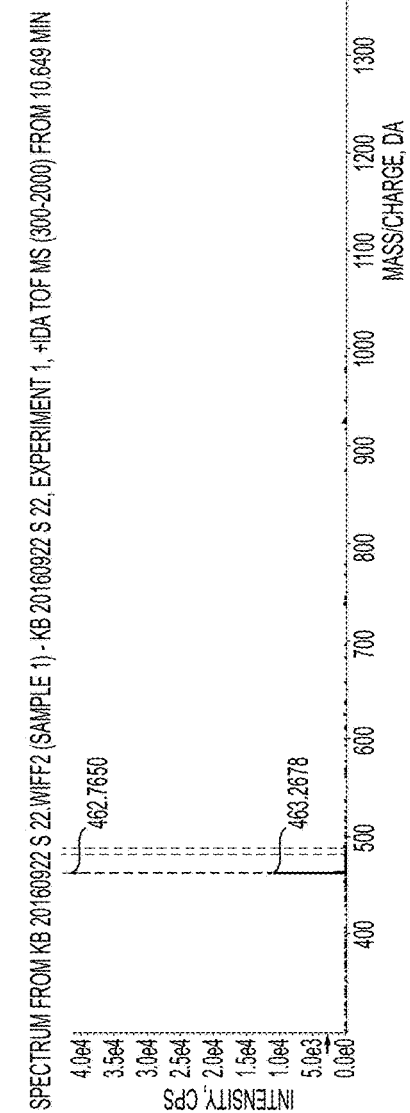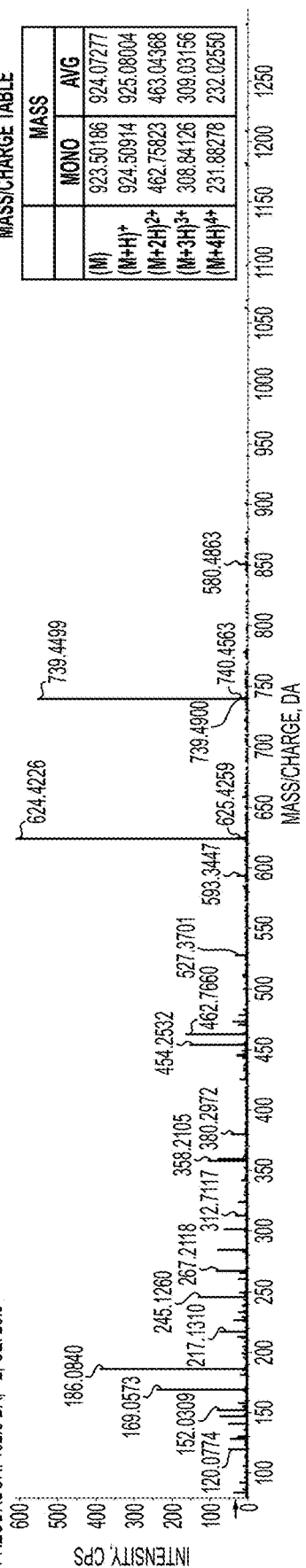
FIG. 6B (CONT.)

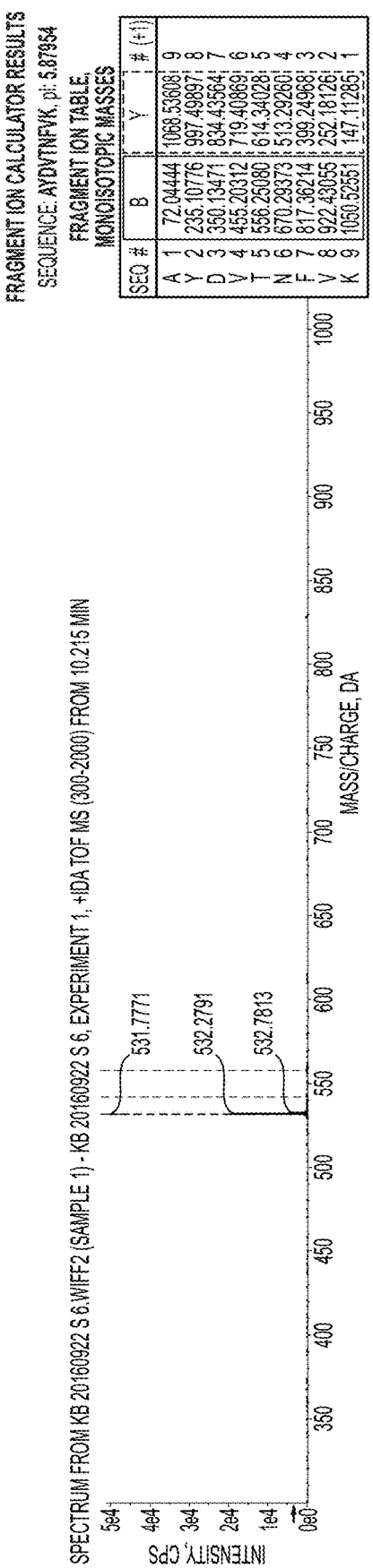
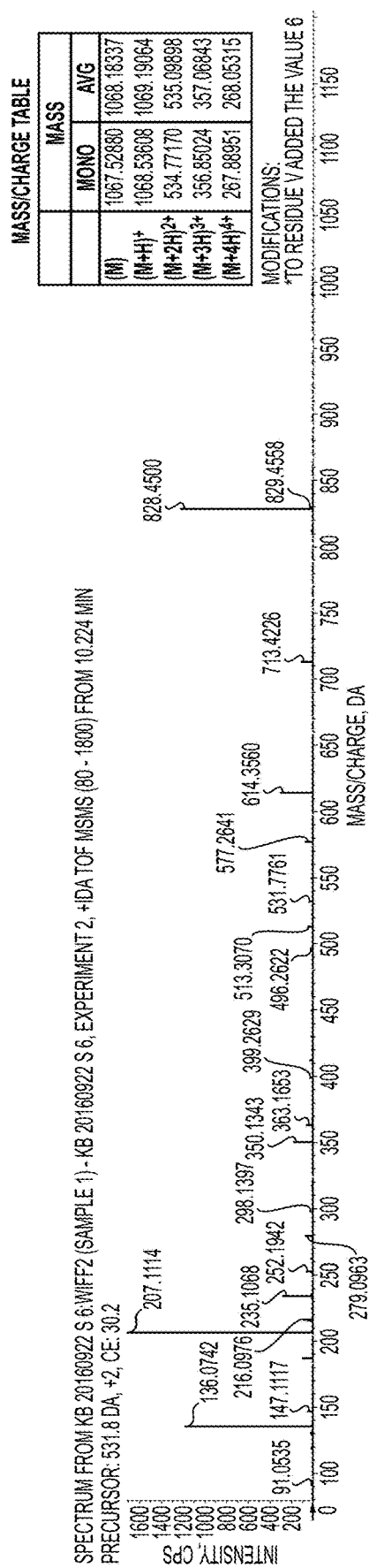
FIG. 7B (CONT.)

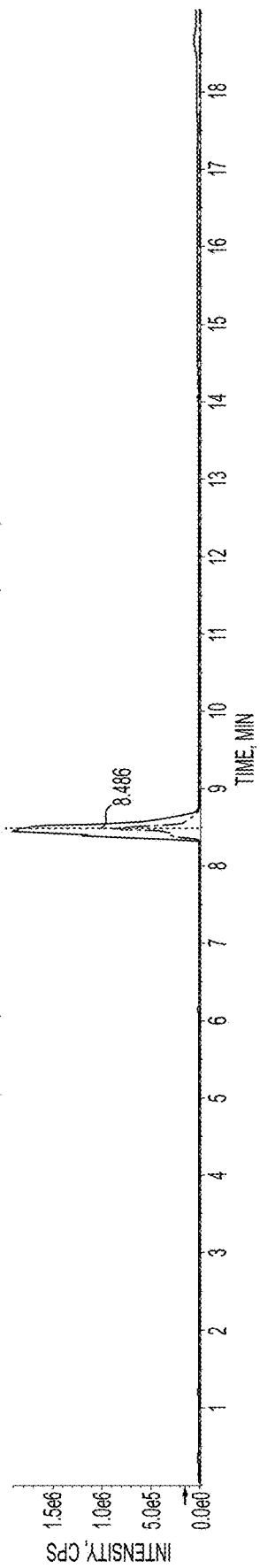
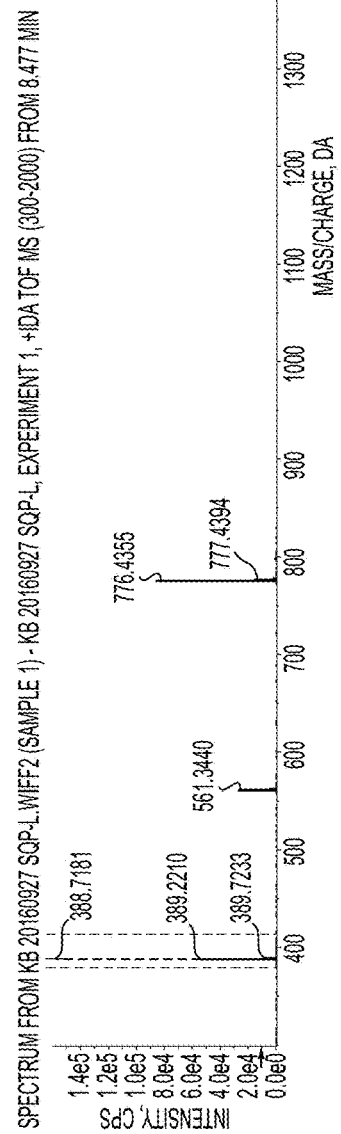
FIG. 8A

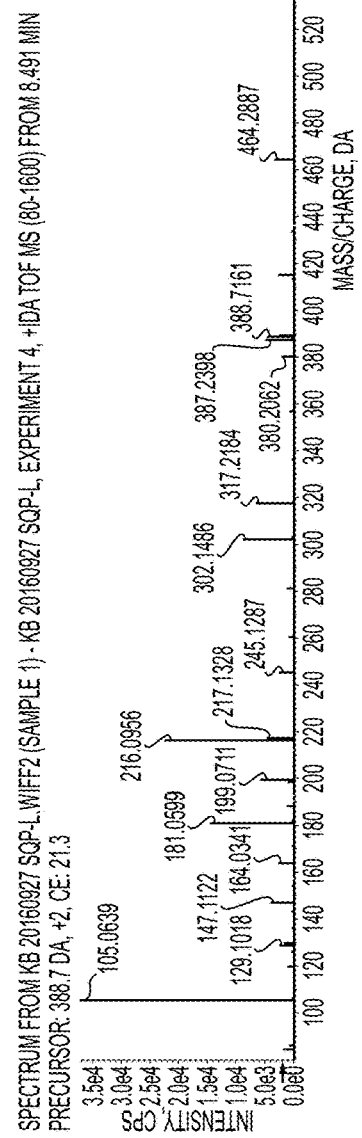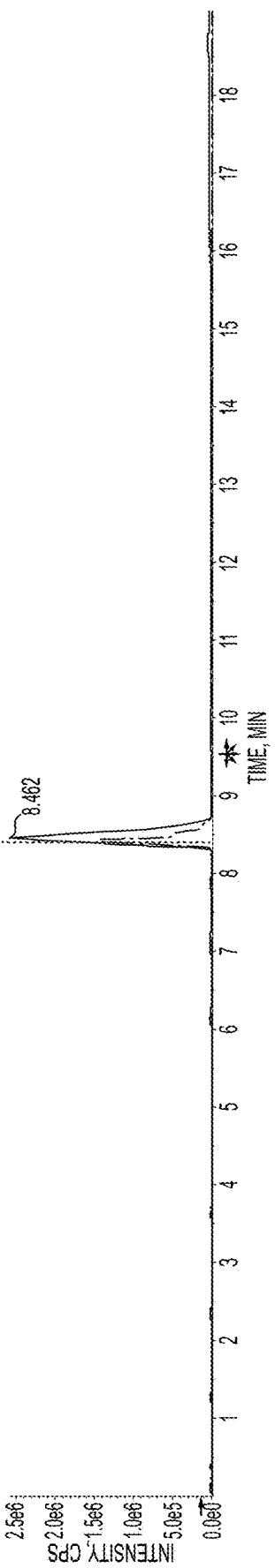
FIG. 8A (CONT.)
FIG. 8B

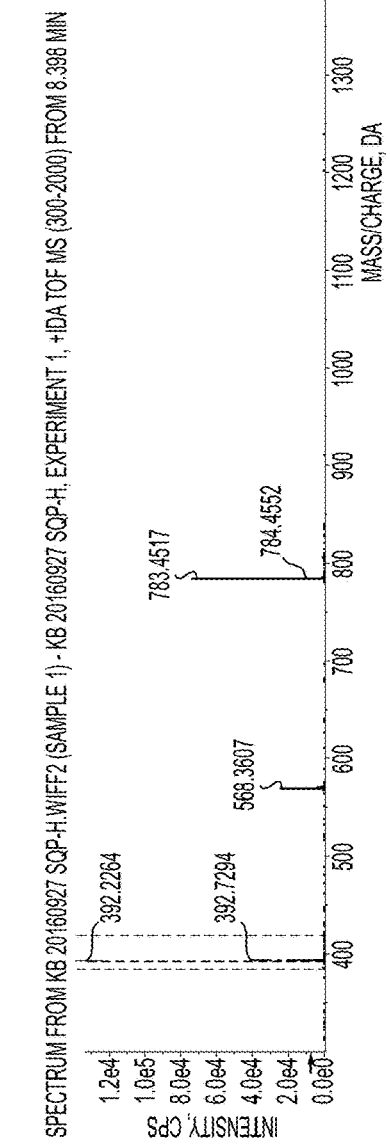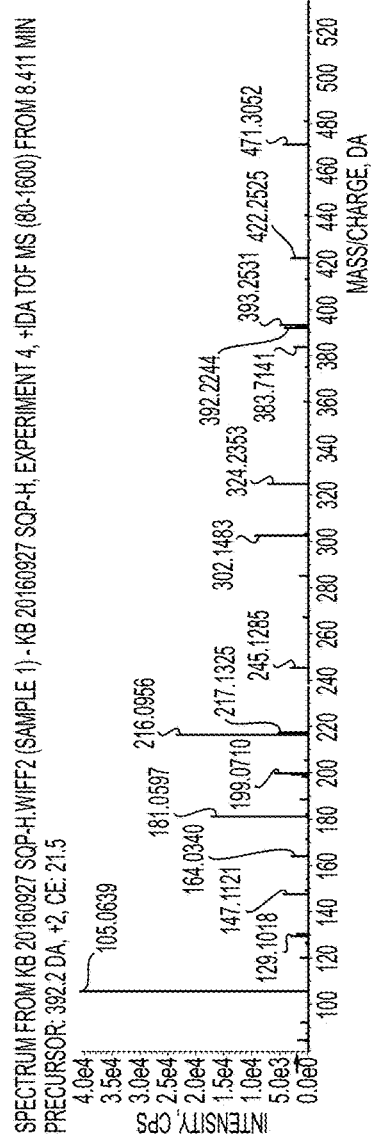
FIG. 8B (CONT.)

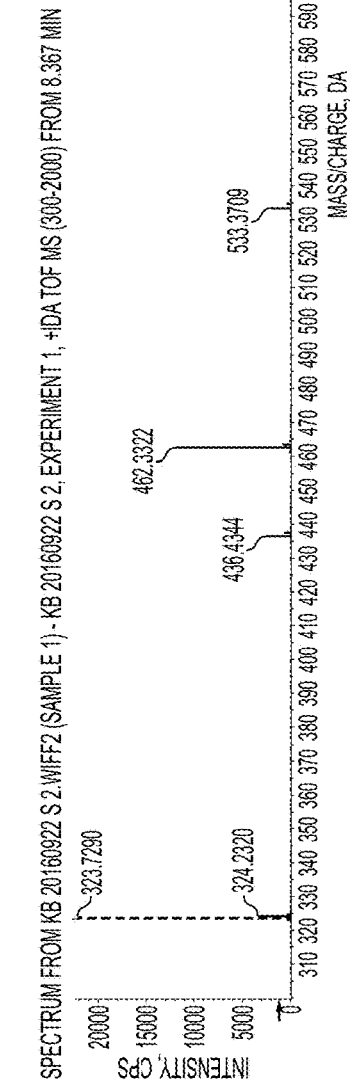
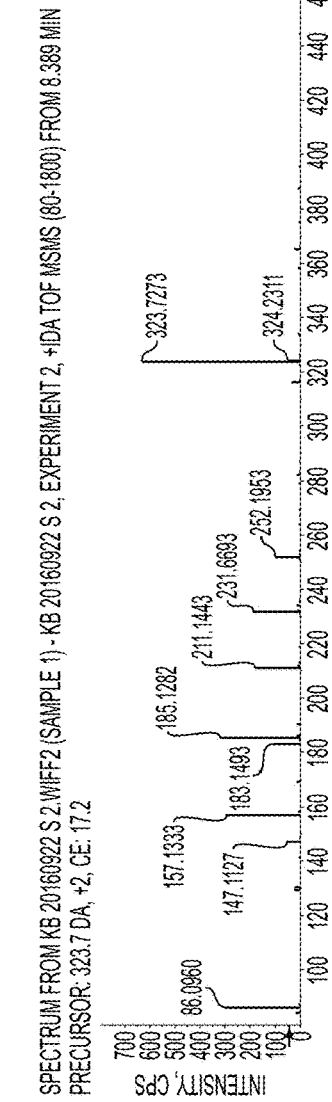
FIG. 9B *(CONT.)*

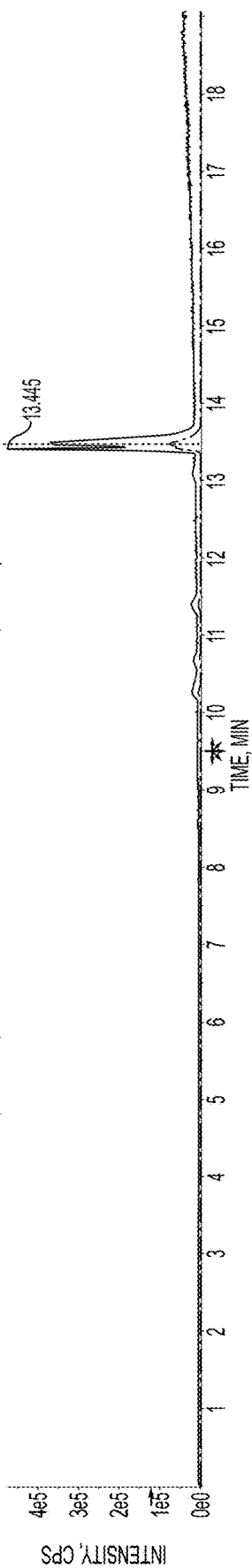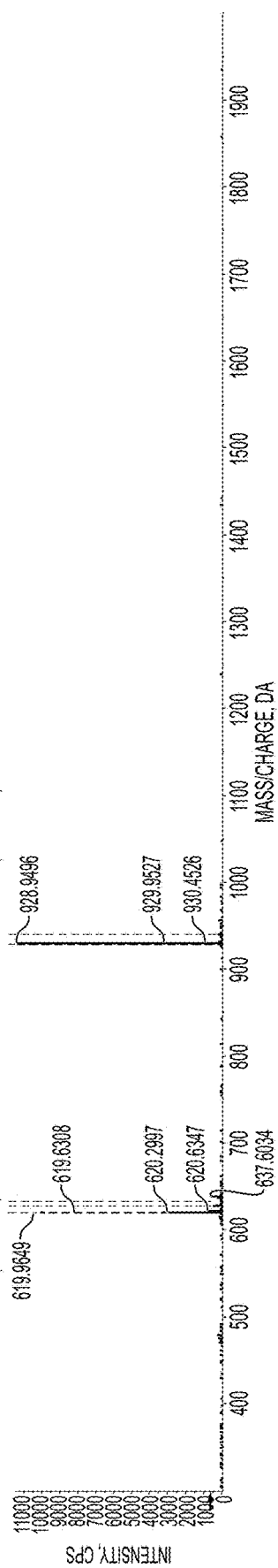
FIG. 10A

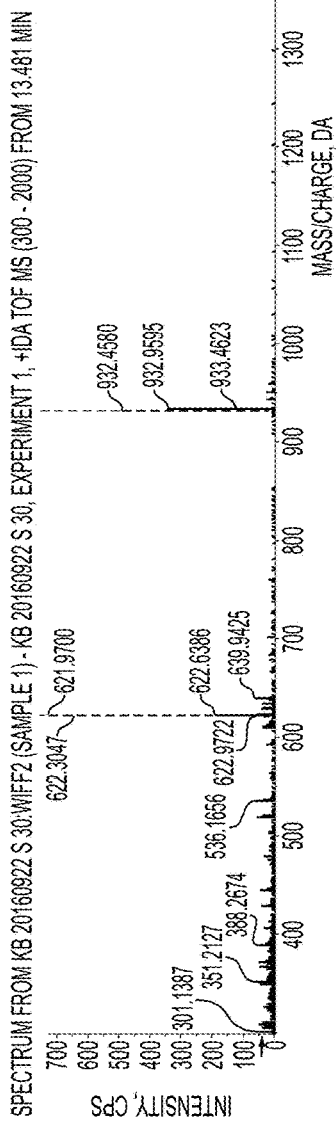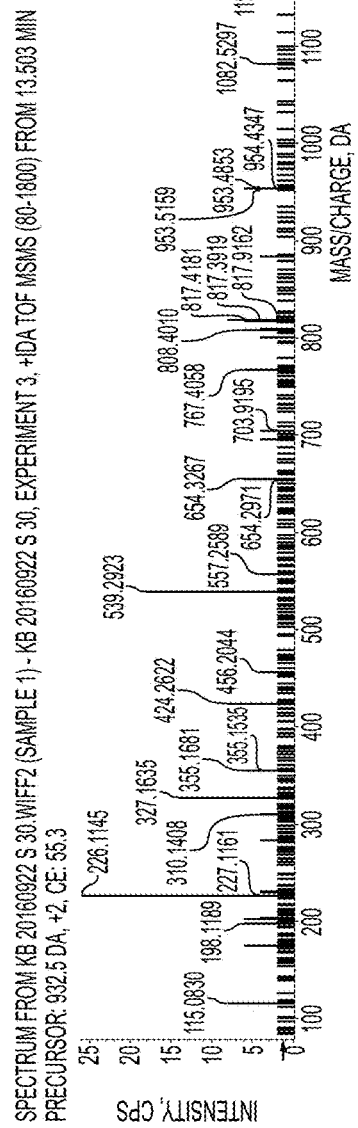
FIG. 10B (CONT.)

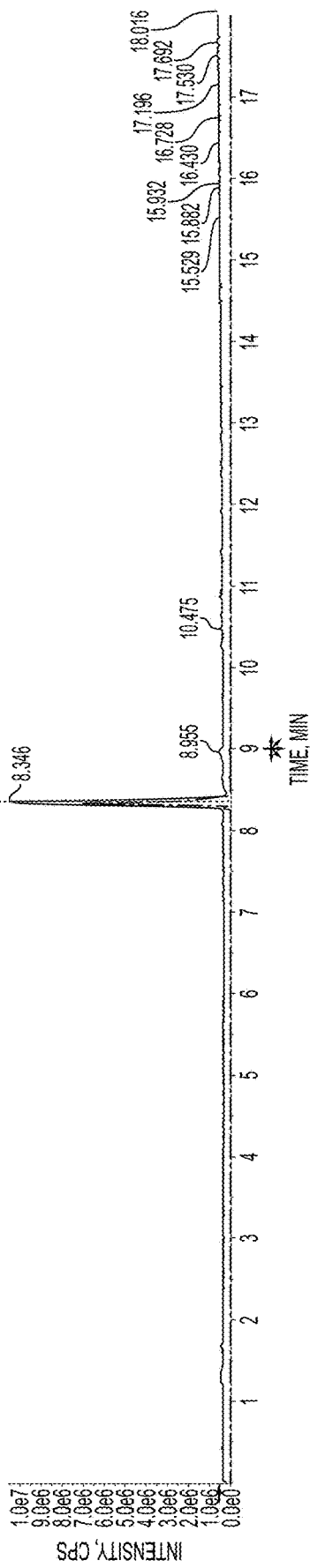
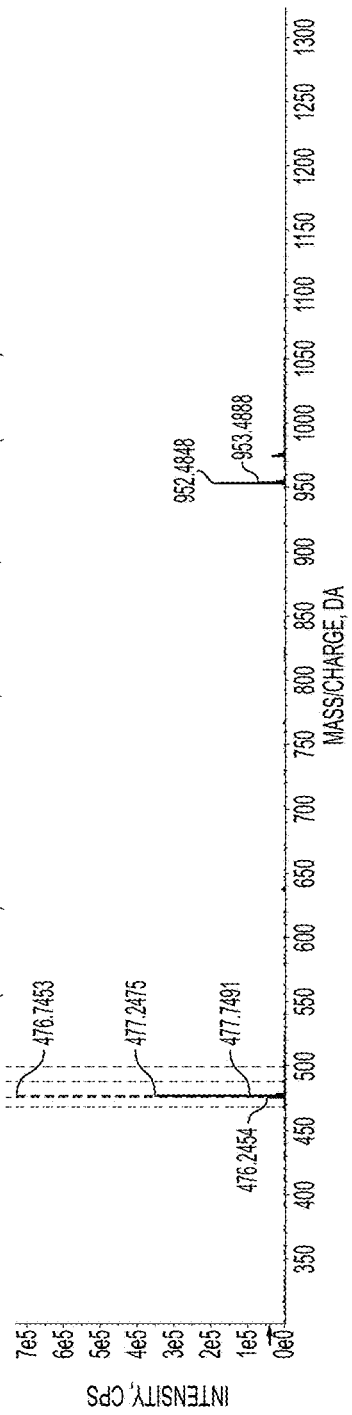
FIG. 11

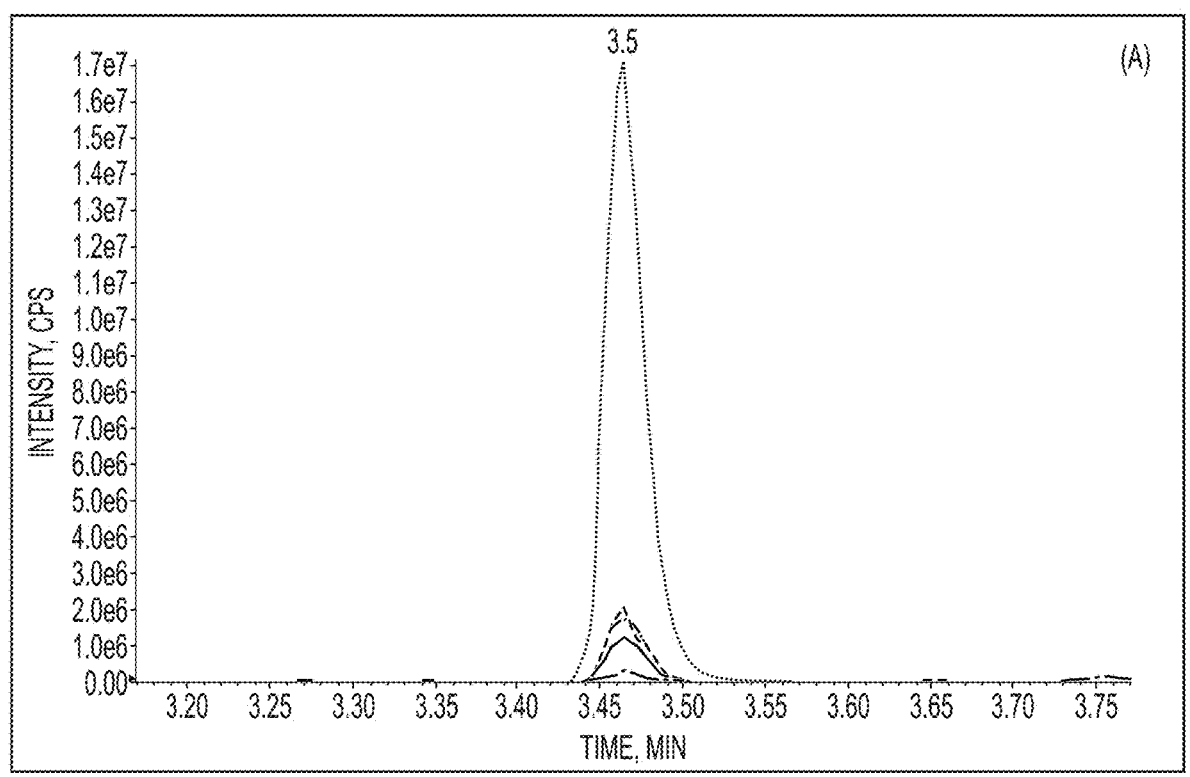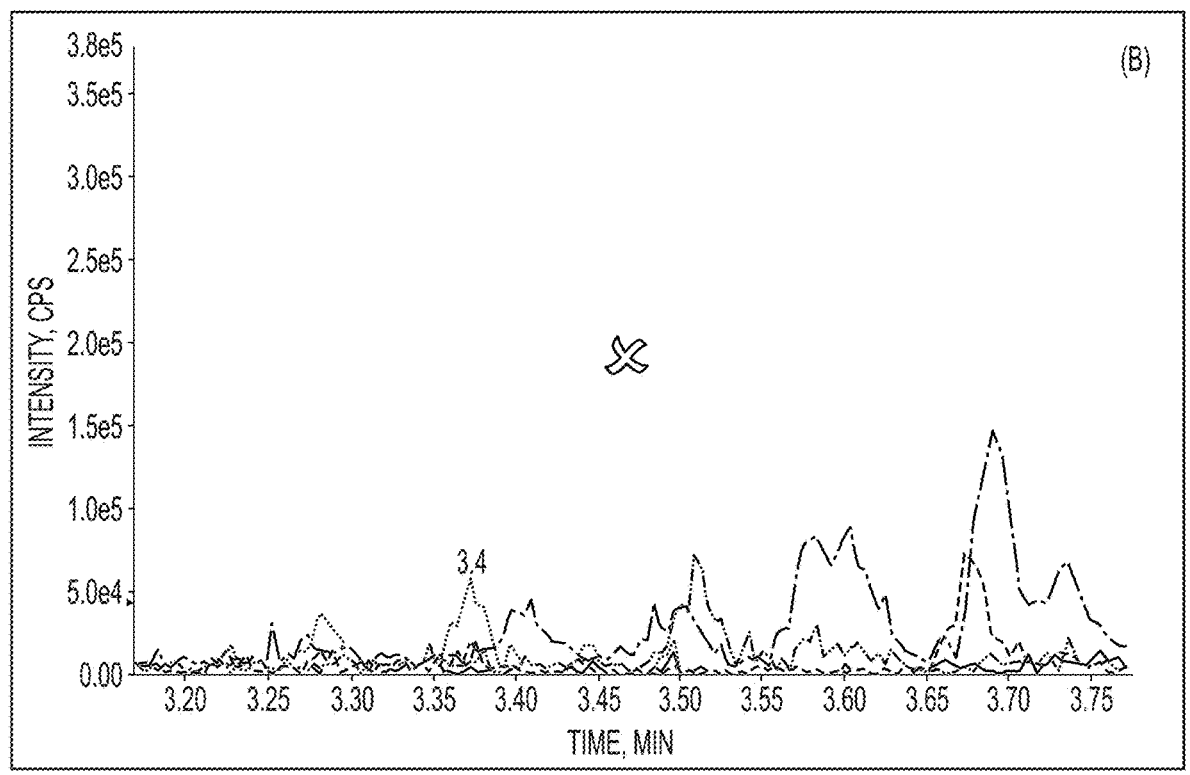
FIG. 18

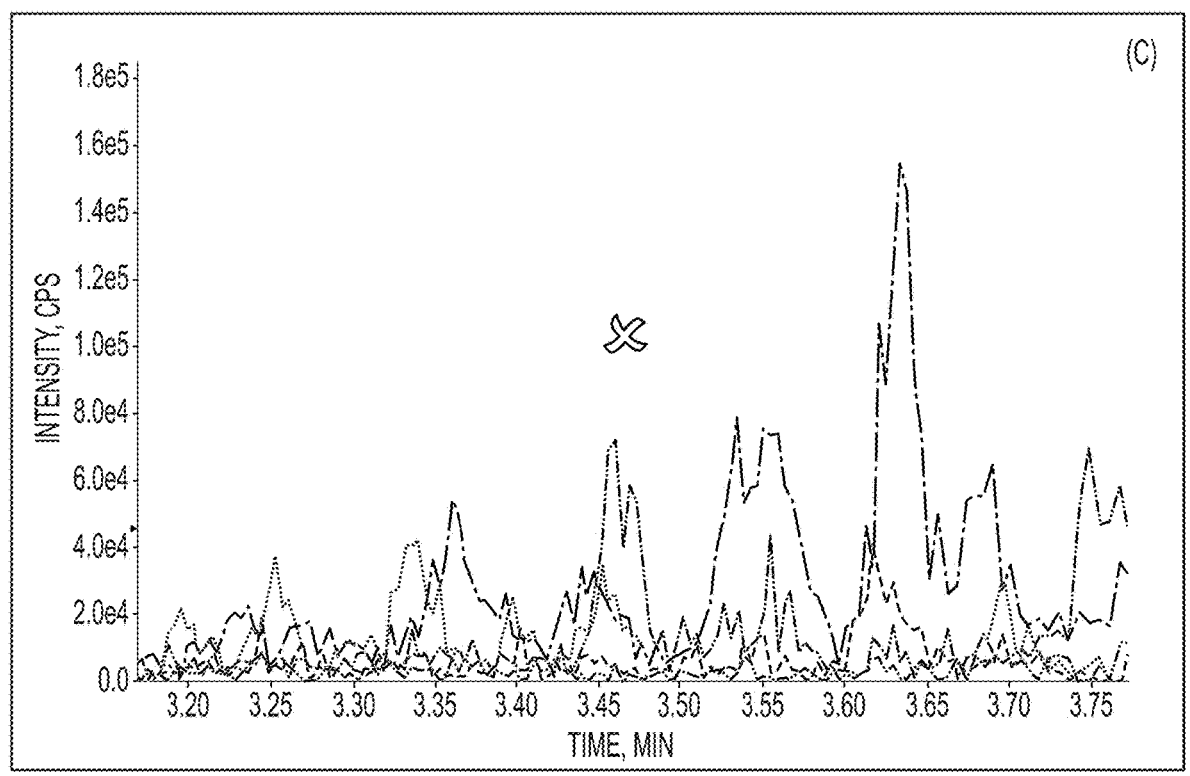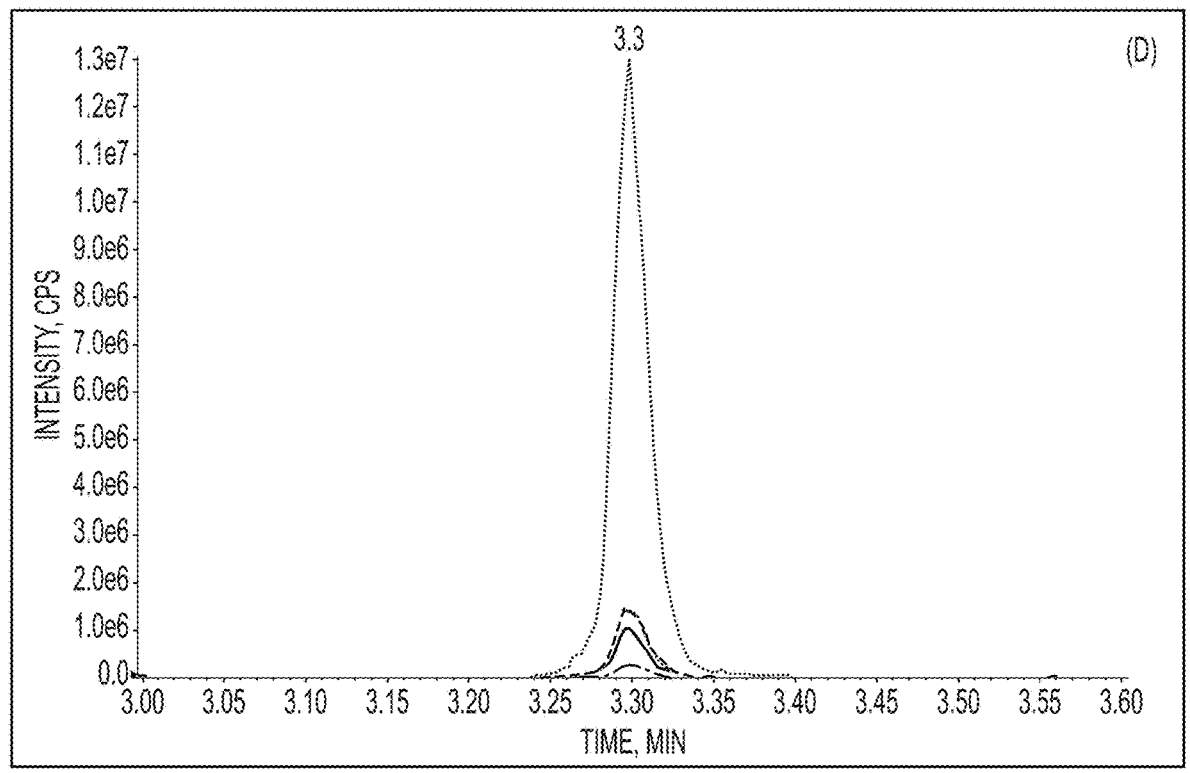
FIG. 18 (CONT. 1)

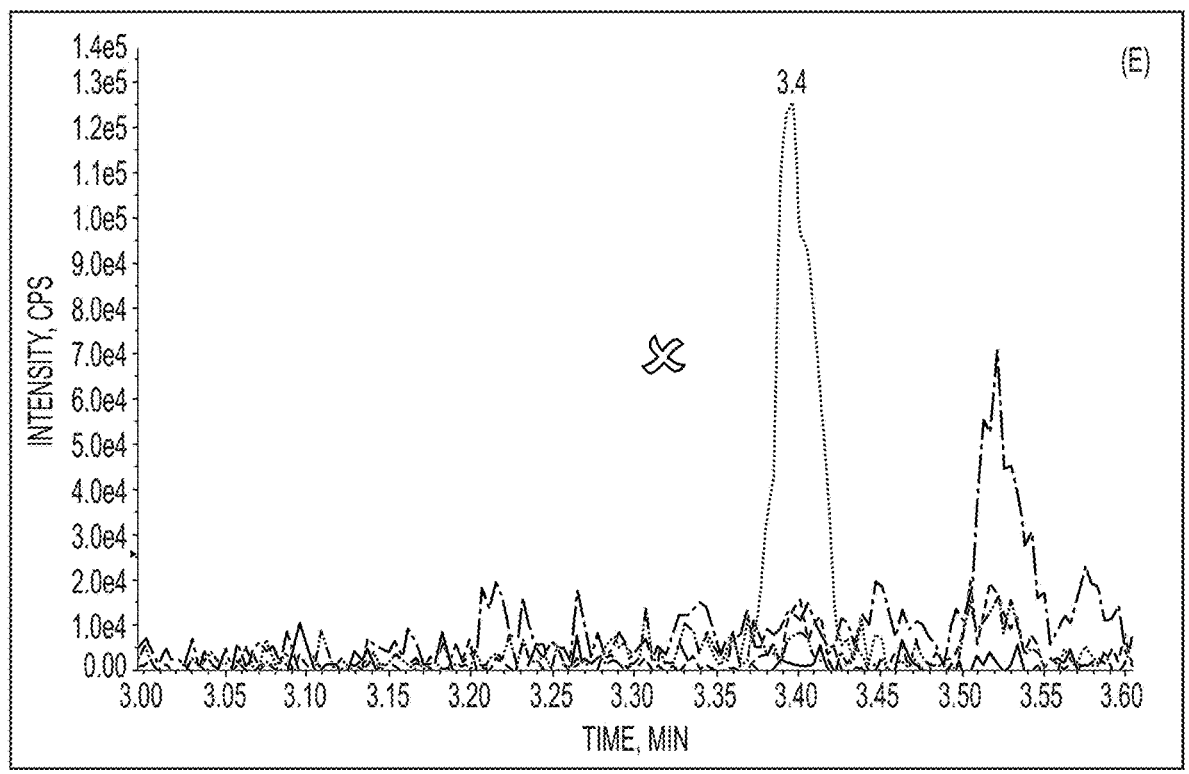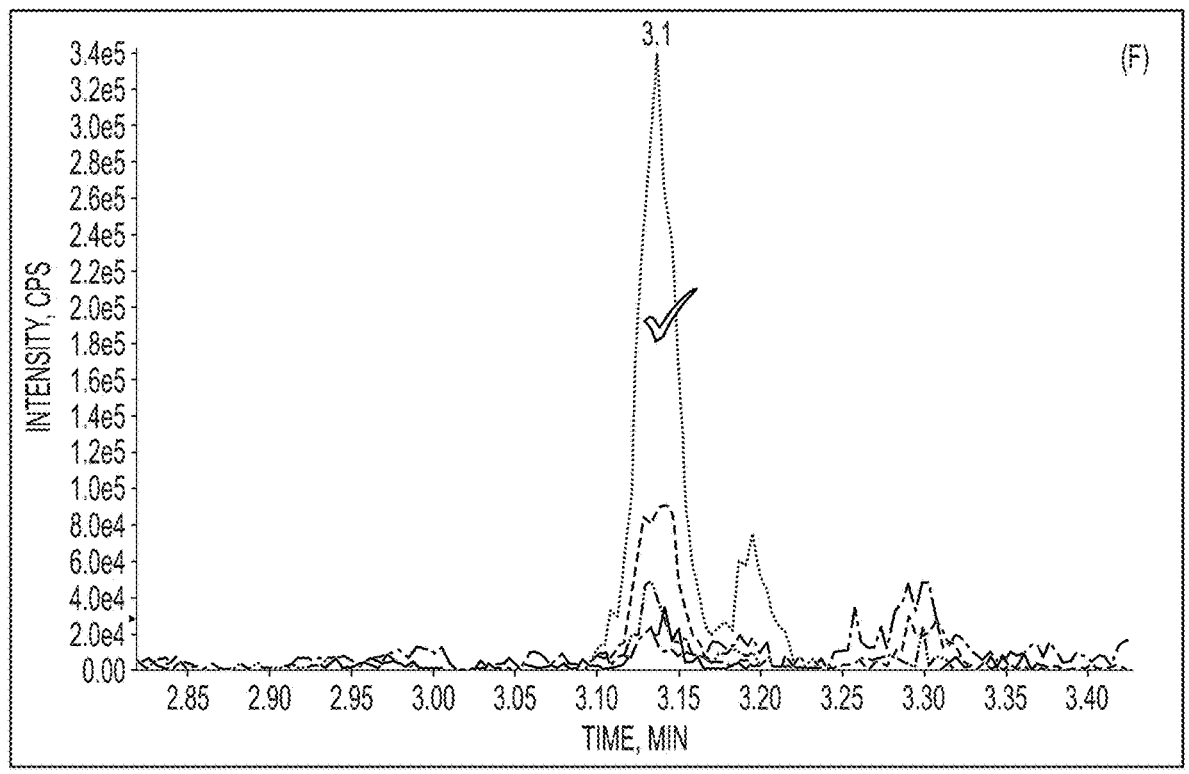
FIG. 18 (CONT. 2)

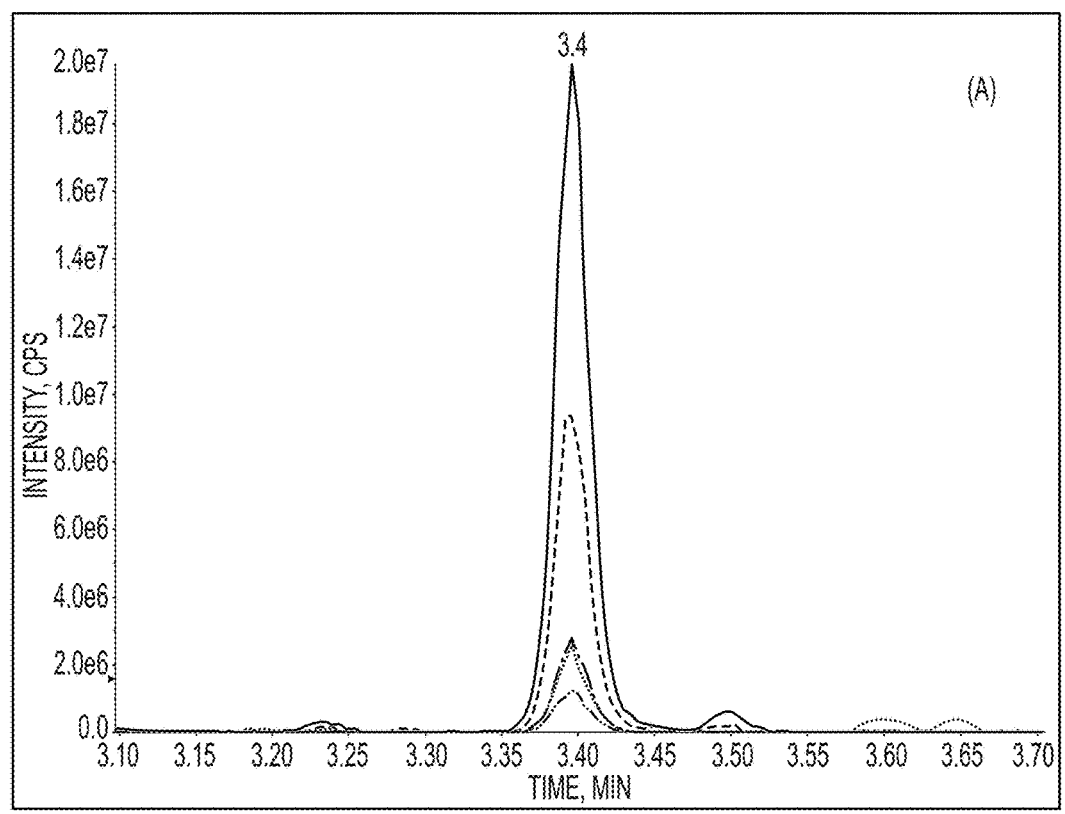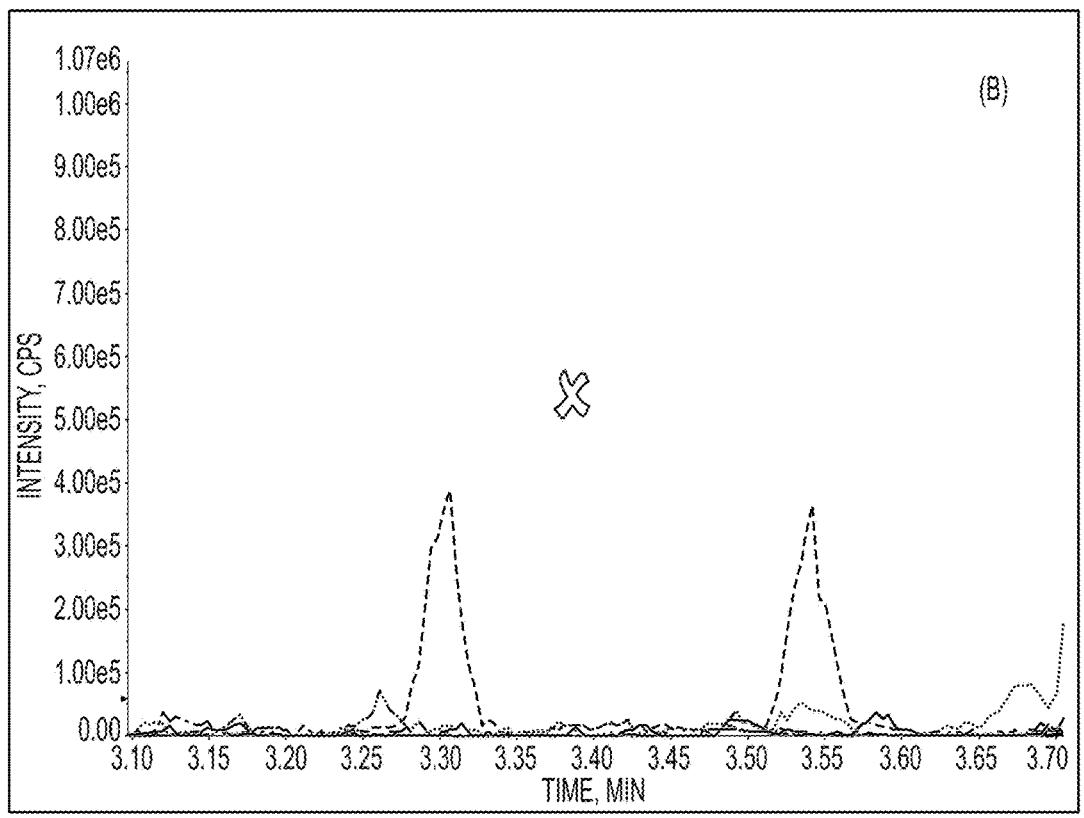
FIG. 19

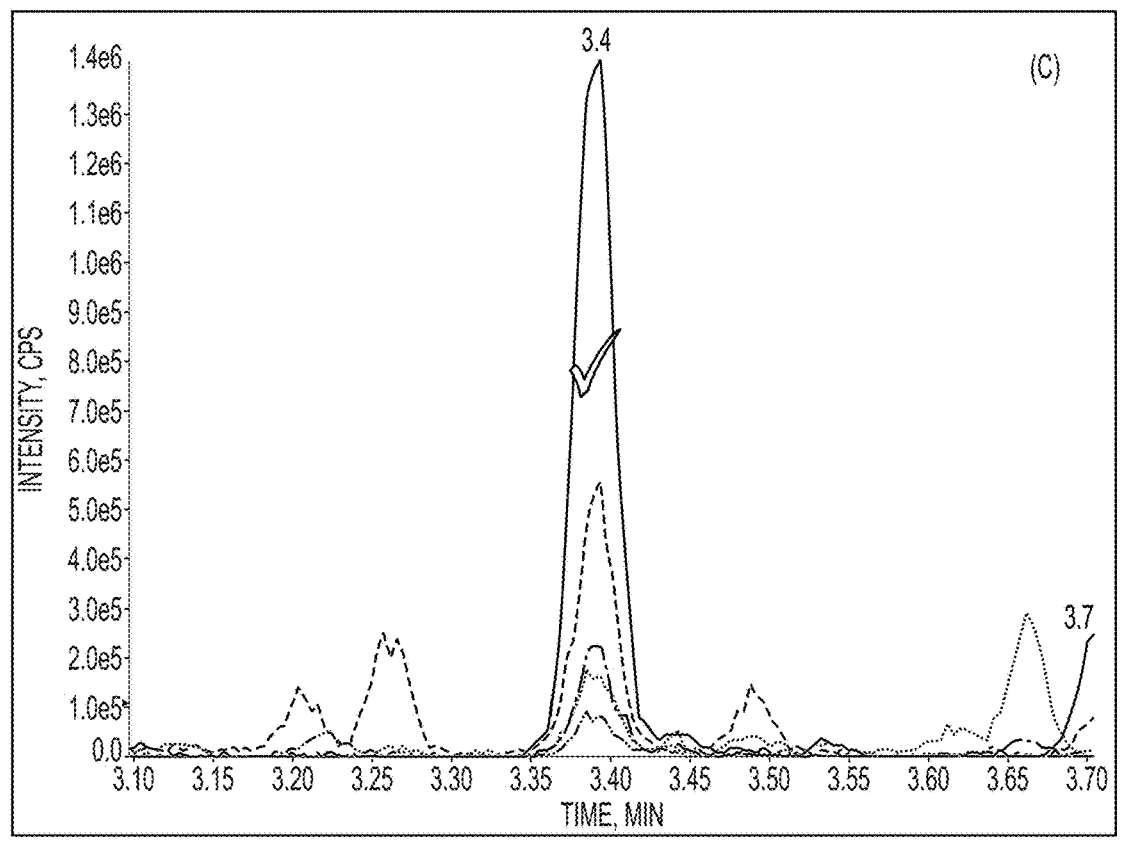
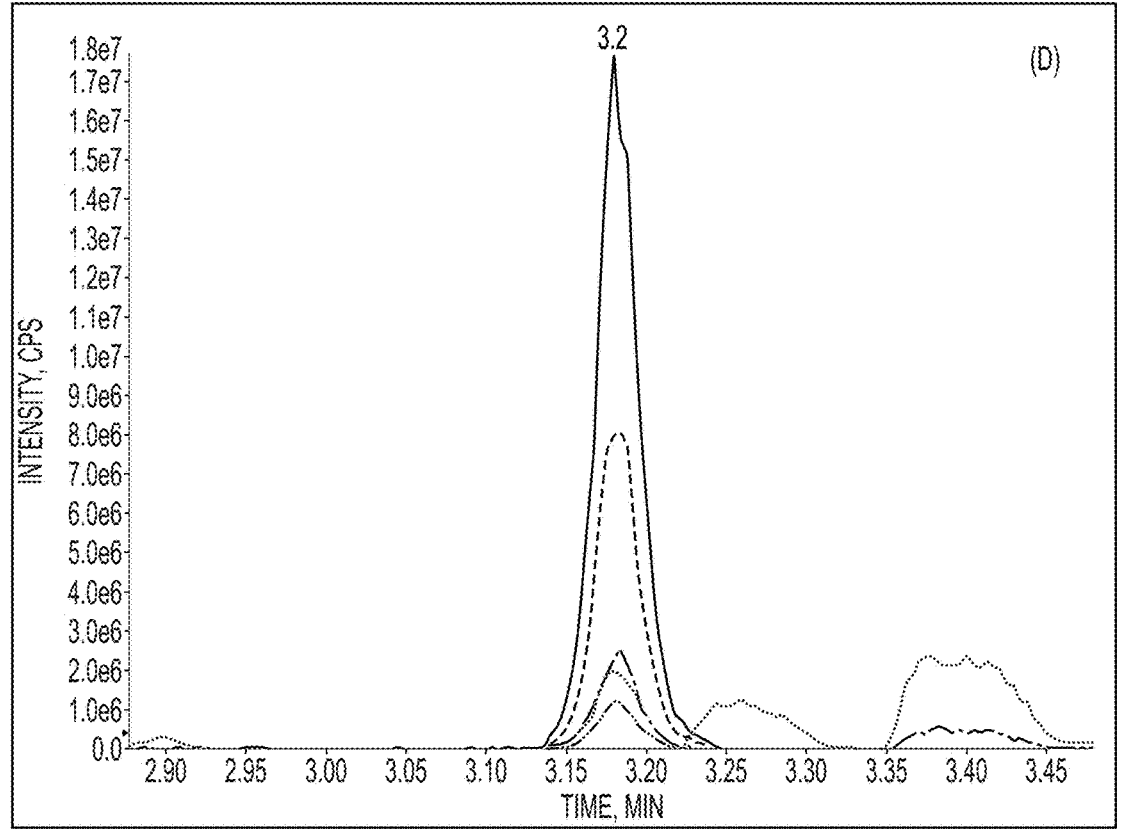
FIG. 19 (CONT. 1)

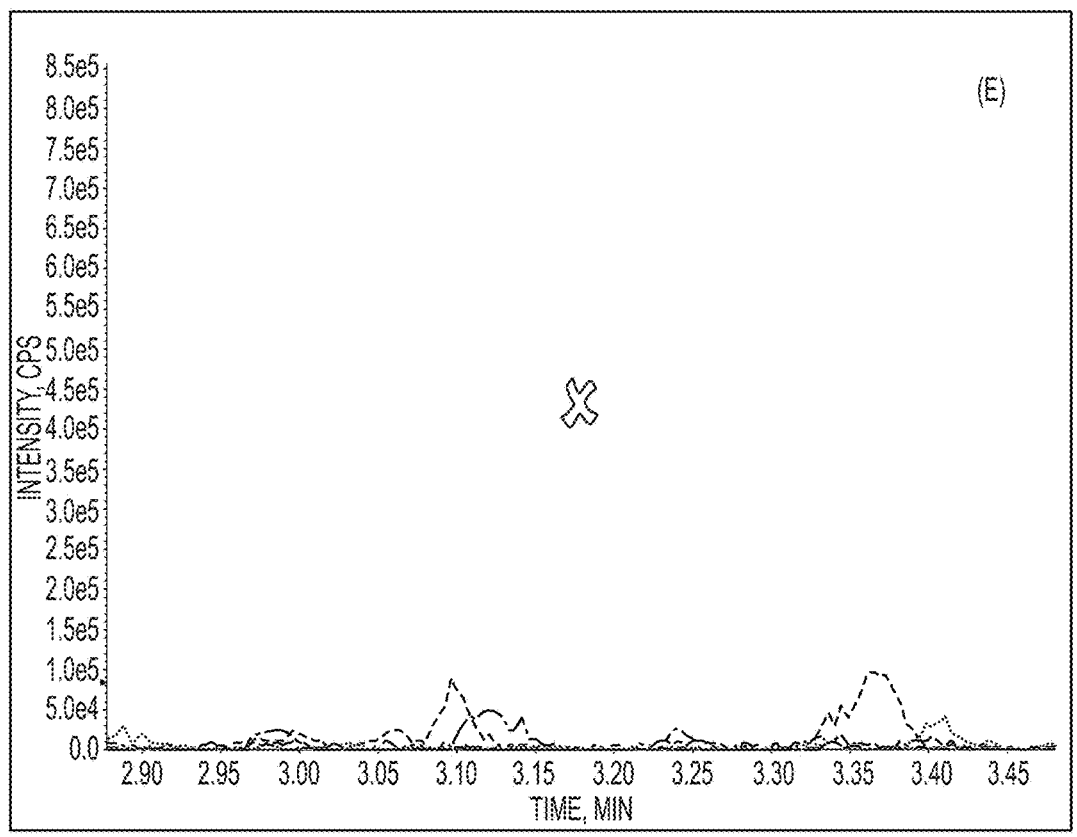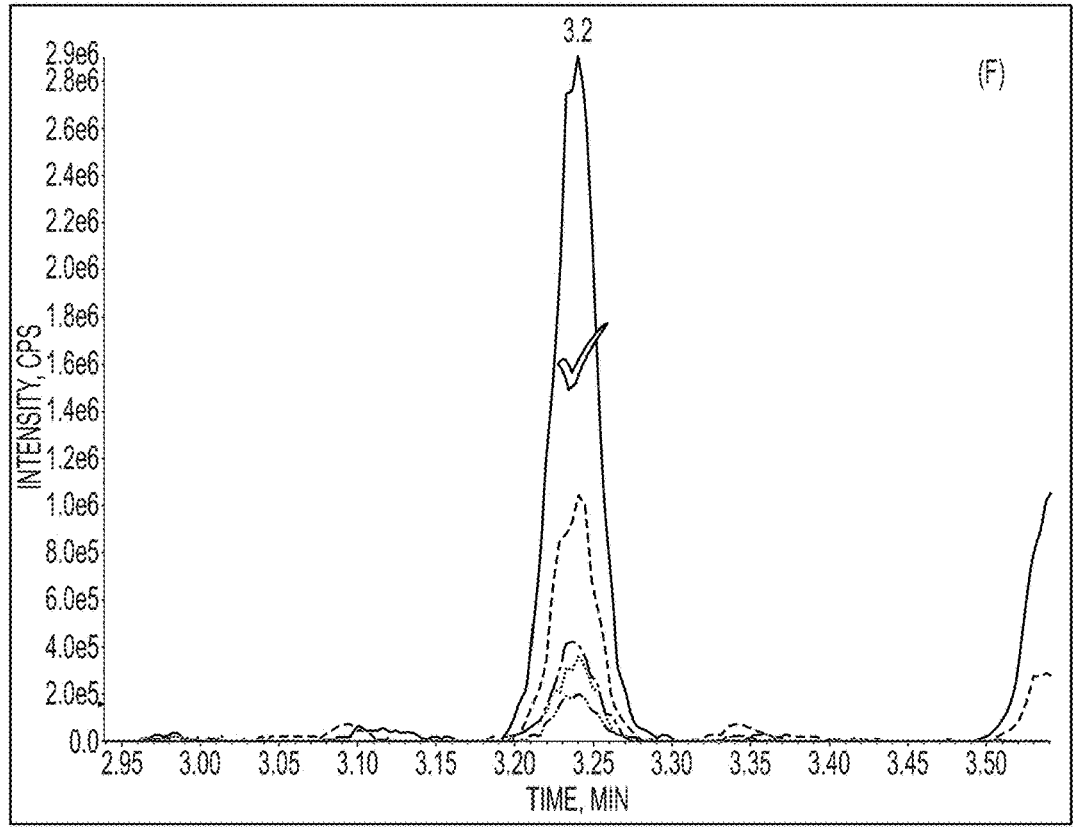
FIG. 19 (CONT. 2)

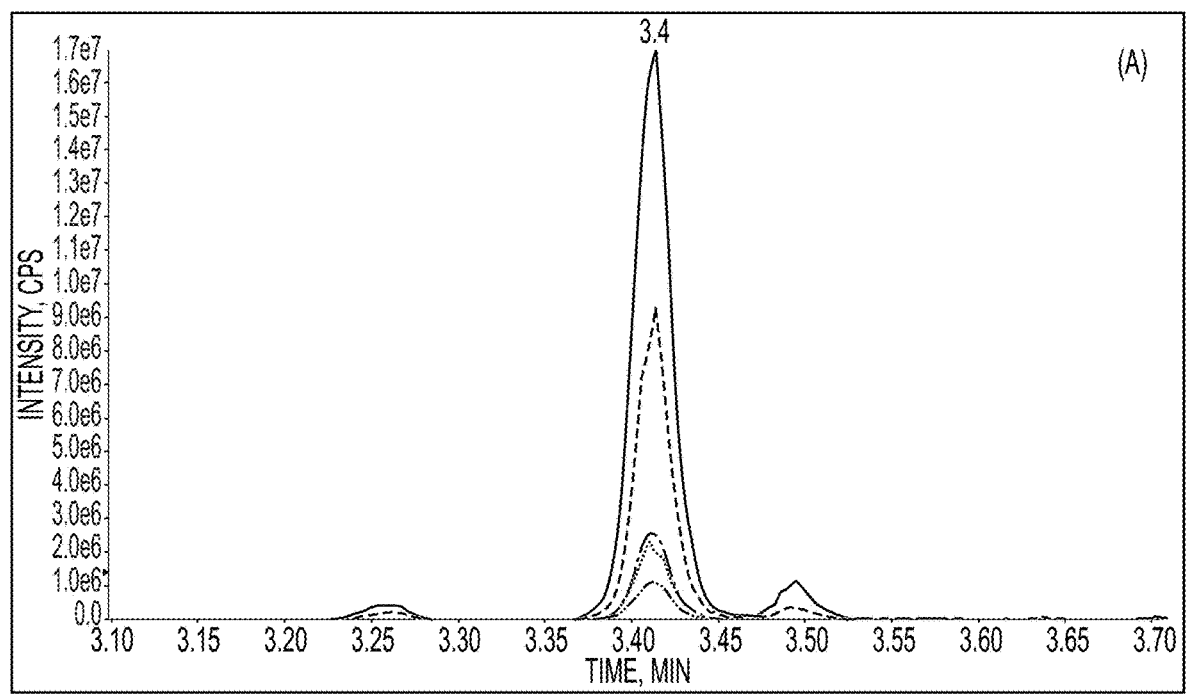
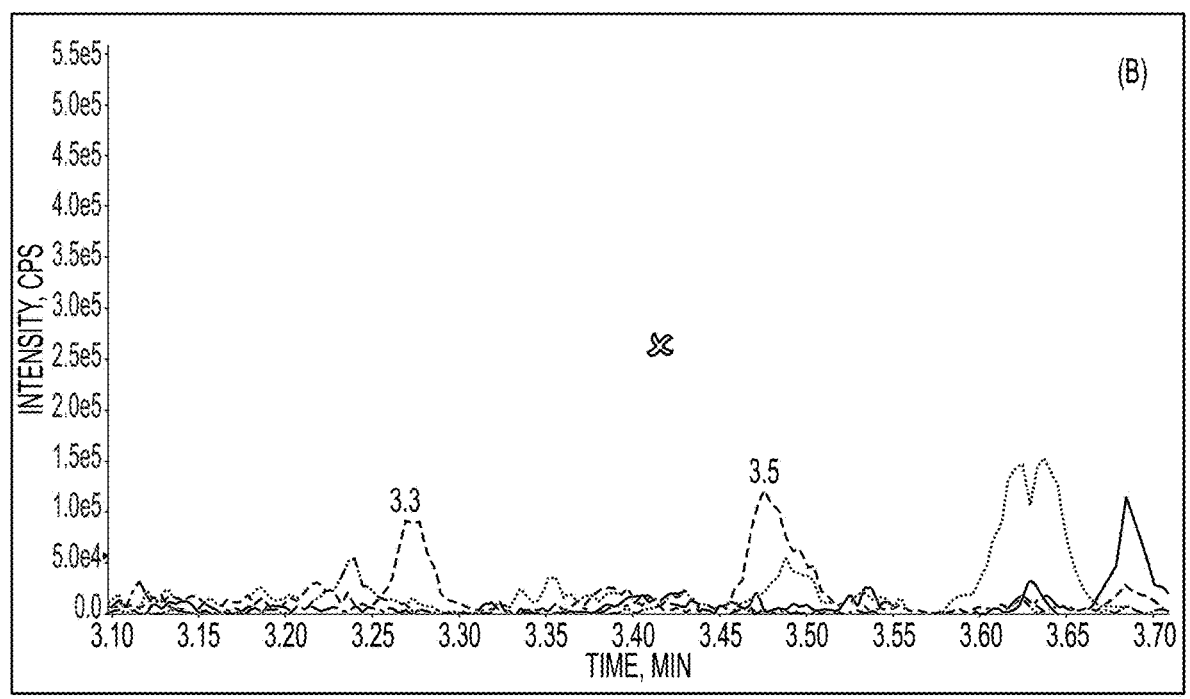
FIG. 20

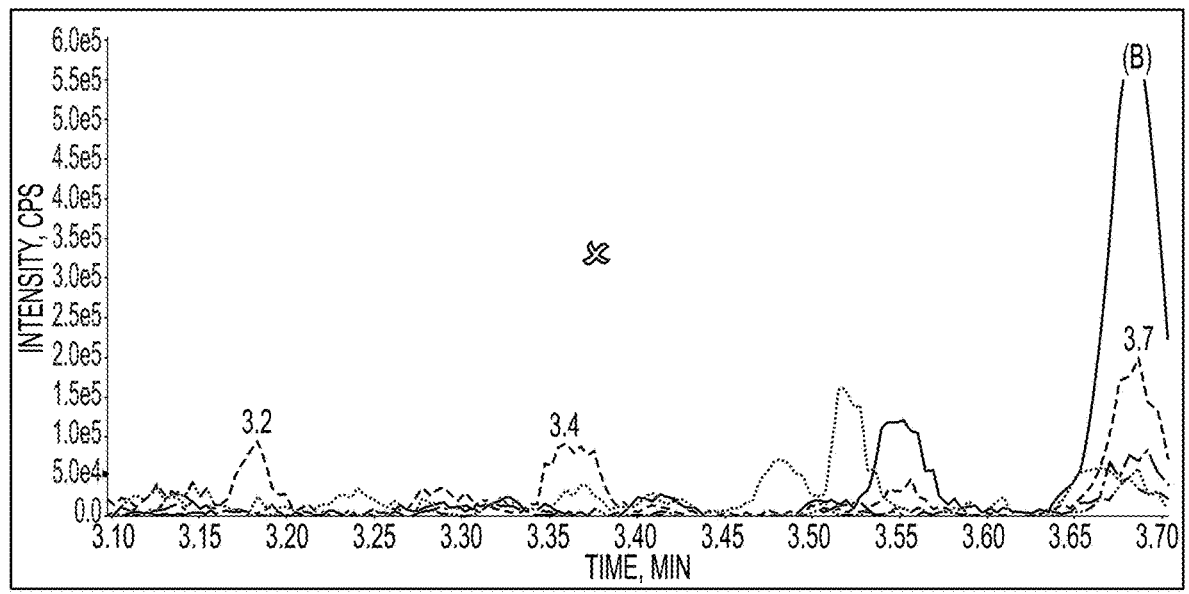
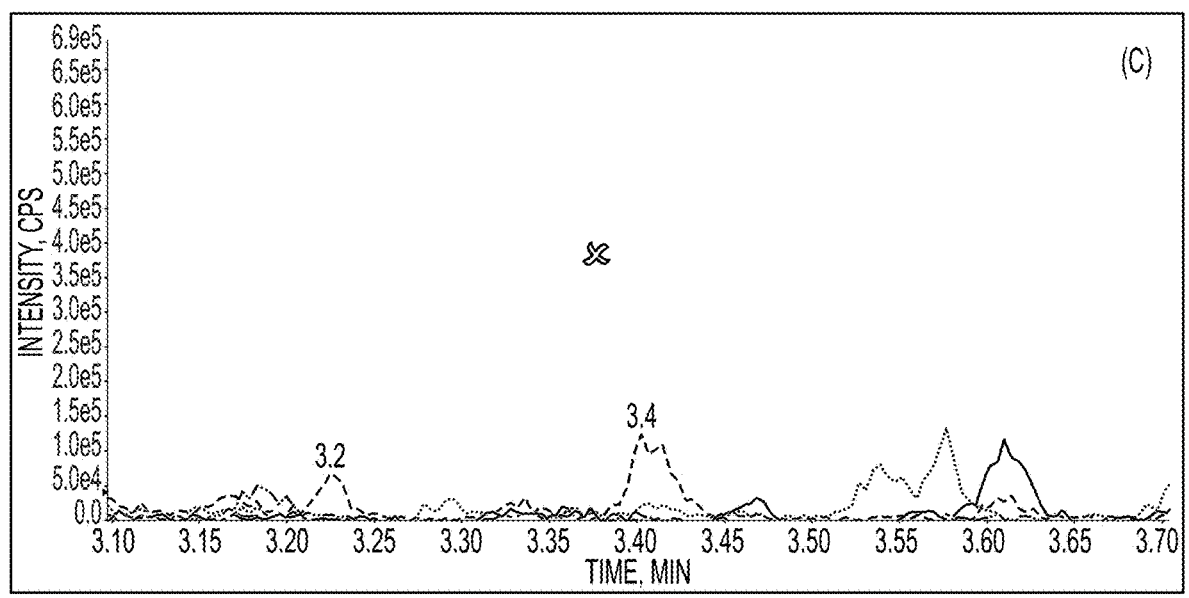
*FIG. 21 (CONT.)*

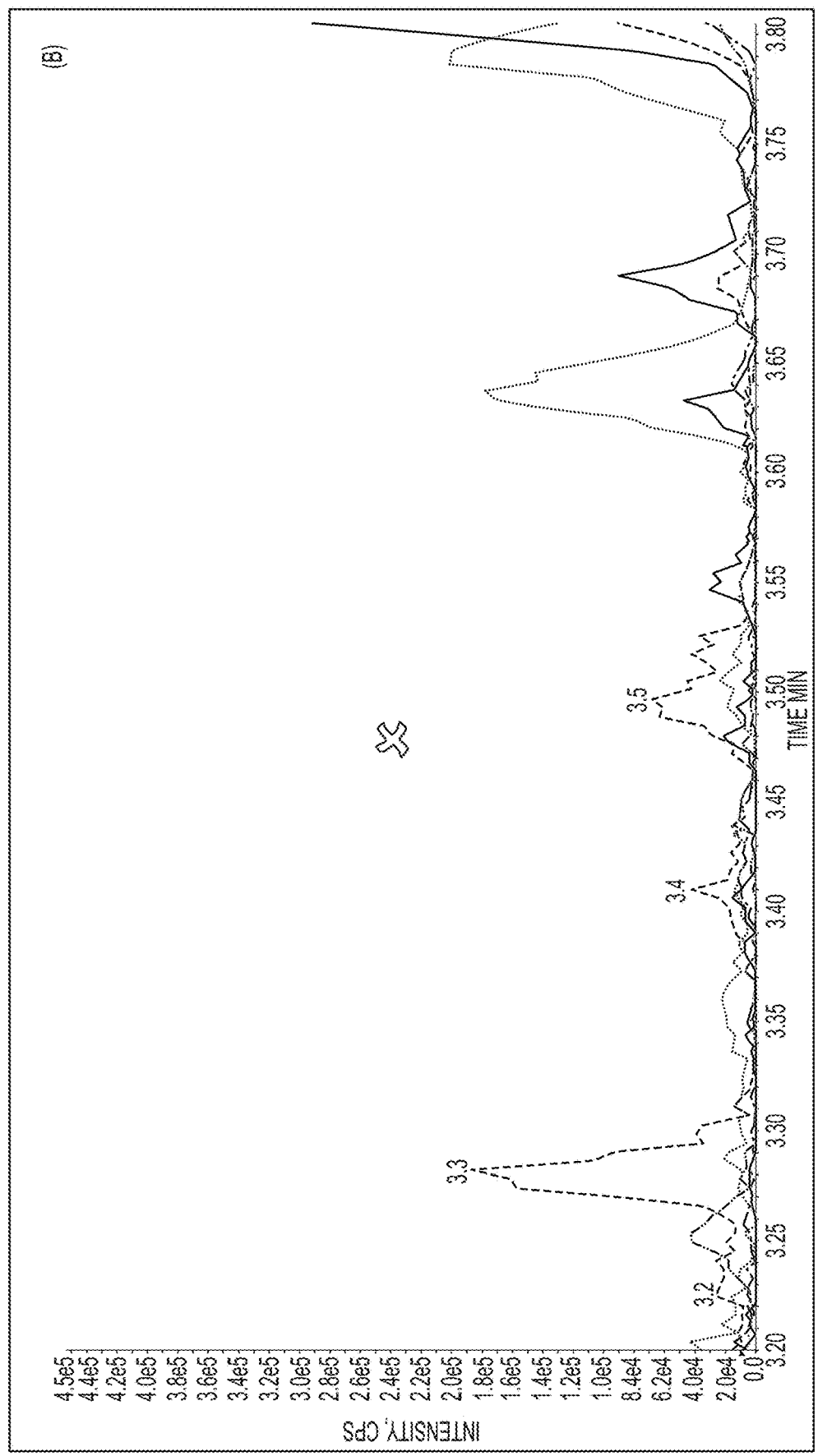
FIG. 24 (CONT. 1)

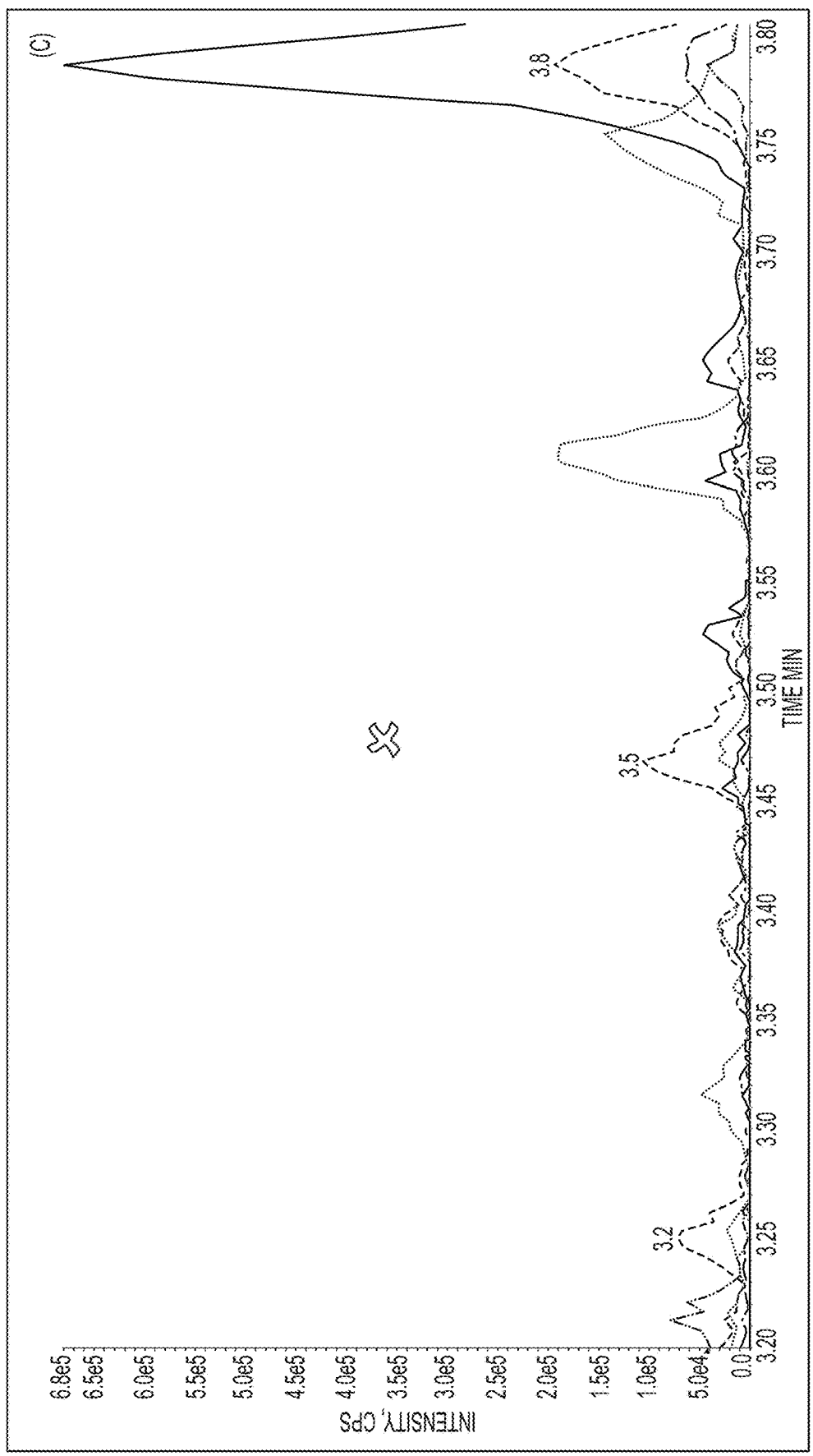
FIG. 24 (CONT. 2)

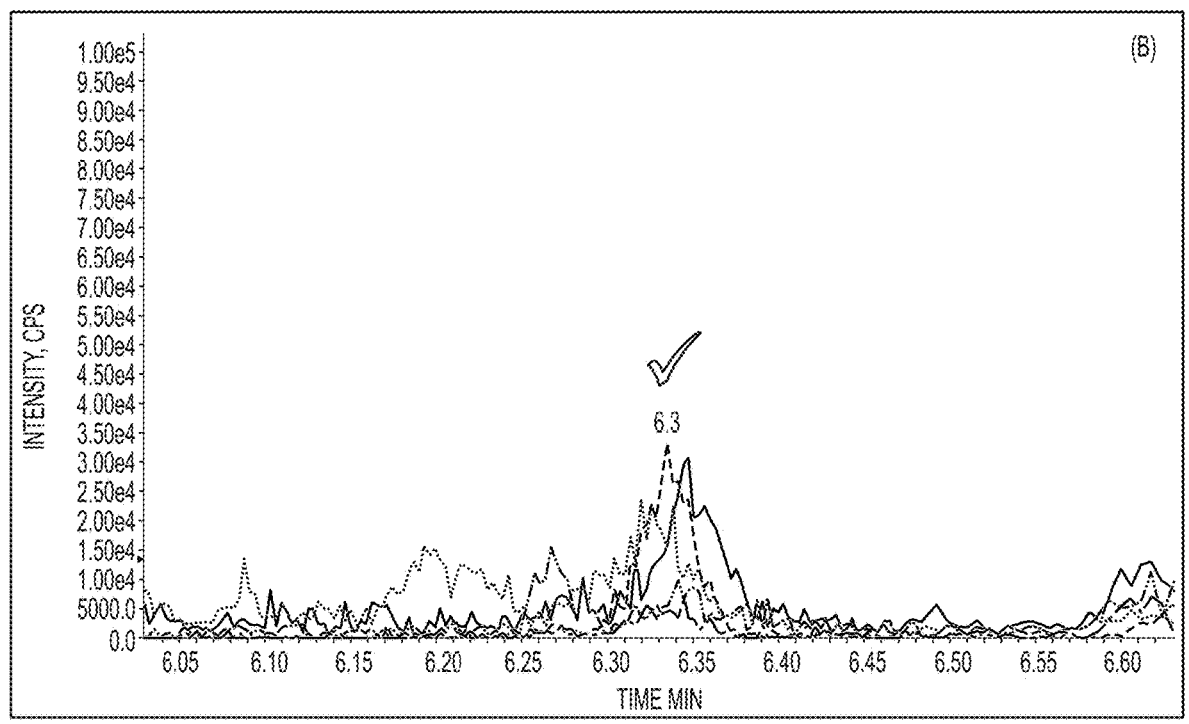
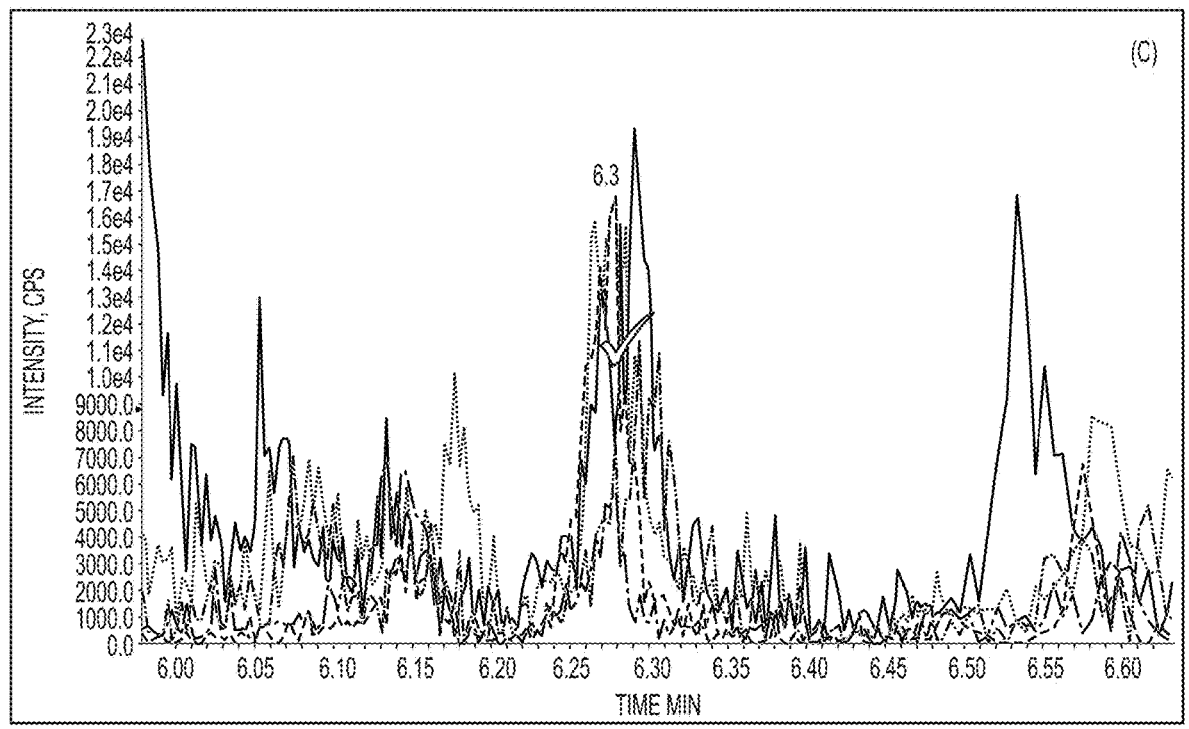
FIG. 25 (CONT. 1)

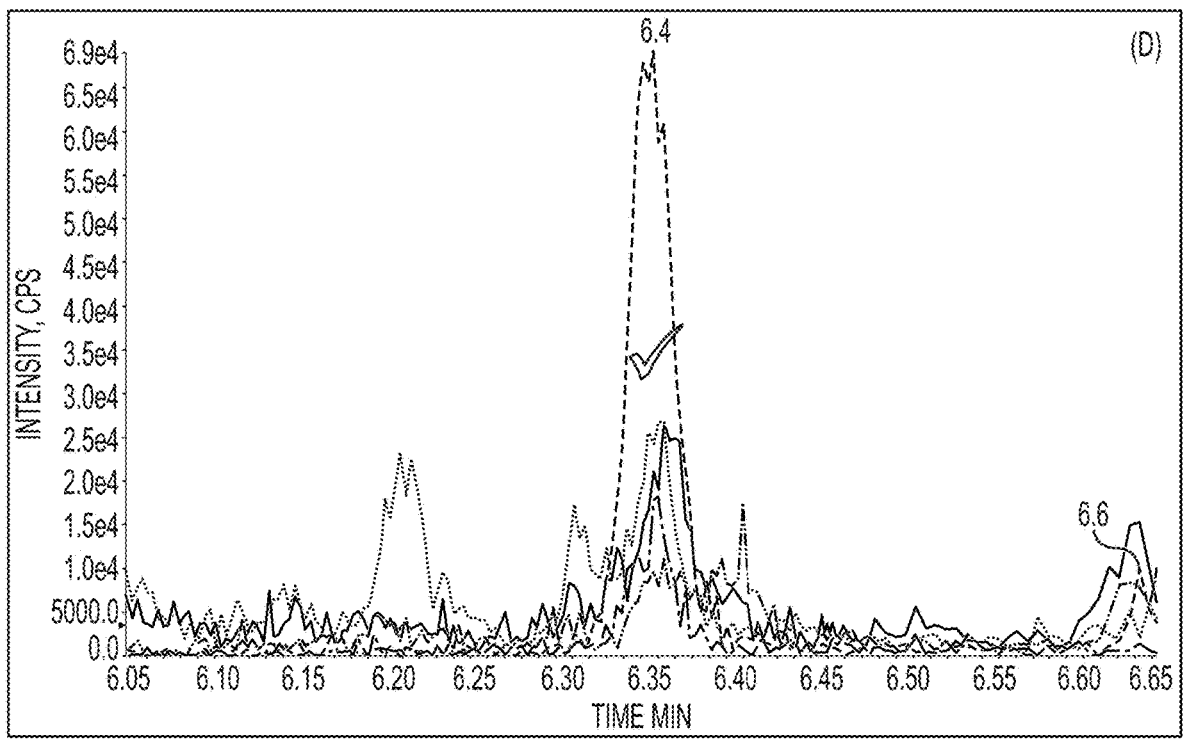
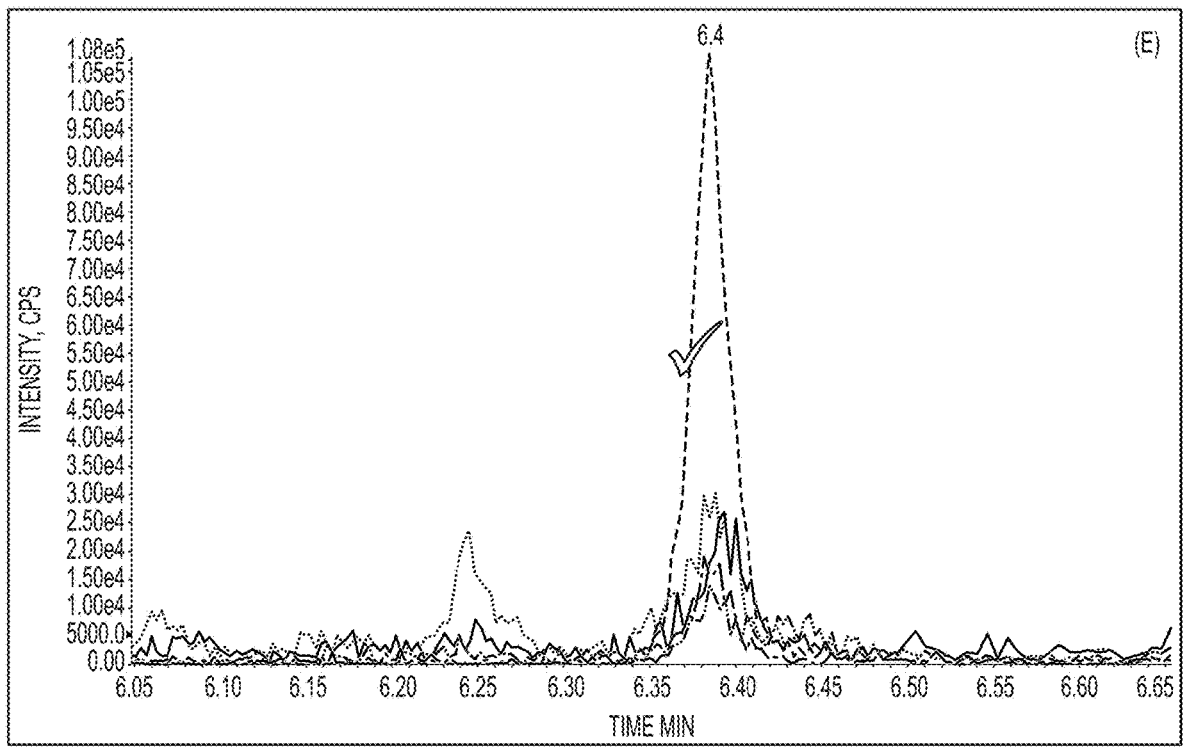
*FIG. 25* (CONT. 2)

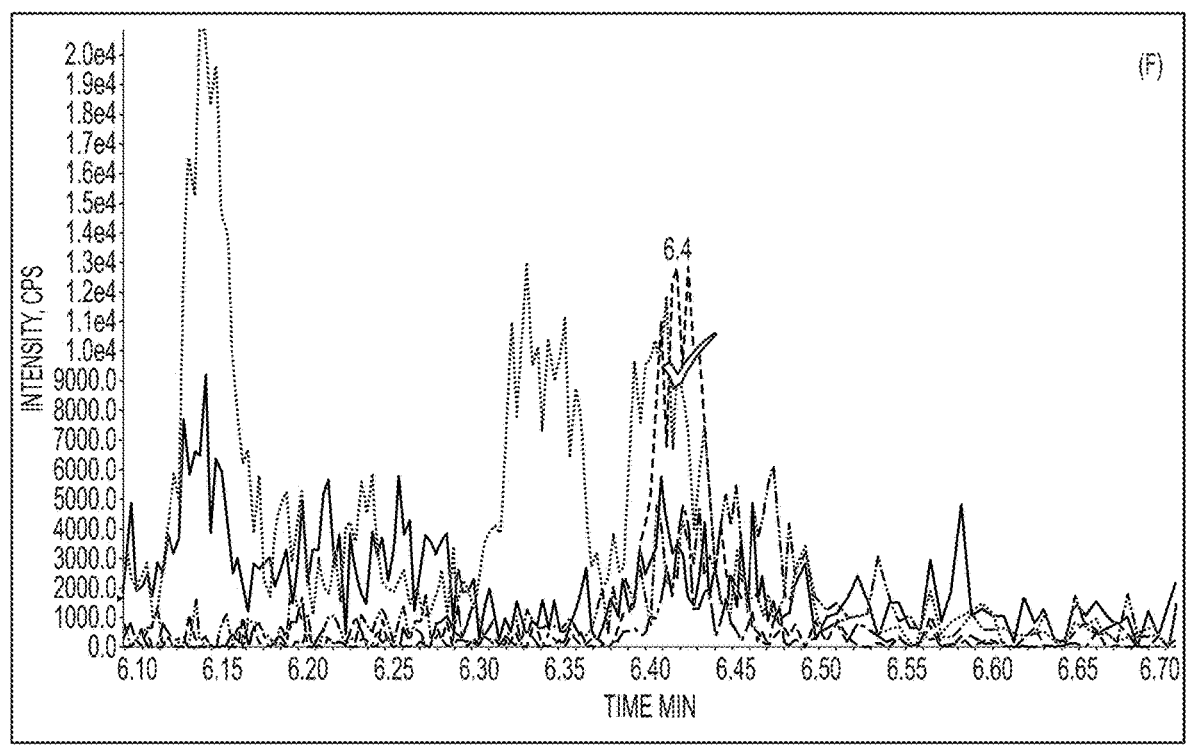
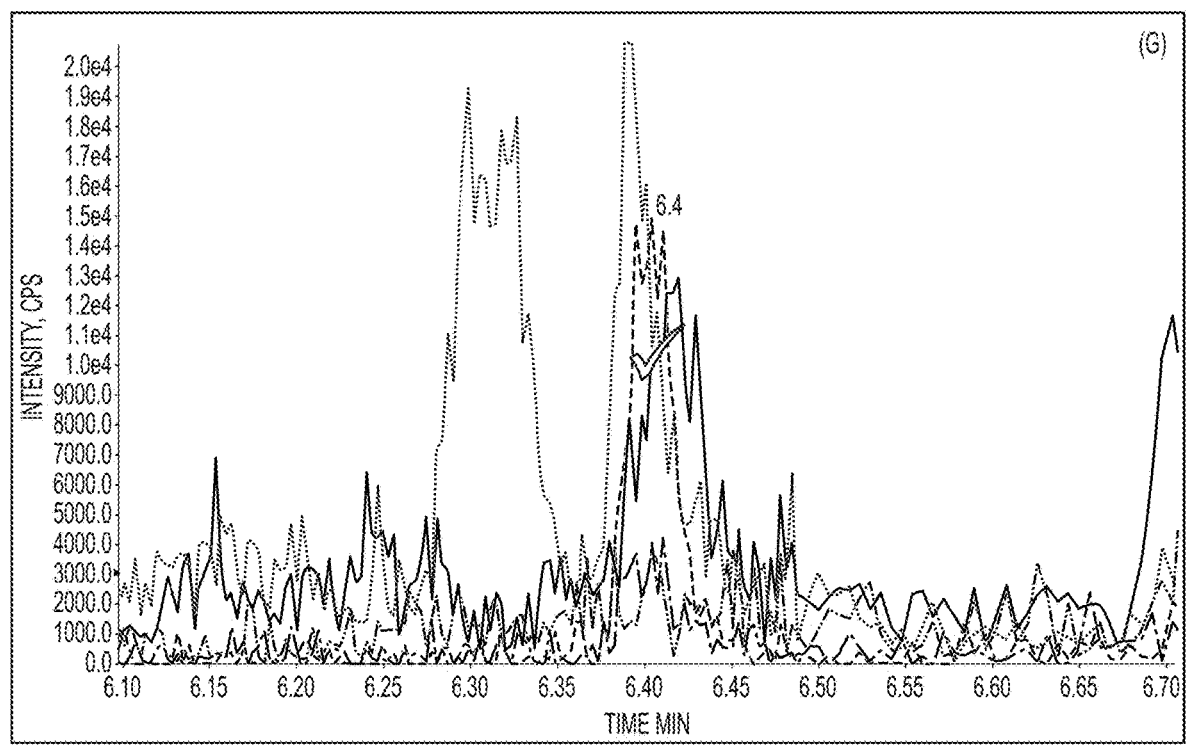
FIG. 25 (CONT. 3)

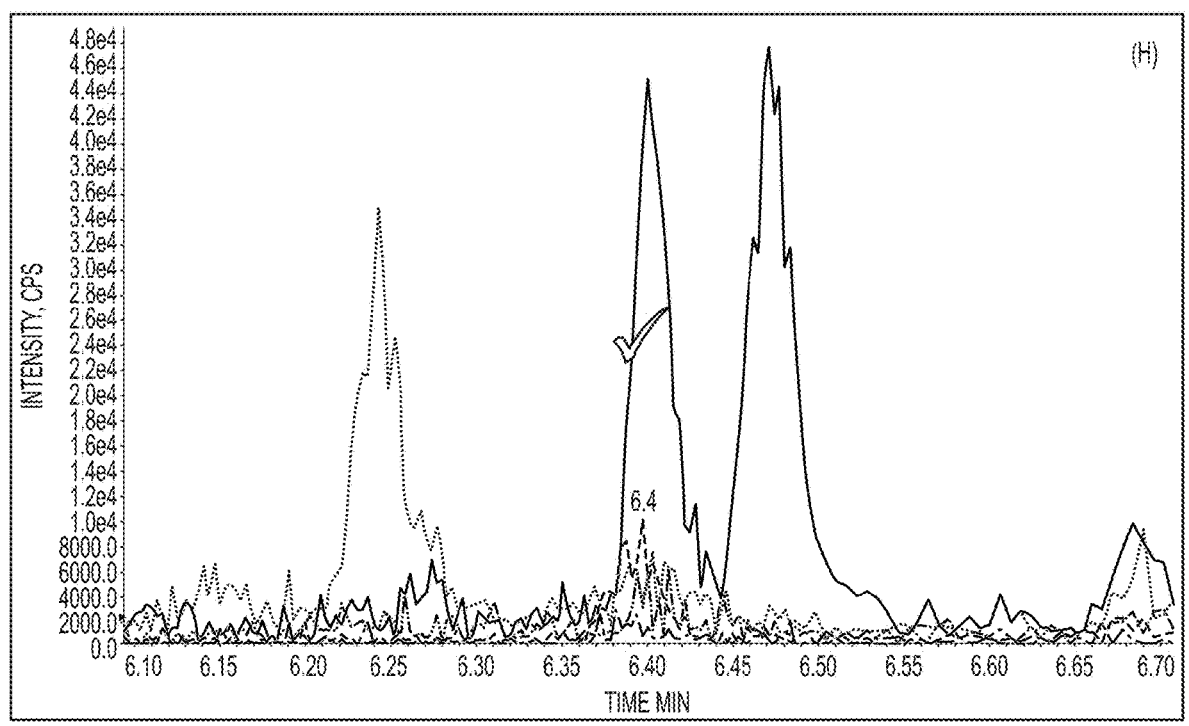
FIG. 25 (CONT. 4)

FIG. 30A

MHHHHHHHHHHSLEV<u>L</u>FQGPMPPSAAKQMGASTGVHAGVTDSSA<u>F</u>TRKDVADRPD<u>L</u>TI
VGDS<u>VY</u>DAKA<u>F</u>RSEHPGGAH<u>F</u>VS<u>LF</u>GGRDATEA<u>F</u>MEYHRRA<u>W</u>PKSRMSR<u>F</u>HVGS<u>L</u>AST
EEPVAADEG<u>YLQL</u>CARIAKMVPSVSSG<u>F</u>APAS<u>YW</u>VKAG<u>LI</u>LGSAIA<u>L</u>EA<u>YM</u>L<u>Y</u>AGK<u>RL</u>
LPSIV<u>LGWLFAL</u>IG<u>L</u>NIQHDANHGA<u>L</u>SKSASVN<u>L</u>A<u>L</u>G<u>L</u>CQD<u>W</u>IGGSMI<u>LWL</u>QEHVVMH
H<u>L</u>HTNDVDKDPDQKAHGA<u>LRL</u>KPTDA<u>W</u>SPMH<u>WL</u>QH<u>LYLL</u>PGETM<u>Y</u>A<u>F</u>K<u>LLFL</u>DISE<u>L</u>V
M<u>W</u>R<u>W</u>EGEPISK<u>L</u>AG<u>YL</u>FMPS<u>LLLKL</u>T<u>FW</u>AR<u>F</u>VA<u>L</u>P<u>LYL</u>APSVHTAVCIAATVMTGS<u>FY</u>
<u>LAFFFF</u>ISHN<u>F</u>EGVASVGPDGSITSMTRGAS<u>FL</u>KRQAETSSNVGGP<u>LLATL</u>NGG<u>L</u>N<u>Y</u>Q
IEHH<u>LF</u>PRVHHG<u>FY</u>P<u>RL</u>A<u>P</u>L<u>VKAEL</u>EARGIE<u>Y</u>KH<u>Y</u>PTI<u>W</u>SN<u>L</u>AST<u>L</u>RHM<u>YAL</u>GRRPRS
KAE

FIG. 30B

MHHHHHHHHHHSLEV**LFQGPMPPSAAKQMGASTGVHAGVTDSSAFTRKDVADRPDLTI
VGDSVYDAKAFRSEHPGGAHFVSLFGGRDATEAFMEYHRRAWPKSRMSRFHVGSLAST
EEPVAADEGYLQLCARIAKMVPSVSSGFAPASY**WVKAGLILGSAIALEAYMLYAGKRL
LPSIVLGWLFALIGLNIQHDANHGALSKSASVNLALGLCQDWIGGSMILWLQE**HVVMH
HLHTNDVDKDPDQKAHGALRLKPTDAWSPMHWLQHLYLLPGETM**YAFKLLFLDISELV
MWRWEGEPISKLAGYLFMPSLLLKLTFWARFVALPLYLAPSVHTAVCIAATVMTGSFY
LAFFFFISHNFEGVASVGPDGSITSMTRGASFLKRQAETSSNVGGPLL**ATLNGGLNYQ
IEHHLFPRVHHGFYPRLAPLVKAELEARGIEYKHYPTIW**SNLASTLRHMYALGRRPRS
KAE

FIG. 30C

MHHHHHHHHHHSLEV<u>L</u>FQGPMPPSAA<u>K</u>QMGASTGVHAGVTDSSAFT<u>RK</u>DVADRPDLTI
VGDSVYDA<u>K</u>AF<u>R</u>SEHPGGAHFVSLFGG<u>R</u>DATEAFMEYH<u>RR</u>AWP<u>K</u>S<u>R</u>MS<u>R</u>FHVGSLAST
EEPVAADEGYLQLCA<u>R</u>IA<u>K</u>MVPSVSSGFAPASYWV<u>K</u>AGLILGSAIALEAYMLYAG<u>KR</u>L
LPSIVLGWLFALIGLNIQHDANHGAL<u>K</u>SASVNLALGLCQDWIGGSMILWLQEHVVMH
HLHTNDVD<u>K</u>DPDQ<u>K</u>AHGAL<u>R</u>L<u>K</u>PTDAWSPMHWLQHLYLLPGETMYAF<u>K</u>LLFLDISELV
MWRWEGEPISK<u>L</u>AGYLFMPSLLL<u>K</u>LTFWA<u>R</u>FVALPLYLAPSVHTAVCIAATVMTGSFY
LAFFFFISHNFEGVASVGPDGSITSMT<u>R</u>GASFL<u>KR</u>QAETSSNVGGPLLATLNGGLNYQ
IEHHLFP<u>R</u>VHHGFYP<u>R</u>LAPLV<u>K</u>AELEA<u>R</u>GIEY<u>K</u>HYPTIWSNLASTL<u>R</u>HMYALG<u>RR</u>P<u>R</u>S
<u>K</u>AE

FIG. 30D

MHHHHHHHHHHSLEVLFQGPMPPSAAK**QMGASTGVHAGVTDSSAFTRKDVADRPDLTI
VGDSVYDAKAFRSEHPGGAHFVSLFGGRDATEAFMEYHR**RAWPKSRMSRFHVGSLAST
EEPVAADEGYLQLCARIAKMVPSVSSGFAPASYWVKAGLILGSAIALEAYMLYAGKRL
LPSIVLGWLFALIGLNIQHDANHGALSKSASVNLALGLCQDWIGGSMILWLQEHVVMH
HLHTNDVDKDPDQKAHGALRLKPTDAWSPMHWLQHLYLLPGETMYAFK**LLFLDISELV
MWRWEGEPISKLAGYLFMPSLLLK**LTFWARFVALPLYLAPSVHTAVCIAATVMTGSFY
LAFFFFISHNFEGVASVGPDGSITSMTR*GASFLK*RQAETSSNVGGPLLATLNGGLNYQ
IEHHLFPRVHHGFYPRLAPLVKAELEARGIEYKHYPTIWSNLASTLRHMYALGRRPRS
KAE

FIG. 31C

MPPSAAKQMGASTGVHAGVTDSSAFTRKDVADRPDLTIVGDSVYDAKAFRSEHPGGAHFVSLFG
GRDATEAFMEYHRRAWPKSRMSRFHVGSLASTEEPVAADEGYLQLCARIAKMVPSVSSGFAPAS
YWVKAGLILGSAIALEAYMLYAGKRLLPSIVLGWLFALIGLNIQHDANHGALSKSASVNLALGL
CQDWIGGSMILWLQEHVVMHHLHTNDVDKDPDQKAHGALRLKPTDAWSPMHWLQHLYLLPGETM
YAFKLLFLDISELVMWRWEGEPISKLAGYLFMPSLLLKLTFWARFVALPLYLAPSVHTAVCIAA
TVMTGSFYLAFFFFISHNFEGVASVGPDGSITSMTRGASFLKRQAETSSNVGGPLLATLNGGLN
YQIEHHLFPRVHHGFYPRLAPLVKAELEARGIEYKHYPTIWSNLASTLRHMYALGRRPRSKAE

FIG. 32A

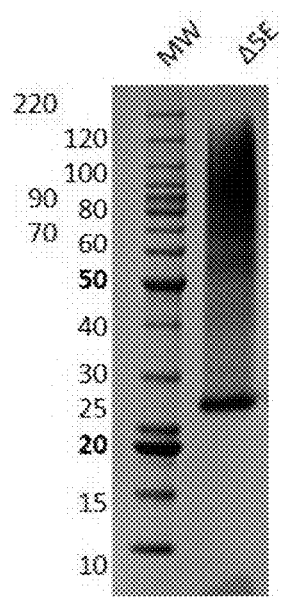

FIG. 32B

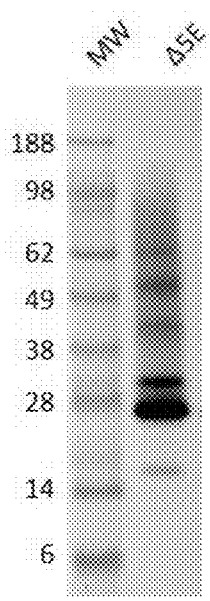

FIG. 33A
MASIAIPAALAGTLGYVTYNVANPDIPASEKVPAYFMQVEYWGPTIGTIGYLLFIYFGKR
IMQNRSQPFGLKNAMLVYNFYQTFFNSYCIYLFVTSHRAQGLKVWGNIPDMTANSWGISQ
VIWLHYNNKYVELLDTFFMVRKKFDQLSFLHIYHHTLLIWSWFVVMKLEPVGDCYFGSS
VNTFVHVIMYSYYGLAALGVNCFWKKYITQIQMLQFCICASHSIYTAYVQNTAFWLPYLQ
LWVMVNMFVLFANFYRKRYKSKGAKKQ

FIG. 33B
MHHHHHHHHHSLEVLFQGPMASIAIPAALAGTLGYVTYNVANPDIPASEKVPAYFMQVE
YWGPTIGTIGYLLFIYFGKRIMQNRSQPFGLKNAMLVYNFYQTFFNSYCIYLFVTSHRAQ
GLKVWGNIPDMTANSWGISQVIWLHYNNKYVELLDTFFMVRKKFDQLSFLHIYHHTLLI
WSWFVVMKLEPVGDCYFGSSVNTFVHVIMYSYYGLAALGVNCFWKKYITQIQMLQFCICA
SHSIYTAYVQNTAFWLPYLQLWVMVNMFVLFANFYRKRYKSKGAKKQ

FIG. 33C
MASIAIPAALAGTLGYVTYNVANPDIPASEKVPAYFMQVEYWGPTIGTIGYLLFIYFGKR
IMQNRSQPFGLKNAMLVYNFYQTFFNSYCIYLFVTSHRAQGLKVWGNIPDMTANSWGISQ
VIWLHYNNKYVELLDTFFMVRKKFDQLSFLHIYHHTLLIWSWFVVMKLEPVGDCYFGSS
VNTFVHVIMYSYYGLAALGVNCFWKKYITQIQMLQFCICASHSIYTAYVQNTAFWLPYLQ
LWVMVNMFVLFANFYRKRYKSKGAKKQ

FIG. 33D
MHHHHHHHHHSLEVLFQGPMASIAIPAALAGTLGYVTYNVANPDIPASEKVPAYFMQV
EYWGPTIGTIGYLLFIYFGKRIMQNRSQPFGLKNAMLVYNFYQTFFNSYCIYLFVTSHR
AQGLKVWGNIPDMTANSWGISQVIWLHYNNKYVELLDTFFMVRKKFDQLSFLHIYHHT
LLIWSWFVVMKLEPVGDCYFGSSVNTFVHVIMYSYYGLAALGVNCFWKKYITQIQMLQF
CICASHSIYTAYVQNTAFWLPYLQLWVMVNMFVLFANFYRKRYKSKGAKK

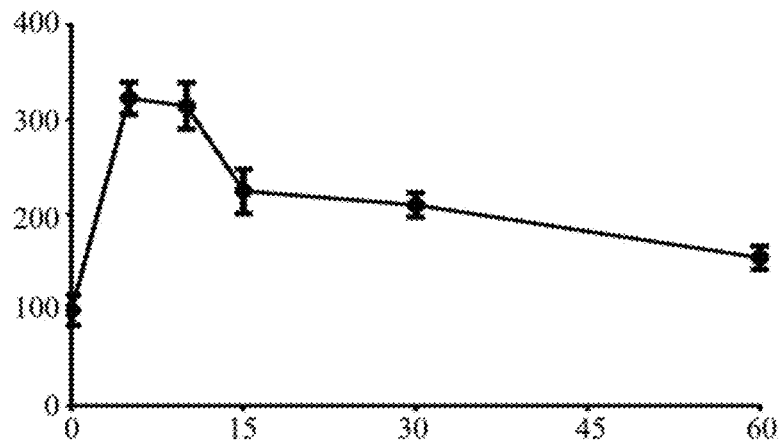
FIG. 36
FIG. 37
MASIAIPAALAGTLGYVTYNVANPDIPASEKVPAYFMQVEYWGPTIGTIGYLLFIYFGKRIMQNRS
QPFGLKNAMLVYNFYQTFFNSYCIYLFVTSHRAQGLKVWGNIPDMTANSWGISQVIWLHYNNKYVE
LLDTFFMVMRKKFDQLSFLHIYHHTLLIWSWFVVMKLEPVGDCYFGSSVNTFVHVIMYSYYGLAAL
GVNCFWKKYITQIQMLQFCICASHSIYTAYVQNTAFWLPYLQLWVMVNMFVLFANFYRKRYKSKGA
KKQ
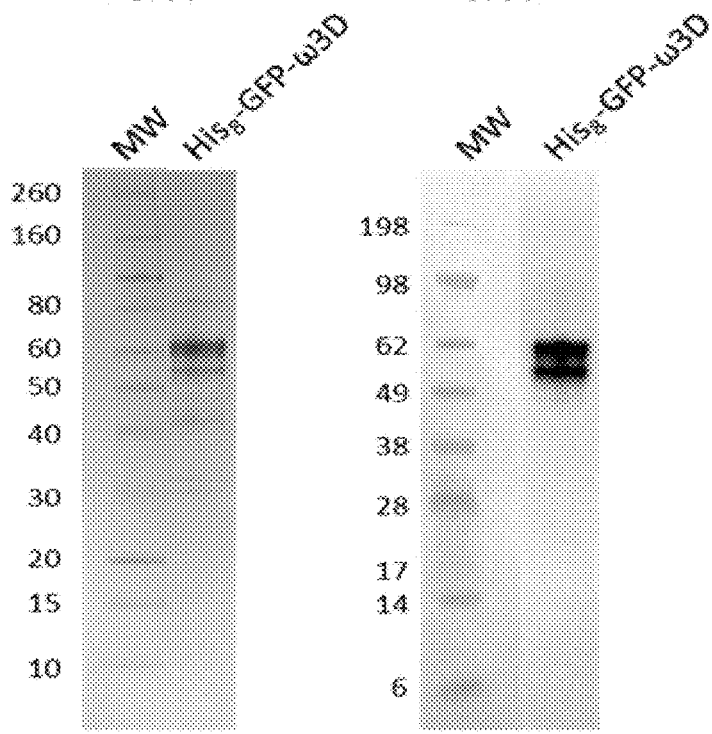
FIG. 38A  FIG. 38B

FIG. 39A

MSKVTVSGSEILEGSTKTVRRSGNVASFKQQKTAIDTFGNVFKVPDYTIKDILDAIPKHCYERSLV
KSMSYVVRDIVAISAIAYVGLTYIPLLPNEFLRFAAWSAYVFSISCFGFGIWILGHECGHSAFSNY
GWVNDTVGWVLHSLVMVPYFSWKFSHAKHHKATGHMTRDMVFVPYTAEEFKEKHQVTSLHDIAEET
PIYSVFALLFQQLGGLSLYLATNATGQPYPGVSKFFKSHYWPSSPVFDKKDYWYIVLSDLGILATL
TSVYTAYKVFGFWPTFITWFCPWILVNHWLVFVTFLQHTDSSMPHYDAQEWTFAKGAAATIDREFG
ILGIIFHDIIETHVLHHYVSRIPFYHAREATECIKKVMGEHYRHTDENMWVSLWKTWRSCQFVENH
DGVYMFRNCNNVGVKPKDT

FIG. 39B

HHHHHHHHSKGEEL**FTGVVPILVELDGDVNGHKFSVRGEGEGDATNGKLTLKFICTTGKLPVPWPT
LVTTLTYGVQCFSRYPDHMKRHDFFKSAMPEGYVQERTISFKDDGTYKTRAEVKFEGDTL**VNRIEL
KGID**FKEDGNILGHKLEYNFNSHNVYITADKQKNGIKANFKIRHNVEDGSVQLADHYQQNTPIGDG
PVLLPDNHYLSTQSVLSKDFNEKRDHMVLLEFVTAAGITHGMDELYKENLYFQGGSSKVTVSGSEI
LEGSTKTVRRSGNVASFKQQKTAIDTFGNVFKVPDYTIKDILDAIPKHCYERSL**VKSMSYVVRDIV
AISAIAYVGLTYIPLLPNEFLRFAAWSAYVFSISCFGFGIWILGHECGHSAF**SNYGWVNDTVGWVL
HSLVMVPYFSWKFSHAKHHKATGHMTRDM**VFVPYTAEEFKEKHQVTSLHDIAEETPIYSVFALLFQ
QLGGLSLYLATNATGQPYPGVSKFFKSHYWPSSPVFDKKDYWYIVLSDLGILATLTSVYTAYKVFG
FWPTFITWFCPWILVNHWLVFVTFLQHTDSSMPHYDAQEWTFAKGAAATIDREFGILGIIFHDIIE
THVLHHYVSRIPFYHAREATECIKKVMGEHYRHTDENMWVSLWKTWRSCQFVENHDGVY**MFRNCNN
VGVKPKDT

FIG. 39C

MSKVTVSGSEILEGSTKTVRRSGNVASFKQQKTAIDTFGNVFKVPDYTIKDILDAIPKHCYERSLV
KSMSYVVRDIVAISAIAYVGLTYIPLLPNEFLRFAAWSAYVFSISCFGFGIWILGHECGHSAFSNY
GWVNDTVGWVLHSLVMVPYFSWKFSHAKHHKATGHMTRDMVFVPYTAEEFKEKHQVTSLHDIAEET
PIYSVFALLFQQLGGLSLYLATNATGQPYPGVSKFFKSHYWPSSPVFDKKDYWYIVLSDLGILATL
TSVYTAYKVFGFWPTFITWFCPWILVNHWLVFVTFLQHTDSSMPHYDAQEWTFAKGAAATIDREFG
ILGIIFHDIIETHVLHHYVSRIPFYHAREATECIKKVMGEHYRHTDENMWVSLWKTWRSCQFVENH
DGVYMFRNCNNVGVKPKDT

FIG. 39D

HHHHHHHHSK**GEELFTGVVPILVELDGDVNGHKFSVRGEGEGDATNGKLTLKFICTTGKLPVPWPT
LVTTLTYGVQCFSRYPDHMKRHDFFKSAMPEGYVQERTISFKDDGTYKTRAEVKFEGDTLVNRIEL
KGIDFKEDGNILGHKLEYNFNSHNVYITADKQKNGIKANFKIRHNVEDGSVQLADHYQQNTPIGDG
PVLLPDNHYLSTQSVLSKDPNEKRDHMVLLEFVTAAGITHGMDELYKENLYFQGGSSKVTVSGSEI
LEGSTKTVRRSGNVASFKQQKTAIDTFGNVFKVPDYTIKDILDAIPKHCYERSL**VKSMSYVVRDIV
AISAIAYVGLTYIPLLPNEFLRFAAWSAYVFSISCFGFGIWILGHECGHSAFSNYGWVNDTVGWVL
HSLVMVPYFSWK**FSHAKHHKATGHMTRDMVFVPYTAEEFKEKHQVTSLHDIAEETPIYSVFALLFQ
QLGGLSLYLATNATGQPYPGVSKFFKSHYWPSSPVFDKKDYWYIVLSDLGILATLTSVYTAYKVFG
FWPTFITWFCPWILVNHWLVFVTFLQHTDS**SMPHYDAQEWTFAKGAAATIDREFGILGIIFHDIIE
THVLHHYVSRIPFYHAREATECIKKVMGEHYRHTDENMWVSLWKTWRSCQFVENHDGVYMFRNCNN
VGVKPKDT

FIG. 43

MSKVTVSGSEIL<u>EGSTKTVRRSGNVA</u>SFKQQKTAIDTFGNVFKVPDYTIKDILDAIPKHCYERSLV
KSMSYVVRDIVAISAIAYVGLTYIPLLPNEFLRFAAWSAYVFSISCFGFGIWILGHECGHSAFSNY
GWVNDTVGWVLHSLVMVPYFSWKFSHAKHHKATGHMTRDMVFVPYTAEEFKEKHQVTSLHDIAEET
FIYSVFALLFQQLGGLSLYLATNATGQPYPGVSKFFKSHYWPSSPVFDKKDYWYIVLSDLGILATL
TSVYTAYKVFGFWPTFITWFCPWILVNHWLVFVTFLQHTDSSMPHYDAQEWTFAKGAAATIDREFG
ILGIIFHDIIETHVLHHYVSRIPFYHAREATECIKKVMGEHYRHTDENMWVSLWKTWRSCQFVENH
DGVYMFRNCNNVGVKPKDT

LC-MS/MS-BASED METHODS FOR CHARACTERIZING PROTEINS

RELATED APPLICATION

This Application is a National Phase entry of PCT/US2018/021423, filed Mar. 8, 2018, which claims priority benefit of U.S. Provisional Patent Application No. 62/468,331, filed Mar. 7, 2017, both of which are incorporated fully herein by reference for all purposes.

SEQUENCE LISTING

This Application contains a Sequence Listing, having a file named "87376.0008US_ST25.txt" that is 44 kilobytes in size, which has been submitted in ASCII format via EFS-Web and is hereby incorporated by reference in its entirety.

FIELD

The embodiments described herein provide methods, assays, and compositions for characterizing the stability and quantity of target proteins, particularly recalcitrant target proteins.

BACKGROUND

There remains a need for methods and assays that characterize the stability and quantity of target proteins, particularly recalcitrant transgenic proteins or membrane-associated proteins not easily characterized by current approaches.

SUMMARY

The embodiments described herein provide novel techniques to characterize the stability (digestibility) and quantity of target proteins using high sensitivity LC-MRM-MS. For example, food, feed, and environmental risk assessments require a full evaluation of transgenic proteins, including protein stability and expression levels within plant tissues and seeds. Antibodies are not always useful for characterizing transgenic proteins because, for example, the amount of target protein in a practical sample may deceed detection levels; the amount of target protein may deceed amounts required to raise antibodies; or the target protein may not provide selective or sensitive epitopes. Indeed, the similarity of certain enzymatic proteins leads to non-specific antibody cross-reactions. Additionally, antibodies are not always useful for characterizing many membrane proteins because tight membrane associations mask epitopes, and such membrane proteins are often expressed at low levels. Because the present embodiments utilize total protein extractions with minimal processing, the LC-MS/MS methods described herein can be scaled-up, allowing for high throughput. The present embodiments thus provide advantageous alternative approaches for evaluating recalcitrant target proteins.

The present embodiments provide LC-MS/MS based methods to evaluate target proteins, including transgenic or membrane proteins, such as recalcitrant transgenic membrane-associated proteins expressed in transgenic canola.

An aspect of the present embodiments provides for characterization of the expression, stability (as digestibility), and quantity of transgenic membrane-associated proteins in plant tissues and seeds. At least one embodiment provides a method to assess the in vitro digestibility of transgenic, membrane-associated proteins using a simulated gastric fluid (SGF) proteolytic degradation by pepsin, in combination with a dual pepsin-trypsin degradation assay, employing mass spectrometry to directly monitor precise degradation products.

In one embodiment of the method, target proteins are digested with pepsin, followed by complete digestion with trypsin. The decline of tryptic peptides can be used as a proxy for intact protein, and the appearance and disappearance of peptic peptides can be used to indicate the in vitro digestibility of the target protein. This time-course comparison provides detailed stability characterization of the target protein. This approach is particularly advantageous when characterizing recalcitrant/intractable proteins.

In at least one embodiment, the dual pepsin and pepsin/trypsin protein digestibility assays can be used as one aspect of the overall allergenicity assessment of newly introduced proteins into genetically modified crops. The methods described herein provide additional evidence in a weight-of-evidence approach to predicting the allergenic potential of a target protein.

At least one embodiment provides an assay for determining the quantity of target protein(s) in various tissues of a transgenic organism, such as plants, using peptide markers in a known quantity of total protein with spiked internal standard and direct LC-MS/MS analysis. For example, the methods described herein can be used to characterize recalcitrant transgenic, membrane associated proteins expressed in tissues and seed of transgenic canola. In a particular embodiment, the methods described herein can be used to characterize the transgenic enzyme of Brassica that produce significant levels of omega-3 long-chain ($\geq$C20) polyunsaturated fatty acids ($\omega$3LCPUFA).

At least one embodiment provides a method for characterizing the stability of a target protein comprising the steps of: subjecting a target protein to pepsin digestion, obtaining a time-course of samples from the pepsin digestion, subjecting a portion of each time-course sample to trypsin digestion, obtaining a time-course of samples from the pepsin-trypsin digestion, collecting LC-MS/MS data for each pepsin and pepsin-trypsin sample; and determining from the LC-MS/MS data the kinetics of target protein digestion and the susceptibility to proteolysis of specific regions of the target protein.

At least one embodiment provides a method for quantifying a target protein comprising the steps of: subjecting a target protein to trypsin digestion, selecting a peptides to act as a proxy for the target protein, generating light and heavy synthetic versions of the selected proxy peptide, obtaining LC-MS/MS data for synthetic light and heavy versions of the proxy peptide, obtaining LC-MS/MS data for the trypsin-digested target protein, and determining from the LC-MS/MS data the concentration of the proxy peptide, wherein the concentration of the proxy peptide correlates with the amount of target protein.

More specifically, for example, metabolic engineering of $\omega$3LCPUFA in oilseed crops requires expression of several transgenic fatty acid desaturases and elongases that exhibit both high sequence homology and membrane association. Applying the LC-MS/MS-based method to such transgenic plants, as described herein, demonstrated that seed-specific promoters correctly limited expression of transgenes to developing and mature seed, and that the enzymatic proteins were present at low levels (ng target per mg total protein). By examining specific peptides (unique to the target transgenic proteins), this approach provides highly selective and sensitive measurement of recalcitrant and, in this case, membrane proteins. The LC-MS/MS based methods described herein are widely applicable to food, feed, and environmental safety assessment.

DESCRIPTION OF THE DRAWINGS

FIG. 2 shows amino acid sequences of tryptic peptides in the biosynthetic enzymes of FIG. 1. Using a variety of host expression systems, the recombinant enzymes were characterized by LC-MS/MS after tryptic digestion, and tryptic peptide embodiments were selected to quantify proteins in transgenic plant tissues and seeds. Bold text: example peptides identified with >95% confidence; bold italics: example peptides identified with 50-95% confidence; regular text: peptides identified with <50% confidence; italics: not detected. Solid and dashed underline are used to distinguish adjacent fully tryptic peptides (6-20 amino acids in length).

FIGS. 3A and 3B are chromatograms reflecting quality control of synthetic Lack1-Δ12D peptide. FIG. 3A: (top panel) LC-ESI-MS/MS total ion chromatogram ("TIC") of Lack1-Δ12D peptide GSSSNTEQEVPK (amino acid residues ["aa"]16-26 of SEQ ID NO: 2) 5.38 min, no other significant peaks were detected; (middle panel) determined m/z value of $631.79^{2+}$ for the peak at 5.38 min matches theoretical m/z value $631.79^{2+}$; (bottom panel) MS/MS spectrum of correct peptide sequence, theoretical m/z values are shown (inset). FIG. 3B: (top panel) LC-ESI-MS/MS TIC of GSSSNTEQEV*PK (aa 16-26 of SEQ ID NO: 2) at 5.39 min, no other significant peaks were detected; (middle panel) determined m/z value of $634.80^{2+}$ for peak at 5.38 min matches theoretical m/z value $634.80^{2+}$; (bottom panel) MS/MS spectrum of correct peptide sequence, theoretical m/z values are shown (inset).

FIG. 4A: (top panel) LC-ESI-MS/MS TIC of Picpa-ω3D peptide IPFYHAR (aa 351-358 of SEQ ID NO: 1) at 8.34 min, no other significant peaks detected; (middle panel) determined m/z value of $452.24^{2+}$ for peak at 8.34 min matches theoretical m/z value $452.24^{2+}$; (bottom panel) MS/MS spectrum of correct peptide sequence and theoretical m/z values are shown (inset). FIG. 4B: (top panel) LC-ESI-MS/MS TIC of peptide IPFYHA*R (aa 351-358 of SEQ ID NO: 1) at 8.36 min, no other significant peaks detected; (middle panel) determined m/z value for peak at 8.36 min of $454.25^{2+}$ matches theoretical m/z value $454.25^{2+}$; (bottom panel) MS/MS spectrum of correct peptide sequence and theoretical m/z values are shown (inset).

FIG. 5A: (top panel) LC-ESI-MS/MS TIC of Micpu-Δ6D peptide DASTAPVDLK (aa 30-39 of SEQ ID NO: 3) at 7.96 min, no other significant peaks detected; (middle panel) determined m/z value for the peak at 7.96 min of $508.76^{2+}$ matches theoretical m/z value $508.76^{2+}$; (bottom panel) MS/MS spectrum revealing the correct peptide sequence and the theoretical m/z values are shown (inset). FIG. 5B: (top panel) LC-ESI-MS/MS TIC of peptide DASTAPVDL*K (aa 30-39 of SEQ ID NO: 3) at 7.94 min. No other significant peaks were detected; (middle panel) the determined m/z value for the peak at 7.94 min of $512.27^{2+}$ is shown and matches the theoretical m/z value $512.27^{2+}$; (bottom panel) MS/MS spectrum revealing the correct peptide sequence and the theoretical m/z values (inset).

FIG. 6A: (top panel) LC-ESI-MS/MS TIC of Pyrco-Δ6E peptide GQDPFLLK (aa 83-90 of SEQ ID NO: 4) at 10.64 min, no other significant peaks were detected; (middle panel) determined m/z value for peak at 10.64 min of $459.26^{2+}$ is shown and matches theoretical m/z value of $459.26^{2+}$; (bottom panel) MS/M S spectrum of correct peptide sequence and theoretical m/z values are shown (inset). FIG. 6B: (top panel) LC-ESI-MS/MS TIC of peptide GQDPFLL*K (aa 83-90 of SEQ ID NO: 4) at 10.63 min; no other significant peaks were detected; (middle panel) determined m/z value for peak at 10.64 min of $462.76^{2+}$ is shown and matches theoretical m/z value of $462.76^{2+}$; (bottom panel) MS/MS spectrum of correct peptide sequence and theoretical m/z values (inset).

FIG. 7A: (top panel) LC-ESI-MS/MS TIC of Pavsa-Δ5D peptide AYDVTNFVK (aa 37-45 of SEQ ID NO: 5) at 10.14 min, no other significant peaks were detected; (middle panel) determined m/z value for peak at 10.14 min of $528.77^{2+}$ matches the theoretical m/z value $528.77^{2+}$; (bottom panel) MS/MS spectrum of correct peptide sequence and theoretical m/z values (inset). FIG. 7B: (top panel) LC-ESI-MS/MS TIC of peptide AYDVTNFV*K (aa 37-45 of SEQ ID NO: 5) at 10.18 min, no other significant peaks were detected; (second panel) determined in value of $531.77^{2+}$ for peak at 10.18 min matches theoretical m/z value $531.77^{2+}$; (third panel) MS/MS spectrum of correct peptide sequence and theoretical m/z values (inset).

FIGS. 8A and 8B are quality control chromatograms of Pyrco-Δ5E peptide. FIG. 8A: (top panel) LC-ESI-MS/MS TIC of Pyrco-Δ5E peptide SQPFGLK (aa 66-72 of SEQ ID NO: 6) at 8.44 min, no other significant peaks detected; (middle panel) determined m/z values for the peak at 8.44 min, $388.72^{2+}$ and $776.43^{1+}$, match the theoretical m/z values: $388.72^{2+}$ and $776.43^{1+}$; (bottom panel) MS/MS spectrum of correct peptide sequence and theoretical m/z values (inset). FIG. 8B: (top panel) LC-ESI-MS/NMS TIC of peptide SQPFGL*K (aa 66-72 of SEQ ID NO: 6) at 8.46 min, no other significant peaks detected; (second panel) determined m/z values for peak at 8.46 min, $392.22^{2+}$ and $783.45^{1+}$, match theoretical m/z values $392.22^{2+}$ and $783.43^{1+}$; (third panel) MS/MS spectrum of correct peptide sequence and theoretical m/z values (inset).

FIG. 9A: (top panel) LC-ESI-MS/MS TIC of Pavsa-Δ4D peptide LAPLVK (aa 403-408 of SEQ ID NO: 7) at 8.36 min, no other significant peaks were detected; (second panel) determined m/z values for the peak at 8.36 min, $320.72^{2+}$ and $640.44^{1+}$, match theoretical m/z values: $320.72^{2+}$ and $639.44^{1+}$ (representing ≤1 ppm mass error respectively); (bottom panel) MS/MS spectrum revealing correct peptide sequence and theoretical m/z values (inset). FIG. 9B: (top panel) LC-ESI-MS/MS TIC show the LAPLV*K (aa 403-408 of SEQ ID NO: 7) peptide at 8.35 min, no other significant peaks were detected; (middle panel) determined m/z values for peak at 8.35 min, $323.73^{2+}$ and $646.45^{1+}$, match theoretical m/z values $323.73^{2+}$ and $645.45^{1+}$ (representing ≤1 ppm mass error respectively); (bottom panel) MS/MS spectrum of correct peptide sequence and theoretical m/z values (inset).

FIG. 10A: (top panel) LC-ESI-MS/MS TIC of peptide TEPQTPQEWIDDLER (SEQ ID NO: 8) at 13.45 min; (middle panel) determined m/z values for the peak at 13.45 min, 619.63$^{3+}$ and 928.95$^{2+}$, match theoretical m/z values 619.63$^{3+}$ and 928.94$^{2+}$; (bottom panel) MS/MS spectrum revealing correct peptide sequence (bottom panel) and theoretical m/z values (inset). FIG. 10B: (top panel) LC-ESI-MS/MS TIC show the TEPQTPQEWIDDL*ER (SEQ ID NO: 8) peptide at 13.46 min, three peaks were detected at 10.25, 10.67 and 11.39 min caused by artefactual modification of Trp; (second panel) determined m/z values for the peak at 13.46 min, 621.97$^{3+}$ and 932.462$^{2+}$, match theoretical m/z values 621.96$^{3+}$ and 932.44$^{2+}$; (bottom panel) MS/MS spectrum of correct peptide sequence and theoretical m/z values (inset).

FIG. 18 shows detection of Pyrco-Δ5E peptide SQPFGLK (aa 66-72 of SEQ ID NO: 6) in transgenic canola. Panels: (A) Heavy labeled reference standard SQPFGL*K (aa 66-72 of SEQ ID NO: 6) spiked into developing embryo protein background from WT canola (2 pmol on-column); (B) developing embryo protein from WT canola; (C) developing embryo protein from transgenic canola; (I)) heavy labeled reference standard SQPFGL*K (aa 66-72 of SEQ II) NO: 6) spiked into mature seed protein background from WT canola (2 pmol on-column); (E) mature seed protein from WT canola; (F) mature seed protein from transgenic canola.

FIG. 19 shows detection of Pavsa-Δ4D peptide LAPLVK (aa 403-408 of SEQ ID NO: 7) in canola. Panels: (A) Heavy labeled reference standard LAPLV*K (aa 403-408 of SEQ ID NO: 7) spiked into developing embryo protein background from WT canola (2 pmol on-column); (B) developing embryo protein from WT canola; (C) developing embryo protein from transgenic canola; (D) heavy labeled reference standard LAPLV*K (aa 403-408 of SEQ ID NO: 7) spiked into mature seed protein background from WT canola (2 pmol on-column); (E) mature seed protein from WT canola; (F) mature seed protein from transgenic canola.

FIG. 27A shows a trypsin cleavage site K (lysine) or R (arginine) at position P1. The amino acid P (proline) in position P1' (#5) hinders proteolysis. FIG. 27B shows pepsin cleavage sites at both sides of aromatic and hydrophobic amino acids, F (phenylalanine), L (leucine), W (tryptophan), and Y (tyrosine). Amino acids K, R, and H (histidine) at position P3 (#2) hinder proteolysis, while amino acid P at P3 (#2), or P4 (#1) promotes proteolysis. The images were created using WebLogo. See Crooks et al., *WebLogo: A sequence logo generator,* 14 Genome Res. 1188 (2004).

FIG. 28A: theoretical digestion curves for pepsin; ●, solid line: rapid and complete digestion; ▼, broken line: slow and complete digestion; ○, solid line: rapid but incomplete digestion; \/, broken line: slow but incomplete digestion. FIG. 28B: theoretical digestion curves for trypsin post-pepsin; ●, broken line: undigestible protein; ■, broken line: partially digestible protein; ▼, solid line: digestible protein.

FIG. 29A: SDS-PAGE of total proteins from baculovirus infected cells. FIG. 29B: Western blot analysis of His-Pavsa-Δ4D developed with anti His-tag antibody (1:1000 dilution). M: protein markers with molecular weight indicated aside; lane 1: total pellet protein; lane 2: total protein in supernatant.

FIG. 30A is a theoretical pepsin cleavage map of Pavsa-Δ4D. The potential pepsin cleavage sites are shown in underlined bold, and pepsin cleaves at both the amino and carboxyl sides of these residues. FIG. 30B shows protein sequence coverage of Pavsa-Δ4D obtained after pepsin digestion. Bold: peptides identified with >95% confidence; bold italics: peptides identified with 50-95% confidence; underlined: peptides identified with <50% confidence; plain: not detected. Wave underlined (both figures) is the N-terminal His-tag and protease cleavage site followed by M of native Pavsa-Δ4D in the fusion protein. FIG. 30C shows the theoretical trypsin cleavage map of Pavsa-Δ4D. The potential trypsin cleavage sites are indicated in underlined bold font. Trypsin cleaves at the carboxyl side of the bold residues. FIG. 30D shows protein sequence coverage obtained after trypsin digestion. Bold: peptides identified with >95% confidence; bold italics: peptides identified with 50-95% confidence; underlined: peptides identified with <50% confidence; plain: not detected. Wave underlined (both figures) indicates the N-terminal His-tag and protease cleavage site followed by the M of the native Pavsa-Δ4D in the fusion protein.

FIG. 31C is the sequence of Pavsa-Δ4D peptides selected for antibody production (GenScript, Piscataway, New Jersey, USA). Peptides used to raise polyclonal antibodies are underlined, and the peptide for both polyclonal and monoclonal antibodies is double-underlined.

FIGS. 32A and 32B are photographs showing gel characterization of His-Pyrco-Δ5E protein expressed in baculovirus-infected insect cells. FIG. 32A: SDS-PAGE of total proteins from baculovirus infected cells. FIG. 32B B: western blot analysis of His-Pyrco-Δ5E with anti-His-tag antibody (1.1000 dilution). MW: protein markers with molecular weights indicated.

FIG. 33A shows a theoretical pepsin cleavage map of Pyrco-Δ5E protein, in which potential pepsin cleavage sites are underlined. FIG. 33B shows the protein sequence coverage obtained after pepsin digestion. Bold: peptides identified with >95% confidence; italics: peptides identified with 50-95%₀ confidence; underlined: peptides identified with <50% confidence; grey: not detected; wave underlined is the N-terminal His-tag and protease cleavage site followed by M of native Pyrco-Δ5E in the fusion protein. FIG. 33C shows the theoretical trypsin cleavage map of Pyrco-Δ5E protein, in which the potential trypsin cleavage sites are underlined. FIG. 33D shows the protein sequence coverage obtained after trypsin digestion. Bold: peptides identified with >95% confidence; italics: peptides identified with 50-95% confidence; underlined: peptides identified with <50% confidence; grey: not detected; wave underlined is the N-terminal His-tag and protease cleavage site followed by M of native Pyrco-Δ5E in the fusion protein. The two peptides identified in bold (>95% confidence) were not fully tryptic (cleaved at K/R).

FIG. 36 is a graph showing quantification of the single tryptic peptide product of His-Pyrco-Δ5E after combined pepsin-trypsin digestion. LC-MRM-MS analysis of the single trypsin proteolytic fragment that was detected. The response in the LC-MS system (measured as peak area) was converted to a percentage reduction relative to the experimental control (time 0, no pepsin). The peptide sequence (and calculated molecular weight) is denoted above the graph, in which the potential sites for pepsin cleavage are F and L.

FIG. 37 shows peptides of Pyrco-Δ5E selected for antibody production. Italicized: peptides for polyclonal antibodies; underlined: peptide for both polyclonal and monoclonal antibodies.

FIGS. 38A and 38B are photographs characterizing His-GFP-Picpa-ω3D protein expressed in *E. coli* C41. Molecular weight markers and 5 μL of His-GFP-Picpa-ω3D were run on NuPAGE 4-12% Bis-Tris gels. FIG. 38A: SDS-PAGE stained with coomassie blue; FIG. 38B: western blot developed with anti His-tag antibody (1:1000 dilution). MW: protein markers with molecular weights indicated.

FIG. 39A shows the theoretical pepsin cleavage map for Pica-ω3D. The potential pepsin cleavage sites are underlined. FIG. 39B presents amino acid sequence coverage obtained after pepsin digestion. Bold: peptides identified with >95% confidence; italics: peptides identified with 50%-95% confidence; underlined: peptides identified with <50% confidence; grey: not detected; wave underlined includes all amino acids from the N-terminus to " . . . GGS" and shows the N-terminal His-GFP region followed by the second amino acid residue of native Picpa-ω3D (i.e., no M) in the fusion protein. FIG. 39C shows the theoretical trypsin cleavage map, in which potential trypsin cleavage sites are underlined. FIG. 39D depicts protein sequence coverage obtained after trypsin digestion. Bold: peptides identified with >95% confidence; italics: peptides identified with 50%-95% confidence; grey: not detected; wave underlined is the N-terminal His-GFP region followed by the second amino acid of native Picpaω3D (i.e., no methionine) in the fusion protein.

FIG. 43 shows peptides selected for antibody production. Italicized: peptides for polyclonal antibodies; underlined: peptide for both polyclonal and monoclonal antibodies.

DETAILED DESCRIPTION

Figure 1:
FIG. 1 illustrates an example transgenic biosynthesis pathway engineered into Brassica (canola). More specifically, seven recombinant enzymes expressed in canola convert oleic acid (OA) to docosahexaenoic acid (DHA): two fatty acid desaturases from yeast (Δ12-Desaturase and ω3/Δ15-Desaturase), two elongases from microalgae (Δ6-Elongase and Δ5-Elongase), and three "front-end" desaturases from microalgae (Δ6-Desaturase, Δ5-Desaturase, and Δ4-Desaturase).
Figure 4A:
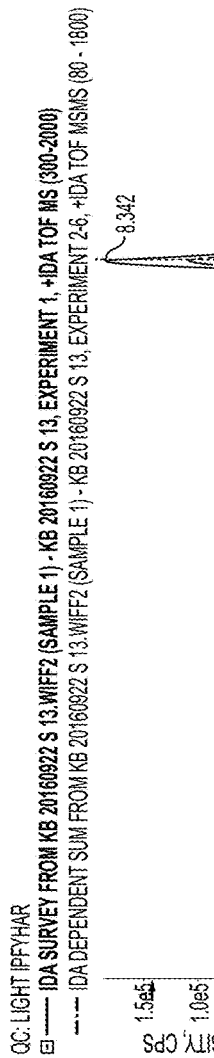
FIGS. 4A and 4B are chromatograms reflecting quality control of Picpa-ω3D peptide.
Figure 4A:
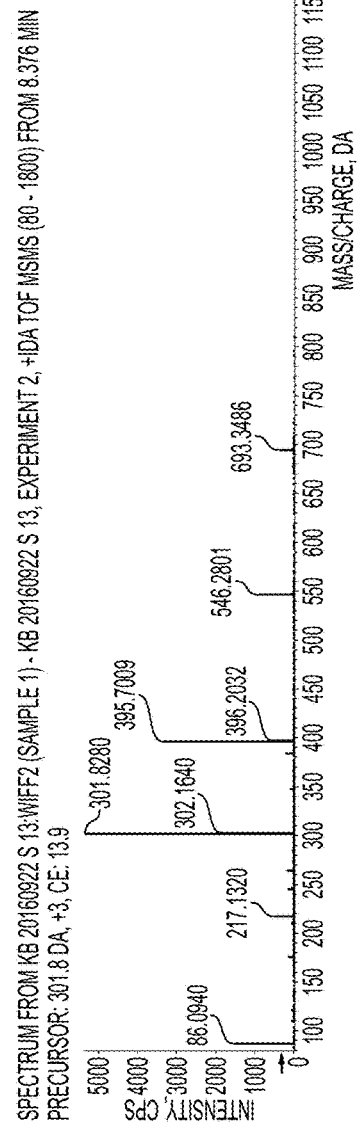
Figure 4B:
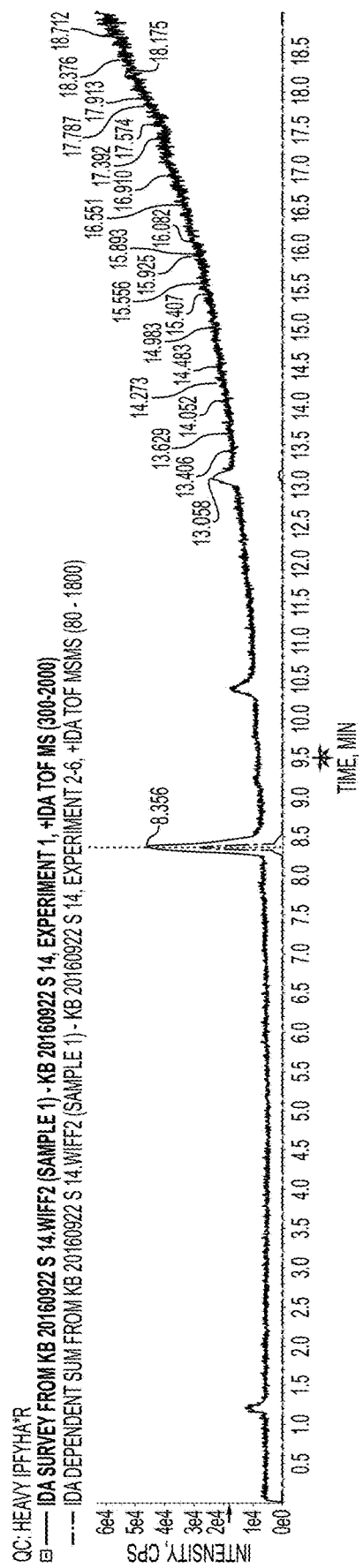
Figure 5A:
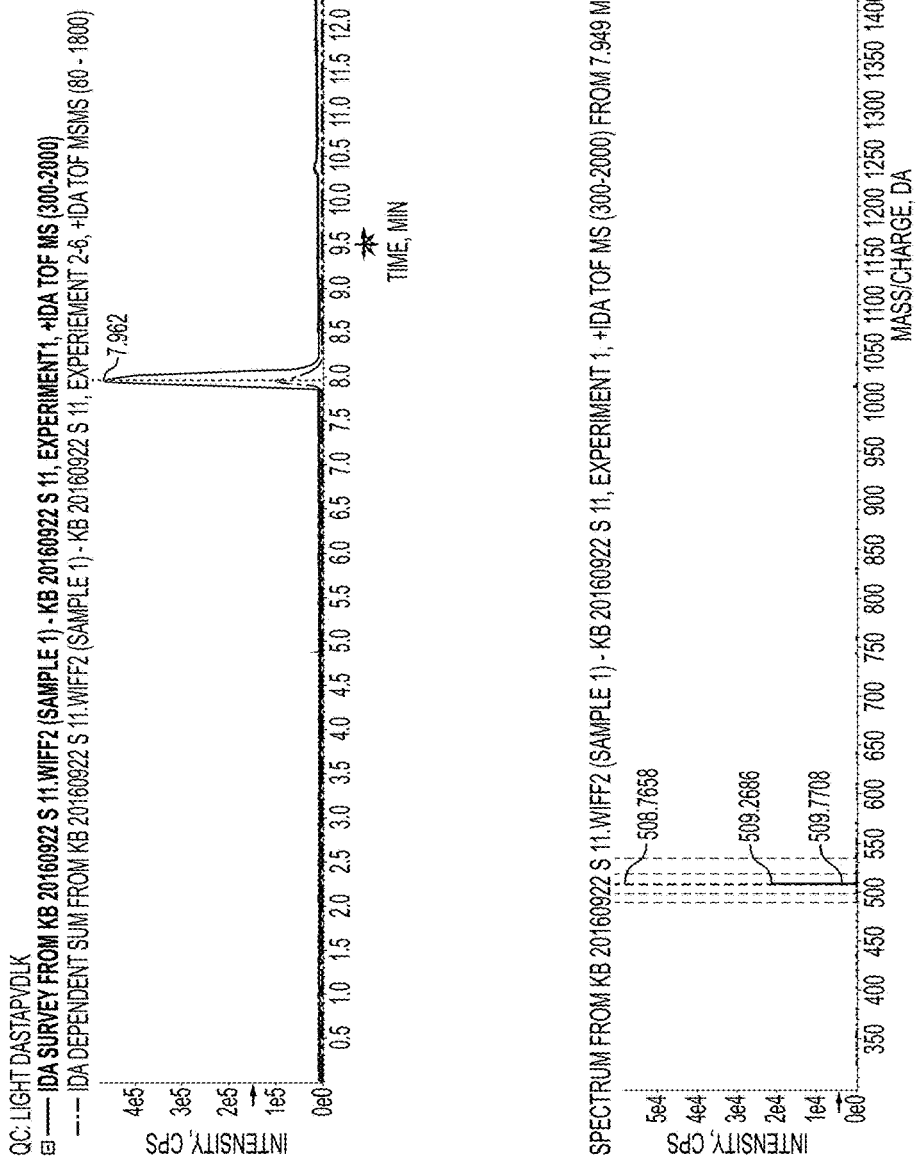
FIGS. 5A and 5B are quality control chromatograms for Micpu-Δ6D peptide.
Figure 5A:
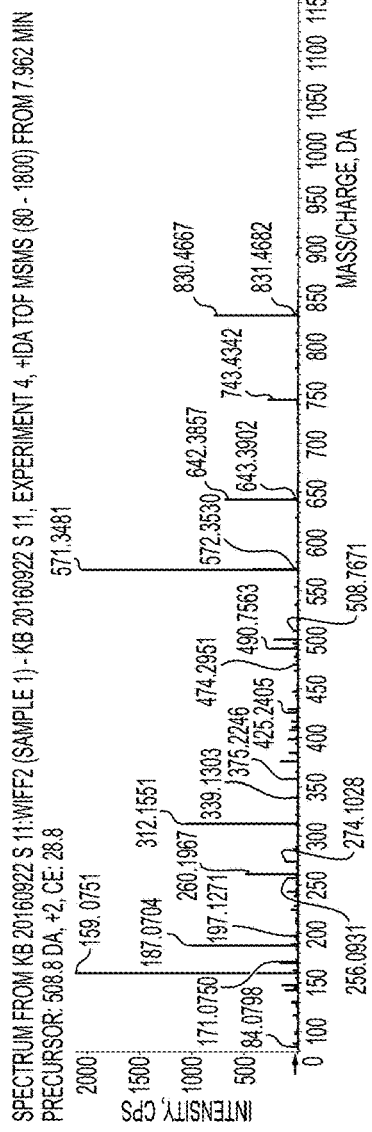
Figure 5B:
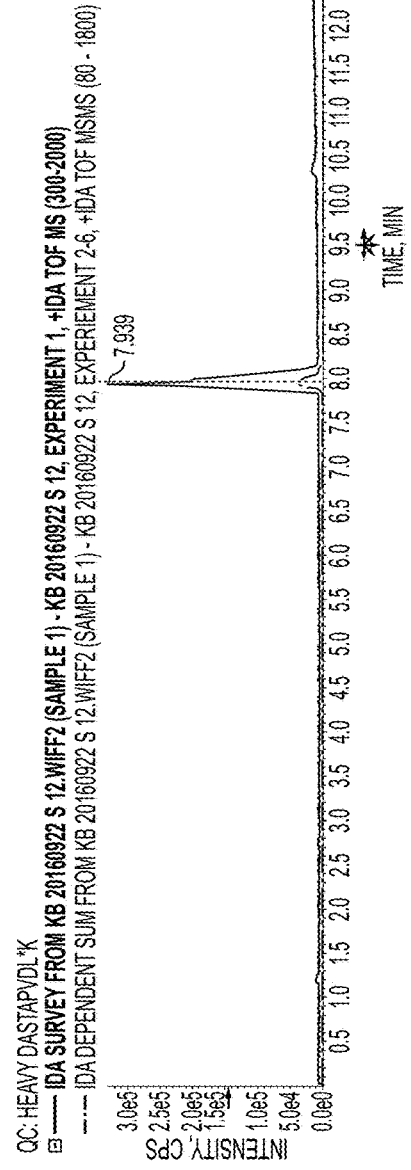
Figure 6A:
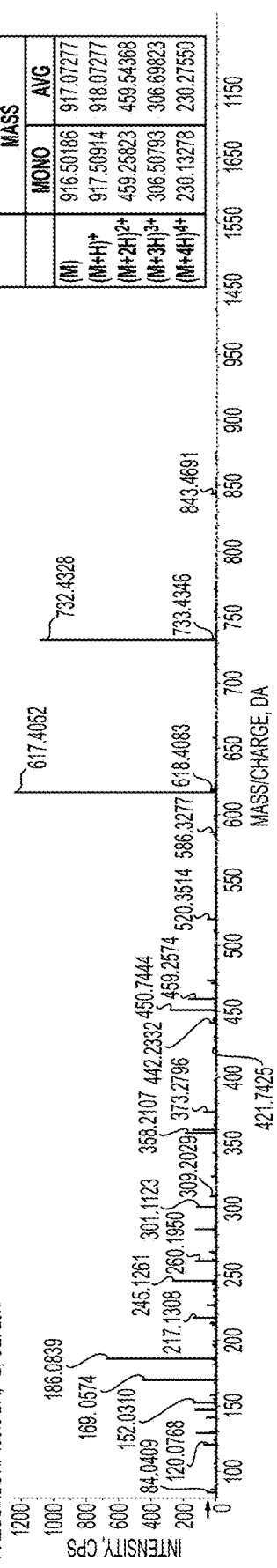
FIGS. 6A and 6B are chromatograms showing quality control of Pyrco-Δ6E peptide.
Figure 6B:
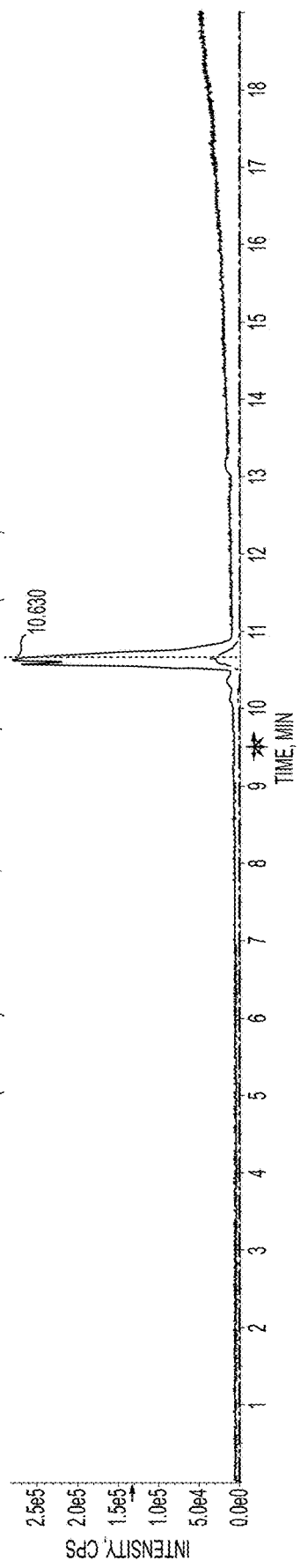
Figure 7A:
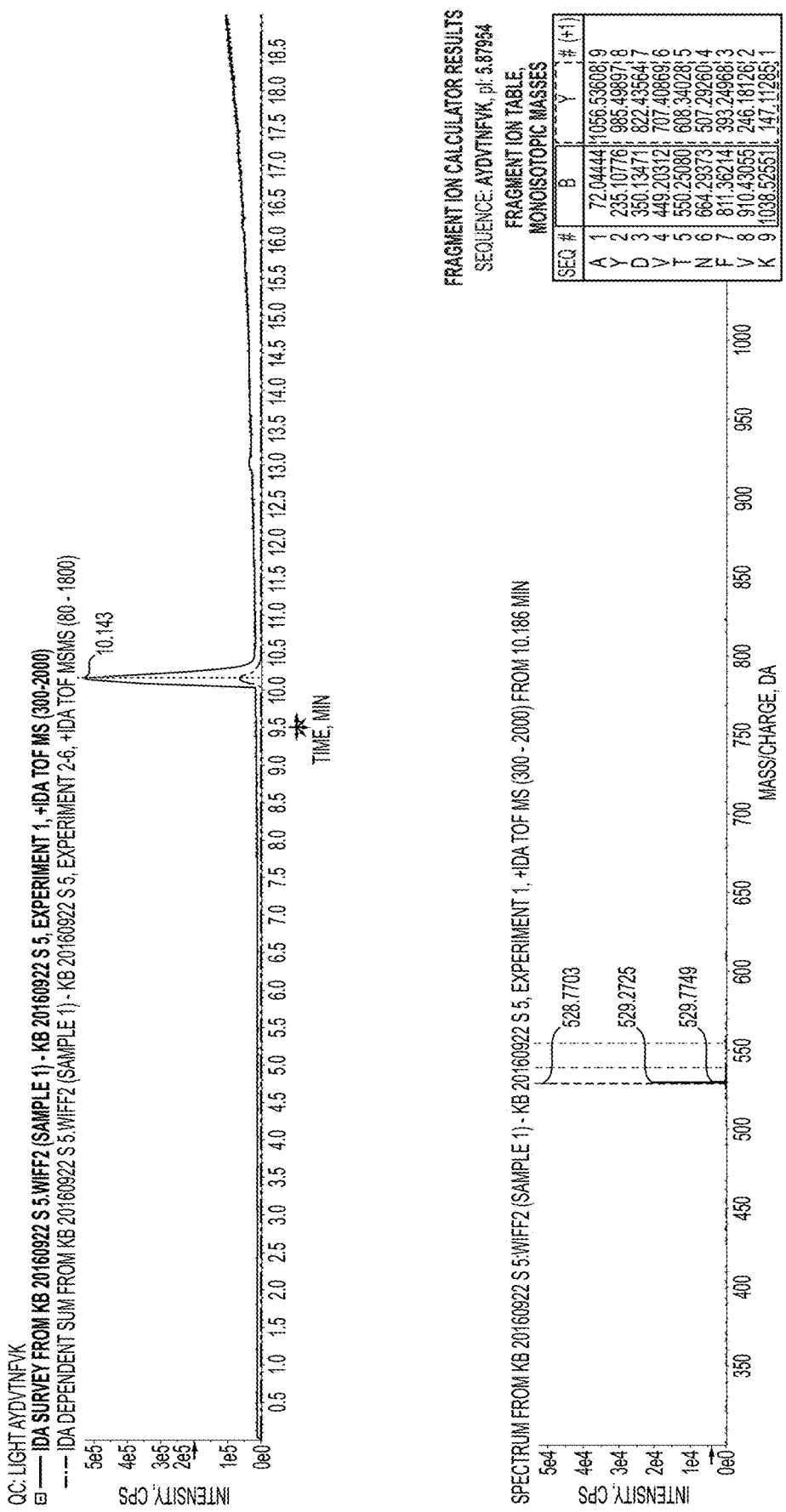
FIGS. 7A and 7B are quality control chromatograms for Pavsa-Δ5D peptide.
Figure 7A:
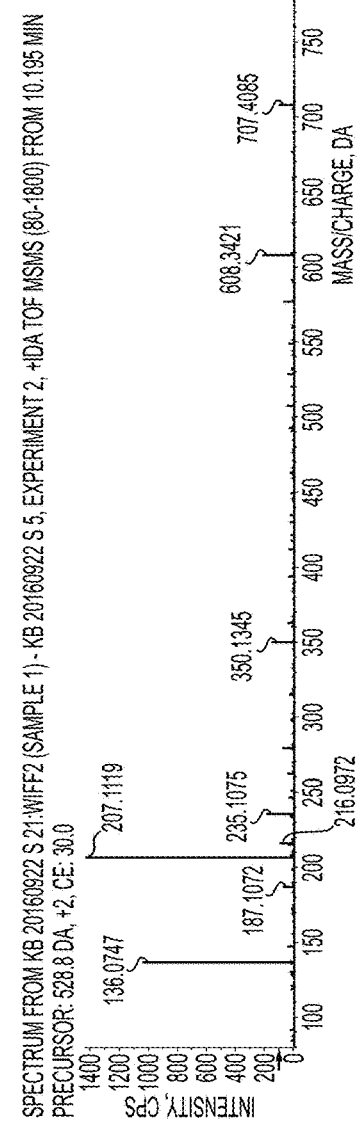
Figure 7B:
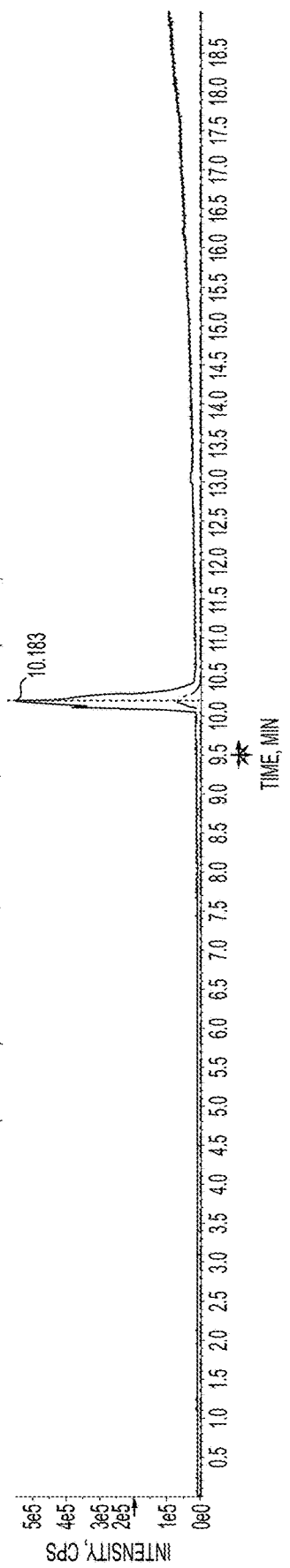
Figure 9A:
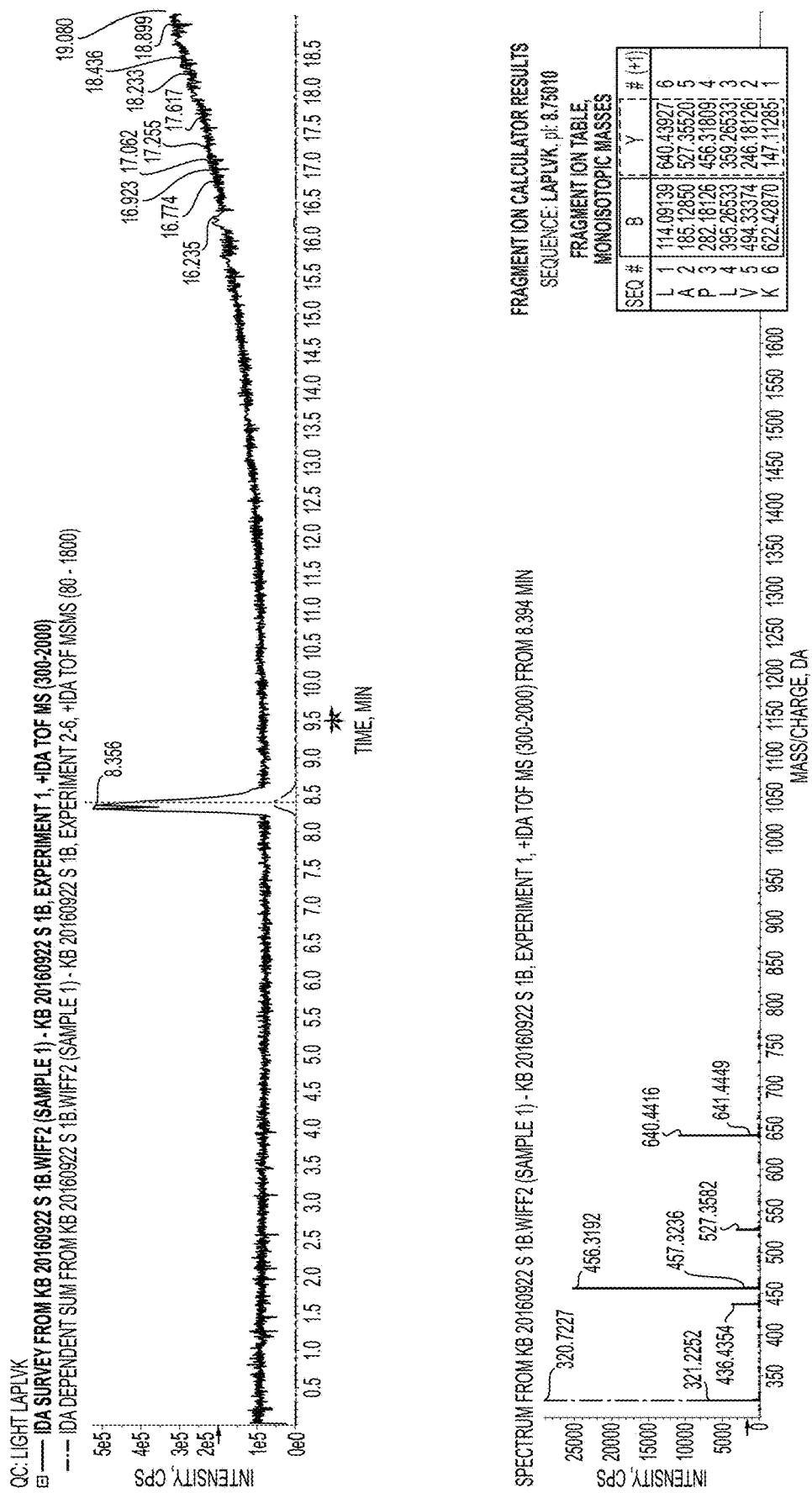
FIGS. 9A and 9B are quality control chromatograms of Pava-Δ4D peptide.
Figure 9A:
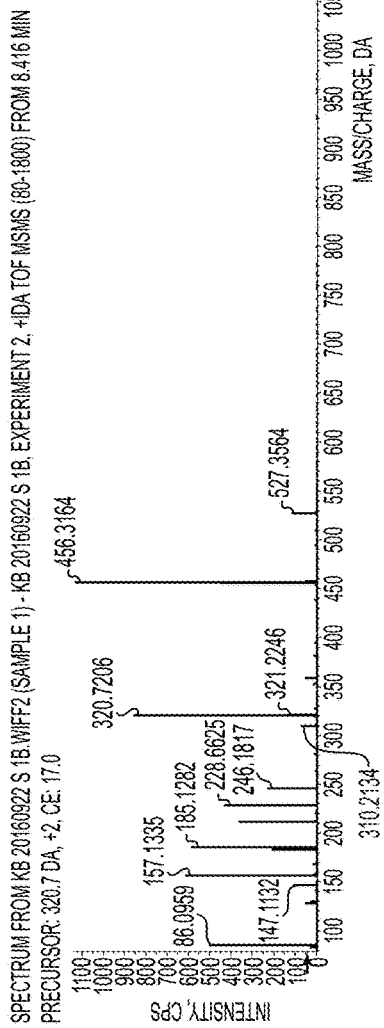
Figure 9B:
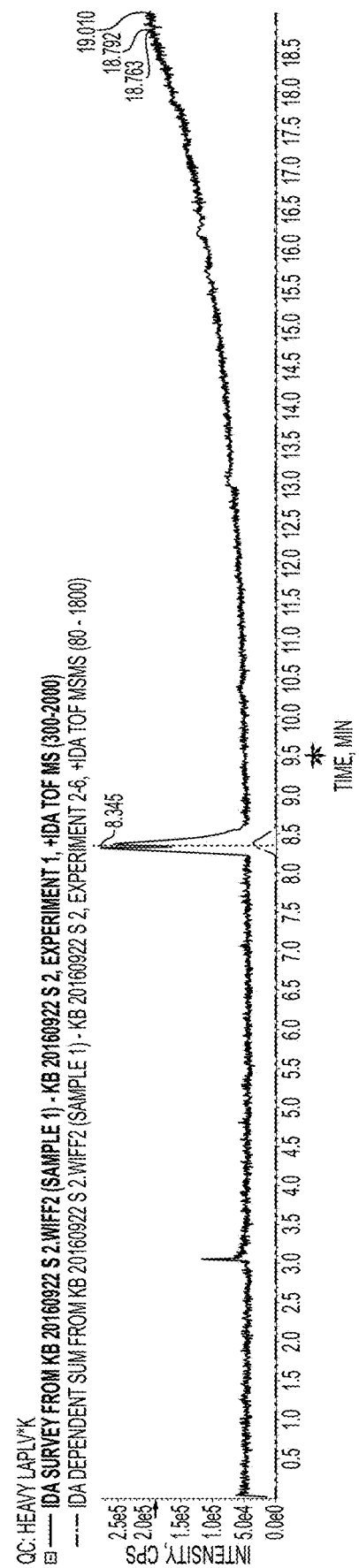
Figure 10A:
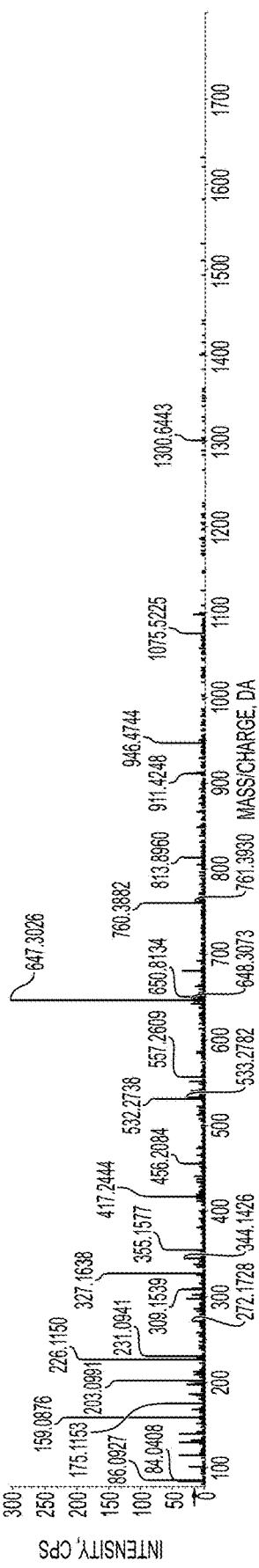
FIGS. 10A and 10B are chromatograms showing quality control for marker peptide, R.
Figure 10B:
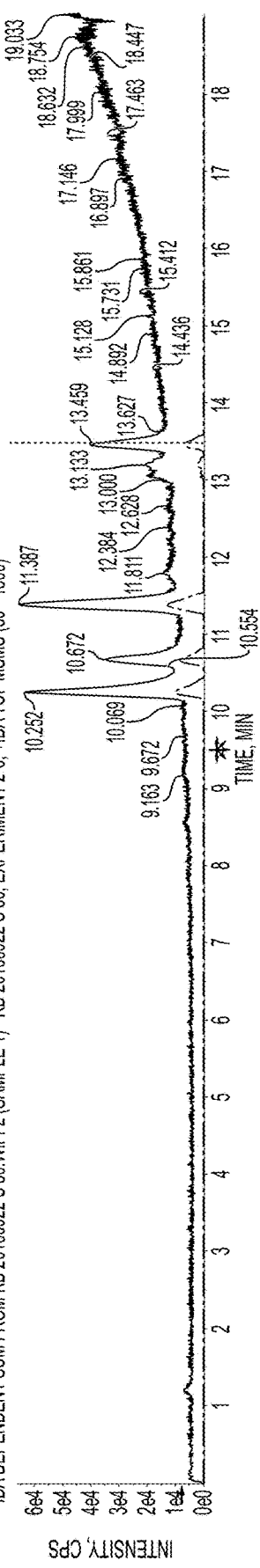
Figure 11:
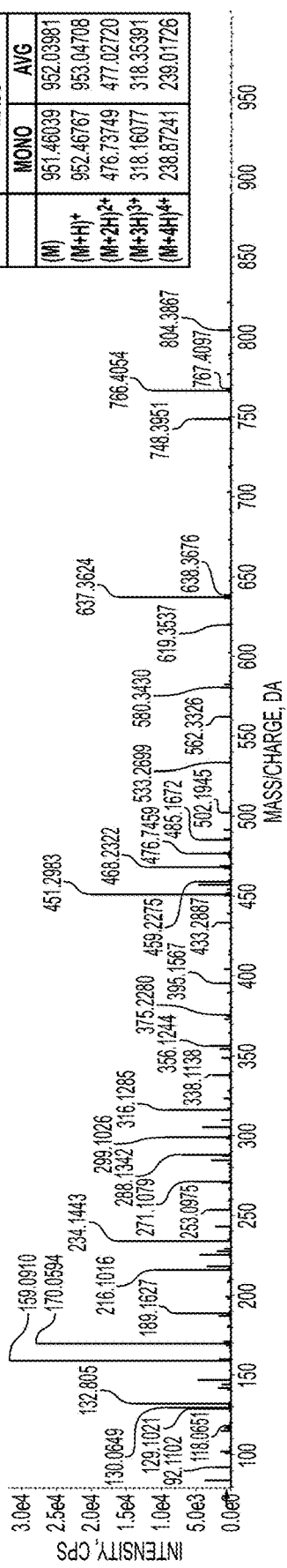
FIG. 11 shows quality control chromatograms of IS peptide: (top panel) LC-ESI-MS/MS TIC showing the IS peptide WEGEPI*SK (aa 274-281 of SEQ ID NO: 7) at 8.35 min, and no other significant peaks were detected; (second panel) determined m/z values for the peak at 8.35 min: 476.75$^{2+}$ and 952.48$^{3+}$ are shown and match the theoretical m/z values. 476.742$^{+}$ and 952.47$^{1+}$ (representing ≤0.01 ppm mass error respectively); (bottom panel) MS/MS spectrum revealing the correct peptide sequence and the theoretical m/z values are shown (inset).

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where otherwise indicated, all numbers expressing quantities of ingredients or reaction conditions used herein should be understood as modified in all instances by the term "about," which is generally ±1% to +10%, depending on context as determined by one of skill in the art.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

The embodiments described herein provide novel techniques to quantify and characterize target membrane proteins using high sensitivity LC-MRM-MS. In particular, transgenic proteins of the ω3LCPUFA synthesis pathway cloned into *Brassica*, and often associated with membranes in vivo, are currently not adequately characterized by antibodies as used, for example, in traditional western blot analysis. Regarding the characterization of protein content and function, solubilization (using detergents to replace the lipid of the membrane), and purification can increase levels of protein, but dissociation from membranes typically eliminates desaturase or elongase activity, likely due to a requirement for other proteins co-localized in the membrane, as well as cofactors, some as yet unknown. The present approach can be used to analyze recalcitrant proteins directly, without first enriching for membrane fractions, such as microsomes, or separating/enriching putative target proteins by electrophoresis, before employing the LC-MS/MS system. See Skinner et al., 64 J. Ag. Food Chem. 5251 (2016). Thus, in comparison with current LC-MS/MS detection, the present embodiments provide high throughput methods that enable analysis of many samples. Additionally, membrane or microsomal enrichment may exclude characterization of proteins that are not captured in a specific cell fraction. For example, "debris" discarded after initial centrifugation of cell lysates at 12 k×g may contain target proteins: supposed ER protein, Δ4-desaturase, was detected in the 15 k×g pellet and would have been excluded from the subsequent 100 k×g microsomal pellet. Se Skinner et al., 2016.

The method described herein was employed to characterize seven transgenic enzymes—fatty acid desaturases and elongases—that provided a biosynthetic pathway to convert oleic acid to DHA. More specifically, metabolic engineering of the ω3LCPUFA, like eicosapentaenoic acid (EPA, 20:5ω3) and docosahexaenoic acid (DHA, 22:6ω3), in oil crops involved in the transgenic expression of several fatty acid desaturases and elongases in ω3LCPUFA biosynthesis pathway. The transgenic enzymes (FIG. 1) consisted of *Lachancea kluyveri* Δ12-desaturase (Lack1-Δ12D; Watanabe et al., 68 Biosci. Biotechnol. Biochem. 721 (2004)); *Pichia pastoris* ω3-/Δ15-desaturase (Picpa-ω3D; Zhang et al., 25 Yeast 21 (2008)); *Micromonas pusilla* Δ6-desaturase (Micpu-Δ6D; Petrie et al., 12 Metab. Eng. 233 (2010b)); *Pyramimonas cordata* Δ6-elongase (Pyrco-Δ6; Petrie et al., 12 Mar. Biotechnol. 430 (2010a)); *Pavlova* salina Δ5-desaturase (Pavsa-Δ5D; Zhou et al., 68 Phytochem. 785 (2007)); *P. cordata* (a Δ5-elongase (Pyrco-Δ5E; Petrie et al., 2010a); and *P. salina* Δ4-desaturase (Pavsa-Δ4D; Zhou et al., 2007). The enzymes were each expressed independently under control of seed-specific promoters and other appropriate genetic regulatory regions.

The functionalities and activities of these enzymes have been demonstrated in different heterologous expression systems including transgenic *Arabidopsis, Camelina*, and *Brassica* seeds. Petrie et al., PLoS One 7: e49165 (2012); Petrie et al., PLoS One 9: e85061 (2014). Based on the sequence similarity and functionality, these seven proteins can be classified into three groups, (1) yeast acyl-CoA type fatty acid desaturases including Lack1-Δ12D and Picpa-ω3D that introduce a double bond at the Δ12 and Δ15 positions, respectively; (2) algae fatty acid elongases including Pyrco-Δ6E and Pyrco-Δ5E that add two carbons to the carboxyl end of fatty acids; and (3) algae "front-end" fatty acid desaturases that introduce a double bond between an existing double bond and the carboxyl end of fatty acids including Micpu-Δ6D, Pavsa-Δ5D and Pavsa-Δ4D. Zhou et al., 2007. Although the engineered D-IA synthesis pathway genes were under the control of seed-specific promoters, other tissues in addition to seed were also assessed as described herein.

The likelihood of allergic oral sensitization to a protein is first affected by the stability of the protein to gastrointestinal digestion. Astwood et al., 14 Nature Biotechnol. 1269 (1996). Full evaluation of each transgenic protein, including expression levels and protein stability, provides valuable information when assessing allergenic potential using a weight of evidence approach. These transgenic ω3LCPUFA enzymes are tightly associated with membranes and expressed at low levels, however, hampering characterization by traditional means such as immunoassays. The present embodiments provide LC-MS/MS based methods to evaluate membrane proteins. An aspect of the present embodiments assesses the in vitro digestibility of the fatty acid biosynthesis enzymes introduced into ω3LCPUFA-producing canola by digesting with pepsin.

In vitro digestion models are used widely to assess the nutritional value of ingested proteins based on their amino acid bioavailability. The correlation between protein allergenicity and protein stability in an in vitro pepsin digestion assay has been reported previously. Astwood et al., 1996. When proteins are found to be highly digestible, the potential for systemic exposure is reduced. The current safety assessment strategy (Codex, 2003) is based on a weight-of-evidence approach recognizing that no single endpoint can predict human allergenicity potential. Based on this strategy, a number of factors are evaluated in the context of genetic plants: the gene source, determining the similarity of amino acid sequence of the newly expressed protein to known allergens, the abundance of the protein in the crop and the digestibility of the protein to in vitro digestion.

Protein quantification by multiple reaction monitoring (MRM), using a triple quadrupole mass spectrometer, has been applied to clinical laboratory studies. Rauh, 883 J. Chromatog. B, 59 (2012); Gillette & Carr, 10 Nat. Meth. 28 (2013). Current analysis of proteins by MRM is based on detection of peptides derived from proteolytic digestion of the target protein, typically by trypsin. The measurement of tryptic peptides in a complex sample matrix may be achieved by adding a known concentration of an isotope-labelled peptide isomer as an internal standard (IS) to the sample before analysis. The labeled peptide isomer (referred to as "heavy") contains an amino acid labelled with the stable isotopes, typically $^{15}N$ or $^{13}C$, resulting in a mass increase compared to that of the native peptide isomer (referred to as "light"). When subjected to chromatographic separation, the heavy and light peptides show nearly identical elution profiles, allowing the detection of the light peptides (analytes) in the matrix background. When subjecting the peptides to MS/MS under conditions of collision-induced dissociation, the light and heavy peptides also undergo an identical fragmentation mechanism (transition) providing an additional level of quality control in confirming the peptide identity.

Figure 28A:
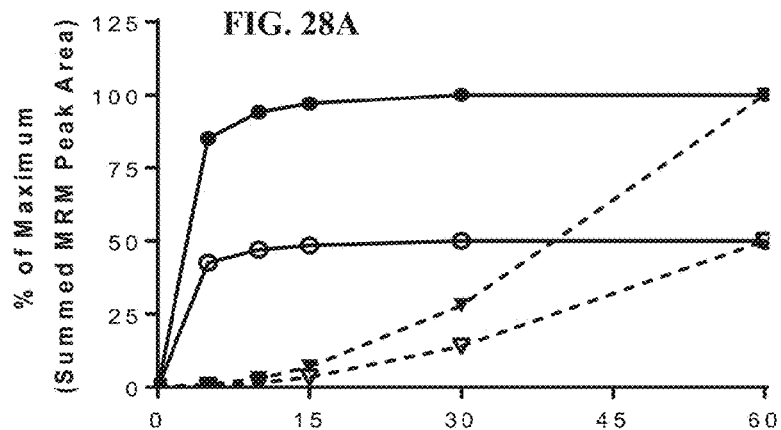
FIGS. 28A and 28B present theoretical digestion curves that could be generated using LC-MS and the proposed digestibility assay.

Upon digestion with pepsin alone, there are a number of scenarios that may occur (FIG. 28A). The simplest is when the protein is rapidly digested to produce fully peptic fragments in which the response increases rapidly, reaching a maximum and creating a plateau (filled circle). The second involves the slow digestion that does not reach a plateau within the experimental duration (filled triangles). This scenario is difficult to judge for completeness as LC-MS monitors the peptide response (peptide peak intensity or area). The third involves a rapid, but incomplete digestion that may appear to be complete as judged by the plateau in peptide response (empty circles). Lastly, slow and incomplete digestion may be observed (hollow triangles).

Figure 28B:
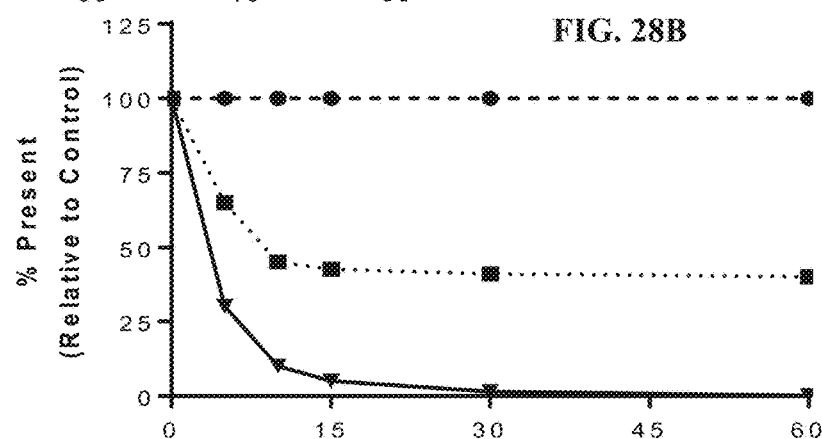

By employing trypsin post-pepsin (see FIG. 28B), it is possible to judge the completeness of the digestion by comparison to an experimental control (time 0, no pepsin added) wherein the tryptic peptides liberated appear at the maximum value (in this instance as the MRM peak area). If the protein is not digested, then no decrease in peptide response will be observed (circles, dashed line). If the protein is partially digested, a partial decrease in the peptide response will be observed (squares, dotted line). If the protein is completely digested, the peptide response will drop to zero within the experiment duration (triangles, solid line).

Thus, by examining the pepsin proteolytic fragments, the breakdown of a protein could be monitored, but it is noted that determining whether degradation had reached completion is a difficult task. To overcome this deficiency, the tryptic peptide products were used as a proxy for intact protein, wherein in the absence of pepsin, the amount of tryptic peptide was equivalent to 100% of protein being present. In the presence of pepsin (at varying time points during digestion), the level of tryptic peptides would be expected to decrease for peptides that contained a pepsin cleavage site. In this way the complete degradation of the protein can be monitored.

In one specific embodiment, transgenic enzymes of the ω3LCPUFA pathway were digested with pepsin for 0 minutes to 60 minutes, followed by complete trypsin digestion, while collecting samples at timed intervals. The decline of tryptic peptides was used as a proxy for intact protein, and the appearance and disappearance of peptic peptides was used to indicate the in vitro digestibility of transgenic proteins. Additionally, the level of tryptic peptide markers in a known quantity of total protein was quantified using a spiked internal standard (IS). By examining specific peptides (unique to the target transgenic proteins), this approach provides highly selective and sensitive measurement of the target membrane proteins.

A similar principle employing LC-MS/MS was used to quantify each target protein in different plant tissues and seed. Applying the LC-MS/MS based method in transgenic plants demonstrated that seed-specific promoters correctly directed expression of transgenes only in developing and mature seed, in which seed the transgenic proteins were present at low levels (ng target/mg protein).

More specifically, in some embodiments, calibration curves were generated in which the analyte concentration was varied, and a defined amount of IS was spiked into the standards. The response of the mass spectrometer was the integrated peak area for each MRM transition. The top three MRM transitions were summed (for both analyte and IS). The ratios of (summed analyte peak area)/(summed IS peak area) were plotted against the known analyte concentration. The endogenous peptide response was determined and the concentration interpolated from the calibration curve, thus allowing the quantification of the peptide as fmol target peptide per 100 μg total protein. This value was converted to a ng equivalent per mg total protein based on the molecular mass of each target protein.

Using protein extracts from a variety of sources including total protein extracts from canola and recombinant proteins expressed in either yeast, bacterial or baculovirus expression systems, the peptides liberated after tryptic digestion were assessed. The ω3 LC-PUFA biosynthetic enzymes were thus characterized, allowing selection of peptides as biomarkers of each protein for quantification. The amino acid sequences of the enzymes are given in FIG. 2, in which fully tryptic peptides, potentially useful as peptide markers, are underlined. FIG. 2 presents the score, protein sequence coverage (at 95% confidence), and number of detected peptides for each enzyme. Peptides were excluded as markers, where possible, if they contained methionine (M, commonly modified by oxidation), or contained adjacent dibasic sites (KK, KR, RK, RR, which inhibit cleavage), thus limiting variability in digestion efficiency. Peptides were selected for use in protein quantification according to, for example, (a) size amenable to LC-MS/MS analysis (6 to 20 amino acids), and (b) highest signal intensity consistently detected (in multiple digests).

Protein extracts from a variety of sources including total protein extracts from canola, recombinant proteins expressed in either yeast, bacterial or baculovirus expression systems were used. The proteins were either provided in-solution or as excised gel slices. Gel bands were digested. See Byrne et al., 12 Proteomics 1 (2012). The solutions were subjected to filter-assisted sample preparation (FASP). Wisniewski et al., 6 Nature Meth. 359 (2009); Colgrave et al., 1370 J. Chromatog. A 105 (2014).

Proteolytically digested proteins were analyzed with chromatographic separation using a nano HPLC system directly coupled to a mass spectrometer, and software used for protein identification. See, Shilov et al., 6 Mol. Cell Proteom. 1638 (2007). Tandem mass spectrometry data was searched against in silico tryptic digests of a database comprising the transgenic proteins, using parameters defined as iodoacetamide modified for cysteine alkylation and trypsin as the digestion enzyme.

Total protein extracts from ω3LCPUFA transgenic canola tissues or seed or from recombinant proteins expressed in yeast, bacterial, or baculovirus expression systems were first analyzed by non-targeted LC-MS for detection of the tryptic peptides generated for each target protein, e.g., desaturase or elongase, of the ω3LCPUFA pathway. Total protein from Nicotiana benthamiana leaf with a transiently expressed marker protein was also used for detection of the tryptic peptides of the marker protein. After searching all generated data against the custom protein database, two peptides were selected from each target protein as proxies for use in quantification. The selection of peptides was based on the criteria: good MS response (high intensity); where possible, absence of amino acids within the peptide sequence that are likely to be modified (for example, oxidation of methionine) or miscleaved (presence of dibasic residues at either terminus); specific/unique to the target protein; and of a size amenable to LC-MS (~6 to 20 amino acids in length). For each selected peptide, both the endogenous (light) peptides and $^{15}$N and $^{13}$C labelled (heavy) peptides were synthesized.

The peptides liberated after tryptic digestion were assessed using protein extracts from a variety of sources including total protein extracts from canola or recombinant proteins expressed in either yeast, bacterial or baculovirus expression systems. The ω3LCPUFA biosynthetic enzymes were thus characterized, allowing selection of peptides as biomarkers of each protein for quantification. See FIG. 2.

EXAMPLES

Example 1. Peptide Selection

Target Proteins—All seven transgenic biosynthesis pathway enzymes expressed in ω3LCPUFA canola were targeted for characterization, including quantification of protein content in various tissues of transgenic canola across the growing season.

Using protein extracts from a variety of sources including total protein extracts from canola or recombinant proteins expressed in either yeast, bacterial or baculovirus expression systems, peptides liberated after tryptic digestion were assessed. The protein sequences are given in FIG. 2 wherein fully tryptic peptides potentially useful as peptide markers are underlined. The figure provides the score, protein sequence coverage (at 95% confidence) and number of detected peptides for each target protein. Peptides were excluded as markers, where possible, if they contained methionine (M), which is commonly modified by oxidation, or contained adjacent dibasic sites (KK, KR, RK, RR), which commonly cause missed cleavage and hence variability in digestion efficiency. Peptides were selected, ideally, for size amenable to LC-MS/MS analysis: 6-20 amino acids in length. Peptides that (a) gave the highest signal intensity and (b) were detected consistently in multiple digests, were selected for peptide synthesis for protein quantification.

Selection of Peptides for Quantification—The total protein extracts from DHA canola seed or from recombinant proteins expressed in either yeast, bacterial, or baculovirus expression systems were analyzed by non-targeted LC-MS for detection of the tryptic peptides generated for each target protein (i.e., desaturase or elongase of the ω3LCPUFA biosynthesis pathway). Total protein from N. benthamiana leaf with transiently expressed R was also used for detection of the tryptic peptides of R protein. After searching all generated data against the custom protein database, two peptides were selected from each target protein as proxies to be used for quantification. The selection of peptides was based on several criteria: (a) good MS response (high intensity), (b) absence of amino acids within a peptide sequence likely to be modified (for example, oxidation of methionine) or miscleaved (presence of dibasic residues at either terminus), (c) amino acids specific/unique to the target protein, and (d) of a size amenable to LC-MS (~6-20 amino acids in length). For each selected peptide, both the endogenous (light) peptides and $^{15}$N and $^{13}$C labelled (heavy) peptides were synthesized.

Based on the preliminary results from both the quality control assessment and determination of linearity of response for the synthetic peptides, the peptide with optimal performance characteristics (e.g., high signal intensity, good chromatographic properties) for each protein was selected as the protein proxy for quantification. The final selected peptides for the DHA synthesis pathway enzymes (see FIG. 1) are shown in Table 2.

TABLE 2

Peptides used for protein quantification of the DHA biosynthesis pathway enzymes

| Protein | Light Peptide Sequence | MW Light Peptide (Da) | Heavy Peptide Sequence | MW Heavy Peptide (Da) |
|---|---|---|---|---|
| Lackl-Δ12D | GSSSNTEQEVPK[1] | 1261.58 | GSSSNTEQEV*PK[1] | 1267.58 |
| Picpa-ω3D | IPFYHAR[2] | 902.48 | IPFYHA*R[2] | 906.48 |
| Micpu-Δ6D | DASTAPVDLK[3] | 1015.52 | DASTAPVDL*K[3] | 1022.52 |
| Pyrco-Δ6E | GQDPFLLK[4] | 916.50 | GQDPFLL*K[4] | 923.50 |
| Pavsa-Δ5D | AYDVTNFVK[5] | 1055.53 | AYDVTNFV*K[5] | 1061.53 |
| Pyrco-Δ5E | SQPFGLK[6] | 775.42 | SQPFGL*K[6] | 782.42 |
| Pavsa-Δ4D | LAPLVK[7] | 639.43 | LAPLV*K[7] | 645.44 |
| IS | | | WEGEPI*SK[8] | 951.46 |
| Additional peptides for use in protein quantification: | | | | |
| Lackl-Δ12D | GSSSNTEQEVPK[1] | 1261.58 | GSSSNTEQEVPK*[1] | 1269.58 |
| Lackl-Δ12D | NINNCGVGAAEK[9] | 1189.3 | NINNC[CAM]GVGAAEK[9] | 1245.56 |
| Lackl-Δ12D | NINNCGVGAAEK[9] | 1189.3 | NINNC[CAM]GVGAAEK*[9] | 1253.56 |
| Picpa-ω3D | DILDAIPK[10] | 883.50 | DILDAIPK*[10] | 891.50 |
| Picpa-ω3D | IPFYHAR[2] | 902.48 | IPFYHAR*[2] | 912.48 |
| Micpu-Δ6D | ALPSRPAEIK[11] | 1081.29 | ALPSRPAEIK*[11] | 1088.63 |
| Micpu-Δ6D | DASTAPVDLK[3] | 1015.52 | DASTAPVDLK*[3] | 1023.52 |
| Pyrco-Δ6E | GQDPFLLK[4] | 916.50 | GQDPFLLK*[4] | 924.50 |
| Pavsa-Δ5D | AYDVTNFVK[5] | 1055.53 | AYDVTNFVK*[5] | 1063.53 |
| Pyrco-Δ5E | SQPFGLK[6] | 775.42 | SQPFGLK*[6] | 783.42 |
| Pavsa-Δ4D | LAPLVK[7] | 639.43 | LAPLVK*[7] | 647.43 |
| Pavsa-Δ4D | WEGEPISK[8] | 945.04 | WEGEPISK*[8] | 952.46 |

*Amino acid residues labeled with isotope $^{15}$N or $^{13}$C. Heavy peptides were used as reference standards for determining the correct retention time and fragmentation pattern.
[1]GSSSNTEQEVPK: residues 16-26 of SEQ ID NO: 2;
[2]IPFYHAR: aa 351-358 of SEQ ID NO: 1;
[3]DASTAPVDLK: aa 30-39 of SEQ ID NO: 3;
[4]GQDPFLLK: aa 83-90 of SEQ ID NO: 4;
[5]AYDVTNFVK: aa 37-45 of SEQ ID NO: 5;
[6]SQPFGLK: aa 66-72 of SEQ ID NO: 6;
[7]LAPLVK: aa 403-408 of SEQ ID NO: 7;
[8]WEGEPISK: aa 274-281 of SEQ ID NO: 7;
[9]NINNCGVGAAEK: aa 405-416 of SEQ ID NO: 2, [CAM] is carbamidomethylated Cys;
[10]DILDAIPK: (aa 51-58 of SEQ ID NO: 1);
[11]ALPSRPAEIK: residues 06-115 of SEQ ID NO: 3.

Synthesis of peptides—Selected peptides were synthesized at Creative Proteomics (Shirley, N.Y., US) at 90% c purity. The amount of each synthesized peptide was determined by high sensitivity amino acid analysis (AAA) at the Australian Proteomics Analysis Facility (Sydney, AU). All samples were analyzed in duplicate. The calculated amount of amino acid (µg/ML) was based on the amino acid residue mass in the protein (molecular weight minus $H_2O$). Using the determined concentrations, stock solutions were prepared at 100 pmol/µL. The purity of synthesized peptides was analyzed by LC-MS. Dilutions equivalent to ~5 pmol/µL were prepared in aqueous solution (1% formic acid) and analyzed by LC-ESI-MS/MS. Any peptides showing significant contamination including the presence of the truncated, modified or synthesis by-products were excluded from further analysis.

The purity of synthesized peptides was analyzed by LC-MS, and the results are shown in FIG. 3 to FIG. 11. In each figure, the top panel shows the total ion chromatogram (TIC) for the light (A) and heavy (B) peptide, in blue (MS) and pink (MS/MS). The middle panel shows the determined m/z values for the light (A) and heavy (B) peptide. The bottom panel shows the MS/MS spectrum of the correct amino acid sequence, and the theoretical m/z values are shown in the insert.

The concentrations of the synthetic peptides were determined by high sensitivity amino acid analysis and results were expressed as averages of duplicate measurements (Tables 3-11). The calculated amount of amino acid (µg/mL) is based on the amino acid residue mass in the protein (molecular weight minus $H_2O$). Using the determined concentrations, stock solutions were prepared at 100 pmol/µL peptide.

TABLE 3

Amino Acid Analysis: GSSSNTEQEVPK[1]

| | GSSSNTEQEVPK[1] MW 1261.58 Da | | | | GSSSNTEQEV*PK[1] MW 1267.58 Da | | | |
|---|---|---|---|---|---|---|---|---|
| Amino acid[a] | Amount (µg/mL) | nmol/mL | Exp. mol % | Theor. mol % | Amount (µg/mL) | nmol/mL | Exp. mol % | Theor. mol % |
| Ser | 14.07 | 161.6 | 22.7 | 25.0 | 15.96 | 183.3 | 22.7 | 25.0 |
| Gly | 3.49 | 61.2 | 8.6 | 8.3 | 3.99 | 70.0 | 8.7 | 8.3 |
| Asp | 7.06 | 61.3 | 8.6 | 8.3 | 7.99 | 69.4 | 8.6 | 8.3 |
| Glu | 23.69 | 183.4 | 25.7 | 25.0 | 26.91 | 208.4 | 25.8 | 25.0 |
| Thr | 5.81 | 57.5 | 8.1 | 8.3 | 6.59 | 65.2 | 8.1 | 8.3 |
| Pro | 5.97 | 61.5 | 8.6 | 8.3 | 6.75 | 69.5 | 8.6 | 8.3 |

TABLE 3-continued

Amino Acid Analysis: GSSSNTEQEVPK[1]

| | GSSSNTEQEVPK[1] MW 1261.58 Da | | | | GSSSNTEQEV*PK[1] MW 1267.58 Da | | | |
|---|---|---|---|---|---|---|---|---|
| Amino acid[a] | Amount (µg/mL) | nmol/mL | Exp. mol % | Theor. mol % | Amount (µg/mL) | nmol/mL | Exp. mol % | Theor. mol % |
| Lys | 7.87 | 61.4 | 8.6 | 8.3 | 8.84 | 69.0 | 8.5 | 8.3 |
| Val | 6.44 | 65.0 | 9.1 | 8.3 | 7.30 | 73.7 | 9.1 | 8.3 |
| Total | 74.40 | 712.9 | 100.0 | 100.0 | 84.33 | 808.4 | 100.0 | 100.0 |

[a]Ser, serine; Gly, glycine; Asp, aspartic acid; Glu, glutamic acid; Thr, threonine; Pro, proline; Lys, lysine; Val, valine;
[1]GSSSNTEQEVPK: residues 16-26 of SEQ ID NO: 2.

TABLE 4

Amino Acid Analysis: IPFYHAR[1]

| | IPFYHAR[1] MW 902.48 Da | | | | IPFYHA*R[1] MW 906.48 Da | | | |
|---|---|---|---|---|---|---|---|---|
| Amino acid[a] | Amount (µg/mL) | nmol/mL | Exp. mol % | Theor. mol % | Amount (µg/mL) | nmol/mL | Exp. mol % | Theor. mol % |
| His | 9.66 | 70.5 | 14.2 | 14.3 | 2.38 | 17.4 | 14.3 | 14.3 |
| Arg | 11.47 | 73.4 | 14.8 | 14.3 | 2.82 | 18.1 | 14.9 | 14.3 |
| Ala | 4.80 | 67.6 | 13.6 | 14.3 | 1.19 | 16.8 | 13.8 | 14.3 |
| Pro | 6.83 | 70.3 | 14.2 | 14.3 | 1.65 | 17.0 | 14.0 | 14.3 |
| Tyr | 11.58 | 71.0 | 14.3 | 14.3 | 2.83 | 17.3 | 14.3 | 14.3 |
| Ile | 8.00 | 70.7 | 14.3 | 14.3 | 1.93 | 17.1 | 14.1 | 14.3 |
| Phe | 10.60 | 72.0 | 14.5 | 14.3 | 2.58 | 17.5 | 14.5 | 14.3 |
| Total | 62.95 | 495.5 | 100.0 | 100.0 | 15.39 | 121.2 | 100.0 | 100.0 |

[a]His, histidine; Arg, argininine; Ala, alanine; Pro, proline; Tyr, tyrosine; Ile, isoleucine; Phe, phenylalanine;
[1]IPFYHAR: residues 351-358 of SEQ ID NO: 1.

TABLE 5

Amino Acid Analysis: DASTAPVDLK[1]

| | DASTAPVDLK[1] MW 1015.51 Da | | | | DASTAPVDL*K[1] MW 1022.52 Da | | | |
|---|---|---|---|---|---|---|---|---|
| Amino acid[a] | Amount (µg/mL) | nmol/mL | Exp. mol % | Theor. mol % | Amount (µg/mL) | nmol/mL | Exp. mol % | Theor. mol % |
| Ser | 5.47 | 62.9 | 8.9 | 10.0 | 3.44 | 39.5 | 9.0 | 10.0 |
| Asp | 16.50 | 143.4 | 20.4 | 20.0 | 10.47 | 91.0 | 20.6 | 20.0 |
| Thr | 6.86 | 67.9 | 9.7 | 10.0 | 4.30 | 42.6 | 9.7 | 10.0 |
| Ala | 9.73 | 136.9 | 19.5 | 20.0 | 6.08 | 85.6 | 19.4 | 20.0 |
| Pro | 6.92 | 71.3 | 10.1 | 10.0 | 4.34 | 44.7 | 10.2 | 10.0 |
| Lys | 9.22 | 72.0 | 10.2 | 10.0 | 5.66 | 44.2 | 10.0 | 10.0 |
| Val | 7.64 | 77.1 | 11.0 | 10.0 | 4.78 | 48.2 | 10.9 | 10.0 |
| Leu | 8.09 | 71.5 | 10.2 | 10.0 | 5.08 | 44.9 | 10.2 | 10.0 |
| Total | 70.45 | 702.9 | 100.0 | 100.0 | 44.16 | 440.6 | 100.0 | 100.0 |

[a]Ser, serine; Asp, aspartic acid; Thr, threonine; Ala, alanine; Pro, proline; Lys, lysine; Val, valine; Leu, leucine;
[1]DASTAPVDLK: residues 30-39 of SEQ ID NO: 3.

TABLE 6

Amino Acid Analysis: GQDPFLLK[1]

| Amino acid[a] | GQDPFLLK[1] MW 916.50 Da | | | | GQDPFLL*K[1] MW 923.5 Da | | | |
|---|---|---|---|---|---|---|---|---|
| | Amount (μg/mL) | nmol/mL | Exp. mol % | Theor. mol % | Amount (μg/mL) | nmol/mL | Exp. mol % | Theor. mol % |
| Gly | 4.34 | 76.2 | 12.6 | 12.5 | 2.70 | 47.3 | 12.4 | 12.5 |
| Asp | 8.75 | 76.0 | 12.6 | 12.5 | 5.53 | 48.0 | 12.6 | 12.5 |
| Glu | 9.84 | 76.2 | 12.6 | 12.5 | 6.11 | 47.3 | 12.4 | 12.5 |
| Pro | 7.33 | 75.4 | 12.5 | 12.5 | 4.62 | 47.6 | 12.5 | 12.5 |
| Lys | 9.58 | 74.7 | 12.3 | 12.5 | 6.15 | 48.0 | 12.6 | 12.5 |
| Leu | 17.01 | 150.3 | 24.8 | 25.0 | 10.79 | 95.3 | 25.0 | 25.0 |
| Phe | 11.22 | 76.2 | 12.6 | 12.5 | 7.04 | 47.8 | 12.5 | 12.5 |
| Total | 68.06 | 605.0 | 100.0 | 100.0 | 42.94 | 381.4 | 100.0 | 100.0 |

[a]Gly, glycine; Asp, aspartic acid; Glu, glutamic acid; Pro, proline; Lys, lysine; Leu, leucine; Phe, phenylalanine;
[1]GQDPFLLK: residues 83-90 of SEQ ID NO: 4.

TABLE 7

Amino Acid Analysis: AYDVTNFVK[1]

| Amino acid[a] | AYDVTNFVK[1] MW 1055.52 Da | | | | AYDVTNFV*K[1] MW 1061.52 Da | | | |
|---|---|---|---|---|---|---|---|---|
| | Amount (μg/mL) | nmol/mL | Exp. mol % | Theor. mol % | Amount (μg/mL) | nmol/mL | Exp. mol % | Theor. mol % |
| Asp | 15.38 | 133.6 | 22.3 | 22.2 | 15.02 | 130.5 | 22.3 | 22.2 |
| Thr | 6.32 | 62.6 | 10.5 | 11.1 | 6.18 | 61.2 | 10.4 | 11.1 |
| Ala | 4.48 | 63.0 | 10.5 | 11.1 | 4.36 | 61.4 | 10.5 | 11.1 |
| Lys | 8.41 | 65.6 | 11.0 | 11.1 | 8.24 | 64.3 | 11.0 | 11.1 |
| Tyr | 10.66 | 65.3 | 10.9 | 11.1 | 10.62 | 65.1 | 11.1 | 11.1 |
| Val | 13.92 | 140.4 | 23.5 | 22.2 | 13.59 | 137.1 | 23.4 | 22.2 |
| Phe | 9.97 | 67.7 | 11.3 | 11.1 | 9.77 | 66.4 | 11.3 | 11.1 |
| Total | 69.14 | 598.3 | 100.0 | 100 | 67.78 | 585.8 | 100.0 | 100 |

[a]Asp, aspartic acid; Thr, threonine; Ala, alanine; Lys, lysine; Tyr, tyrosine; Val, valine; Phe, phenylalanine;
[1]AYDVTNFVK: residues 37-45 of SEQ ID NO: 5.

TABLE 8

Amino Acid Analysis: SQPFGLK[1]

| Amino acid[a] | SQPFGLK[1] MW 775.42 Da | | | | SQPFGL*K[1] MW 782.42 Da | | | |
|---|---|---|---|---|---|---|---|---|
| | Amount (μg/mL) | nmol/mL | Exp. mol % | Theor. mol % | Amount (μg/mL) | nmol/mL | Exp. mol % | Theor. mol % |
| Ser | 8.1 | 93 | 13.0 | 14.3 | 10.4 | 119 | 13.1 | 14.3 |
| Gly | 6.0 | 106 | 14.7 | 14.3 | 7.6 | 134 | 14.7 | 14.3 |
| Glu | 13.4 | 104 | 14.4 | 14.3 | 16.9 | 131 | 14.4 | 14.3 |
| Pro | 10.1 | 104 | 14.5 | 14.3 | 12.8 | 132 | 14.5 | 14.3 |
| Lys | 13.2 | 103 | 14.3 | 14.3 | 16.6 | 129 | 14.2 | 14.3 |
| Leu | 11.7 | 104 | 14.4 | 14.3 | 14.8 | 131 | 14.4 | 14.3 |
| Phe | 15.4 | 105 | 14.6 | 14.3 | 19.7 | 134 | 14.7 | 14.3 |
| Total | 78.0 | 718 | 100.0 | 100.0 | 98.8 | 909 | 100.0 | 100.0 |

[a]Ser, serine; Glu, glutamic acid; Pro, proline; Lys, lysine; Leu, leucine; Phe, phenylalanine;
[1]SQPFGLK: residues 66-72 of SEQ ID NO: 6

TABLE 9

Amino Acid Analysis: LAPLVK[1]

| | LAPLVK[1] MW 639.43 Da | | | | LAPLV*K[1] MW 645.43 Da | | | |
|---|---|---|---|---|---|---|---|---|
| Amino acid[a] | Amount (μg/mL) | nmol/mL | Exp. mol % | Theor. mol % | Amount (μg/mL) | nmol/mL | Exp. mol % | Theor. mol % |
| Ala | 8.13 | 114.3 | 16.0 | 16.7 | 4.69 | 66.0 | 15.8 | 16.7 |
| Pro | 11.63 | 119.7 | 16.8 | 16.7 | 6.71 | 69.1 | 16.6 | 16.7 |
| Lys | 15.19 | 118.5 | 16.6 | 16.7 | 8.78 | 68.5 | 16.5 | 16.7 |
| Val | 12.37 | 124.7 | 17.5 | 16.7 | 7.45 | 75.2 | 18.1 | 16.7 |
| Leu | 26.76 | 236.5 | 33.1 | 33.3 | 15.58 | 137.7 | 33.1 | 33.3 |
| Total | 74.07 | 713.8 | 100.0 | 100.0 | 43.21 | 416.4 | 100.0 | 100.0 |

[a]Ala, alanine; Pro, proline; Lys, lysine; Val, valine; Leu, leucine;
[1]LAPLVK; residues 403-408 of SEQ ID NO: 7.

TABLE 10

Amino Acid Analysis of IS: WEGEPISK[1]

| | WEGEPISK[1] MW 944.46 Da | | | | WEGEPI*SK[1] MW 951.46 Da | | | |
|---|---|---|---|---|---|---|---|---|
| Amino acid[a] | Amount (μg/mL) | nmol/mL | Exp. mol % | Theor. mol % | Amount (μg/mL) | nmol/mL | Exp. mol % | Theor. mol % |
| Ser | 6.6 | 76 | 12.8 | 14.3 | 6.8 | 78 | 13.0 | 14.3 |
| Gly | 4.9 | 86 | 14.4 | 14.3 | 5.0 | 88 | 14.8 | 14.3 |
| Glu | 22.1 | 171 | 28.8 | 28.6 | 22.1 | 171 | 28.7 | 28.6 |
| Pro | 8.4 | 87 | 14.6 | 14.3 | 8.4 | 87 | 14.5 | 14.3 |
| Lys | 11.3 | 88 | 14.8 | 14.3 | 10.9 | 85 | 14.2 | 14.3 |
| Ile | 9.8 | 87 | 14.6 | 14.3 | 9.9 | 88 | 14.7 | 14.3 |
| Total | 63.2 | 595 | 100.0 | 100.0 | 63.1 | 596 | 100.0 | 100.0 |

[a]Ser, serine; Gly, glycine; Glu, glutamic acid; Pro, proline; Lys, lysine; Ile, isoleucine;
[1]WEGEPISK: residues 274-281 of SEQ ID NO: 7.

TABLE 11

Amino Acid Analysis of R Marker: TEPQTPQEWIDDLER[1]

| | TEPQTPQEWIDDLER[1] MW 1855.86 Da | | | | TEPQTPQEWIDDL*ER[1] MW 1862.86 Da | | | |
|---|---|---|---|---|---|---|---|---|
| Amino acid[a] | Amount (μg/mL) | nmol/mL | Exp. mol % | Theor. mol % | Amount (μg/mL) | nmol/mL | Exp. mol % | Theor. mol % |
| Arg | 6.12 | 39.2 | 7.3 | 7.1 | 4.90 | 31.4 | 7.5 | 7.1 |
| Asp | 9.43 | 82.0 | 15.3 | 14.3 | 6.98 | 60.6 | 14.5 | 14.3 |
| Glu | 25.1 | 194.4 | 36.4 | 35.7 | 19.35 | 149.9 | 35.8 | 35.7 |
| Thr | 7.12 | 70.4 | 13.2 | 14.3 | 5.75 | 56.9 | 13.6 | 14.3 |
| Pro | 7.15 | 73.7 | 13.8 | 14.3 | 5.74 | 59.1 | 14.1 | 14.3 |
| Ile | 4.16 | 36.8 | 6.9 | 7.1 | 3.32 | 29.4 | 7.0 | 7.1 |
| Leu | 4.25 | 37.6 | 7.0 | 7.1 | 3.50 | 31.0 | 7.4 | 7.1 |
| Total | 63.35 | 534.0 | 100.0 | 100.0 | 49.55 | 418.3 | 100.0 | 100.0 |

[a]Arg, arginine; Asp, aspartic acid; Glu, glutamic acid; Thr, threonine; Pro, proline; Ile, isoleucine; Leu, leucine;
[1]TEPQTPQEWIDDLER: SEQ ID NO: 8.
An alternative peptide for use as a proxy of marker, R, expression in N. benthamiana is SVVAVIGLPNDPSVR (SEQ ID NO: 13), MW1521.85 (light) and SVVAVIGLPNDPSVR* (SEQ ID NO: 13), MW 1531.85 (heavy).

Figure 12A:
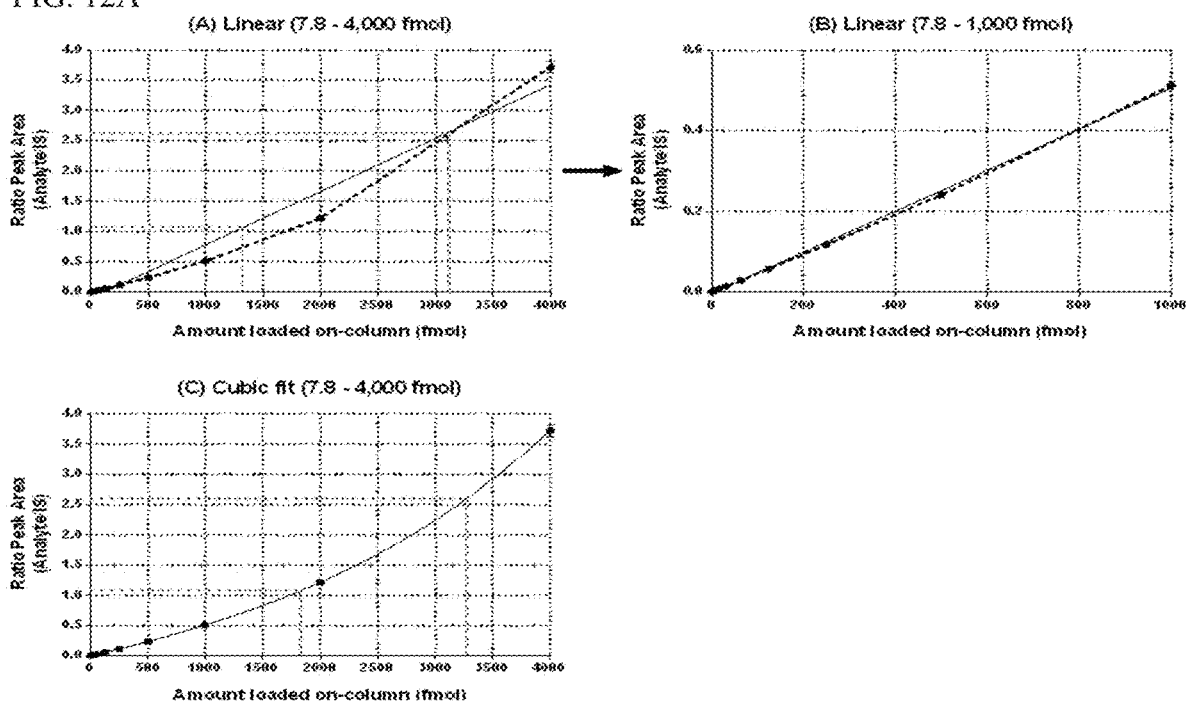
FIG. 12A presents graphs that provide justification for use of cubic (3rd order polynomial) fit for interpolation of peptide concentration. The dashed black line is a point-to-point graph through the plotted standards. The data for the ratio of the MRM peak area (analyte/IS) (see Table 13) was noted to deviate from a linear relationship above 1,000 fmol on-column, R2=0.9664 (A). Plotting a reduced peptide range improved the goodness of fit, R2=0.9984 (B). The Δ4D peptide LAPLVK was observed with an MS response requiring an extended concentration range (up to 4,000 fmol). The cubic fit provided a better interpolation with a goodness of fit of R2=0.9993 (C). The dashed gray lines indicate the peptide amount that Would be determined using the two models at two examples of experimentally determined MS responses.

As depicted in FIG. 12A, a linear regression model was unsuitable for quantitation of Δ4D peptide LAPLVK. Examining two experimentally determined MS responses it was noted that the interpolated results differed from the graphical interpretation. Using the linear regression model (FIG. 3A), the segregant 14E-0368-04-03 mature seed with a peak area ratio of 1.083 would yield an amount of 1,345 fmol and the NS-B50027-4 seed with a peak area ratio of 2.642 would yield 3,115 fmol. Comparing this to the cubic regression model which would yield amounts of 1,836 and 3,307, fmol, it was apparent that the segregant 14E-0368-04-03 seed amount was underestimated (by 270 and 6% respectively). The analytical parameters for quantitation of canola peptides wherein limit of detection (LOD), lower limit of quantification (LLOQ) and upper limit of quantification (ULOQ) are given in femtomoles for the non-linear regression model with the adjusted ULOQ, the standard deviation of the residuals (Sy.x), and the sum-of-the-squares (SS) are listed in Table A:

TABLE A

Goodness of fit for quantitation of canola peptides (femtomoles)

| Protein | Peptide Sequence | LOD | LLOQ | ULOQ | Sy.x | SS | R² |
|---|---|---|---|---|---|---|---|
| Lack1-Δ12D | NINNC[CAM]GVGAAEK | 15.62 | 31.25 | 4,000 | 0.02143 | 0.01378 | 0.9996 |
| Picpa-ω3D | DILDAIPK | 7.80 | 15.62 | 4,000 | 0.02249 | 0.17710 | 0.9997 |
| Micpu-Δ6D | ALPSRPAEIK | 7.80 | 15.62 | 4,000 | 0.08970 | 0.27360 | 0.9950 |
| Pyrco-Δ6E | GQDPFLLK | 7.80 | 15.62 | 4,000 | 0.02772 | 0.02767 | 0.9995 |
| Pavsa-Δ5D | AYDVTNFVK | 7.80 | 15.62 | 4,000 | 0.02695 | 0.02615 | 0.9988 |
| Pyrco-Δ5E | SQPFGLK | 7.80 | 15.62 | 4,000 | 0.02213 | 0.01764 | 0.9997 |
| Pavsa-Δ4D | LAPLVK | 7.80 | 7.80 | 4,000 | 0.03003 | 0.03608 | 0.9993 |
| PAT | SVVAVIGLPNDPSVR | 7.80 | 31.25 | 4,000 | 0.00972 | 0.00302 | 0.9998 |

LOD, limit of detection;
LLOQ, lower limit of quantification;
ULOQ, upper limit of quantification;
Sy.x, standard deviation of residuals, sum of the squares (SS);
$R^2$, non-linear regression, polynomial-cubic.
Units in femtomoles loaded on-column.

Example 2. Sample Preparation

All seven biosynthesis pathway enzymes expressed in the ω3LCPUFA producing transgenic canola were targeted for quantification in various tissues and seed of transgenic canola throughout the growing season in separate planting locations.

Collection of Canola Samples—Wild-type (WT) and transgenic canola were planted at field trial sites. The tissues that were sampled for both WT and transgenic plants at each site are listed in Table B. The sampling times represent specific growth stages of canola allowing for various tissue types, including leaves, roots, pods, and reproductive tissues. See Lancashire et al., 119 Annals Appl. Biol. 561 (1991). The plant tissues harvested were maintained in dry ice to keep frozen, and transferred into −80° C. freezer until further processing.

TABLE B

Canola tissues sampled at different stages

| Growth stage | Timing | Tissue sampled | Replicates |
|---|---|---|---|
| TG15 | 5 True leaves | 3 Whole plants | 3 |
| TG35 | 3 Visibly extended internodes | 1 Whole plant | 3 |
| TG65 | 50% Full flowering | All flowers from 1 plant | 3 |
| | | All roots from 1 plant | 3 |
| | | All leftover from 1 plant | 3 |
| TG79 | Developing seed | All pods form 1 plant | 3 |
| TG90 | Senescence | All grain from 1 plant | 3 |

Total Protein Extraction from Canola—The collected samples (previously stored at −80° C.) were ground with mortar and pestle into fine powder with liquid nitrogen; all samples were maintained frozen on dry ice during the process. To avoid cross contamination, WT samples were processed first, then transgenic samples, in the order: TG15, TG35, TG65 root, TG other tissues, TG flower, TG79, and lastly TG90. Total protein was extracted from multiple aliquots of 100 mg in 2 mL plastic tubes in order to obtain more than 1 mg of total protein. Each tube was filled with 1 mL of 10% TCA in acetone and vortexed, then sonicated at frequency of 25% amplitude for 20 sec using a digital probe sonicator (Branson, St. Louis, Mo., US). Samples were centrifuged at 16,000×g for 3 min at 4° C. The supernatant was removed by careful decanting. The pellet was resuspended in 1 mL of 0.1 M ammonium acetate ($NH_4CH_3CO_2$) in 80% MeOH, mixed by vortexing, and centrifuged at 16,000×g for 3 min at 4° C. The supernatant was discarded by careful decanting. The pellet was then resuspended in 1 mL 80% acetone, vortexed until the pellet was fully dispersed, and centrifuged at 16,000×g for 3 min at 4° C. The supernatant was discarded, and the pellet air dried to remove the residual acetone.

The air-dried pellet was re-suspended in 0.6 mL of UltraPure buffer-saturated phenol (Invitrogen, Carlsbad, Calif., US) and 0.6 mL freshly prepared SDS buffer (30% sucrose, 2% SDS, 0.1 M Tris-HC pH 8.8, 0.1 M DTT), mixed thoroughly, and incubated for 5 Min at room temp. The samples were then centrifuged at 16,000×g for 5 min at room temp. The upper phenol phase was transferred to a new 2 mL tube, and 1 mL of 0.1 M $NH_4CH_3CO_2$ in 80% MeOH was added. The proteins were precipitated at −20° C. overnight. Samples were centrifuged at 16,000×g for 5 min at 4° C. The supernatant was carefully discarded, and the pellet was washed with 100% MeOH, then washed with 80% acetone. The proteins were pelleted by centrifuging at 16,000×g for 5 min at 4° C. The final protein pellet was left to air dry.

Canola Protein Digestion—The proteins extracted from different plant tissue or seed were dissolved in UA buffer (8 M urea, 0.1 M Tris-HCl, pH 8.5). Protein estimations were performed using a microtiter Bradford protein assay (Bio-Rad Labs., Hercules, Calif., US), following the reagent manufacturer instructions (version: Lit 33 Rev C). Samples were diluted in water over three dilutions, in duplicate, and measurements were made at 595 nm using a SpectraMax Plus. Bovine serum albumin (BSA) standard was used in the linear range 0.05 mg/mL to ~0.5 mg/mL. The BSA standard concentration was determined by high sensitivity AAA at a commercial laboratory (Australian Proteomics Analysis Facility, Sydney, AU). Blank-corrected standard curves were run in duplicate. Linear regression was used to fit the standard curve.

Protein Samples—Protein samples were stored at −80° C. prior to processing. Protein was subjected to FASP, wherein the protein extract (250 μg) in UA buffer was applied to a 10 kDa molecular weight cut-off (MWCO) filter (Millipore, Sydney, AU) and diluted to 200 μL with UA buffer before centrifugation (20,800×g, 15 min). The protein on the filter was washed with two 200 μL volumes of UA buffer with centrifugation (20,800×g, 15 min). To reduce the protein on the filter, DTT (100 mM, 100 μL) was added and the solution incubated at room temp for 50 min with shaking. The filter was washed with two 200 µL volumes of UA buffer with centrifugation (20,800×g, 15 min).

To alkylate the cysteine residues, iodoacetamide (IAM) (50 mM, 100 µL) was applied to the protein on the filter with incubation for 20 min at room temp in the dark. The filter was washed with two 200 µL volumes of UA buffer with centrifugation (20,800×g, 15 min). The buffer was exchanged using 50 mM (NH$_4$)HCO$_3$ (pH 8.0) by two consecutive wash/centrifugation cycles. Then, 25 µg sequencing grade porcine trypsin (Promega Corp., Alexandria, AU) (0.125 µg trypsin/µL in 200 µL of 50 mM (NH$_4$)HCO$_3$, 1 mM CaCl$_2$)) was added to the protein on the 10 kDa MWCO filters and incubated for 16 hr at 37° C. in a wet chamber. The filters were then transferred to fresh centrifuge tubes and the filtrate (digested peptides) collected following centrifugation (20,800×g, 10 min). The filters were washed with 200 µL of 100 mM (NH$_4$)HCO$_3$ and the filtrates combined and lyophilized. The resultant peptides were resuspended in 62.5 µL of 1% formic acid containing 0.04 pmol/µL of the IS peptide WEGEPI*SK (aa 274-281 of SEQ ID NO: 7) and 25 µL (equivalent to ~100 µg of total protein and 1 pmol of IS) was analyzed by LC-MS/MS.

Sample Preparation for LC-MS Method Development—Protein extracts from a variety of sources, including total protein extracts from canola, recombinant proteins expressed in either yeast, bacterial or baculovirus expression systems, were tested. Proteins were either provided in solution or as excised gel slices. The solutions were subjected to FA SP as described previously. See Colgrave et al., 2014; Colgrave et al., 147 J. Proteom. 169 (2016). Gel bands were digested as described previously. Byrne et al., 2012.

Example 3. LC-MS Analysis

Preliminary LC-MS Analysis—Proteolytically digested proteins were analyzed with chromatographic separation (2%/min linear gradient of 2%-40% acetonitrile) using a nanoflow HPLC system (Prominence Nano, Shimadzu Corp., Rydalmere, Australia) directly coupled to a TripleTOF 5600+MS/MS system (AB Sciex LLC, Redwood City, Calif., US). ProteinPilot Software v4.0 (AB Sciex) with the Paragon Algorithm (Shilov et al., 2007) was used for protein identification. Tandem mass spectrometry data was searched against an in silico tryptic digest database comprising the transgenic proteins. The search parameters were defined as iodoacetamide modified for cysteine alkylation and trypsin as the digestion enzyme.

LC-MRM-MS Quantification—A series of standards (n=4 replicates) comprising a double blank (no analyte, no IS), a blank (IS only) and seventeen standards containing a known, but varied amount (0.08 to 5,000 fmol) of each peptide and 1 pmol of the IS peptide (WEGEPI*SK, aa 274-281 of SEQ ID NO: 7) were analyzed by LC-MRM-MS. The data were acquired using the Analyst 1.6.3 software on a QTRAP 6500+ LC-MS/MS system (AB Sciex). The data were imported into MultiQuant v3.0 (AB Sciex) and the peak areas for each of five monitored MRM transitions were integrated. The peak area of each of the top three MRM transitions (quantifiers) was summed and the remaining two MRM transitions were used as qualifiers (allowing confirmation of peptide identification by assessment of retention time (RT) and the order of intensity of the MRM transitions). Using preliminary data, the best-performing peptide per protein was selected as the proxy for each enzyme based on criteria such as chromatographic performance (good peak shape), intensity in MS, free from interference (as assessed in sample matrix). Heavy peptides were spiked into pooled (n=6) WT or transgenic canola samples of each tissue and these served as reference standards for determining the correct retention time (RT, min) and MRM transition order. The heavy peptide WEGEPI*SK (aa 274-28 of SEQ ID NO: 7) derived from Pavsa-Δ4D was selected as an IS based on its high MS response, reproducible detection, and excellent chromatographic performance (elution at 3.2 min with ~1.6 see peak width at half-maximum).

LC-MRM-MS Quantification of Canola Proteins—The extracted and digested protein samples representing five growth stages (seven samples) from two growing sites, comprising both WT and transgenic canola (n=3 replicates, total 84 samples) containing the spiked IS were analyzed by LC-MRM-MS alongside aqueous peptide standards. An aliquot (25 µL) of aqueous standard or canola peptide extract were chromatographically separated on a Nexera UHPLC (Shimadzu) and analyzed on a QTRAP 6500+ mass spectrometer. See Colgrave et al., 2014. Quantification was achieved using scheduled MRM scanning experiments using a 120 sec-detection window for each MRM transition and a 0.3 sec cycle time. Peaks were integrated using MultiQuant v3.0 (AB Sciex) in which all three transitions were required to co-elute at the same retention time (RT, min) with a signal-to-noise (S/N)>3 for detection and a S/N>5 for quantification. The graphs showing the calibration curves for the synthetic peptides were generated in GraphPad Prism v6 (GraphPad Software, Inc., San Diego, Calif., US). The sum of the peak area for the top three MRM interference-free transitions for each targeted light peptide was compared to sum of MRM peak area of the IS peptide to generate a MRM response ratio. The amount of each target peptide (as fmol per 100 µg total protein) was determined by interpolation from the appropriate calibration curve. The amount of protein detected in these samples was then calculated based on the protein molecular mass, by conversion to a ng equivalent per mg total protein.

Development of Quantitative LC-MRM-MS Method—Using the data collected from the tryptic digests of the enzymes in the transgenic ω3LCPUFA biosynthetic pathway, the peptide mass, and hence precursor mass-to-charge (m/z) ratio, was determined. Subsequently, five fragment ions were selected that were representative of the target peptide. Together, the Q1 m/z and Q3 m/z are termed the "MRM transition," and the MRM transitions are presented in Table 12A for the light peptides, and Table 12B for the heavy peptides, heavy peptides were used as reference standards for qualitative assessment. Additional transitions information is in Table 13.

TABLE 12A

| MRM transitions of light peptides (analytes) | | | | | | | |
|---|---|---|---|---|---|---|---|
| Protein | Peptide | RT | Q1 m/z | Z | Q3 m/z | Fragment | CE |
| Δ12D | GSSSNTEQEVPK (aa 16-26 of SEQ ID NO: 2) | 1.62 | 631.797 | 2+ | 729.380 | y6+ | 32.0 |
| | | | | | 944.468 | y8+ | 28.0 |
| | | | | | 1019.428 | b10+ | 28.0 |

TABLE 12A-continued

MRM transitions of light peptides (analytes)

| Protein | Peptide | RT | Q1 m/z | Z | Q3 m/z | Fragment | CE |
|---|---|---|---|---|---|---|---|
| ω3D | IPFYHAR (aa 351 358 of SEQ ID NO: 1) | 3.56 | 452.245 | 2+ | 546.278<br>693.347<br>395.703 | y4+<br>y5+<br>y6++ | 27.2<br>27.2<br>23.2 |
| Δ6D | DASTAPVDLK (aa 30-39 of SEQ ID NO: 3) | 3.63 | 508.767 | 2+ | 571.345<br>642.382<br>743.430 | y5+<br>y6+<br>y7+ | 23.9<br>23.9<br>21.9 |
| Δ6E | GQDPFLLK (aa 83-90 of SEQ ID NO: 4) | 5.07 | 459.258 | 2+ | 260.197<br>617.402<br>732.429 | y2+<br>y5+<br>y6+ | 28.5<br>21.5<br>19.5 |
| Δ5D | AYDVTNFVK (aa 37-45 of SEQ ID NO: 5) | 4.85 | 528.772 | 2+ | 608.34<br>707.409<br>822.436 | y5+<br>y6+<br>y7+ | 22.9<br>22.9<br>22.9 |
| Δ5E | SQPFGLK (aa 66-72 of SEQ ID NO: 6) | 3.84 | 388.719 | 2+ | 216.098<br>317.218<br>561.34 | b2+<br>y3+<br>y5+ | 18.9<br>26.9<br>18.9 |
| Δ4D | LAPLVK (aa 403-408 of SEQ ID NO: 7) | 3.72 | 320.723 | 2+ | 185.128<br>246.181<br>456.318 | b2+<br>y2+<br>y4+ | 14.0<br>22.0<br>14.0 |

RT, retention time (min);
Q1 m/z, precursor ion mass-to-charge ratio;
z, charge state;
Q3 m/z, fragment ion m/z;
CE, collision energy in V.
Collision energy settings were also optimized for all targeted transitions by analyzing 2 μL of each peptide chromatographically separated on a Nexera UHPLC and analyzed on a QTRAP 6500+ mass spectrometer. See Colgrave et al., 2014.

TABLE 12B

MRM transitions of heavy peptides (reference standards) including IS peptide

| Protein | Peptide | RT | Q1 m/z | Z | Q3 m/z | Fragment | CE |
|---|---|---|---|---|---|---|---|
| Δ12D | GSSSNTEQEV*PK (aa 16-26 of SEQ ID NO: 2) | 1.62 | 634.79 | 2+ | 735.380<br>950.470<br>1025.420 | y6+<br>y8+<br>b10+ | 32.0<br>28.0<br>28.0 |
| ω3D | IPFYHA*R (aa 351 358 of SEQ ID NO: 1) | 3.56 | 454.245 | 2+ | 550.278<br>697.346<br>397.703 | y4+<br>y5+<br>y6++ | 27.3<br>27.3<br>23.3 |
| Δ6D | DASTAPVDL*K (aa 30-39 of SEQ ID NO: 3) | 3.63 | 512.266 | 2+ | 578.345<br>649.382<br>750.429 | y5+<br>y6+<br>y7+ | 23.9<br>23.9<br>21.9 |
| Δ6E | GQDPFLL*K (aa 83-90 of SEQ ID NO: 4) | 5.07 | 462.758 | 2+ | 267.196<br>624.402<br>739.429 | y2+<br>y5+<br>y6+ | 27.7<br>21.7<br>19.7 |
| Δ5D | AYDVTNFV*K (aa 37-45 of SEQ ID NO: 5) | 4.85 | 531.771 | 2+ | 614.340<br>713.408<br>828.435 | y5+<br>y6+<br>y7+ | 22.9<br>22.9<br>22.9 |
| ΔSE | SQPFGL*K (aa 66-72 of SEQ ID NO: 6) | 3.84 | 392.218 | 2+ | 216.098<br>324.218<br>568.339 | b2+<br>y3+<br>y5+ | 24.9<br>26.9<br>18.9 |
| Δ4D | LAPLV*K (aa 403-408 of SEQ ID NO: 7) | 3.72 | 323.723 | 2+ | 185.128<br>252.181<br>462.318 | b2+<br>y2+<br>y4+ | 14.0<br>22.0<br>14.0 |
| IS | WEGEPI*SK (aa 274-281 of SEQ ID NO: 7) | 3.26 | 476.737 | 2+ | 451.281<br>637.346<br>766.388 | y4+<br>y6+<br>y7+ | 28.0<br>24.0<br>26.0 |

RT, retention time (min);
Q1 m/z, precursor ion mass-to-charge ratio (m/z);
z, charge state;
Q3 m/z, fragment ion m/z;
CE, collision energy in V.
Collision energy settings were also optimized for all targeted transitions by analyzing 2 μL of each peptide were chromatographically separated by UHPLC and analyzed on a 6500 QTRAP mass spectrometer.

TABLE 13

| Q1 m/z | Q3 m/z | Peptide Name | CE |
|---|---|---|---|
| \multicolumn{4}{l}{Additional Transitions} |

| Q1 m/z | Q3 m/z | Peptide Name | CE |
|---|---|---|---|
| 476.737 | 451.281 | IS.XR2-d4D.WEGEPI*SK.+ 2y4 | 28 |
| 476.737 | 580.324 | IS.XR2-d4D.WEGEPI*SK.+ 2y5 | 26 |
| 476.737 | 637.346 | IS.XR2-d4D.WEGEPI*SK.+ 2y6 | 24 |
| 476.737 | 766.388 | IS.XR2-d4D.WEGEPI*SK.+ 2y7 | 26 |
| 476.737 | 502.193 | IS.XR2-d4D.WEGEPI*SK.+ 2b4 | 20 |
| 452.245 | 383.215 | XR1-w3D.IPFYHAR. + 2y3 | 27.2 |
| 452.245 | 546.278 | XR1-w3D.IPFYHAR. + 2y4 | 27.2 |
| 452.245 | 693.347 | XR1-w3D.IPFYHAR. + 2y5 | 27.2 |
| 452.245 | 790.399 | XR1-w3D.IPFYHAR. +2y6 | 23.2 |
| 452.245 | 395.703 | XR1-w3D.IPFYHAR. + 2y6++ | 23.2 |
| 442.76 | 244.17 | XR1-w3D.DILDAIPK. + 2y2 | 20.7 |
| 442.76 | 428.29 | XR1-w3D.DILDAIPK. + 2y4 | 20.7 |
| 442.76 | 528.27 | XR1-w3D.DILDAIPK. + 2b5 | 20.7 |
| 442.76 | 543.31 | XR1-w3D.DILDAIPK. + 2y5 | 20.7 |
| 442.76 | 656.4 | XR1-w3D.DILDAIPK . + 2y6 | 20.7 |
| 320.723 | 185.128 | XR2-d4D.LAPLVK. + 2b2 | 14 |
| 320.723 | 246.181 | XR2-d4D.LAPLVK. + 2y2 | 22 |
| 320.723 | 359.265 | XR2-d4D.LAPLVK. + 2y3 | 22 |
| 320.723 | 456.318 | XR2-d4D.LAPLVK. + 2y4 | 14 |
| 320.723 | 527.355 | XR2-d4D.LAPLVK. + 2y5 | 14 |
| 338.175 | 272.172 | XR2-d4D.VHHGFYPR. + 3y2 | 18.2 |
| 338.175 | 582.304 | XR2-d4D.VHHGFYPR. + 3y4 | 20.2 |
| 338.175 | 639.325 | XR2-d4D.VHHGFYPR. + 3y5 | 18.2 |
| 338.175 | 578.283 | XR2-d4D.VHHGFYPR. + 3b5 | 16.2 |
| 506.759 | 776.384 | XR2-d4D.VHHGFYPR. + 2y6 | 25.8 |
| 528.772 | 235.108 | XR3-d5D.AYDVTNFVK. + 2b2 | 22.9 |
| 528.772 | 350.135 | XR3-d5D.AYDVTNFVK. + 2b3 | 22.9 |
| 528.772 | 608.34 | XR3-d5D.AYDVTNFVK. + 2y5 | 22.9 |
| 528.772 | 707.409 | XR3-d5D.AYDVTNFVK. + 2y6 | 22.9 |
| 528.772 | 822.436 | XR3-d5D.AYDVTNFVK. + 2y7 | 22.9 |
| 401.227 | 243.13 | XR3-d5D.ELVIGDR. + 2b2 | 18.7 |
| 401.227 | 342.2 | XR3-d5D.ELVIGDR. + 2b3 | 18.7 |
| 401.227 | 460.251 | XR3-d5D.ELVIGDR. + 2y4 | 18.7 |
| 401.227 | 559.32 | XR3-d5D.ELVIGDR. + 2y5 | 18.7 |
| 401.227 | 672.4 | XR3-d5D.ELVIGDR. + 2y6 | 18.7 |
| 388.719 | 216.098 | XR4-d5E.SQPFGLK. + 2b2 | 18.9 |
| 388.719 | 260.197 | XR4-d5E.SQPFGLK. + 2y2 | 26.9 |
| 338.719 | 317.218 | XR4-d5E.SQPFGLK. + 2y3 | 26.9 |
| 388.719 | 464.287 | XR4-d5E.SQPFGLK. + 2y4 | 26.9 |
| 388.719 | 561.34 | XR4-d5E.SQPFGLK. + 2y5 | 18.9 |
| 631.797 | 729.38 | XRS-d12D.GSSSNTEQEVPK. + 2y6 | 32 |
| 631.797 | 830.425 | XR5-d12D.GSSSNTEQEVPK. + 2y7 | 30 |
| 631.797 | 944.468 | XR5-d12D.GSSSNTEQEVPK. + 2y8 | 28 |
| 631.797 | 1031.5 | XR5-d12D.GSSSNTEQEVPK. + 2y9 | 32 |
| 631.797 | 1019.428 | XR5-d12D.GSSSNTEQEVPK. + 2b10 | 28 |
| 623.796 | 475.251 | XR5-d12D.NINNC[CAM]GVGAAEK. + 2y5 | 29.6 |
| 623.796 | 631.341 | XR5-d12D.NINNC[CAM]GVGAAEK. + 2y7 | 29.6 |
| 623.796 | 791.372 | XR5-d12D.NINNC[CAM]GVGAAEK. + 2y8 | 29.6 |
| 623.796 | 905.415 | XRS-d12D.NINNC[CAM]GVGAAEK. + 2y9 | 29.6 |
| 623.796 | 1019.458 | XR5-d12D.NINNC[CAM]GVGAAEK. + 2y10 | 29.6 |
| 459.258 | 260.197 | XR6-d6E.GQDPFLLK. + 2y2 | 28.5 |
| 459.258 | 373.281 | XR6-d6E.GQDPFLLK. + 2y3 | 27.5 |
| 459.258 | 520.349 | XR6-d6E.GQDPFLLK. + 2y4 | 27.5 |
| 459.258 | 617.402 | XR6-d6E.GQDPFLLK. + 2y5 | 21.5 |
| 459.258 | 732.429 | XR6-d6E.GQDPFLLK. + 2y6 | 19.5 |
| 577.834 | 234.145 | XR6-d6E.VIWIFYVSK. + 2y2 | 33.3 |
| 577.834 | 496.277 | XR6-d6E.VIWIFYVSK. + 2y4 | 33.3 |
| 577.834 | 643.345 | XR6-d6E.VIWIFYVSK. + 2y5 | 29.3 |
| 577.834 | 756.429 | XR6-d6E.VIWIFYVSK. + 2y6 | 27.3 |
| 577.34 | 942.508 | XR6-d6E.VIWIFYVSK. + 2y7 | 25.3 |
| 361.217 | 400.735 | XR7-d6D.ALPSRPAEIK. + 3y7++ | 21.3 |
| 361.217 | 449.261 | XR7-d6D.ALPSRPAEIK. + 3y8++ | 15.3 |
| 361.217 | 557.329 | XR7-d6D.ALPSRPAEIK. + 3y5 | 21.3 |
| 541.322 | 822.447 | XR7-d6D.ALPSRPAEIK. + 2b8 | 29.5 |
| 541.322 | 897.515 | XR7-d6D.ALPSRPAEIK. + 2y8 | 29.5 |
| 508.767 | 474.292 | XR7-d6D.DASTAPVDLK. + 2y4 | 29.9 |
| 508.767 | 571.345 | XR7-d6D.DASTAPVDLK. + 2y5 | 23.9 |
| 508.767 | 642.382 | XR7-d6D.DASTAPVDLK. + 2y6 | 23.9 |
| 508.767 | 743.43 | XR7-d6D.DASTAPVDLK. + 2y7 | 21.9 |
| 508.767 | 901.499 | XR7-d6D.DASTAPVDLK. + 2y9 | 27.9 |
| 619.627 | 647.299 | XR8-PAT.TEPQTPQEWIDDLER. + 3y5 | 29.7 |
| 619.627 | 650.812 | XR8-PAT.TEPQTPQEWIDDLER. + 3y10++ | 27.7 |
| 619.627 | 813.892 | XR8-PAT.TEPQTPQEWIDDLER. + 3y12++ | 25.7 |
| 928.937 | 946.463 | XR8-PAT.TEPQTPQEWIDDLER. + 2y7 | 50.5 |
| 928.937 | 1300.617 | XR8-PAT.TEPQTPQEWIDDLER. + 2y10 | 48.5 |
| 761.933 | 458.272 | XR8-PAT.SVVAVIGLPNDPSVR. + 2y4 | 36.3 |

TABLE 13-continued

Additional Transitions

| Q1 m/z | Q3 m/z | Peptide Name | CE |
|---|---|---|---|
| 761.933 | 784.395 | XR8-PAT.SVVAVIGLPNDPSVR. + 2y7 | 36.3 |
| 761.933 | 897.479 | XR8-PAT.SVVAVIGLPNDPSVR. + 2y8 | 36.3 |
| 761.933 | 954.5 | XR8-PAT.SVVAVIGLPNDPSVR. + 2y9 | 36.3 |
| 761.933 | 1067.584 | XR8-PAT.SVVAVIGLPNDPSVR. + 2y10 | 36.3 |

Figure 12B:
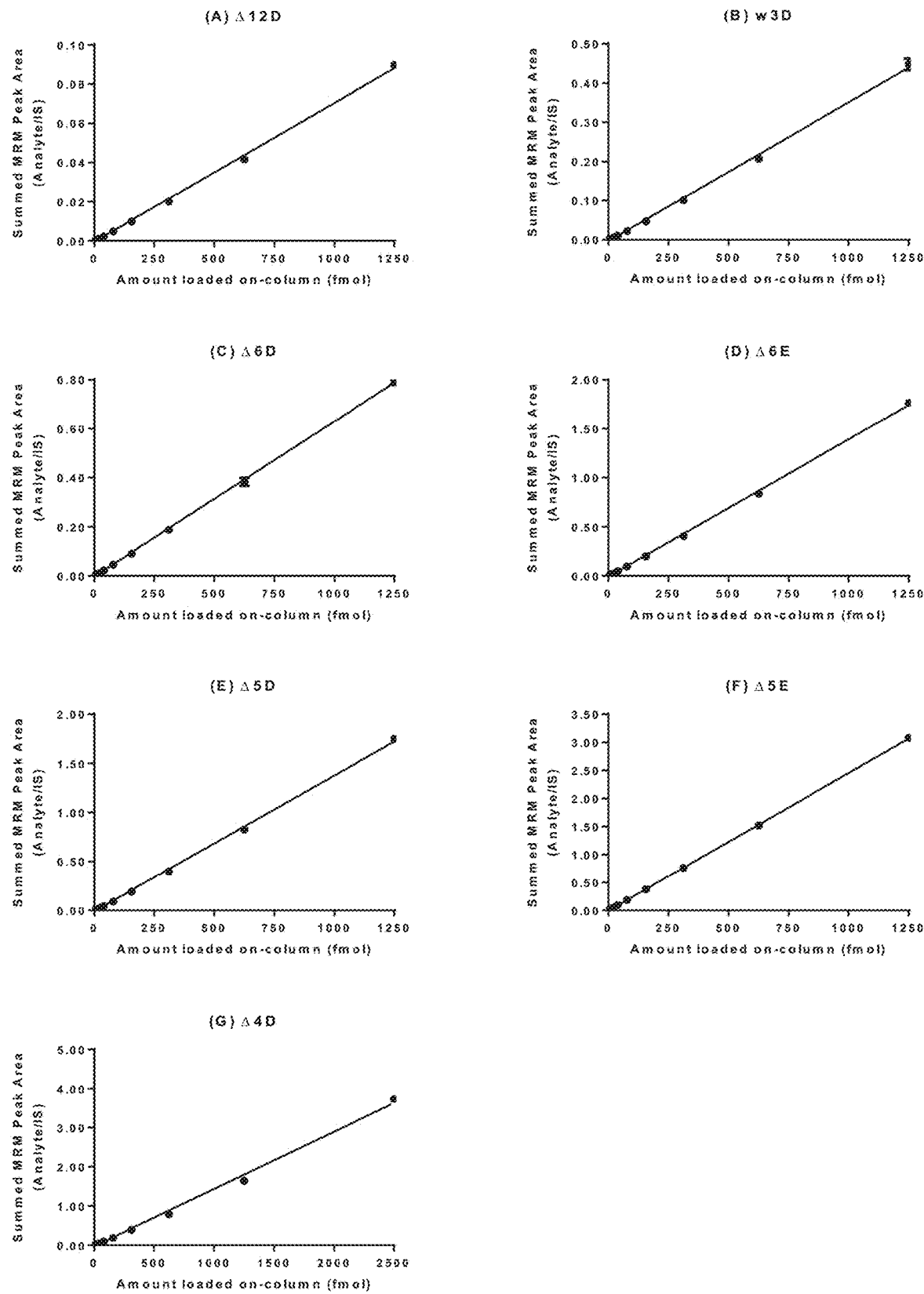
FIG. 12B shows calibration curves for quantifier peptides for each enzyme in an example transgenic pathway that biosynthesizes DHA in transgenic plants. Panels: (A) Lack1-Δ12D; (B) Picpaω3D; (C) Micpu-Δ6D; (D) Pyrco-Δ6E; (E) Pavsa-Δ5D; (F) Pyrco-Δ5-E; and (G) Pavsa-Δ4D.
Figure 13:
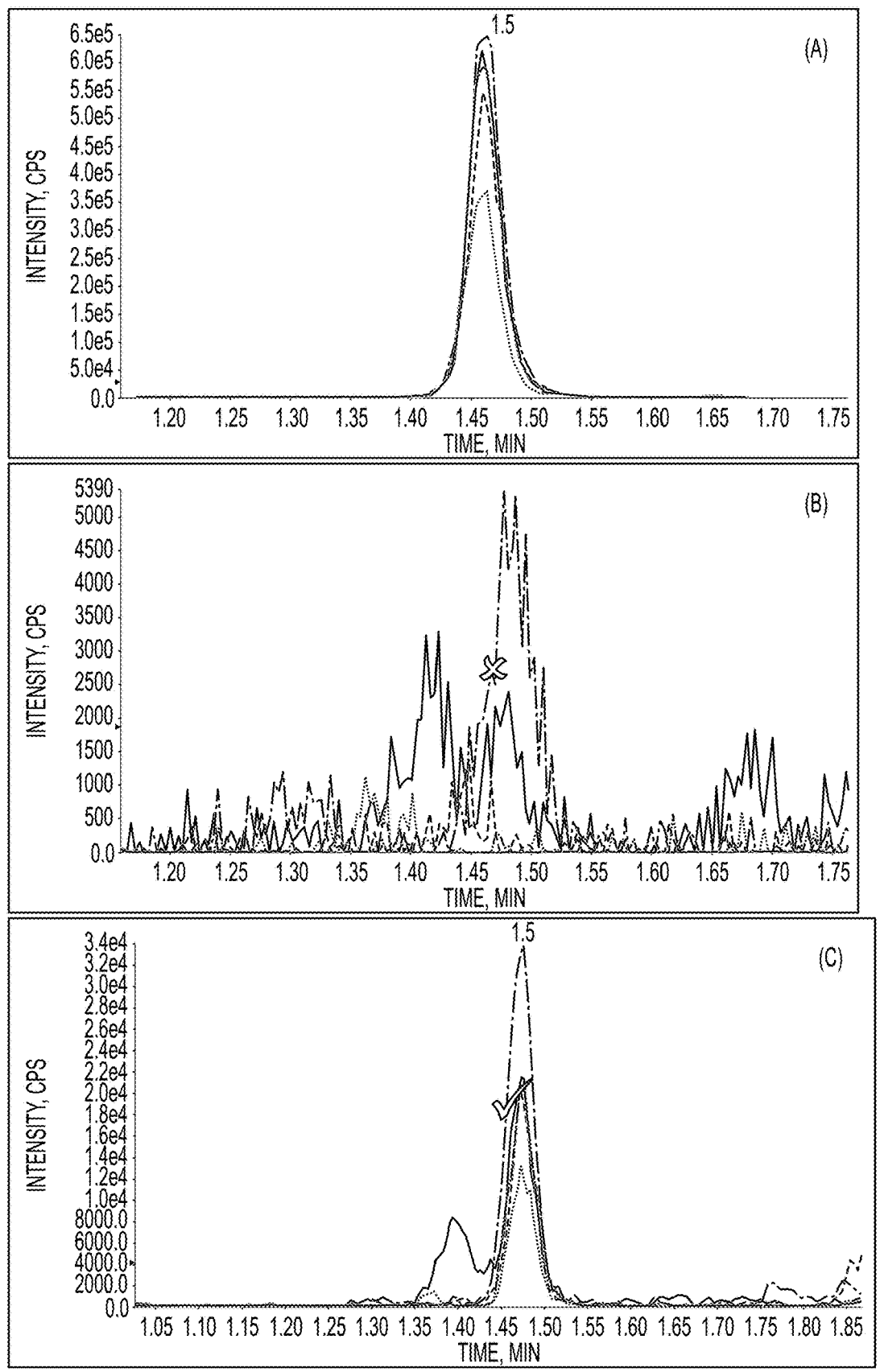
FIG. 13 shows detection of Lack1-Δ12D peptide GSSSNTEQEVPK (aa 16-26 of SEQ ID NO: 2) in transgenic canola. Panels: (A) Heavy labeled reference standard GSSSNTEQEVP*K (aa 16-26 of SEQ ID NO: 2) spiked into developing embryo protein background from wild-type ("WT") canola (2 pmol on-column); (B) developing embryo protein from WT canola; (C) developing embryo protein from transgenic canola; (D) heavy labeled reference standard GSSSNTEQEVP*K (aa 16-26 of SEQ ID NO: 2) spiked into mature seed protein background from WT canola (2 pmol on-column); (E) mature seed protein from WT canola; (F) mature seed protein from transgenic canola.
Figure 13:
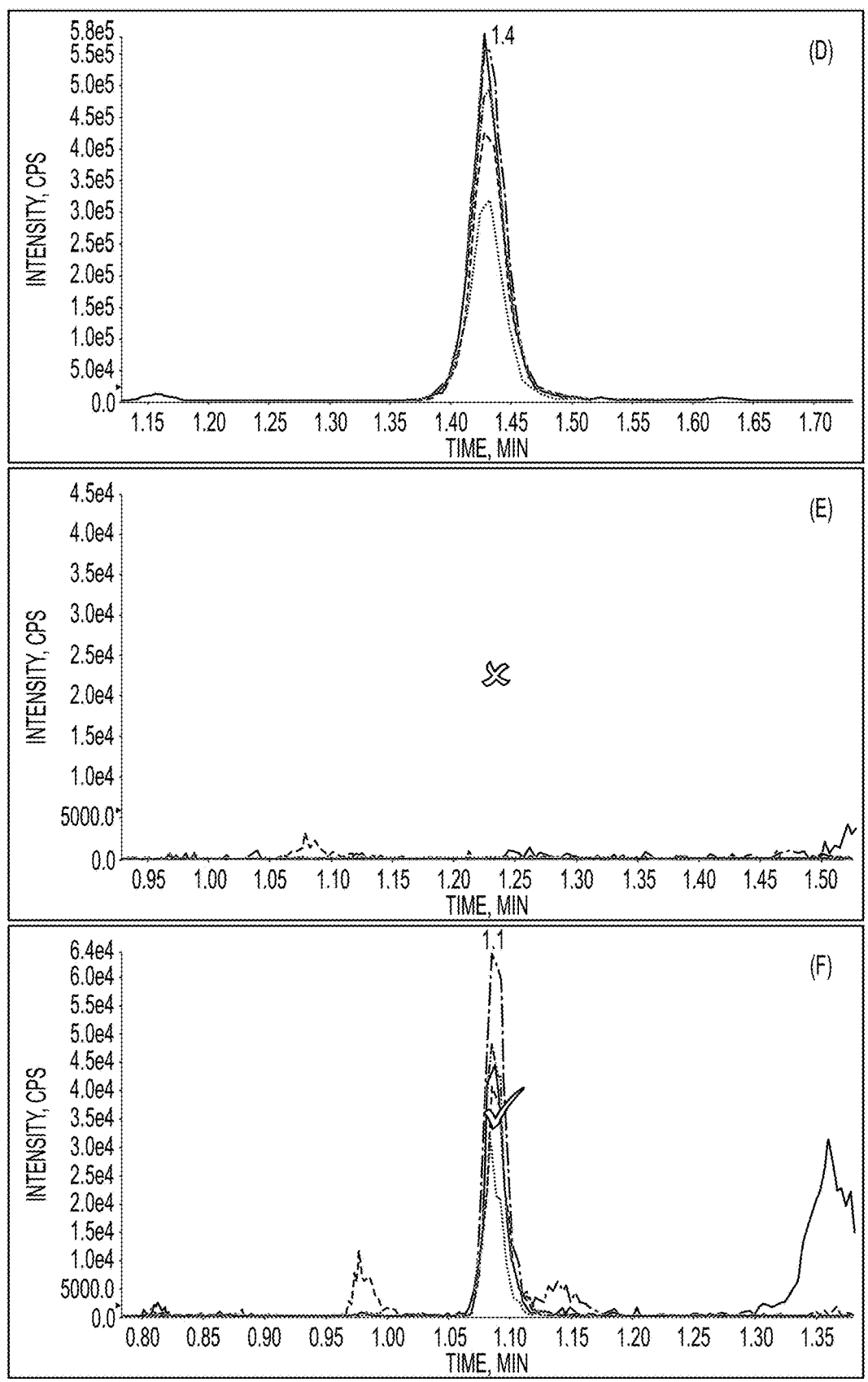
Figure 14:
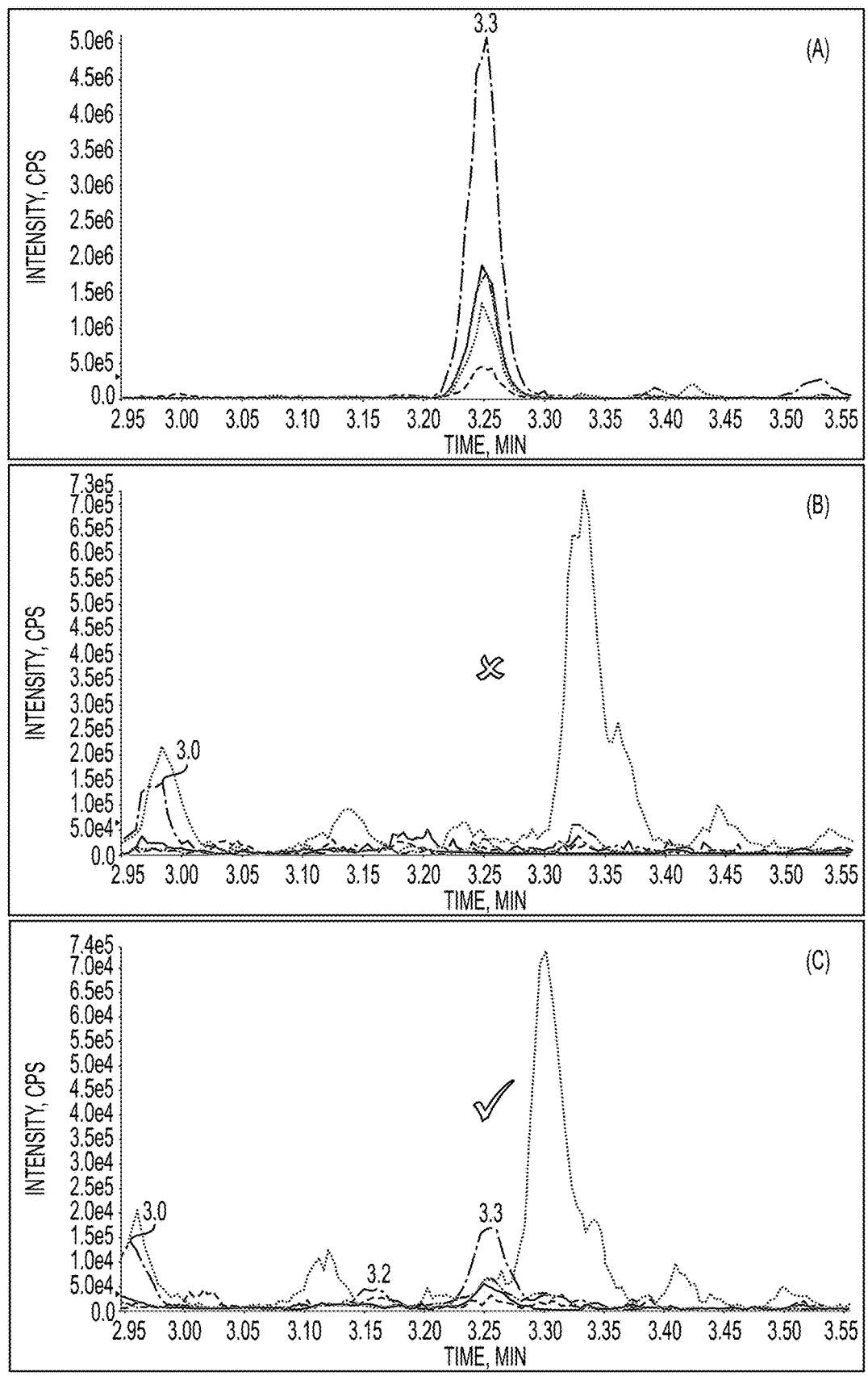
FIG. 14 shows detection of Picpa-ω3D peptide IPFYHAR (aa 351-358 of SEQ ID NO: 1) in transgenic canola. Panels: (A) Heavy labeled reference standard IPFYIHA*R spiked into developing embryo protein background from WT canola (2 pmol on-column); (B) developing embryo protein from WT canola; (C) developing embryo protein from DHA canola; (D)) heavy labelled reference standard IPFYHA*R (aa 351-358 of SEQ ID NO: 1) spiked into mature seed protein background from WT canola (2 pmol on-column); (E) mature seed protein from WT canola; (F) mature seed from transgenic canola.
Figure 14:
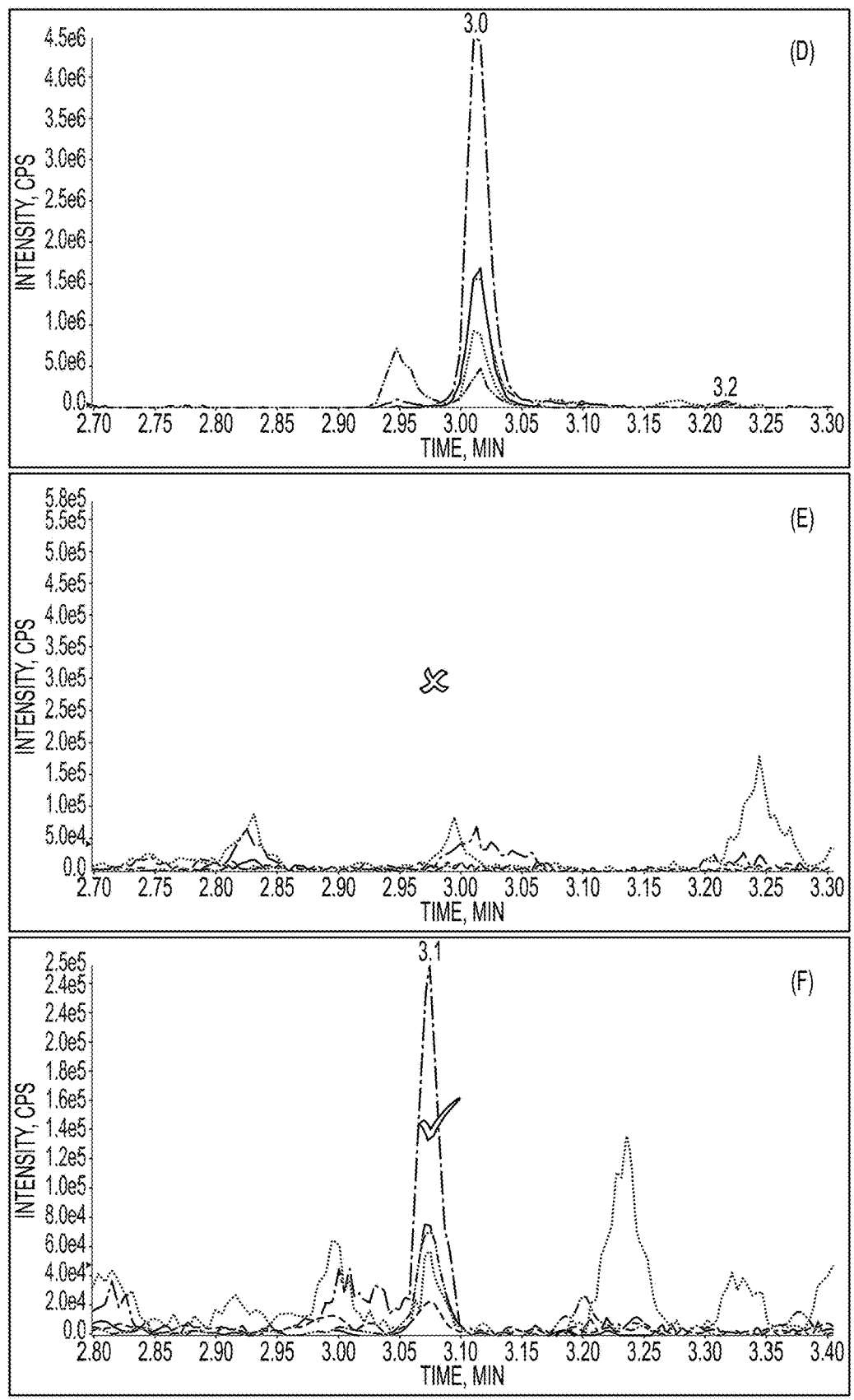
Figure 15:
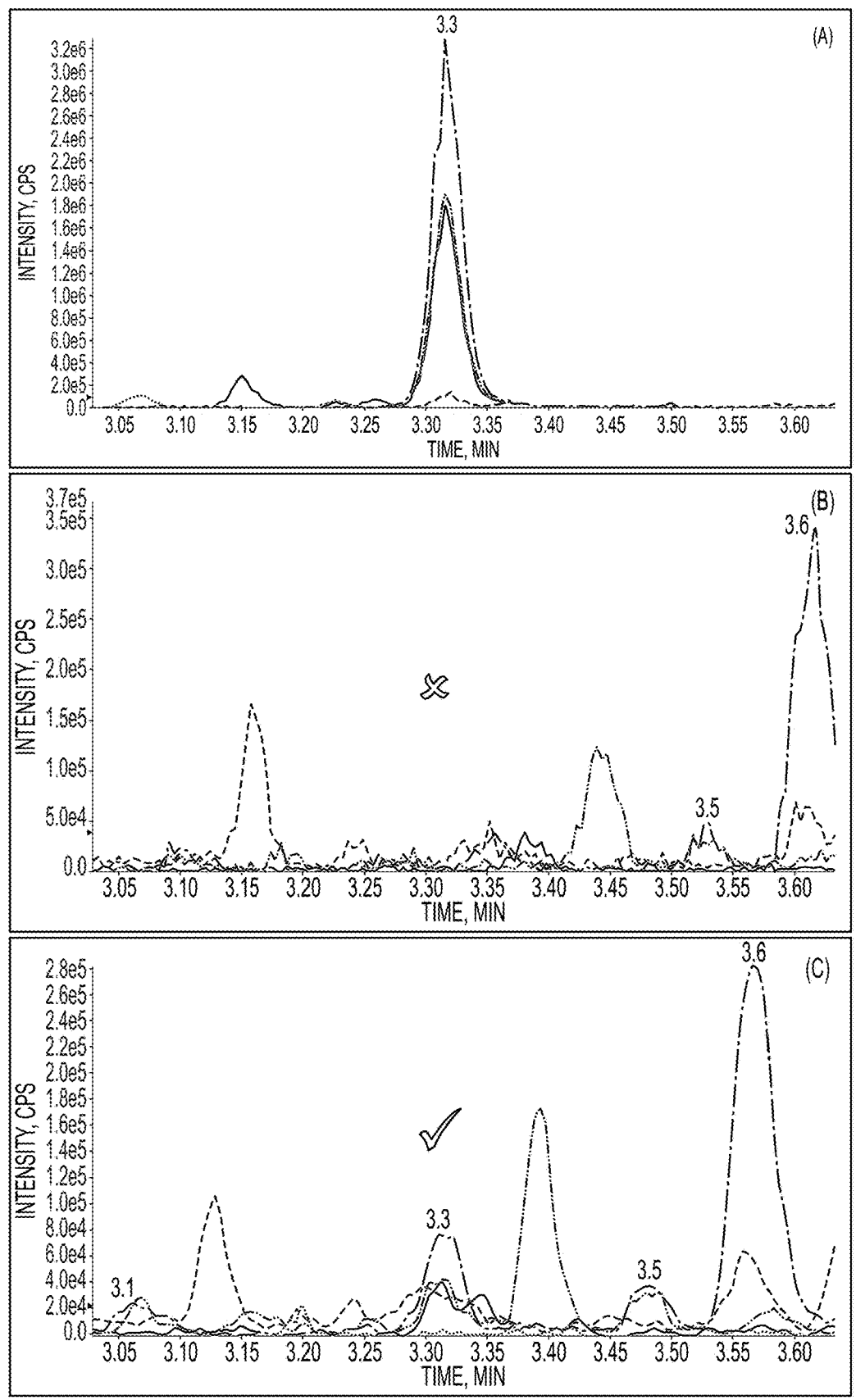
FIG. 15 shows detection of Micpu-Δ6D peptide DASTAPVDLK (residues 30-39 of SEQ ID NO: 3) in transgenic canola. Panels: (A) Heavy labeled reference standard DASTAPVDL*K (aa 30-39 of SEQ ID NO: 3) spiked into developing embryo protein background from WT canola (2 pmol on-column); (B) developing embryo protein from WT canola; (C) developing embryo protein from transgenic canola; (D) heavy labeled reference standard DASTAPVDL*K (aa 30-39 of SEQ ID NO: 3) spiked into mature seed protein background from WT canola (2 pmol on-column); (E) mature seed protein from WT canola; (F) mature seed protein from transgenic canola.
Figure 15:
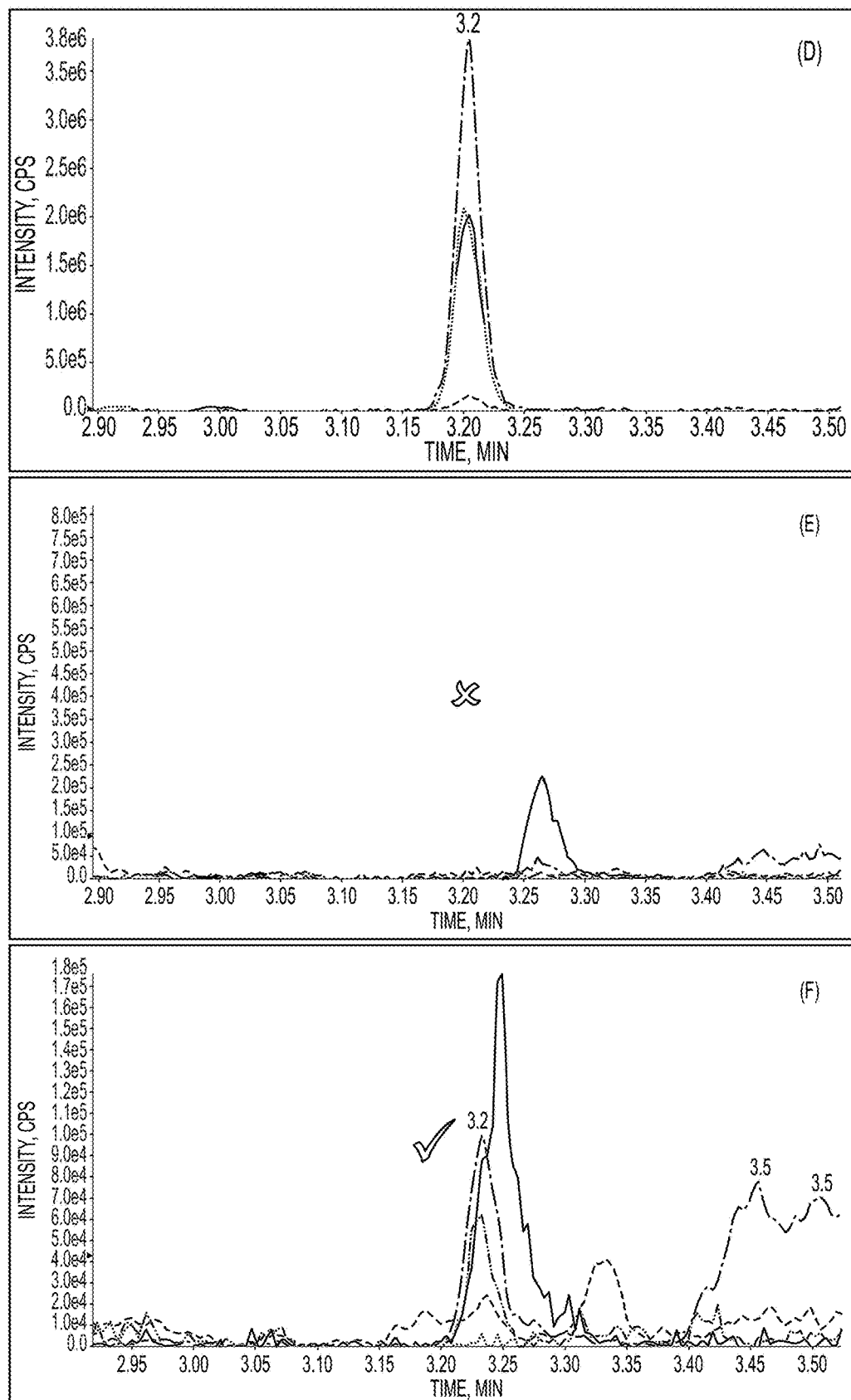
Figure 16:
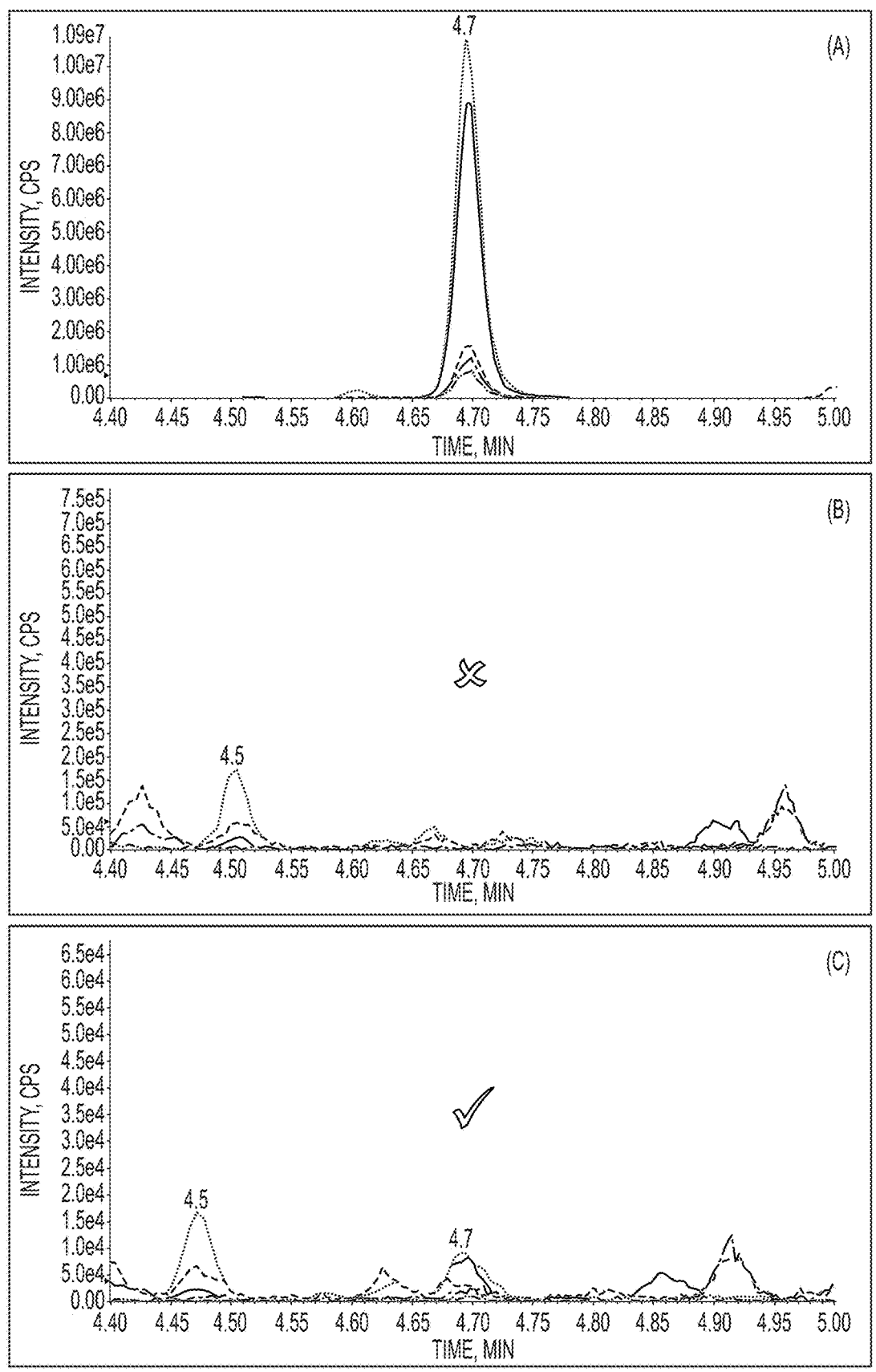
FIG. 16 shows detection of Pyrco-Δ6E peptide GQDPFLLK (aa 83-90 of SEQ ID NO: 4) in transgenic canola. Panels: (A) Heavy labeled reference standard GQDPFLL*K (aa 83-90 of SEQ ID NO: 4) spiked into developing embryo protein background from WT canola (2 pmol on-column); (B) developing embryo protein from WT canola; (C) developing embryo from transgenic canola; (D) heavy labeled reference standard GQDPFLL*K (aa 83-90 of SEQ ID NO: 4) spiked into mature seed background from WT canola (2 pmol on-column); (E) mature seed from WI canola; (F) mature seed from transgenic canola.
Figure 16:
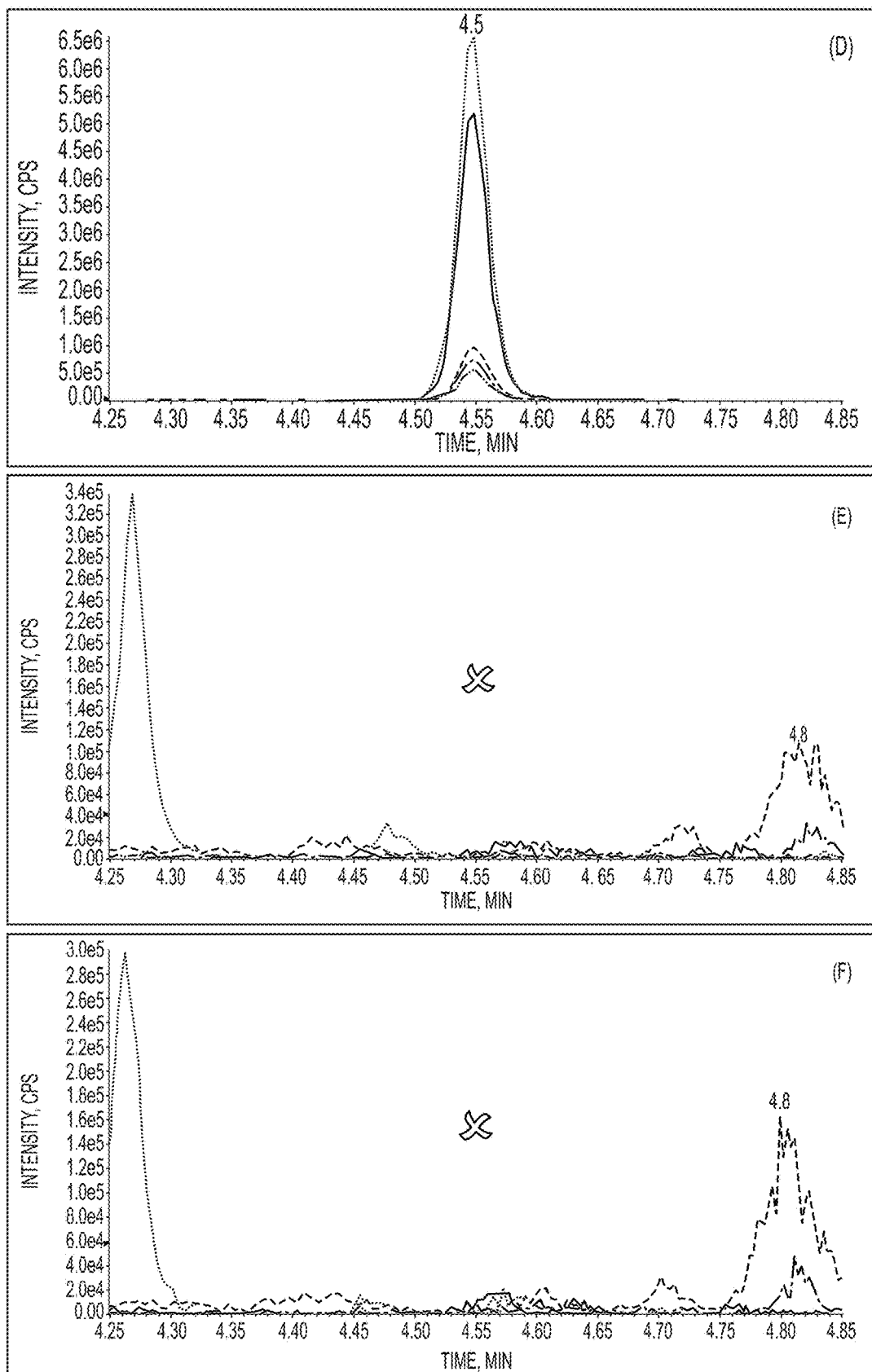
Figure 17:
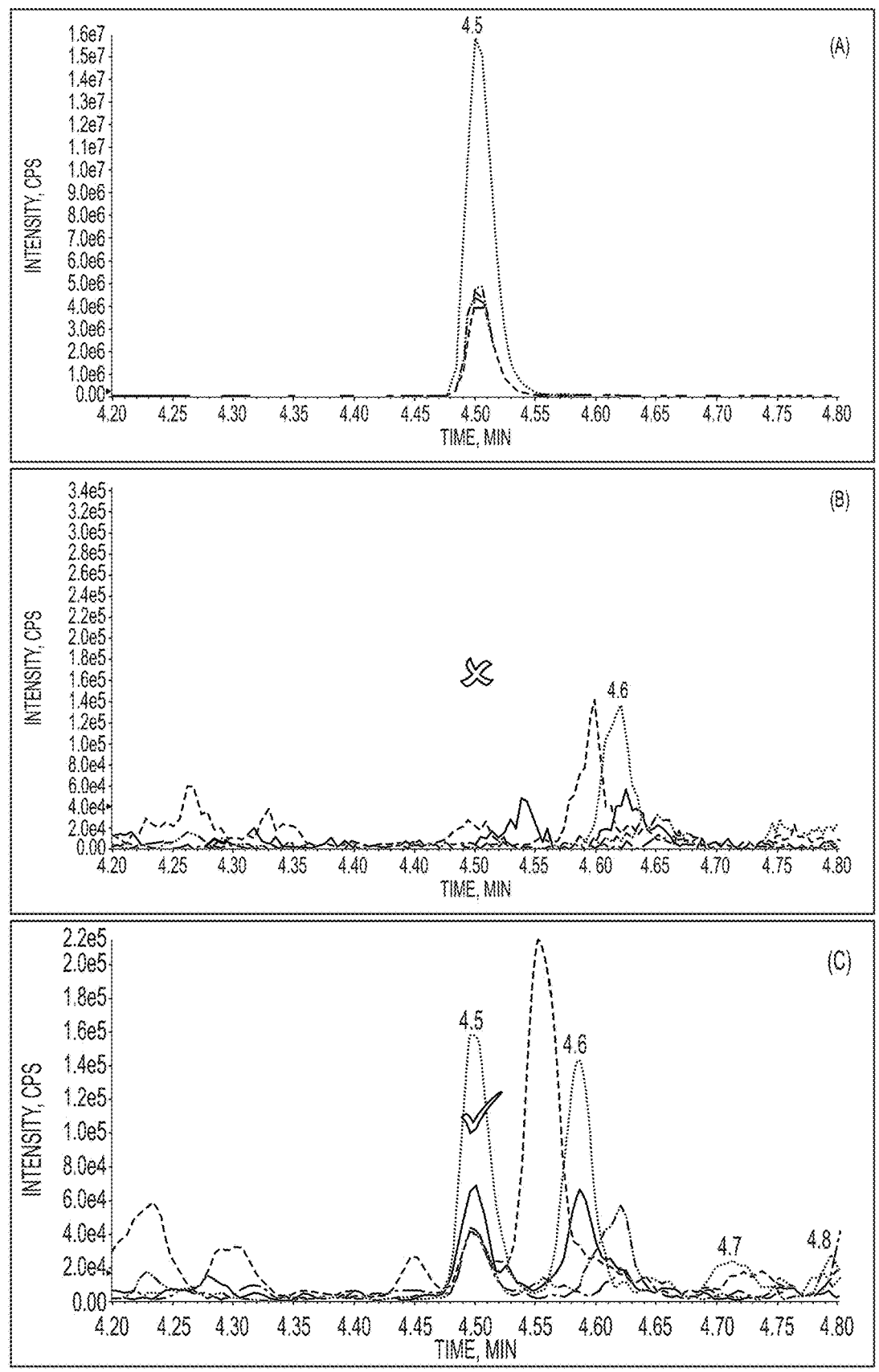
FIG. 17 shows detection of Pavsa-Δ5D peptide AYDVTNFVK (aa 37-45 of SEQ ID NO: 5) in transgenic canola. Panels: (A) Heavy labeled reference standard AYDVTNFV*K (aa 37-45 of SEQ ID NO: 5) spiked into developing embryo protein background from WT canola (2 pmol on-column); (B) developing embryo protein from WT canola; (C) developing embryo protein from transgenic canola; (D) heavy labeled reference standard AYDVTNFV*K (aa 37-45 of SEQ ID NO: 5) spiked into mature seed protein background from WT canola (2 pmol on-column); (E) mature seed protein from WT canola; (F) mature seed protein from transgenic canola.
Figure 17:
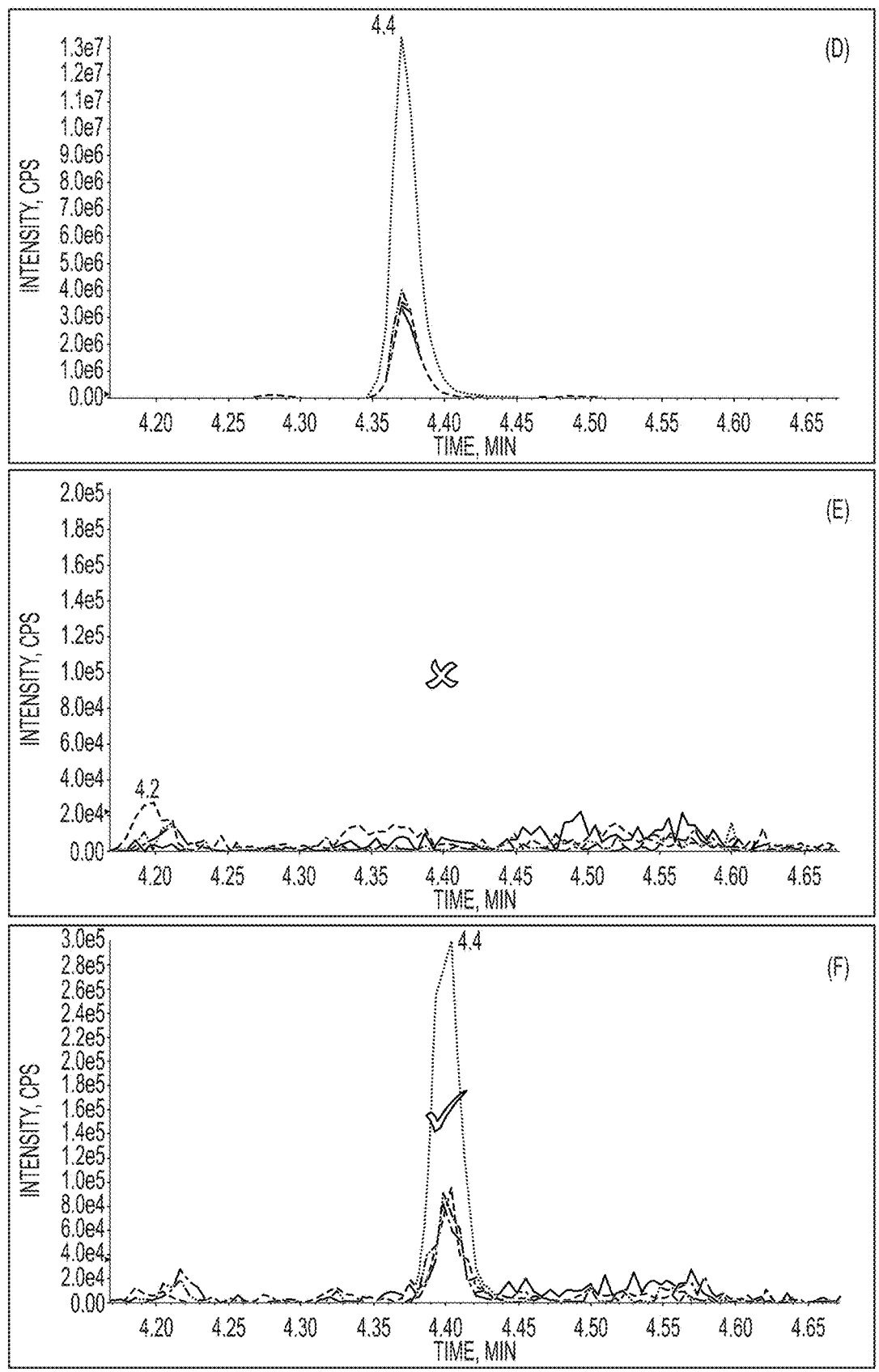
Figure 20:
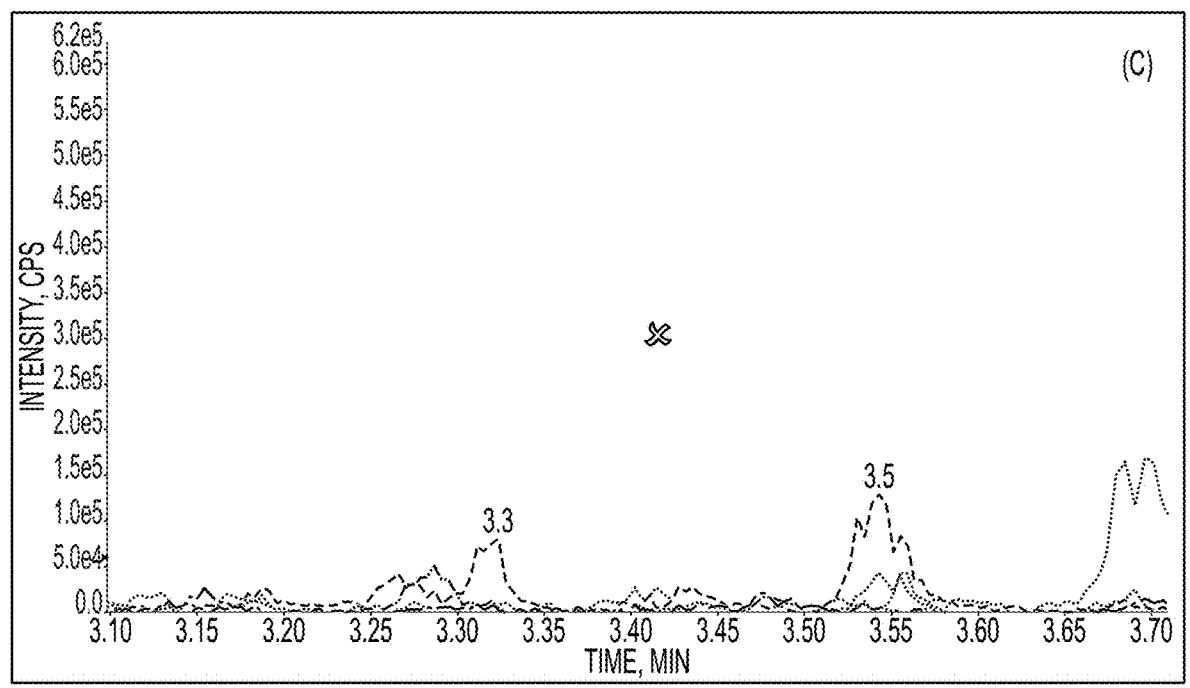
FIG. 20 shows Pavsa-Δ4D was not detected in transgenic canola TG15 whole plant. The Pavsa-Δ4D was most abundant of the seven transgene products detected in seed, but undetected canola TG15 whole plant. Panels: (A) Heavy labeled reference standard spiked into WT canola protein; (B) WT canola protein; (C) transgenic canola protein.
Figure 21:
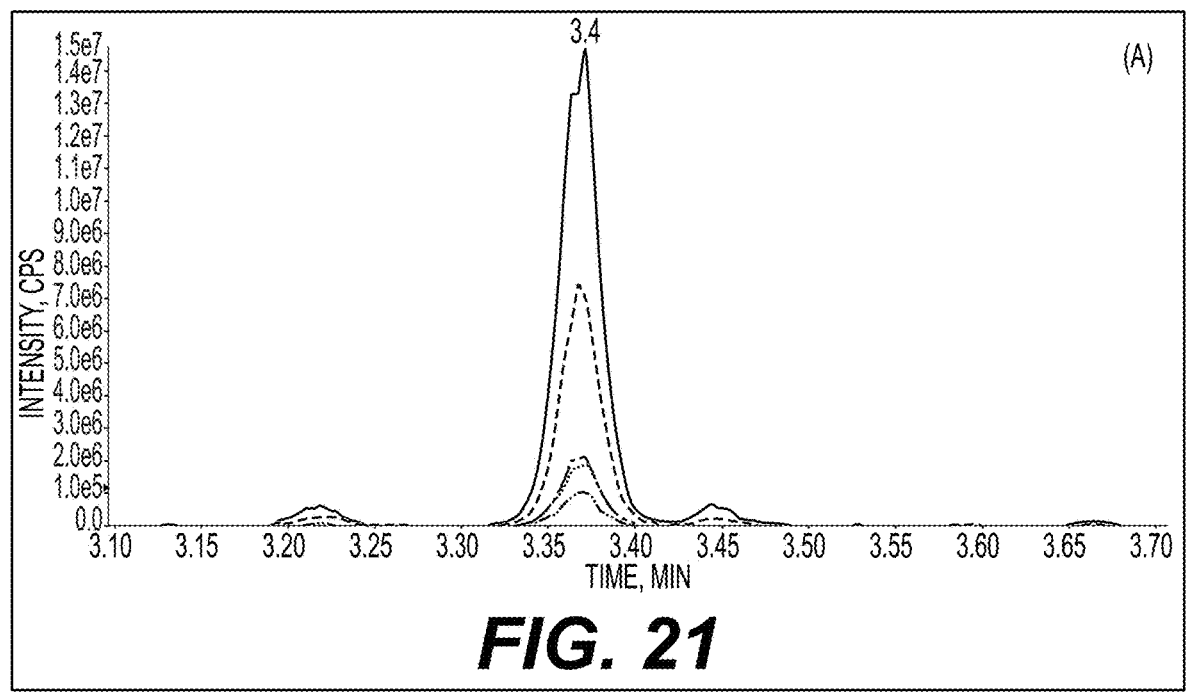
FIG. 21 shows Pavsa-Δ4D was not detected in transgenic canola TG35 whole plant. The Pavsa-Δ4D was most abundant of the seven transgene products detected in seed, but undetected canola TG35 whole plant. Panels: (A) heavy labeled reference standard spiked into WT canola protein; (B) WT canola protein; (C) transgenic canola protein.
Figure 22:
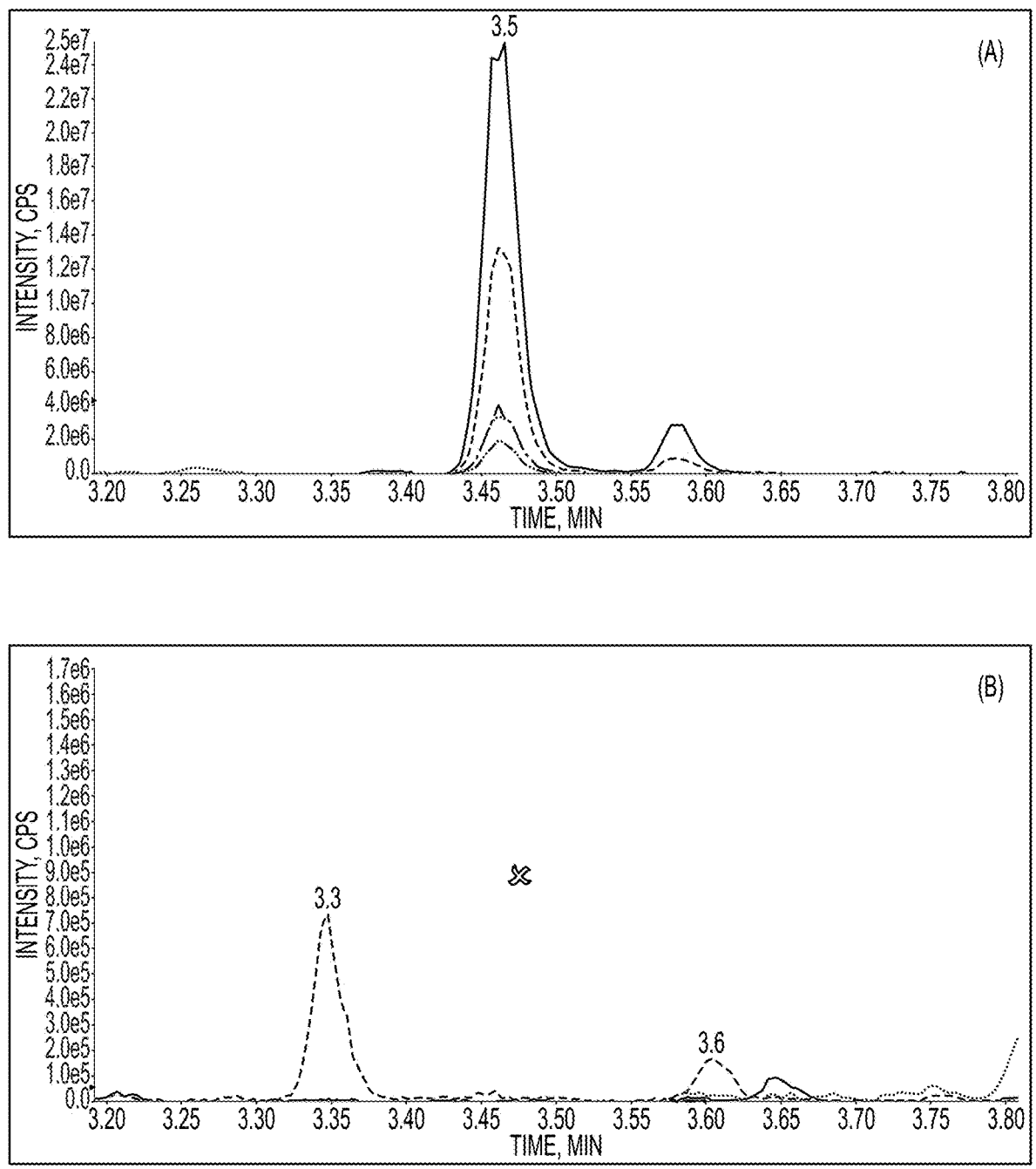
FIG. 22 shows Pavsa-Δ4D was not detected in transgenic canola TG65 root. The Pavsa-Δ4D was most abundant of the seven transgene products detected in canola seed, but undetected in TG65 root. Panels: (A) heavy labeled reference standard spiked into WT canola protein; (B) WT canola protein; (C) transgenic canola protein.
Figure 22:
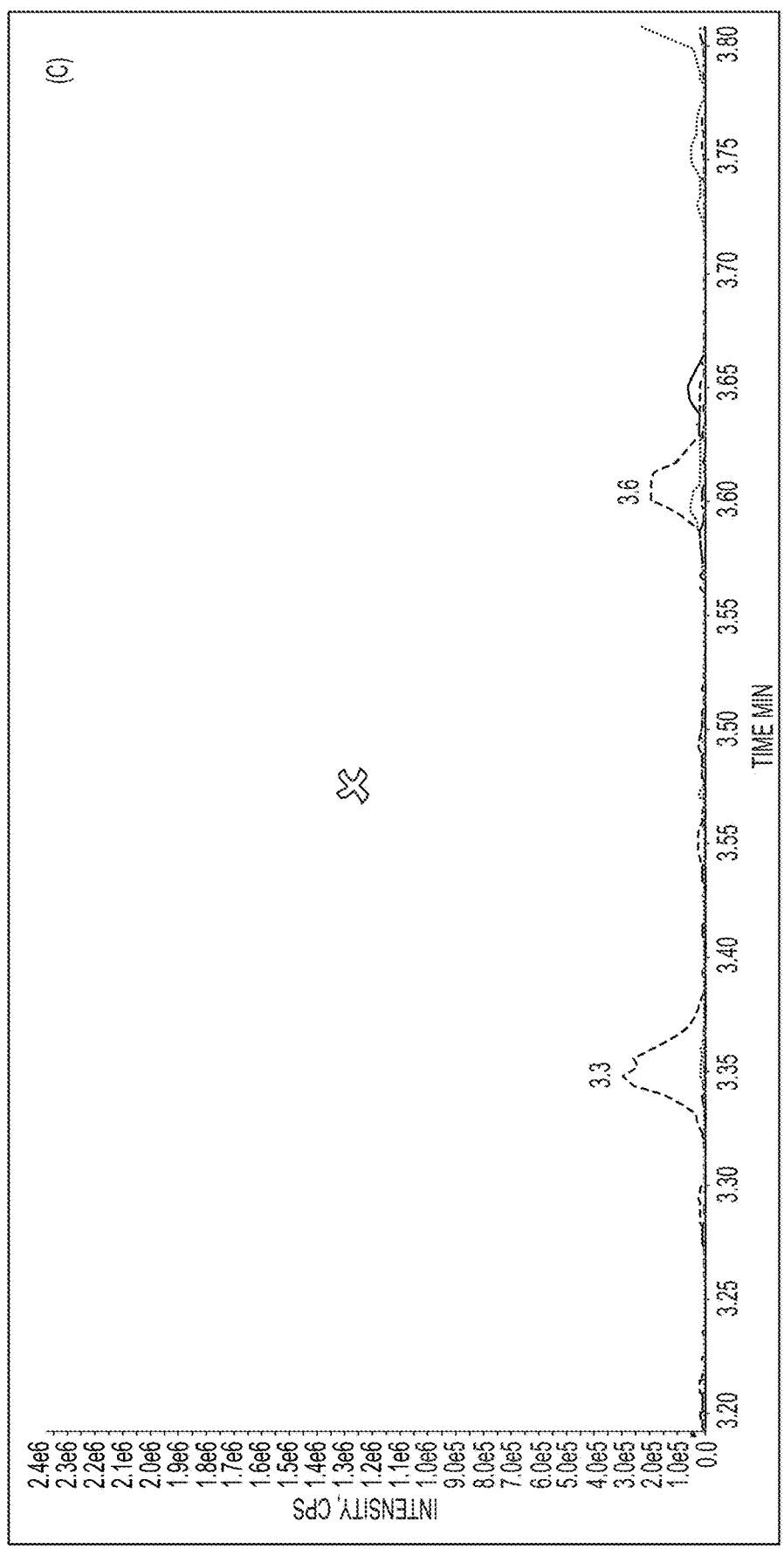
Figure 23:
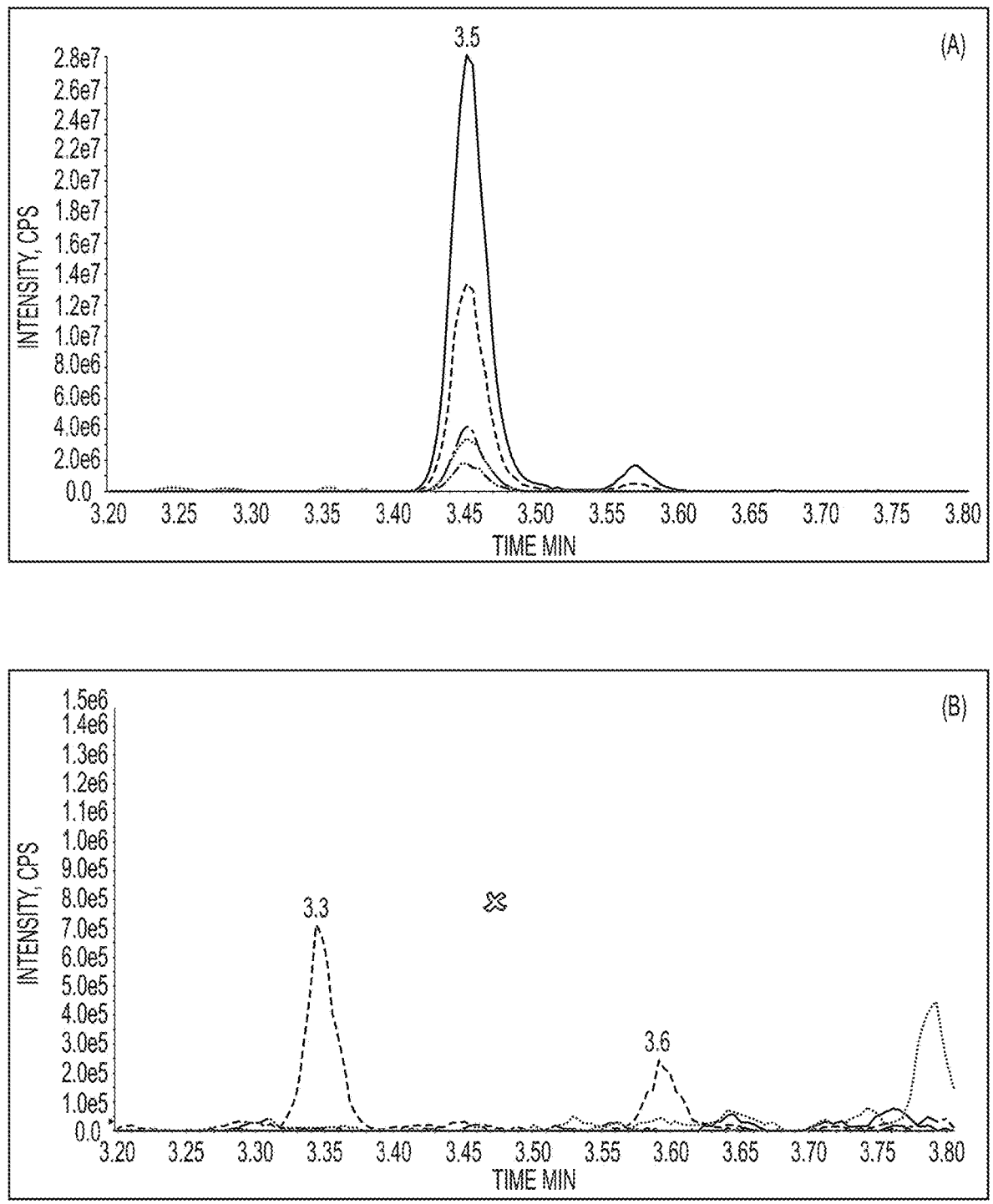
FIG. 23 shows that Pavsa-Δ4D was not detected in transgenic canola TG65 flower. The Pavsa-Δ4D was most abundant of the seven transgene products detected in seed, but undetected canola TG65 flower. Panels: (A) Heavy labeled reference standard spiked into WT canola protein; (B) WT canola protein; (C) transgenic canola protein.
Figure 23:
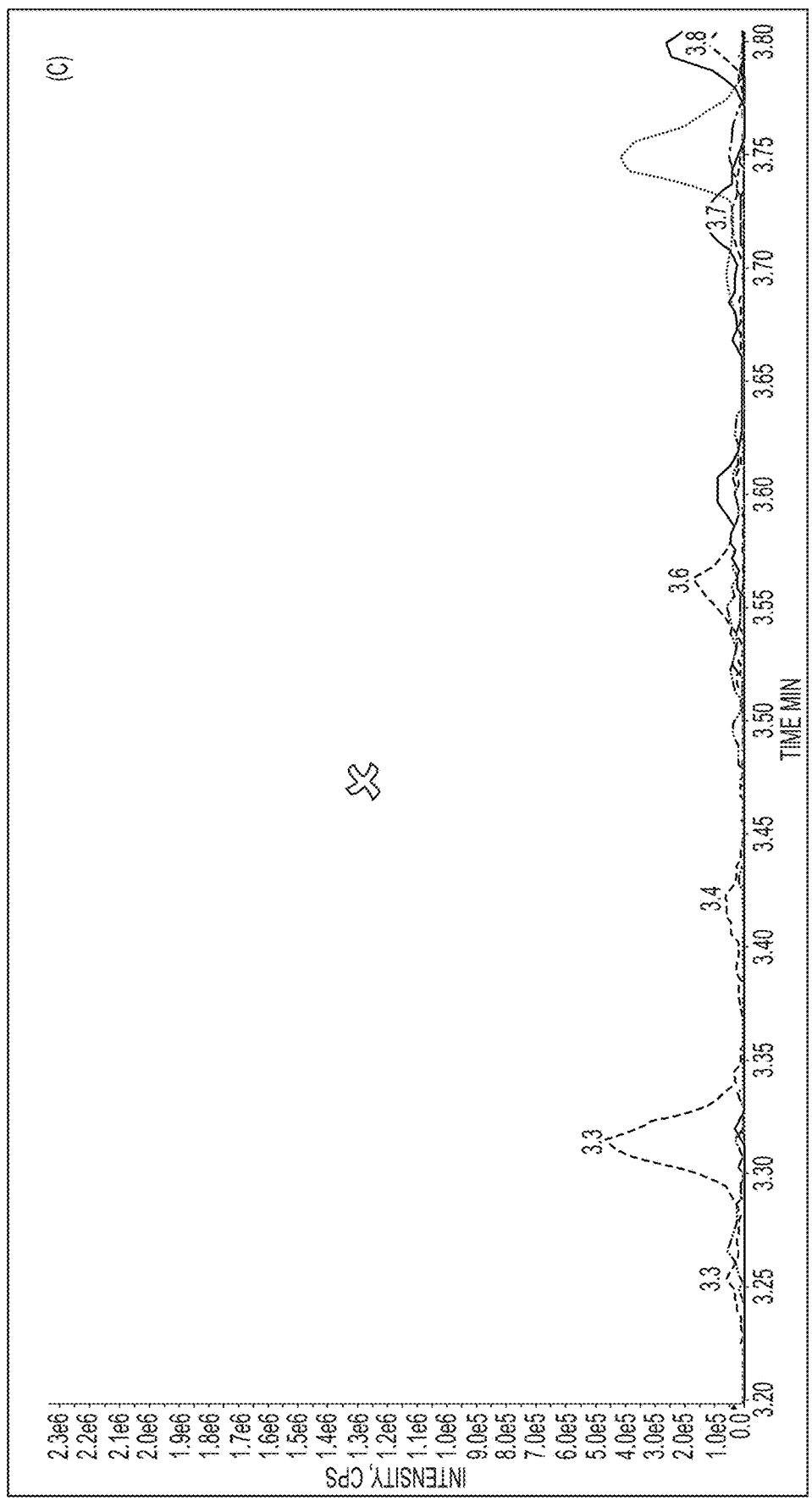
Figure 24:
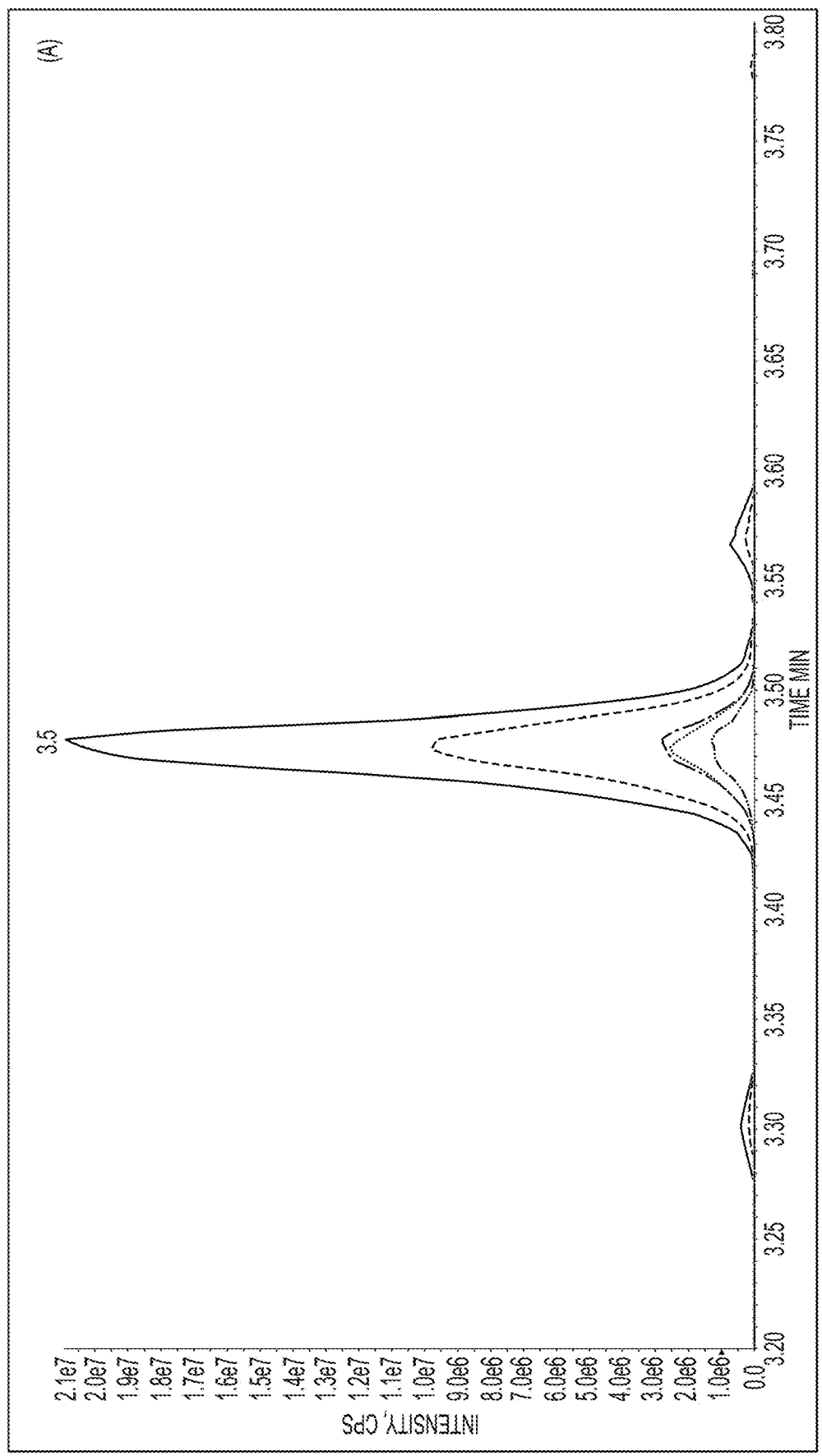
FIG. 24 shows that Pavsa-Δ4D was not detected in transgenic canola TG65 tissues. The Pavsa-Δ4D was most abundant of the seven transgene products detected in seed, but undetected in other canola TG65 tissues. Panels: (A) Heavy labeled reference standard spiked into WT canola protein; (B) WT canola protein; (C) transgenic canola protein.

Validation of Protein Quantification by LC-MRM-MS—The MS responses (peak area) of the light peptides (analytes) were measured and plotted relative to the amount of peptide loaded onto the LC-MS system. All peptides gave a linear response over the range 0 fmol to 1,250 fmol, with the exception of the Pavsa-Δ4D peptide LAPLV*K (aa 403-408 SEQ ID NO: 7), for which the linear range extended to 2,500 fmol as shown in FIG. 12B. The analytical parameters for quantification of canola peptides, wherein limit of detection (LOD), lower limit of quantification (LLOQ) and upper limit of quantification (ULOQ) are given in fmol, and listed in Table 14.

TABLE 14

Analytical parameters for quantification of canola peptides

| Protein | Peptide Sequence | LOD | LLOQ | ULOQ | m | b | $R^2$ |
|---|---|---|---|---|---|---|---|
| Lack1-Δ12D | GSSSNTEQEVPK1 | 0.31 | 0.31 | 1,250 | 7.088e−5 | −0.0004562 | 0.9980 |
| Picpa-@3D | IPFYHAR2 | 0.61 | 1.22 | 1,250 | 0.0003545 | −0.003352 | 0.9974 |
| Micpu-Δ6D | DASTAPVDLK3 | 0.08 | 0.15 | 1,250 | 0.006326 | −0.002506 | 0.9989 |
| Pyrco-Δ6E | GQDPFLLK4 | 0.08 | 0.31 | 1,250 | 0.001400 | −0.007894 | 0.9989 |
| Pavsa-Δ5D | AYDVTNFVKS | 0.15 | 0.15 | 1,250 | 0.001385 | −0.008230 | 0.9988 |
| Pyrco-Δ5E | SQPFGLK6 | 0.08 | 0.15 | 1,250 | 0.002457 | −0.002724 | 0.9996 |
| Pavsa-Δ4D | LAPLVK7 | 0.08 | 0.31 | 2,500 | 0.001461 | −0.02667 | 0.9958 |

LOD, limit of detection;
LLOQ, lower limit of quantification;
ULOQ, upper limit of quantification;
m, slope or gradient;
b, y-intercept;
$R^2$, linear regression.
Units in fmol loaded on-column.
[1]GSSSNTEQEVPK: residues 16-26 of SEQ ID NO: 2;
[2]IPFYHAR: residues 351-358 of SEQ ID NO: 1;
[3]DASTAPVDLK: residues 30-39 of SEQ ID NO: 3;
[4]GQDPFLLK: residues 83-90 of SEQ ID NO: 4;
[5]AYDVTNFVK: residues 37-45 of SEQ ID NO: 5;
[6]SQPFGLK: residues 66-72 of SEQ ID NO: 6;
[7]LAPLVK: residues 403-408 of SEQ ID NO: 7.

Levels of the ω3LCPUFA Biosynthesis Pathway Enzymes in Transgenic Canola—LC-MRM-MS quantification confirmed that none of the target peptides were detected in total protein extracts from WT canola obtained at all seven sampling points at five growth stages collected from two field trial sites. Further, none of the target peptides were detected in total protein extracts in the non-seed tissues of transgenic ω3LCPUFA canola obtained from the seven sampling points at five growth stages collected from two field trial sites (Table 15).

TABLE 15

Detection of peptides in transgene proteins in canola plant parts

| Protein | Peptide Sequence | Whole plant TG15 | Whole plant BTG35 | Root TG65 | Flower TG65 | Other TG65 | Devel. Seed TG79 | Mature Seed TG90 |
|---|---|---|---|---|---|---|---|---|
| Lack1-Δ12D | GSSSNTEQEVPK[1] | ND | ND | ND | ND | ND | ✓ | ✓ |
| Picpa-@3D | IPFYHAR[2] | ND | ND | ND | ND | ND | ✓ | ✓ |
| Micpu-Δ6D | DASTAPVDLK[3] | ND | ND | ND | ND | ND | ✓ | ✓ |
| Pyrco-Δ6E | GQDPFLLK[4] | ND | ND | ND | ND | ND | ✓ | ND |

TABLE 15-continued

Detection of peptides in transgene proteins in canola plant parts

| Protein | Peptide Sequence | Whole plant TG15 | Whole plant BTG35 | Root TG65 | Flower TG65 | Other TG65 | Devel. Seed TG79 | Mature Seed TG90 |
|---|---|---|---|---|---|---|---|---|
| Pavsa-Δ5D | AYDVTNFVK[5] | ND | ND | ND | ND | ND | ✓ | ✓ |
| Pyrco-Δ5E | SQPFGLK[6] | ND | ND | ND | ND | ND | ND | ✓ |
| Pavsa-Δ4D | LAPLVK[7] | ND | ND | ND | ND | ND | ✓ | ✓ |

[1]GSSSNTEQEVPK: residues 16-26 of SEQ ID NO: 2;
[2]IPFYHAR: residues 351-358 of SEQ ID NO: 1;
[3]DASTAPVDLK: residues 30-39 of SEQ ID NO: 3;
[4]GQDPFLLK: residues 83-90 of SEQ ID NO: 4;
[5]AYDVTNFVK: residues 37-45 of SEQ ID NO: 5;
[6]SQPFGLK: residues 66-72 of SEQ ID NO: 6;
[7]LAPLVK: residues 403-408 of SEQ ID NO: 7.

All seven peptides representing the ω3LCPUFA biosynthesis pathway enzymes were detected in developing or mature seeds of transgenic canola, and were quantified as shown in Table 16.

TABLE 16

Transgenic protein quantification in developing and mature canola seed

| | | Developing seed (TG79) | | Mature seed (TG90) | |
|---|---|---|---|---|---|
| Protein | Peptide Sequence | Site A | Site B | Site A | Site B |
| Lackl-Δ12D | GSSSNTEQEVPK[1] | 507.1 ± 14.1 | 461.6 ± 149.5 | 441.0 ± 89.6 | 551.0 ± 87.3 |
| Picpa-ω3D | IPFYHAR[2] | 351.1 ± 51.9 | 352.0 ± 148.7 | 469.3 ± 189.1 | 551.2 ± 55.1 |
| Micpu-Δ6D | DASTAPVDLK[3] | 166.0 ± 28.7 | 257.1 ± 57.3 | 85.6 ± 7.5 | 80.9 ± 14.9 |
| Pyrco-Δ6E | GQDPFLLK[4] | 79.0 ± 5.3 | 89.9 ± 19.6 | ND | ND |
| Pavsa-Δ5D | AYDVTNFVK[5] | 131.6 ± 34.1 | 136.4 ± 65.7 | 129.2 ± 31.6 | 155.5 ± 41.6 |
| Pyrco-Δ5E | SQPFGLK[6] | ND | ND | 64.1 ± 38.7 | 89.7 ± 15.7 |
| Pavsa-Δ4D | LAPLVK[7] | 974.6 ± 296.6 | 888.7 ± 629.1 | 1500 ± 408.7 | 1470 ± 313.7 |

The amount of peptide detected is reported in units of fmol/100 µg total protein, as mean ± SD, n = 4.
ND, not detected.
[1]GSSSNTEQEVPK: residues 16-26 of SEQ ID NO: 2;
[2]IPFYHAR: residues 351-358 of SEQ ID NO: 1;
[3]DASTAPVDLK: residues 30-39 of SEQ ID NO: 3;
[4]GQDPFLLK: residues 83-90 of SEQ ID NO: 4;
[5]AYDVTNFVK: residues 37-45 of SEQ ID NO: 5;
[6]SQPFGLK: residues 66-72 of SEQ ID NO: 6;
[7]LAPLVK: residues 403-408 of SEQ ID NO: 7

The Pyrco-Δ5E and Pyrco-Δ6E proteins revealed the lowest protein abundance in the transgenic canola (ranging from 64-90 fmol). The Pyrco-Δ5E was below the limit of detection in developing seeds, and the Pyrco-Δ6E protein was below the limit of detection in mature seeds. Pavsa-Δ4D was present in the highest amount of the seven enzymes, with up to 1,500 fmol in mature seeds. Based on the molecular mass of each protein, the level of each transgenic protein was determined (on a per mg total protein basis) as shown in Table 17. Specifically, the lowest protein was Pyrco-Δ5E at 20/mg total protein, and highest Pavsa-Δ4D 740 ng/mg total proteins. All the detected peptides were confirmed, as shown in FIG. 13-FIG. 19.

TABLE 17

Quantification of transgenic proteins in developing and mature canola seed

| | MW | Developing Seed (TG79) | | Mature Seed (TG90) | |
|---|---|---|---|---|---|
| Protein | (Da) | Site A | Site B | Site A | Site B |
| Lackl-Δ12D | 48,158 | 244.2 ± 6.8 | 222.3 ± 72.0 | 212.4 ± 43.2 | 265.4 ± 42.0 |
| Picpa-ω3D | 47,760 | 167.7 ± 24.8 | 168.1 ± 71.0 | 224.1 ± 90.3 | 263.3 ± 26.3 |
| Micpu-Δ6D | 52.935 | 87.9 ± 15.2 | 136.1 ± 30.3 | 45.3 ± 4.0 | 42.8 ± 7.9 |
| Pyrco-Δ6E | 33,078 | 26.1 ± 1.8 | 29.7 ± 6.5 | ND | ND |
| Pavsa-Δ5D | 48,215 | 63.4 ± 16.4 | 65.8 ± 31.7 | 62.3 ± 15.2 | 75.0 ± 20.0 |
| Pyrco-Δ5E | 31,268 | ND | ND | 20.0 ± 12.1 | 28.0 ± 4.9 |
| Pavsa-Δ4D | 49,307 | 480.5 ± 146.2 | 438.2 ± 310.2 | 739.5 ± 201.5 | 724.7 ± 154.7 |

Units are ng of transgene protein per mg total protein extracted.

The seed-specific expression of the ω3LCPUFA biosynthesis pathway enzymes was confirmed by examining a range of plant tissues. There was no detection of the target peptides in the non-seed tissues of the transgenic canola. The Pavsa-Δ4D protein was the most abundant among the seven transgene products detected in developing seed or mature seed, thus was chosen as a representative protein as depicted in FIG. 20-FIG. 24. There was no detection of the Pavsa-Δ4D peptide LAPLVK (aa 403-408, SEQ ID NO: 7) in TG15 whole plant, TG35 whole plant, TG65 root, TG65 flower, or the other tissues of TG65.

Protein content was detected and quantified in transgenic canola for all seven enzymes in the fatty acid biosynthetic pathway. The enzymes driving ω3LCPUFA production, expressed under control of seed-specific promoters, were detected only in developing seed and mature seed, and present in low levels (20-740 ng/mg total protein). Conversely, none of the ω3LCPUFA pathway enzymes were detected in other tissues of transgenic canola, regardless of the sampling time. Finally, no transgenic proteins were detected in WT canola tissues or seed.

Figure 25:
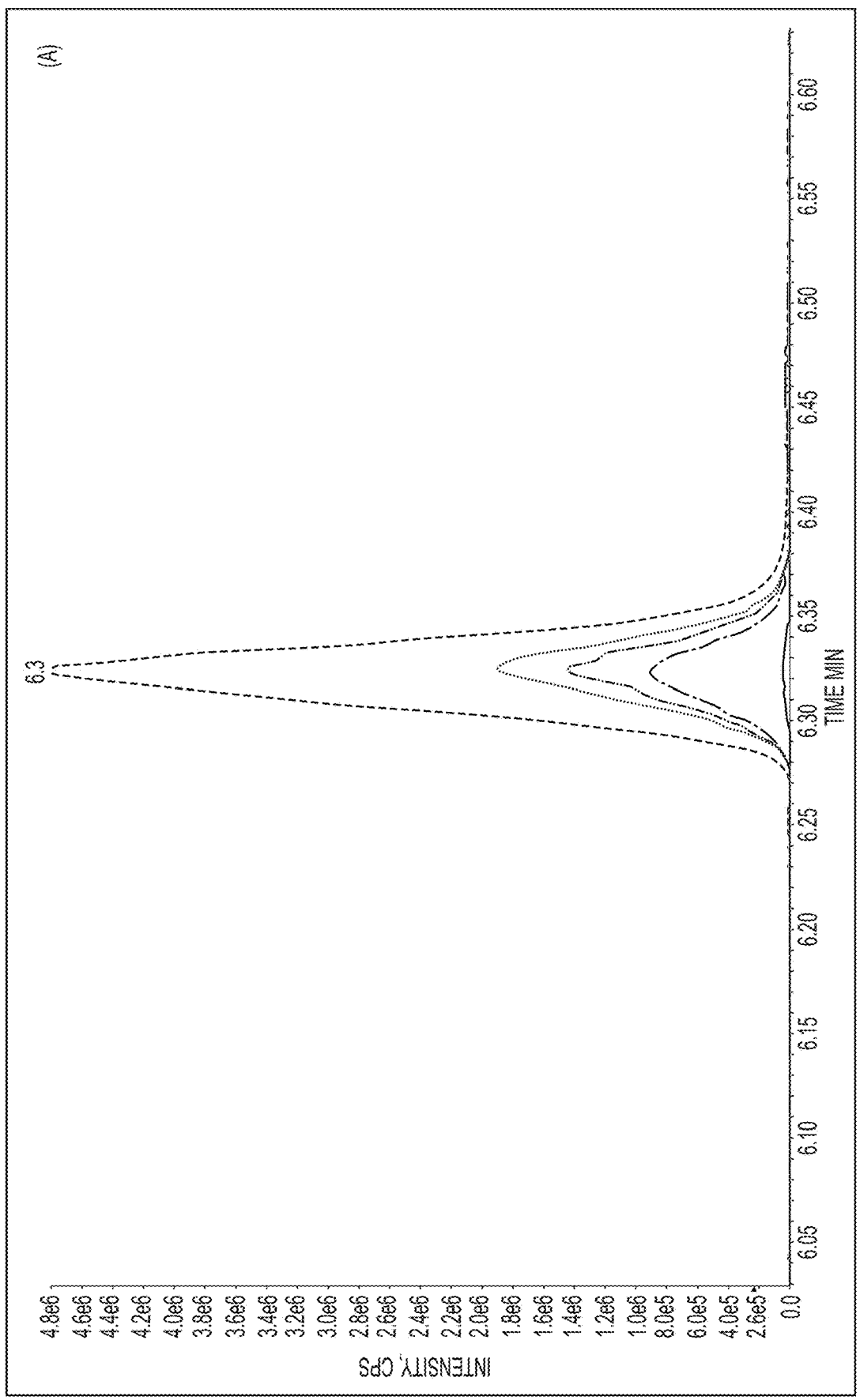
FIG. 25 shows expression of marker, R, in canola seed. Panel (A): heavy labeled reference standard TEPQTPQEWIDDL*ER (SEQ ID NO: 8) spiked into developing embryo background from WT canola (2 pmol on-column). Detection of trace levels of R in transgenic canola plant parts, Panels: (B) developing seed; (C) mature seed; (D) whole plant (TG15); (E) whole plant (TG35); (F) root (TG65); (G) flower (TG65), and other tissue (TG65).
Figure 26:
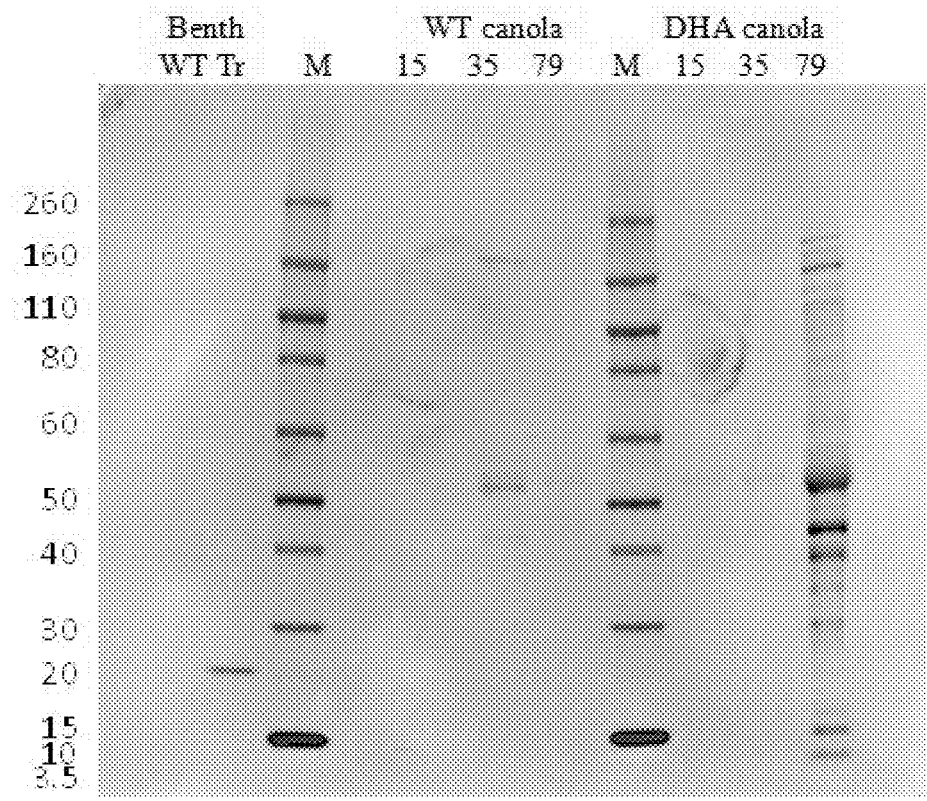
FIG. 26 depicts western blot analysis of marker R expressed in transgenic plants. Left part shows total proteins from *Nicotiana benthamiana* leaf (Benth). WT:WT, untreated; Tr: transient expression of marker protein for 5 days. Middle part shows total proteins from WT canola. Right part shows total protein from transgenic canola. M: molecular weight marker in kDa indicated to the left of the gel. Lanes 15, 35, and 79 represents canola materials of TG15 (whole plant), TG35 (whole plant) and TG79 (developing seed). 20 µg of protein was loaded in each lane, and subsequently developed with anti-R antibody (Sigma) at a 1:1000 dilution.

Detection of Selection Marker protein—Low level expression (below the limit of detection) of a selection marker gene (R) was confirmed in canola, as shown in FIG. 25, wherein a trace amount of marker protein (R) detected in all tested tissues. The highest R signal intensity was detected for whole plant stages TG15 and TG35 (FIG. 25D-FIG. 25E). The low expression of R in test plants was also supported by western blot analysis using anti-R antibody (FIG. 26). Transiently-expressed R protein, at an expected size, was detected in total protein of transgenic *N. benthamiana* leaf, but not in total protein of WT *N. benthamiana* leaf. No specific R band was detected in transgenic canola TG15 whole plant, TG35 whole plant, or TG79 developing seed, suggesting that the amount of R deceeded the detectable level of the western blot assay.

Example 4. In Vitro Stability of *Pavlova Salina* Δ4-Desaturase (Pavsa-Δ4D

This Example provides assessment of the in vitro digestibility of Pavsa-Δ4D protein in SGF containing pepsin, in combination with a novel pepsin-trypsin assay employing state-of-the-art mass spectrometric approaches to monitor the precise degradation products. The extent of protein digestion was evaluated by the appearance and disappearance of peptic peptide products, and the disappearance of tryptic peptide products as a proxy for intact protein. Because no single method can predict the allergenicity of a protein, the allergenic potential of a protein is determined by a weight of evidence approach. Protein digestibility is one aspect of the overall allergenicity assessment that is conducted for proteins newly expressed in genetically modified crops The results of this Example show that Pavsa-Δ4D, a recalcitrant integral membrane protein, was readily digestible in pepsin or trypsin. In a particular embodiment, the results provided herein demonstrate that upon incubation in pepsin and analyzed using LC-MS/MS, >80% of full-length Pavsa-Δ4D protein was digested within 10 mini, and >93% of full-length Pavsa-Δ4D protein was digested within 60 min. In another embodiment, the results provided herein demonstrate that upon incubation in pepsin and analyzed using LC-MS/MS, 99% of full-length Pavsa-Δ4D protein was digested within 10 min, and 99.6% of full-length Pavsa-Δ4) protein was digested within 60 min when analyzed by LC-MS/MS. Rapid digestion of the full-length protein is one of many factors that indicate transgenic protein safety.

The ω3LCPUFA, eicosapentaenoic acid, docosapentaenoic acid, and docosahexaenoic acid (EPA, 20:5ω3; DPA, 22:5ω3; and DHA, 22:6ω3, respectively) are widely recognized for their beneficial roles in human health, particularly those related to cardiovascular and inflammatory health. EPA, DPA and DHA are sourced primarily from wild-caught fish oils and algal oils, with algae being the initial producer in the marine food web. Marine sources are under pressure, however, from increasing demand for ω3LCPUFA by aquaculture, nutraceutical, and pharmaceutical applications.

Additional sources of these fatty acids were produced by engineering land-based oilseed crops to convert native fatty acids to marine-type ω3LCPUFA in seed oil. For example, canola is a commonly grown oilseed with 67 million metric tons (MMT) of rapeseed produced globally in 2015/16, and transgenic canola (*Brassica napus*) lines that produce significant amounts of ω3LCPUFA, including DHA, in seed oil have been developed. As noted above, seven fatty acid desaturases and elongases were introduced into canola in a single expression vector to provide the synthesis pathway for the conversion of oleic acid (OA) to DHA. See, e.g., WO 2010/057246.

Briefly, the Δ4-desaturase gene used in the transgenic ω3LCPUFA canola was cloned from alga *P. salina*, codon optimized (see, e.g., WO 2010/057246), fused with a His-tag and a PreScission Protease cleavage site (SLEVLFQ↓GP) (SEQ ID NO: 12) (GE Healthcare, Parramatta, AU), cloned into baculovirus pFastBac vector (Invitrogen, Germany), expressed in the Sf9 insect cell line, and then purified as follows: about 100 mg of insect cell pellet expressing His-Pavsa-Δ4D was resuspended in 500 μL of lysis buffer (1× phosphate buffer saline (PBS) with imidazole, DTT and PMSF). The final lysis buffer contained 140 mM NaCl, 27 mM KCl, 10 mM $Na_2HPO_4$, 1.8 mM $KH_2PO_4$, 20 mM imidazole, 10 mM DTT, 1 mM PMSF). The cells were sonicated using a Branson Probe Sonicator (Emerson Elec. Co., St. Louis, Mo., US) and centrifuged at 21,700×g for 30 min at 4° C. The pellet protein and leftover protein in supernatant were assessed by SDS-PAGE and western blot analysis using a mouse anti-His-tag antibody (1:1000 dilution). The proteins were stored at −80° C. freezer until assay time.

Digestibility assays employed two enzymes: trypsin and pepsin. Trypsin is a serine protease that is found in the digestive system. Trypsin cleaves polypeptide chains at the carboxyl side of the basic amino acids lysine (K) or arginine (R), but its cleavage is hindered by the presence of proline as the preceding amino acid (P1' position, FIG. 27A). Pepsin is a protease produced in the stomach and is efficient at cleaving, in a non-specific manner, the peptide bonds adjacent to aromatic and hydrophobic amino acids phenylalanine (F), tyrosine (Y), tryptophan (W) and leucine (L) (FIG. 27B). Histidine (H), lysine (K) and arginine (R) at the P3 position act to hinder proteolysis, while proline (P) at P3 or P4 positions promotes proteolysis.

Two test systems, pepsin digestion (representing simulated gastric fluid (SGF)) and a combined pepsin-trypsin digestion, were utilized independently to test the stability of the His-Pavsa-Δ4D protein. SGF contained the proteolytic enzyme pepsin in a buffer adjusted to an acidic pH 1.2, using a highly purified form of pepsin. The SGF was formulated so that an enzyme:protein ratio of 3:1 would be present in the digestion reactions. The digestion of the Pavsa-Δ4D protein was monitored by LC-MS/MS. The pepsin digestibility assay protocol described herein references the protocol standardized by the International Life Sciences Institute (ILS) in a multi-laboratory test and the results demonstrated that the in vitro pepsin digestion assay is reproducible when a common protocol is followed. Thomas et al., 39 Reg. Tox. Pharm. 87 (2004). Sequencing grade porcine trypsin and a highly purified form of pepsin (Catalog #V195A; specific activity >2,500 units/mg) were purchased from Promega (Madison, Wis., US). Mouse anti-His antibody (Catalog #A7058) was purchased from Sigma-Aldrich (Sydney, AU).

SGF was represented by the proteolytic enzyme pepsin in a buffer adjusted to an acidic pH 1.2. The digestion was performed for 5, 10, 15, 30, and 60 min, with 0 min (no pepsin added) as the control, each with five replicates. Because of filtering and washing five replicates after pepsin digestion, the earliest practical time point was 5 min from the addition of pepsin. The increased abundance of targeted peptic peptides was used as indicator of the protein digestibility. Additionally, the SGF digestion at the time points as above was followed by 16 hr digestion with trypsin, designated as the combined pepsin-trypsin digestion. The relative abundance of tryptic peptides compared to the abundance of peptides in no pepsin (0 min) followed by trypsin digestion provided an indicator of the protein digestibility.

For pepsin digestion, thirty µg of protein (30 µL, n=30 comprising five replicate digestions and six time-points) were applied to a 10 kDa molecular weight cut-off filter (Millipore, Australia), and washed twice with 200 µL volumes of UA buffer with centrifugation (20,800×g, 15 min). The buffer was exchanged using 50 mM $(NH_4)HCO_3$ (pH 8.0) by two consecutive wash/centrifugation steps. The pH was lowered by two consecutive wash/centrifugation steps with acidified 50 mM $(NH_4)HCO_3$ (pH 1.2). Numerous acids may be used to acidify buffer and achieve a low pH (i.e., pH~1.2 to pH~3.0) in which pepsin is active, such as HCl, acetic acid, or citric acid. The 10 kDa filters were transferred to fresh centrifuge tubes, and 90 µg pepsin (150 µL, 0.6 µg/mL in acidified 50 mM $(NH_4)HCO_3$, pH 1.2) added to obtain an enzyme:protein ratio of 3:1. The replicate tubes were incubated at 37° C. for five time-points (5, 10, 15, 30, 60 min). Pepsin was not applied to the 0 time-point, which served as an experimental control for acid hydrolysis. The digestion was stopped by the addition of 200 µL of 50 mM $(NH_4)HCO_3$, pH 8.0, which irreversibly inactivated the pepsin. The 10 kDa filters were immediately centrifuged (20,800×g, 15 min) and the filtrates containing digested peptides were collected. The filters were washed twice with 200 µL of 50 mM $(NH_4)HCO_3$, pH 8.0, and the filtrates combined and lyophilized, then stored at −80° C. until further analysis. For LC-MS, the peptic peptides were resuspended in 12 µL of 1% formic acid and run on the QTRAP 6500+ LC-MS system and quantified.

For the dual pepsin-trypsin digestion, 10 kDa filters from each time point were transferred to fresh centrifuge tubes and the residual protein was reduced with 200 µl of 50 mM DTT, 50 mM $(NH_4)HCO_3$, pH 8.5, on mixer at 600 rpm for 45 min prior to centrifugation (20,800×g, 15 min). The protein was alkylated with 200 µL of 50 mM IAM, 50 mM $(NH_4)HCO_3$, pH 8.5, in the dark for 20 min prior to centrifugation (20,800×g, 15 min). The 10 kDa filters were transferred to fresh centrifuge tubes, and 2 µg trypsin (200 µL, 0.01 µg/mL in 50 mM $(NH_4)HCO_3$, pH 8.5, and 1 mM $CaCl_2$) was added to obtain an enzyme:protein ratio of ~1.15. Replicate tubes were incubated at 37° C. for 16 hr. After incubation, the filters were centrifuged (20,800×g, 15 min) and the filtrates containing digested peptides were collected. The filters were washed twice with 200 µL of 50 mM $(NH_4)HCO_3$, pH 8.5, and the filtrates combined, lyophilized, and stored at −80° C. until further analysis. For LC-MS, the tryptic peptides were resuspended in 12 µL of 1% formic acid and run on a QTRAP 6500+ LC-MS and quantified.

For 60 min pepsin digestion, His-Pavsa-Δ4D protein was diluted in UA buffer to ~1.3 µg/µL. An aliquot of the protein extract (equivalent to ~200 µg) was subjected to filter-assisted sample preparation (FASP). See Wisniewski et al., 2009. The protein extract was applied to a 10 kDa MWCO filter (Millipore), washed with two 200 µL volumes of UA buffer with centrifugation (20,800×g, 15 min). The buffer was exchanged using 50 mM $(NH_4)HCO_3$, pH 8.0, by two consecutive wash/centrifugation steps. The pH was adjusted with acidified 50 mM $(NH_4)HCO_3$ (pH 1.2) by two consecutive wash/centrifugation steps. The 10 kDa filters were transferred to fresh centrifuge tubes and 600 µg pepsin (200 µL, 3 µg/µL in 50 mM acidified $(NH_4)HCO_3$, pH 1.2) was added to obtain an enzyme:protein ratio of 3:1. The filters were incubated with the pepsin for 60 min at 37° C., then transferred to clean tubes. The filtrates (containing the digested peptides) were collected following centrifugation (20,800×g, 10 min). The filters were washed with 200 µL of 100 mM $(NH_4)HCO_3$ and the filtrates combined and lyophilized, then stored at −20° C. until further analysis. For LC-MS/MS, the resultant peptides were reconstituted in 12.5 µL of 1% formic acid and a 10 µL aliquot analyzed by LC-MS/MS.

For trypsin digestion, the His-Pavsa-Δ4D protein was diluted in UA buffer (8 M urea, 0.1 M Tris-HCl, pH 8.5) to ~1.3 µg/µL. The protein was reduced by addition of 100 mM DTT with incubation on a shaker for 50 min at room temp. An aliquot of the protein extract (equivalent to ~300 µg) was subjected to F ASP. Wisniewski et al., 2009. The protein extract was applied to a 10 kDa MWCO filter, washed with two 200 µL volumes of UA buffer with centrifugation (20,800×g, 15 min). The buffer was then exchanged using 50 mM $(NH_4)HCO_3$, pH 8.0, by two consecutive wash/centrifugation steps. Then, 30 µL sequencing grade porcine trypsin, at a concentration of 1 µg/µL in 100 mM $(NH_4)HCO_3$, was added to the protein on the 10 kDa filter and incubated for 16 hr at 37° C. in a wet chamber. Each filter was then transferred to a fresh centrifuge tube, and the filtrate containing the digested peptides collected following centrifugation (20,800×g, 10 min). Filters were washed with 200 µL of 100 mM $(NH_4)HCO_3$, and the filtrates combined and lyophilized. The tryptic peptides were subsequently resuspended in 30 µL. of 1% formic acid (FA) and a 12 µL aliquot analyzed by LC-MS/MS.

Proteolytically digested (either pepsin or trypsin) proteins were analyzed with chromatographic separation (2%/min linear gradient from 2%-40% acetonitrile) using a nano HPLC system (Shimadzu Sci., Rydalmere, AU) coupled directly to a TripleTOF 5600 MS (AB SCIEX). See Colgrave et al, 2014. ProteinPilot™ 4.0 software (AB SCIEX) with the Paragon Algorithm was used for protein identification. Shilov et al, 2007. Tandem mass spectrometry data was searched against in silico tryptic digests of a custom-built database. The database (76,110 sequences) comprised the Noctuidae and Baculovirus proteins of the Uniprot-KB database (v2015/11) appended with the transgenic protein, and searched additionally against a database of contaminant proteins (known as the common repository of adventitious proteins). The search parameters were defined as: (1) no modification to cysteine and pepsin as the digestion enzyme; or (2) iodoacetamide modified for cysteine alkylation and trypsin as the digestion enzyme. Additional modifications and cleavages have been defined previously. Colgrave et al., 2014. The database search results were manually curated to yield protein identifications using a 1% global false discovery rate (FDR) determined by the in-built FDR tool within ProteinPilot software. Tang et al., 7 J. Proteome Res. 3661 (2008).

Either 5 μL of native peptic peptides (Table 18) or reduced and alkylated tryptic peptides (Table 19) were chromatographically separated on a Nexera UHPLC (Shimadzu) and analyzed on a QTRAP 6500+ mass spectrometer (AB SCIEX). Colgrave et al, 2014. Quantification was achieved using scheduled MRM scanning experiments using a 60 sec detection window for each MRM transition and a 0.2 sec cycle time. Peaks were integrated using MultiQuant v3.0 (AB SCIEX) wherein all three transitions were required to co-elute at the same retention time (RT, min) with a signal-to-noise (S/N)>3 for detection and a S/N>5 for quantification. The graphs showing digestibility of the Pavsa-Δ4D protein were generated in GraphPad Prism v6 software.

For the tryptic data, peptide summaries generated by ProteinPilot software were used to select peptides that yielded intense peaks and were fully tryptic, i.e., no unusual or missed cleavages. For the pepsin data, peptide summaries generated by ProteinPilot were used to select peptides that (a) yielded intense peaks, (b) were consistently observed in the replicate digests, and (c) were present after 30 min and 60 min incubation with pepsin. As pepsin is non-specific, many of these peptide products were overlapping or contained missed cleavages. MRM transitions (Tables 18 and 19) were determined for each peptide where the precursor ion (Q1) m/z and the fragment ion (Q3) m/z values were determined from the data collected in the discovery experiments. Three transitions were used per peptide (with eight peptides from Pavsa-Δ4D), wherein the peak area of the three MRM transitions were summed.

Allergenic reactions require that a protein or protein fragment simultaneously bind to two IgE molecules in order to induce mast cell degranulation (Lack et al, 2002). This IgE binding places theoretical limits on the peptide size of between 1500 and 3500 Da. The complete digestion of a protein by a single enzyme is difficult to judge, especially when employing a non-specific enzyme such as pepsin. Although it is possible to judge the disappearance of the intact protein on a gel or by western blotting techniques, the protein may be hydrolyzed once (cleaved at a single site), or multiple times, often yielding small and overlapping fragments. Gel analysis using various staining or antibody techniques can typically detect peptides larger than ~3,000 Da. Solely employing gel analysis in order to judge the completeness of digestion requires a high level of purity. When employing antibodies, the hydrolysis of a protein by a proteolytic enzyme may result in cleavage of the epitope, thus rendering antibody-based detection methods unsuitable. Likewise, cleavage of a protein at a single site may yield two protein fragments in which only one fragment contains the epitope while the other fragment does not. In that instance, large protein fragments may evade detection.

By using LC-MS/MS analysis, the peptide products resulting from both pepsin and trypsin digestions can be determined qualitatively and quantitatively. LC-MS analysis can simultaneously monitor peptides spanning the entire protein length that are generated by proteolytic digestion. The combined pepsin trypsin approach to analyze digestibility, as in this Example, mimics the typical mammalian digestive system that exposes food proteins to both pepsin (stomach) and trypsin (intestine) enzymes in transit through the gut.

Figure 29A:
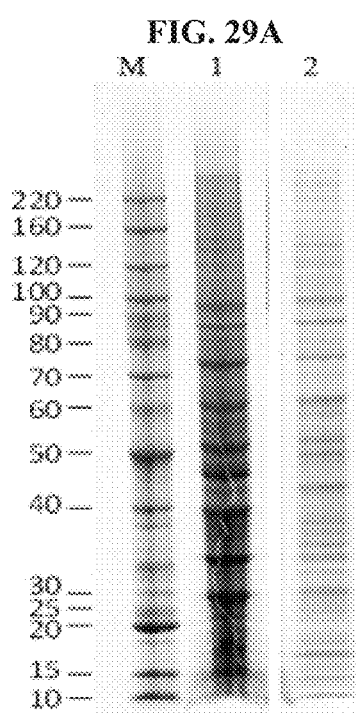
FIGS. 29A and 29B presents photos showing characterization of His-Pavsa-Δ4D protein expressed in baculovirus-infected insect cells.
Figure 29B:
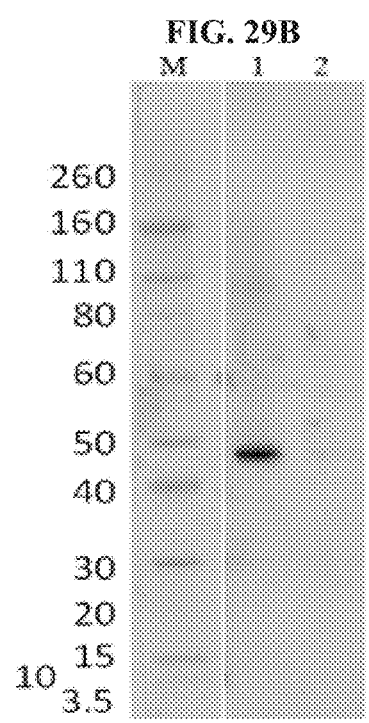

The concentration of total Pavsa-Δ4D protein extracted was estimated at ~5.7 mg/mL, as total protein from the precipitated pellet and supernatant were assessed by SDS-PAGE (FIG. 29A). The protein was also transferred to PVDF membrane and confirmed with western blot using an anti His-tag antibody. The expected molecular weight (MW) of the His-Pavsa-Δ4D fusion protein is 51 kDa (see SEQ ID NO: 16). A specific protein band close to 50 kDa was detected in the protein pellet, but very low levels were detected in the supernatant (FIG. 29B), suggesting good recovery of intact protein by protein precipitation.

Figure 27A:
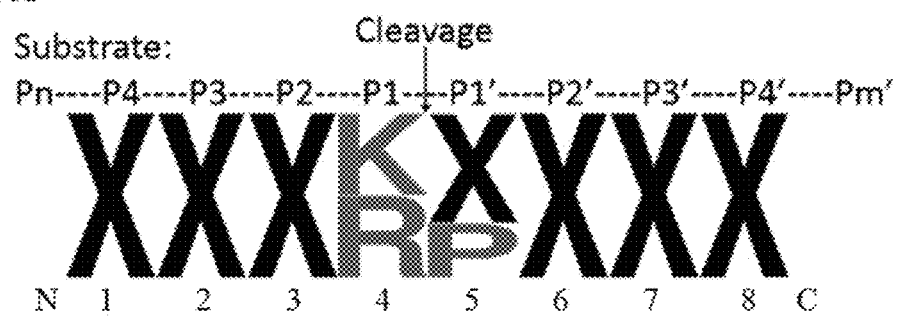
FIGS. 27A and 27B are schemes showing the specificity of proteolytic enzymes used in the Examples, in which the substrate has amino acid residues at positions Pn, P4, etc., to Pm', (also #1 to #8 in the N- to C-terminal direction).
Figure 27B:
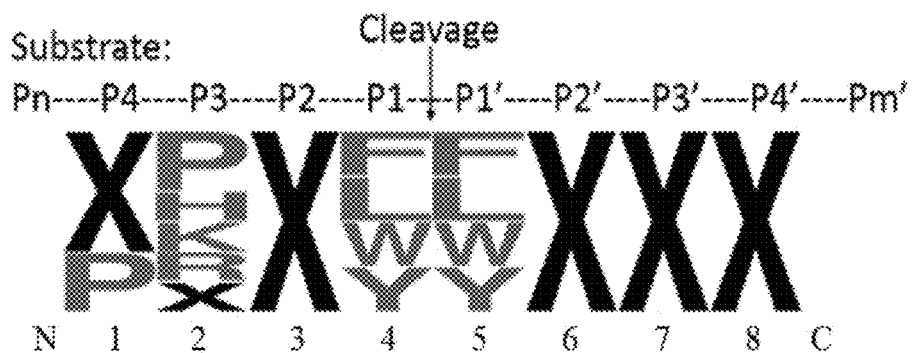

As depicted in FIG. 27A, pepsin results in cleavage at Phe (F), Tyr (Y), Trp (W), and Leu (L) resulting in hundreds of possible Pavsa-Δ4D peptide fragments in which missed cleavages are commonly observed. In silico analysis of the Pavsa-Δ4D protein digested by pepsin suggested the theoretical pepsin cleavage map shown in FIG. 30A. In this Example, the peptide fragments of His-Pavsa-Δ4D persisting after pepsin digestion for 60 min were characterized by untargeted LC-MS/MS, as shown in FIG. 30I. The fully tryptic peptide product, FHVGSLASTEEPVAAD-EGYLQLCAR (residues 88-112 of SEQ ID NO: 7) was not detected in this digest (representative sequence coverage shown); but this peptide was detected in an alternate digest and as such was included in the MRM method.

Trypsin is comparatively specific, and digestion results in cleavage at Lys (K) and Arg (R) resulting in thirty-seven possible Pavsa-Δ4D peptide fragments, of which twenty-two were in the mass range suited to LC-MS/MS analysis. See FIG. 30C. In this Example, the Pavsa-Δ4D peptide fragments present after trypsin digestion (for 16 hr) were characterized by untargeted LC-MS/MS as shown in FIG. 30D.

To assess the digestibility of the His-Pavsa-Δ4D protein, a targeted LC-MS/MS method was developed based on the use of multiple reaction monitoring (MRM) mass spectrometry (MS). See Lange et al., 4 Mol. Syst. Biol. 222 (2008). Both the appearance and the increase of the peptic peptides during the time course of pepsin digestion were used as the evidence of the protein digestibility. Moreover, the rapid decline of the tryptic peptides subsequent to pepsin digestion served as confirmation of the protein digestibility.

In order to select peptides to quantify by this method, the digestion products resulting from both pepsin and trypsin digestion were characterized. Peptides that were identified with 95% confidence and that yielded intense signals in the MS were selected for relative quantification. Eight peptides that spanned the length of the His-Pavsa-Δ4D protein were selected from the digestion of the His-Pavsa-Δ4D protein, and are summarized in Table 18 and Table 19.

TABLE 18

Peptide MRM transitions for Pavsa-Δ4D pepsin products

| Peptide | RT | Q1 m/z | z | Q3 m/z | Fragment | CE |
|---|---|---|---|---|---|---|
| FTRKDVADRPDL (aa 25-36, SEQ ID NO: 7) | 2.97 | 478.256 | 3+ | 615.310 | y5+ | 27.0 |
| | | | | 686.347 | y6+ | 27.0 |
| | | | | 785.415 | y7+ | 27.0 |

TABLE 18-continued

Peptide MRM transitions for Pavsa-Δ4D pepsin products

| Peptide | RT | Q1 m/z | z | Q3 m/z | Fragment | CE |
|---|---|---|---|---|---|---|
| TRKDVADRPDL (aa 26-36, SEQ ID NO: 7) | 2.20 | 429.234 | 3+ | 501.278 | b4+ | 24.6 |
| | | | | 615.310 | y5+ | 24.6 |
| | | | | 686.347 | y6+ | 24.6 |
| FRSEHPGGAHF (aa 49-59, SEQ ID NO: 7) | 2.19 | 414.532 | 3+ | 657.310 | b5+ | 19.9 |
| | | | | 488.225 | y5+ | 23.9 |
| | | | | 585.278 | y6+ | 19.9 |
| YLLPGETM (aa 249-256, SEQ ID NO: 7) | 5.99 | 462.231 | 2+ | 534.223 | y5+ | 21.6 |
| | | | | 673.357 | b6+ | 21.6 |
| | | | | 774.403 | b7+ | 21.6 |
| WRWEGEPISKL (aa 272-282, SEQ ID NO: 7) | 5.70 | 467.582 | 3+ | 557.366 | y5+ | 20.4 |
| | | | | 715.331 | b5+ | 20.4 |
| | | | | 844.374 | b6+ | 20.4 |
| LKRQAETSSNVGGPLL (aa 361-376, SEQ ID NO: 7) | 4.19 | 557.313 | 3+ | 664.850 | b13++ | 24.8 |
| | | | | 769.918 | b15++ | 24.8 |
| | | | | 756.425 | y8+ | 24.8 |
| PRLAPLVKAEL (aa 401-411, SEQ ID NO: 7) | 5.32 | 402.924 | 3+ | 438.282 | b4+ | 19.3 |
| | | | | 559.345 | y5+ | 17.3 |
| | | | | 648.419 | b6+ | 17.3 |
| APLVKAEL (aa 404-411, SEQ ID NO: 7) | 4.51 | 420.763 | 2+ | 460.277 | y4+ | 25.6 |
| | | | | 559.345 | y5+ | 21.6 |
| | | | | 672.429 | y6+ | 19.6 |

Pavsa-Δ4D sequence:[b] (SEQ ID NO: 7)

MPPSAAKQMGASTGVHAGVTDSSAF<u>TRKDVADRPDL</u>TIVGDSVYDAKAF<u>RSEHPGGAHF</u>VSLFGGRDAT
EAFMEYHRRAWPKSRMSRFHVGSLASTEEPVAADEGYLQLCARIAKMVPSVSSGFAPASYWVKAGLILG
SAIALEAYMLYAGKRLLPSIVLGWLFALIGLNIQHDANHGALSKSASVNLALGLCQDWIGGSMILWLQE
HVVMHHLHTNDVDKDPDQKAHGALRLKPTDAWSPMHWLQH<u>LYLLPGETM</u>YAFKLLELDISELVM<u>WRWEG
EPISKL</u>AGYLFMPSLLLKLTEWARFVALPLYLAPSVHTAVCIAATVMTGSFYLAFFFFISHNFEGVASV
GPDGSITSMTRGASF<u>LKRQAETSSNVGGPLL</u>ATLNGGLNYQIEHHLFPRVHHGFYP<u>RL<u>APLVKAEL</u></u>EAR
GIEYKHYPTIWSNLASTIRHMYALGRRPRSKAE

RT, retention time (min); Q1 m/z, precursor ion mass-to-charge ratio (m/z); z, charge state; Q3 m/z, fragment ion m/z; CE, collision energy in V.
[b]Pavsa-Δ4D sequence with mapped peptic peptides (underlined). For pepsin, different cleavage variants were observed owing to the incomplete digestion and these peptides have been differentiated by single or double underline.

TABLE 19

Peptide MRM transitions for Pavsa-Δ4D trypsin products

| Peptide | RT | Q1 m/z | z | Q3 m/z | Fragment | CE |
|---|---|---|---|---|---|---|
| QMGASTGVHAGVTDSSAFTR (aa 8-27, SEQ ID NO: 7) | 4.00 | 660.647 | 3+ | 884.411 | y8+ | 33.1 |
| | | | | 1040.501 | y10+ | 33.1 |
| | | | | 1111.538 | y11+ | 33.1 |
| DVADRPDLTIVGDSVYDAK (aa 29-47, SEQ ID NO: 7) | 5.70 | 683.676 | 3+ | 953.457 | y9+ | 34.8 |
| | | | | 854.389 | y8+ | 34.8 |
| | | | | 797.368 | y7+ | 34.8 |
| SEHPGGAHFVSLFGGR (aa 51-66, SEQ ID NO: 7) | 4.95 | 827.908 | 2+ | 1301.675 | y13+ | 38.7 |
| | | | | 1019.542 | y9+ | 38.7 |
| | | | | 882.483 | y8+ | 38.7 |
| FHVGSLASTEEPVAADEGYLQLC*AR (aa 88-112, SEQ ID NO: 7) | 6.22 | 907.438 | 3+ | 1109.541 | y9+ | 47.0 |
| | | | | 980.498 | y8+ | 47.0 |
| | | | | 923.477 | y7+ | 47.0 |
| DATEAFMEYHR (aa 67-77, SEQ ID NO: 7) | 4.27 | 457.200 | 3+ | 475.242 | y3+ | 24.1 |
| | | | | 604.284 | y4+ | 24.1 |
| | | | | 735.325 | y5+ | 24.1 |
| VHHGFYPR (aa 395-402, SEQ ID NO: 7) | 2.07 | 506.759 | 2+ | 776.384 | y6+ | 27.1 |
| | | | | 639.325 | y5+ | 27.1 |
| | | | | 582.303 | y4+ | 27.1 |

TABLE 19-continued

Peptide MRM transitions for Pavsa-Δ4D trypsin products

| Peptide | RT | Q1 m/z | z | Q3 m/z | Fragment | CE |
|---|---|---|---|---|---|---|
| LAPLVK | 3.72 | 320.720 | 2+ | 456.319 | y4+ | 21.0 |
| (aa 403-408, SEQ ID NO: 7) | | | | 527.356 | y5+ | 21.0 |
| | | | | 359.266 | y3+ | 21.0 |
| HMYALGR | 2.77 | 424.200 | 2+ | 424.216 | y7++ | 26.2 |
| (aa 434-440, SEQ ID NO: 7) | | | | 579.326 | y5+ | 26.2 |
| | | | | 710.366 | y6+ | 26.2 |

Pavsa-Δ4D sequence:[b]

(SEQ ID NO: 7)
MPPSAAKQMGASTGVHAGVTDSSAFTRKDVADRPDLTIVGDSVYDAKAFRSEHPGGAHFVSLFGGRDAT
EAFMEYHRRAWPKSRMSRFHVGSLASTEEPVAADEGYLQLCARIAKMVPSVSSGFAPASYWVKAGLILG
SAIALEAYMLYAGKRLLPSIVIGWLFALIGLNIQHDANHGALSKSASVNLALGLCQDWIGGSMILWLQE
HVVMHHLHTNDVDKDPDQKAHGALRLKPTDAWSPMHWLQHLYLLPGETMYAFKLLFLDISELVMWRWEG
EPISKLAGYLFMPSLLLKLTFWARFVALPLYLAPSVHTAVCIAATVMTGSFYLAFFFFISHNFEGVASV
GPDGSITSMTRGASFLKRQAETSSNVGGPLLATLNGGLNYQIEHHLFPRVHHGFYPRLAPLVKAELEAR
GIEYKHYPTIWSNLASTLRHMYALGRRPRSKAE

RT, retention time (min); Q1 m/z, precursor ion mass-to-charge ratio (m/z); z, charge state;
Q3 m/z, fragment ion m/z; CE, collision energy in V.
[b]Pavsa-Δ4D sequence with mapped tryptic peptides (bold, underlined). For trypsin, all peptides selected were fully tryptic, i.e., contained no missed cleavages. As some of the peptides were adjacent in the sequence, these have been differentiated by single or double underline.

Digestibility of His-Pavsa-Δ4D in SGF was assessed by LC-MRM-MS method as described above. Characterization and quantification of the targeted peptic peptides showed the rapid degradation of His-Pavsa-Δ4D. Pepsin digestion data shown in FIG. 31A as the mean of five replicate digests relative percentage of the maximum detected MRM peak area (sum of three transitions) per peptide across the time points (0, 5, 10, 15, 30, 60 min).

Figure 31A:
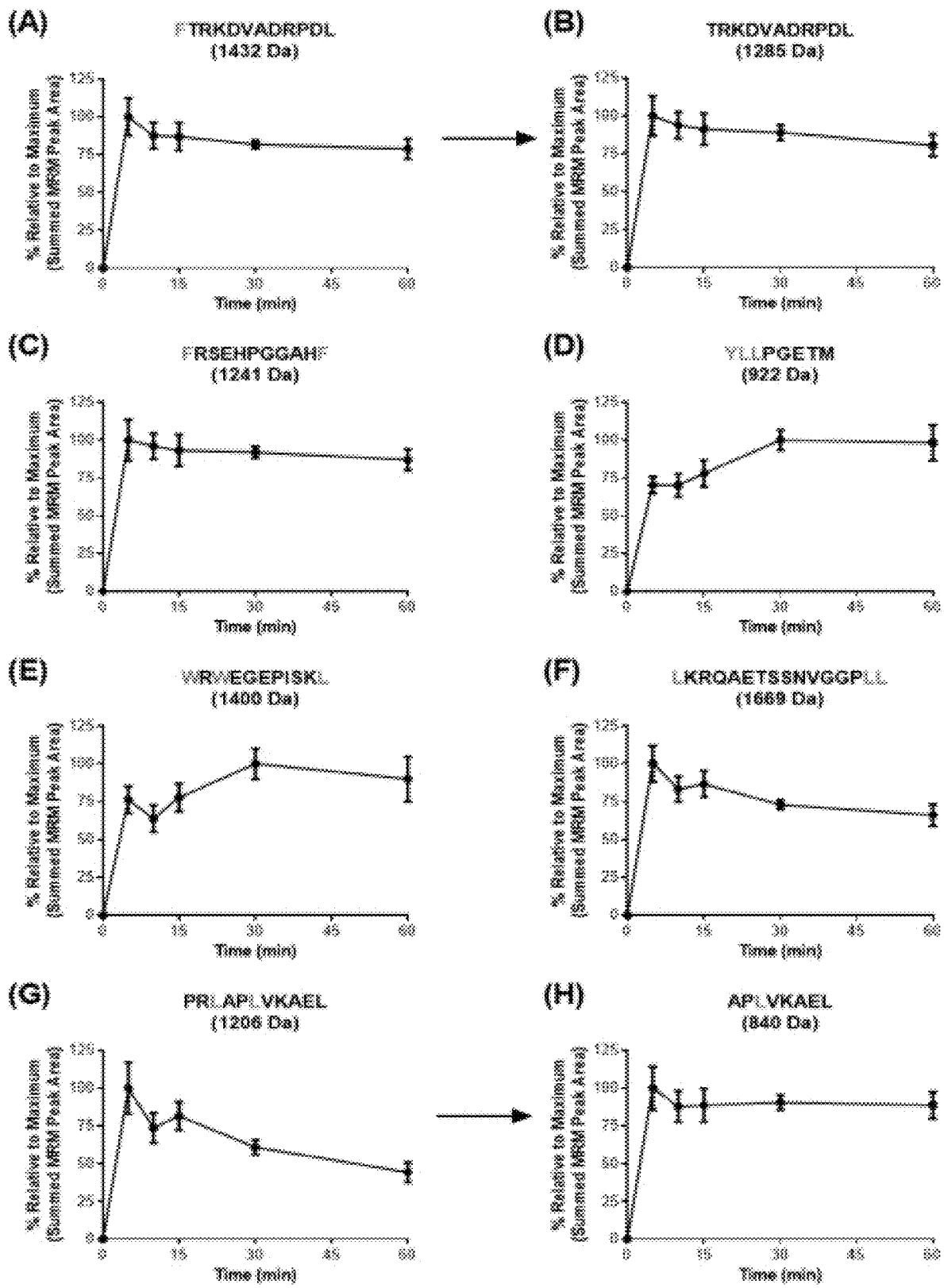
FIG. 31A, Panels (A)-(H), shows LC-MRM-MS analysis of pepsin proteolytic fragments. The response in the LC-MS system (measured as peak area) was converted to a percentage relative to the maximum peak area observed during pepsin digestion. The experimental control was time 0 with no pepsin addition. The peptides are graphed in order from protein N- to C-terminus. The peptide sequence (and calculated molecular weight) are denoted above each graph. Arrows indicate a subsequent cleavage to yield a secondary cleavage variant; error bars denote SD; potential sites for secondary pepsin cleavage are: Panel (A): F; (C): F, F (D): YLL; (E): W, W, L; (F): L, LL; (G): L, L; (H): L; Control: time 0, no pepsin.

Four of the peptides characterized and quantified after pepsin digestion of His-Pavsa-Δ4D were cleavage variants (FIG. 31A) The black arrows in FIG. 31A Panels (A)→(B), and (G)→(H) indicate that the peptide denoted in the left panel was cleaved further by pepsin to yield the peptide in the right panel. All the peptic peptides monitored were produced rapidly (<15 min), and many reached an equilibrium over this time frame. The peptic peptides monitored may not represent the fully cleaved final product, however, because pepsin is relatively non-specific. In some cases, a decrease in peptide amount was noted over time. For example, PRLAPLVKAEL (aa 401-411, SEQ ID NO: 7) (FIG. 31(C)) decreased after 5 min, and its product APLV-KAEL (aa 404-411, SEQ ID NO: 7) increased from 10 min-15 min before also decreasing. Additionally, APLV-KAEL (aa 404-411, SEQ ID NO: 7) could be cleaved further to yield even smaller peptide fragments that were not monitored, e.g., LVKAEL/VKAEL (aa 406-411, SEQ ID NO: 7/(aa 407-411, SEQ ID NO: 7). Several other examples of pepsin proteolysis products containing missed cleavages (indicated by underlined font in peptide sequence), therefore susceptible to further degradation, were monitored (FIG. 31A, Panels (A), (C)-(I)). In fact, only one Pavsa-Δ4D peptide, TRKDVADRPDL (aa 26-36, SEQ ID NO: 7), contains no predicted secondary cleavage site (FIG. 30B). The appearance of these peptides in the digest is taken as evidence of the degradation and therefore digestibility of the Pavsa-Δ4D protein. Six of the eight peptides monitored reached a peak at 5 min. The remaining two peptides had reached 70% of maximum response by 5 min and peaked by 30 min during the pepsin time course (FIG. 30C). These two peptides were located in the central region of the intact Pavsa-Δ4D protein (Table 18).

Figure 31B:
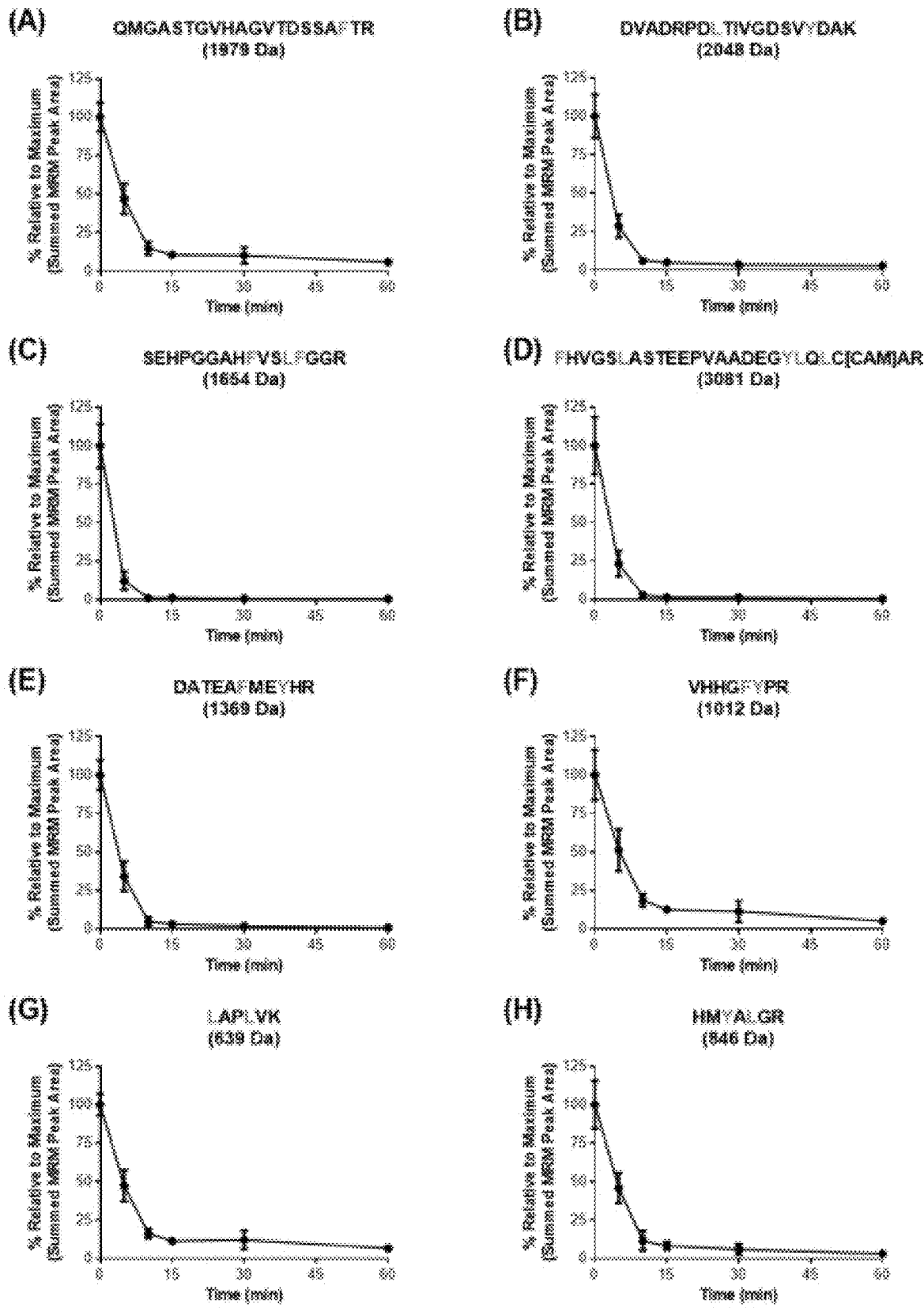
FIG. 31B shows Quantification of the tryptic peptide products of His10::Pavsa-Δ4D after combined pepsin-trypsin digestion. The trypsin data has been presented as the mean percentage (n=5 replicate digests) reduction relative to the experimental control at 0 min (no pepsin addition, measured as MRM peak area, sum of three transitions) per peptide across the time points (0, 5, 10, 15, 30, 60 min). The peptides are graphed in order from protein N- to C-terminus. The peptide sequence (and calculated molecular weight) are denoted above each graph. Error bars denote SD; potential sites for secondary pepsin cleavage are: Panel (A): F; (B): L, Y; (C): F, LF (D): F, L, YL, L; (E): F, Y; (F): Y, L; (G): L, L; (H): Y, L.

The rapid degradation of the His-Pavsa-Δ4D protein, demonstrated by the rapid increase of peptic peptides, was further demonstrated by rapid decline of tryptic peptides in trypsin digestion after pepsin digestion (combined pepsin-trypsin digestion). The tryptic peptides monitored after the pepsin digest show a rapid decline in the first 5-10 min and then a further decline over the remainder of the 60 min duration experiment (FIG. 31B). The summed MRM peak area of the tryptic peptides without pepsin digestion (0 min) as the undigested control. The summed MRM peak area of the tryptic peptides, after digestion by pepsin for 5, 10, 15, 30, 45, and 60 min and followed with digestion by trypsin, were calculated as the percentage relative to the undigested control as the indicator of protein cleavage. It is estimated that >93% of the protein was cleaved after 60 min, on the basis of the disappearance of tryptic peptides. The peptides containing multiple pepsin cleavage sites are (where X↓X represents the pepsin cleavage site) are: DVADRPDL↓TIVGDSVY↓DAK (aa 29-47, SEQ ID NO: 7), SEHPGGAHF↓VSL↓F↓GGR (aa 29-47, SEQ ID NO: 7); F↓HVGSL↓ASTEEPVAADEGY↓L↓QL↓C[CAM]AR (SEQ ID NO: 11); DATEAF↓M↓EY↓HR (aa 67-77, SEQ ID NO: 7), L↓APL↓VK (aa 403-408, SEQ ID NO: 7); and HM↓Y↓AL↓GR (aa 434-440, SEQ ID NO: 7); and these were reduced to 3.0, 0.4, 0.6, 1.2, 6.7, and 2.8% of the undigested control, respectively (FIG. 31B Panels (A)-(H)). This interpretation is supported by analysis of the digested peptides on the TripleTOF 5600 LC-MS/MS, which showed that these peptides are more frequently fragmented to yield smaller fragments after 30 min-60 min. The tryptic peptides containing fewer sites: QMGASTGVHAGVTDSSAF↓TR (aa 8-27, SEQ ID NO: 7) (with a single site) or VHHGF↓Y↓PR (aa 395-402, SEQ ID NO: 7) (where the histidine in position P3 is known to hinder pepsin cleavage) were reduced to 5.8 and 5.1% respectively. The higher percentage of LAPLVK (aa 403-408 of SEQ ID NO: 7) observed, despite containing two potential pepsin cleavage sites (L1 and L4), can be explained in relation to the incomplete peptic digestion product: PRLAPLVKAEL (aa 401-412, SEQ ID NO: 7), noted to persist at 60 min and hence be available for tryptic digestion to yield the fragment LAPLVK (aa 403-408 of SEQ ID NO: 7). Overall, it was observed that the peptides from the N-terminus to center of the protein were liberated rapidly with <15% remaining after 10 min (Table 20).

TABLE 20

Percentage of each tryptic peptide remaining during pepsin time course

| Peptide Sequence | Time (min) | | | | |
|---|---|---|---|---|---|
| | 5 | 10 | 15 | 30 | 60 |
| QMGASTGVHAGVTDSSAFTR[1] | 46.9 | 14.8 | 10.4 | 10.2 | 5.8 |
| DVADRPDLTIVGDSVYDAK[2] | 28.6 | 6.2 | 5.0 | 3.6 | 3.0 |
| SEHPGGAHFVSLFGGR[3] | 12.3 | 1.0 | 1.2 | 0.6 | 0.4 |
| FHVGSLASTEEPV-AADEGYLOLC[CAM]AR[4] | 23.2 | 2.8 | 1.5 | 1.2 | 0.4 |
| DATEAFMEYHR[5] | 34.2 | 4.8 | 3.2 | 1.8 | 0.9 |
| VHHGFYPR[6] | 51.2 | 18.6 | 12.4 | 11.3 | 5.1 |
| LAPLVK[7] | 47.4 | 16.3 | 11.4 | 12.1 | 6.7 |
| HMYALGR[8] | 45.1 | 8.2 | 7.7 | 5.4 | 3.0 |

[1]Residues (aa) 8-27, SEQ ID NO: 7;
[2]aa 29-47, SEQ ID NO: 7;
[3]aa 29-47, SEQ ID NO: 7;
[4]SEQ ID NO: 11;
[5]aa 67-77, SEQ ID NO: 7;
[6]aa 395-402, SEQ ID NO: 7;
[7]aa 403-408, SEQ ID NO: 7;
[8]aa 434-440, SEQ ID NO: 7

Although there were still some peptides remained after 60 min digestion, within as few as 10 min only 1% of the tryptic peptide SEHPGGAHFVSLFGGR (aa 29 47 of SEQ ID NO: 7) remained (Table 20), indicating that 99% of the intact protein was degraded. The existence of some tryptic peptides at low levels after 60 min only suggested that the intact protein was degraded into small peptides by pepsin, and these peptides were detectable. The tryptic peptide SEHPGGAHFVSLFGGR (aa 29 47, SEQ ID NO: 7) was reduced to 0.4% after 60 min, indicating that essentially there was no intact protein remained beyond this pepsin digestion time.

Additionally, although Pavsa-Δ4D, expressed as the His-tag fusion protein, could be analyzed by western blot using an anti-His-tag antibody, western blot analysis can only monitor the fusion region, rather than whole protein, which would be problematic when the His-tag is cleaved off, for example during SGF digestion. In addition, the anti-His-tag antibody is not suitable for quantification of the native Pavsa-Δ4D (unfused) protein in transgenic canola. Thus, an alternative approach using LC-MRM-MS analysis was developed, which can be applied to both the quantification and stability of the target protein. The results herein demonstrate that the LC-MS approach is suitable for such applications. This method is at least as sensitive as traditional western blot, which normally detects in the ng to μg range: the LC-MRM-MS approach detected Pavsa-Δ4D levels as low as 7.8 femtomoles (injected on-column), which equates to ~385 μg on a protein scale. Additionally, although western blot may detect a limited number of epitopes (one or two) from the protein, the present embodiment targeted eight peptides, spanning the intact Pavsa-Δ4D protein, thus providing a more complete understanding of the kinetics of digestion and the susceptibility of specific regions of the Pavsa-Δ4D protein to proteolysis. Because of the filtration and washing steps after pepsin digestion with five replicates, the earliest practical time point during this particular protocol was 5 min. Nevertheless, this example enables use of LC-MRM-MS for protein digestibility analysis.

For stability analysis of transgenic, recalcitrant or membrane-associated ω3LCPUFA enzymes, Pavsa-Δ4D protein was used as the representative of the three front-end desaturases engineered in the ω3LCPUFA canola. Front-end desaturases introduce a double bond between an existing double bond and the carboxyl end of fatty acids. Additionally, front-end desaturases all contain a cytochrome b5-like domain at the N-terminus fused with a desaturase domain with three conserved histidine motifs required for desaturase activity. Zhou et al., 2007. The front-end desaturases, including Δ4-, Δ5-, Δ6- and Δ8-desaturases, exist in a wide range of organisms including algae, diatom, fungi, moss, bacteria and plants. Some of these front-end desaturases are also common in food or in food production. The results of this Example demonstrated that greater than 80% or 99% of the full-length Pavsa-Δ4D protein digested within 10 min, and >93%, or 99.6% of the full-length Pavsa-Δ4D protein was digested within 60 min of incubation in pepsin, when analyzed by LC-MS/MS. The combined pepsin-trypsin assay showed a rapid decline in the tryptic peptides that were used as a proxy for the presence of intact protein. In addition to rapid digestion of the full-length Pavsa-Δ4D protein in SGF, Pavsa-Δ4D protein represents a negligible portion of the total protein present in transgenic canola mature seed.

Example 5. The In Vitro Stability of *Pyramimonas Cordata* Δ5-Elongase (Pyrco-Δ5E) Protein This Example characterizes the microalgae fatty acid elongase, Pyrco-Δ5E, included in the engineering of transgenic canola to catalyze the elongation of EPA into DPA ($20:5^{\Delta 5,8,11,14,17} \rightarrow 22:5^{\Delta 7,10,13,16,19}$) This Example assesses the in vitro stability of this recalcitrant/intractable membrane-associated protein both in SGF comprising pepsin and in combination with the pepsin-trypsin assay, using MS to monitor precise degradation/digestion products. The extent of protein digestion was evaluated by the appearance and disappearance of peptic products and the disappearance of tryptic peptide products as a proxy for intact protein. By using LC-MS/MS analysis, the peptide products resulting from both pepsin and trypsin digestions could first be determined qualitatively and then subsequently a quantitative LC-MS/MS for the detection of these peptide fragments was developed. LC-MS analysis is capable of simultaneously monitoring peptides spanning the entire protein sequence that are generated by proteolytic digestion. The approach to analyze digestibility in this Example mimics the typical mammalian digestive system that exposes food proteins to both pepsin (stomach) and trypsin (intestine) enzymes in transit through the gut. The results described herein show that greater than 75% Pyrco-Δ5E protein was digested within 5 min, and full-length Pyrco-Δ5E protein was rapidly digested within 60 min of incubation in pepsin, producing a suite of pepsin peptide products <3,000 Da that spanned the entire length of the protein when analyzed using LC-MS/MS. The results show that this integral membrane protein was readily digestible in pepsin or trypsin. Rapid digestion of the full-length protein indicates that it is highly unlikely that Pyrco-Δ5E will pose any safety concern to human health.

A codon optimized Pyrco-15E gene was cloned from *P. cordata* and expressed in Sf9 cells using the approach described in Example 4. The Pyrco-Δ5E protein was expressed in Sf9 insect cell line infected with baculovirus as a fusion protein with a ten-histidine residue (His) tag at the N-terminus of the protein (His-Pyrco-Δ5E). Cells were grown by GeneArt (2 L expression in Sf99 cells infected with 1:100 virus dilution and harvested 48 hr post-infection) and the thawed cells were resuspended in lysis buffer (100 mL per 20 g of cell pellet) containing 20 mM Tris, pH 8.0, 150 mM NaCl, 10% glycerol, 5 mM DTT, 5 mM EDTA, 1 mM PMSF and two protease inhibitor tablets per 100 mL (Roche). The cells were lysed by sonication and the cellular debris removed by centrifugation. The resultant supernatant was centrifuged at 200,000×g for 60 min at 4° C. to isolate the membrane fraction. The pellet was resuspended in 50 mL 20 mM Tris, pH 7.5, 150 mM NaCl, 10% glycerol, 5 mM DTT, and 10 mM imidazole. To solubilize the His-Pyrco-Δ5E from the membrane fraction 1% (w/v) FosCholine-16 (Glycon Biochemicals GmbH) was added to the mixture and incubated for 2 hr at 4° C. The mixture was then centrifuged for 60 min at 200,000×g at 4° C. and 10 mL Ni-Sepharose FF (GE Healthcare, AU) was added to the supernatant and the slurry left to bind overnight at 4° C. After binding, the resin was poured into an empty column and washed with the binding buffer. The protein was eluted with an imidazole gradient. Fractions were analyzed by SDS-PAGE and western blots.

Fractions containing the His-Pyrco-Δ5E were pooled and buffer exchanged into MES buffer (20 mM MES pH 6.0, 50 mM NaCl, 10% glycerol, 5 mM DTT and 0.01% FosCholine-16) using a HiPrep 26/10 desalting column (GE Healthcare, AU). The sample was injected onto a 5 mL Hitrap SP column (GE Healthcare, AU) and eluted with a NaCl gradient. The fractions were analyzed by SDS-PAGE, and fractions containing the His-Pyrco-Δ5E pooled and buffer exchanged using a HiPrep 26/10 column into PBS buffer containing 10% glycerol and 0.01% FosCholine-16. The fractions containing the His-Pyrco-Δ5E were pooled and concentrated to 1.7 mg/mL, and flash-frozen in liquid nitrogen and stored at −80° C. Concentrated protein was analyzed by SDS-PAGE and western blotting using an anti-His HRP conjugated antibody (A7058, Sigma-Aldrich) (FIG. 32). The estimated purity was ~90%.

After extraction, the His-Pyrco-Δ5E protein solution contained 1.7 mg/mL in PBS, 0.01% FosCholine-16, and 10% glycerol. An aliquot of the protein extract (equivalent to ~5 µg) was subjected to FASP. Wisniewski et al., 2009. The extract was applied to a 10 kDa MWCO filter (Millipore, AU), diluted to 200 µL with UA buffer (8 M urea, 0.1 M Tris-HCl, pH 8.5) before centrifugation (20,800×g, 15 min), and the filter washed with two 200 µL, volumes of UA buffer with centrifugation (20,800×g, 15 min). The protein on the filter was reduced by DTT (50 mM, 100 µL) incubation at room temp for 50 min with shaking. The filter was washed with two 200 µL volumes of UA buffer with centrifugation (20,800×g, 15 min). Cysteine residues were alkylated by LAM (50 mM, 100 µL) incubation for 20 min at room temp in the dark, then the filter washed with two 200 µL volumes of UA buffer with centrifugation (20,800×g; 15 min). The buffer was exchanged by 50 mM (NH$_4$)HCO$_3$ (pH 8.0) in two consecutive wash/centrifugation steps. Sequencing grade porcine trypsin (Promega, Alexandria, Australia) was added (0.5 µg in 200 µL of 50 mM (NH$_4$)HCO$_3$, 1 mM CaCl$_2$)) to the protein on the 10 kDa filters and incubated for 16 hr at 37° C. in a wet chamber. The filters were transferred to fresh centrifuge tubes and the filtrate (comprising digested peptides) collected following centrifugation (20,800×g, 10 min). The filters were washed with 200 µL of 100 mM (NH$_4$)HCO$_3$ and the filtrate combined and lyophilized. The tryptic peptides were resuspended in 50 µL of 1% formic acid (FA) and 25 µL was injected on the LC-MS/MS system.

An aliquot of the His-Pyrco-Δ5E protein extract (equivalent to ~5 µg) was subjected to FASP digestion. The protein extract was applied to a 10 kDa MWCO filter (Millipore), diluted to 200 µL with UA buffer before centrifugation (20,800×g, 15 min). The protein on the filter was washed with two 200 µL volumes of UA buffer with centrifugation (20,800×g, 15 min). The buffer was exchanged using 50 mM (NH$_4$)HCO$_3$ (pH 8.0) by two consecutive wash/centrifugation steps. The pH was adjusted by further washing with acidified 50 mM (NH$_4$)HCO$_3$ (pH 1.2) by two consecutive wash/centrifugation steps. The 10 kDa filter was transferred to a fresh centrifuge tube and 15 µg pepsin (150 µL, 0.1 µg/µL in 50 mM (NH$_4$)HCO$_3$, pH 1.2) was added to obtain an enzyme to protein ratio of 3:1. The filters were incubated at 37° C. for 120 min. The filtrate (containing the digested peptides) were collected following centrifugation (20,800×g, 10 min). The filters were washed with 200 µL of 100 mM (NH$_4$)HCO$_3$ and the filtrates were combined and lyophilised and stored at 20° C. until analysis. The resultant peptides were reconstituted in 50 µL of 1% formic acid of which 25 µL was analyzed by LC-MS/MS.

Proteolytically digested (either pepsin or trypsin) His-Pyrco-Δ5E protein (25 µL) were analyzed with chromatographic separation (0.23%/min linear gradient from 2%-40% acetonitrile) using a Nexera UHPLC system (Shimadzu Sci., Rydalmere, AU) directly coupled to a TripleTOF 5600 MS (AB Sciex, Foster City, US). ProteinPilot™ 4.0 software (AB Sciex) with the Paragon Algorithm (Shilov et al., 2007) was used for protein identification. Tandem mass spectrometry data was searched against in silico tryptic digests of a custom-built database. The database (76,110 sequences) comprised the Noctuidae and Baculovirus proteins of the Uniprot-KB database (v2015/11) appended with the transgenic proteins and additionally with a database of contaminant proteins (known as the common repository of adventitious proteins). The search parameters were defined as: (a) no modification to cysteine and pepsin as the digestion enzyme; or (b) iodoacetamide modified for cysteine alkylation and trypsin as the digestion enzyme. The database search results were manually curated to yield the protein identifications using a 1% global FDR determined by the in-built FDR tool within ProteinPilot software. Tang et al, 2008.

For the tryptic data, peptide summaries generated by ProteinPilot were used to select peptides that yielded intense peaks and were fully tryptic, i.e., no unusual or missed cleavages. For the pepsin data, peptide summaries generated by ProteinPilot were used to select peptides that yielded intense peaks after 120 min incubation with pepsin. Because pepsin is non-specific, many of these peptide products were overlapping or contained missed cleavages. MRM transitions (Tables 21-22) were determined for each peptide where the precursor ion (Q1) m/z and the fragment ion (Q3) m/z values were determined from the data collected. Three transitions were used per peptide (with eight peptic peptides and a single tryptic peptide from His-Pyrco-Δ5E), wherein the peak area of the three MRM transitions were summed.

Two test systems, pepsin digestion (representing SGF) and a combined pepsin-trypsin digestion, were utilized independently to test the stability of the His-Pyrco-Δ5E protein. SGF contained a highly purified form of the proteolytic enzyme pepsin in a buffer adjusted to an acidic pH 1.2. The SGF was formulated so that an enzyme:protein ratio of 3:1 would be present in the digestion reactions. The digestion of the Pyrco-Δ5E protein was monitored by LC-MS/MS (as described herein).

For pepsin digestion, aliquots of 6.7 µg of protein (67 µL, n=24 comprising four replicate digestions and six time points) were applied to a 10 kDa MWCO filter (Millipore)

and diluted to 200 µL UA buffer before centrifugation (20,800×g, 15 min). The protein on the filter was washed twice with 200 µL volumes of UA buffer with centrifugation (20,800×g, 15 min). The buffer was exchanged using 50 mM $(NH_4)HCO_3$ (pH 8.0) by two consecutive wash/centrifugation steps. The pH was lowered by further washing with acidified 50 mM $(NH_4)HCO_3$ (pH 1.2) by two consecutive wash/centrifugation steps. The 10 kDa filters were transferred to fresh centrifuge tubes and 20 µg pepsin (150 µL, 0.133 µg/µL in acidified 50 mM $(NH_4)HCO_3$, pH 1.2) was added to obtain an enzyme:protein ratio of 3:1. The replicate tubes were incubated at 37° C. for five time-points (5, 10, 15, 30, or 60 min). Pepsin was not applied to the 0 time-point, which served as an experimental control for acid hydrolysis. The digestion was stopped by addition of 200 µL of 50 mM $(NH_4)HCO_3$ (pH 8.0) which irreversibly inactivated the pepsin. The 10 kDa filters were centrifuged immediately (20,800×g, 15 min) and the filtrate containing digested peptides were collected. The filters were washed twice with 200 µL of 50 mM $(NH_4)HCO_3$ (pH 8.0) and the filtrates were combined and lyophilized and stored in a −80° C. freezer until analyzed. The peptic peptides were resuspended in 50 µL of 1% formic acid, and then a 20 µL aliquot was run on the QTRAP 6500+ LC-MS system and quantified.

For trypsin digestion, the 10 kDa filters were transferred to fresh centrifuge tubes and the residual protein reduced with 200 µL of 50 mM DTT, 50 mM $(NH_4)HCO_3$, pH 8.5, on a mixer at 600 rpm for 45 min prior to centrifugation (20,800×g, 15 min). The protein was alkylated with 200 µL of 50 mM IAM, 50 mM $(NH_4)HCO_3$, pH 8.5, in the dark for 20 min prior to centrifugation (20,800×g, 15 min). The 10 kDa filters were transferred to fresh centrifuge tubes and 0.5 µg trypsin (200 µL, 2.5 ng/µL in 50 mM $(NH_4)HCO_3$, pH 8.5, and 1 mM $CaCl_2$)) was added to obtain an enzyme to protein ratio of ~1:15. The replicate tubes were incubated at 37° C. for 16 hr. The filters were centrifuged (20,800×g, 15 min) and the filtrates containing digested peptides were collected. The filters were washed twice with 200 µl of 50 mM $(NH_4)HCO_3$, pH 8.5, and the filtrates were combined and lyophilized and stored in a −80° C. freezer until analyzed. The tryptic peptides were resuspended in 50 µL of 1% formic acid and 20 µL aliquots were run on the QTRAP 6500+ LC-MS and quantified.

Either 20 µL of native peptic peptides (Table 21) or reduced and alkylated tryptic peptides (Table 22) were chromatographically separated on a Nexera UHPLC and analyzed on a QTRAP 6500±mass spectrometer. Quantification was achieved using scheduled MRM scanning experiments using a 60 sec-detection window for each MRM transition and a 0.5 sec cycle-time. Peaks were integrated using MultiQuant v3.0, in which all three transitions were required to co-elute at the same retention time (RT, min) with a signal-to-noise (S/N)>3 for detection and a S/N>5 for quantification. The graphs showing digestibility of the Pyrco-Δ5E protein were generated in Graphpad Prism v6 software.

For the dual pepsin, pepsin-trypsin assay, SGF was represented by the proteolytic enzyme pepsin in a buffer adjusted to an acidic pH 1.2. The digestion was performed for 5, 10, 15, 30 and 60 min, with 0 min (no pepsin added) as the control, each with five replicates. The increased abundance of targeted peptic peptides was used as indicator of the protein digestibility. The SGF digestion was extended by collecting samples of the pepsin digestion at the same time points, followed by 16 hr digestion with trypsin, designated as combined pepsin-trypsin digestion. The relative abundance of tryptic peptides compared to the abundance of peptides in no pepsin digestion (0 min) followed by trypsin digestion was used as indicator of the protein digestibility.

The total protein extracted was estimated to be 1.7 mg/mL. The total protein from purification was assessed by SDS-PAGE (FIG. 32A). The protein was also transferred to PVDF membrane and confirmed with western blot using an anti-$His_{10}$-tag antibody. The expected molecular weight (MW) of $His_{10}$-Pyrco-Δ5E is ~33.7 kDa. A specific protein band close to 27 kDa was detected (FIG. 32B). Above this band and ranging from 30 kDa-120 kDa, there was some smearing apparent in the lane with some faint bands noted within this region. This is duplicated on the western blot, with the faint bands appearing more defined at apparent molecular weights of 30, 40, 50 and 62 kDa. The lower than predicted molecular weight on the SDS-PAGE is a common and well documented phenomenon for membrane proteins, however, and is caused by the presence and binding of detergents to the hydrophobic regions. Rath et al., 2009. Smearing is most likely due to detergent effects upon concentration of the protein in detergent micelles, and larger-than-expected molecular weight His-positive bands could be due to formation of multimers of the His-Pyrco-Δ5E.

The protein was identified/characterized by LC-MS/MS analysis. Five main bands identified in the gel and western blot were excised and subjected to proteolytic digestion with trypsin. All five of the bands were identified with >99% confidence as containing His-Pyrco-Δ5E (w/ or w/o minor contaminating proteins). The higher MW bands may be due to oligomerization (dimer, trimer, hexamer) or protein-protein interactions.

Because of the difficulty of expressing and purifying membrane proteins, in general, in prokaryotic and eukaryotic systems, affinity tags like the histidine tag selected here, are commonly used. The insect cell/baculovirus system was selected because it has been used widely for expression of membrane proteins, although the yields of expressed protein is many folds less than the yields of expressed protein from systems such as E. coli.

Pepsin is a relatively non-specific enzyme and its use results in cleavage at Phe (F), Tyr (Y), Trp (W) and Leu (L) resulting in hundreds of possible peptide fragments wherein missed cleavages are commonly observed. In silico analysis of the Pyrco-Δ5E protein with pepsin digestion suggested the theoretical pepsin cleavage map shown in FIG. 33A. In this Example, the peptide fragments of His-Pyrco-Δ5E persisting after pepsin digestion for 120 min were characterized by untargeted LC-MS/MS. See FIG. 33B.

Trypsin is a relatively specific enzyme and its use results in cleavage at Lys (K) and Arg (R) resulting in twenty-two possible peptide fragments, of which eight were in the mass range suited to LC-MS/MS analysis. See FIG. 33C. In this Example, the peptide fragments present after trypsin digestion for 16 hr were characterized by untargeted LC-MS/MS as shown in FIG. 33D. Owing to the distribution of the tryptic sites within the Pyrco-Δ5E sequence, there were few tryptic peptides of a size amenable to LC-MS/MS. Furthermore, using a 5 µg protein load, only a single fully tryptic peptide was able to be identified with a confidence of 85%: SQPFLGK (residues 66-72 of SEQ ID NO: 6). See FIG. 33D.

Figure 34:
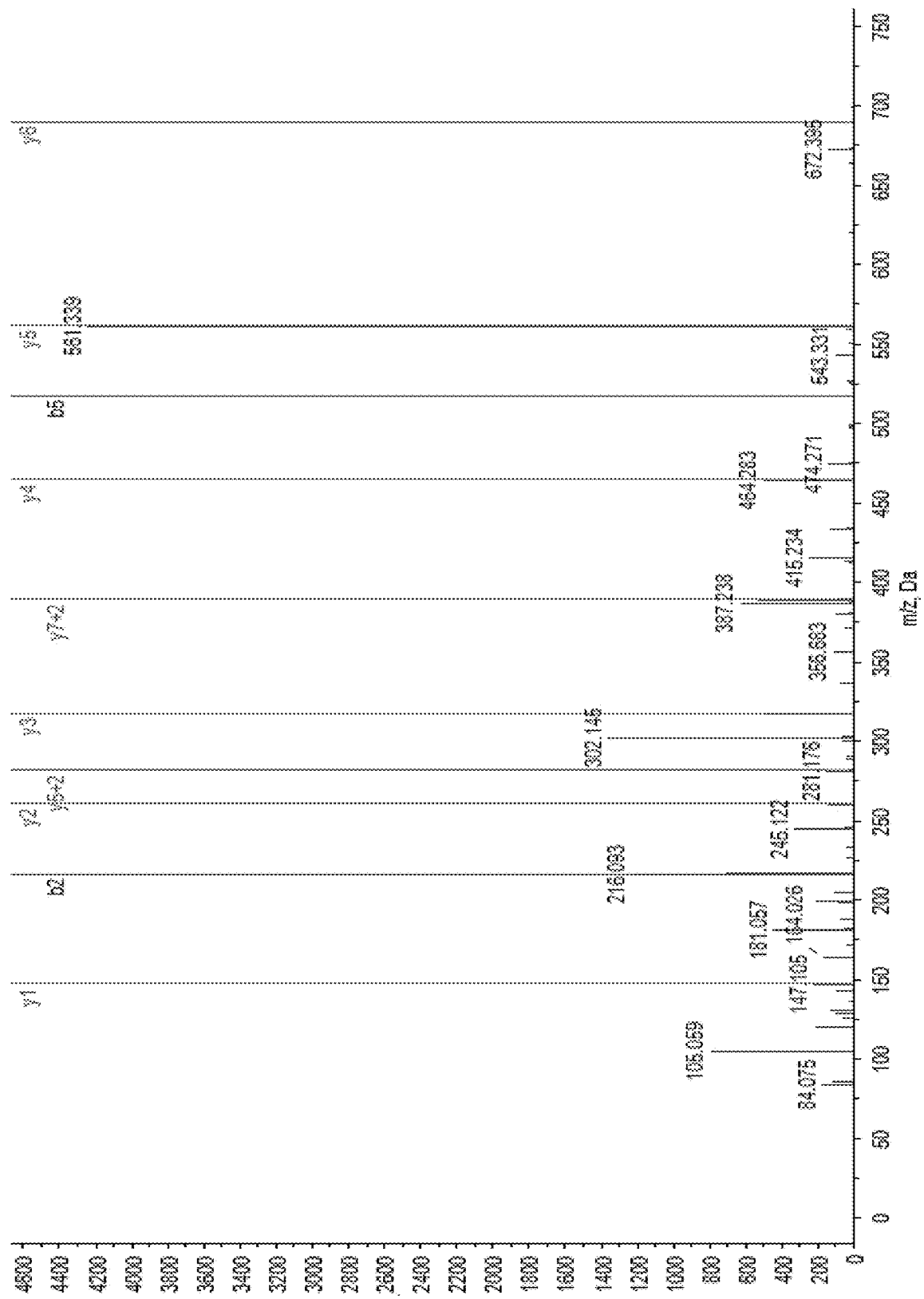
FIG. 34 is a chromatograph showing manual verification of the peptide-spectrum match for the single Pyrco-Δ5E tryptic peptide: SQPFGLK (residues 66-72 of SEQ ID NO: 6).

The peptide-spectrum match was manually verified by de novo peptide sequencing. The presence of six from six possible y-ions and additionally two b-ions confirmed the peptide as confidently identified (FIG. 34).

To assess the digestibility of the His-Pyrco-Δ5E protein, a targeted LC-MS/MS method based on the use of multiple reaction monitoring (NRM), mass spectrometry (MS) was developed. The appearance and the increase of the peptic peptides during the time course of pepsin digestion were used as the evidence of the protein digestibility. Moreover, the rapid decline of the tryptic peptides after the pepsin digestion served as confirmation of the protein digestibility. In order to select peptides to quantify in this method, the digestion products resulting from both pepsin and trypsin digestion were characterized. Pepsin-derived peptides that were identified with 95% confidence and that yielded intense signals in the MS were selected for relative quantification. The eight peptides that were selected from the pepsin digestion of the H-is-Pyrco-Δ5E protein and the single tryptic peptide are summarized in Tables 21-22. The selected pepsin-derived peptides spanned the length of the protein.

TABLE 21

Peptide MRM transitions for Pyrco-Δ5E pepsin products

| Peptide | RT | Q1 m/z | z | Q3 m/z | Fragment | CE |
|---|---|---|---|---|---|---|
| NVANPDIPASEKVPAYF (aa 20-36, SEQ ID NO: 6) | 5.92 | 916.460 | 2+ | 1108.560 | y10+ | 43.9 |
| | | | | 1221.650 | y11+ | 43.9 |
| | | | | 1335.690 | b13++ | 43.9 |
| NVANPDIPASEKVPAY (aa 20-35, SEQ ID NO: 6) | 4.73 | 842.930 | 2+ | 961.500 | y9+ | 40.3 |
| | | | | 1286.660 | y12+ | 40.3 |
| | | | | 724.360 | b7+ | 40.3 |
| GKRIMQNRSQPFGLKNAML (aa 58-76, SEQ ID NO: 6) | 4.49 | 548.050 | 4+ | 600.320 | b10++ | 25.4 |
| | | | | 807.440 | b14++ | 25.4 |
| | | | | 746.420 | y7+ | 25.4 |
| GKRIMQNRSQPFGLKNAM (aa 58-77, SEQ ID NO: 6) | 3.64 | 519.770 | 4+ | 600.320 | b10++ | 24.0 |
| | | | | 633.330 | y6+ | 24.0 |
| | | | | 586.350 | b5+ | 24.0 |
| LFVTSHRAQGLKV (aa 92-104, SEQ ID NO: 6) | 3.89 | 485.950 | 3+ | 548.810 | y10++ | 21.3 |
| | | | | 598.340 | y11++ | 21.3 |
| | | | | 671.880 | y12++ | 21.3 |
| WGNIPDM (aa 105-111, SEQ ID NO: 6) | 5.63 | 416.680 | 2+ | 471.240 | b4+ | 19.4 |
| | | | | 683.310 | b6+ | 19.4 |
| | | | | 362.130 | y3+ | 19.4 |
| LHIYHHTLL (aa 151-159, SEQ ID NO: 6) | 3.99 | 573.824 | 2+ | 896.490 | y7+ | 27.1 |
| | | 382.880 | 3+ | 451.730 | b7++ | 16.4 |
| | | 382.880 | 3+ | 508.270 | b8++ | 16.4 |
| FVHVIM (aa 184-189, SEQ ID NO: 6) | 5.20 | 373.207 | 2+ | 384.200 | b3+ | 17.3 |
| | | | | 483.270 | b4+ | 17.3 |
| | | | | 596.350 | b5+ | 17.3 |

Pyrco-Δ5E sequence[b]:

(SEQ ID NO: 6)
MASIAIPAALAGTLGYVTYNVANPDIPASEKVPAYFMQVEYWGPTIGTIGYLLFIYFGKRIMQNR
SQPFGLKNAMLVYNFYQTFFNSYCIYLFVTSHRAQGLKVWGNIPDMTANSWGISQVIWLHYNNKY
VELLDTFFMVMRKKFDQLSFLHIYHHTLLIWSWFVVMKLEPVGDCYFGSSVNTFVHVIMYSYYGL
AALGVNCFWKKYITQIQMLQFCICASHSIYTAYVQNTAFWLPYLQLWVMVNMFVLFANFYRKRYK
SKGAKKQ

RT, retention time (min); Q1 m/z, precursor ion mass-to-charge ratio (m/z); z, charge state; Q3 m/z, fragment ion m/z; CE, collision energy in V.
[b]Pyrco-Δ5E sequence with mapped peptic peptides (bold, underlined). For pepsin, different cleavage variants were observed owing to the incomplete digestion and these peptides have been differentiated by single or double underline.

The lack of available protein required the digestion protocol to be adjusted to a smaller scale (6.7 μg load). As such, only a single tryptic peptide could be monitored (FIG. 34, Table 22).

TABLE 22

Peptide MRM transitions for Pyrco-Δ5E trypsin product

| Peptide | RT | Q1 m/z | z | Q3 m/z | Fragment | CE |
|---|---|---|---|---|---|---|
| SQPFLGK (residues 66-72 of SEQ ID NO: 6) | 3.84 | 388.719 | 2+ | 561.340 | y5+ | 18.1 |
| | | | | 317.200 | y3+ | 26.0 |
| | | | | 260.200 | y2+ | 26.0 |

TABLE 22-continued

Peptide MRM transitions for Pyrco-Δ5E trypsin product

| Peptide | RT | Q1 m/z | z | Q3 m/z | Fragment | CE |
|---------|----|----|---|--------|----------|----|

Pyrco-Δ5E sequence[b]:

(SEQ ID NO: 6)
MASIAIPAALAGTLGYVTYNVANPDIPASEKVPAYFMQVEYWGPTIGTIGYLLFIYFGKRIMQNRSQPFGLK
NAMLVYNFYQTFFNSYCIYLFVTSHRAQGLKVWGNIPDMTANSWGISQVIWLHYNNKYVELLDTFFMVMRKK
FDQLSFLHIYHHTLLIWSWFVVMKLEPVGDCYFGSSVNTFVHVIMYSYYGLAALGVNCFWKKYITQIQMLQF
CICASHSIYTAYVQNTAFWLPYLQLWVMVNMFVLFANFYRKRYKSKGAKKQ

RT, retention time (min); Q1 m/z, precursor ion mass-to-charge ratio (m/z); z, charge state; Q3 m/z, fragment ion m/z; CE, collision energy in V.
[b]Pyrco-Δ5E sequence with mapped tryptic peptide (bold, underlined). For trypsin, the selected peptide was fully tryptic, i.e. contained no missed cleavages.

Digestibility of His-Pyrco-Δ5E in SGF was assessed by LC-MRM-MS method as described above. Characterization and quantification of the targeted peptic peptides showed the rapid degradation of His-Pyrco-Δ5E. The pepsin digestion data has been presented in FIG. 35 as the mean of four replicate digests relative percentage of the maximum detected MRM peak area (sum of three transitions) per peptide across the time points (0, 5, 10, 15, 30, 60 min).

The rapid degradation of the His-Pyrco-Δ5E protein demonstrated by the rapid liberation of peptic peptides was further confirmed by the decline of the single tryptic peptide after trypsin digestion (in the combined pepsin-trypsin digestion). Four of the peptides characterized and quantified after pepsin digestion were cleavage variants (FIG. 35, Panels (A)-(D)), in which black arrows indicate that the peptide in the left panel is cleaved further by pepsin to yield the peptide in the right panel. The N-terminal peptic peptides monitored were produced rapidly (<5 min) and reached an equilibrium over the experimental duration. The peptic peptides monitored may not represent the fully cleaved final product as pepsin is relatively non-specific. All of the displayed pepsin proteolysis products in FIG. 35 contained missed cleavages and are therefore susceptible to further degradation. A peptide that might be considered a final product of pepsin digestion is NVANPDIPASEKVPAY (aa 20-35, SEQ ID NO: 6) because the lysine (K) located in the P3 position likely hinders further cleavage before tyrosine (Y) (FIG. 35 Panel (B)). This peptide reaches an equilibrium plateau by 15 min. The appearance of these peptides in the digest is taken as evidence of the degradation and therefore digestibility of the 1-is-Pyrco-Δ5E protein.

Figure 35:
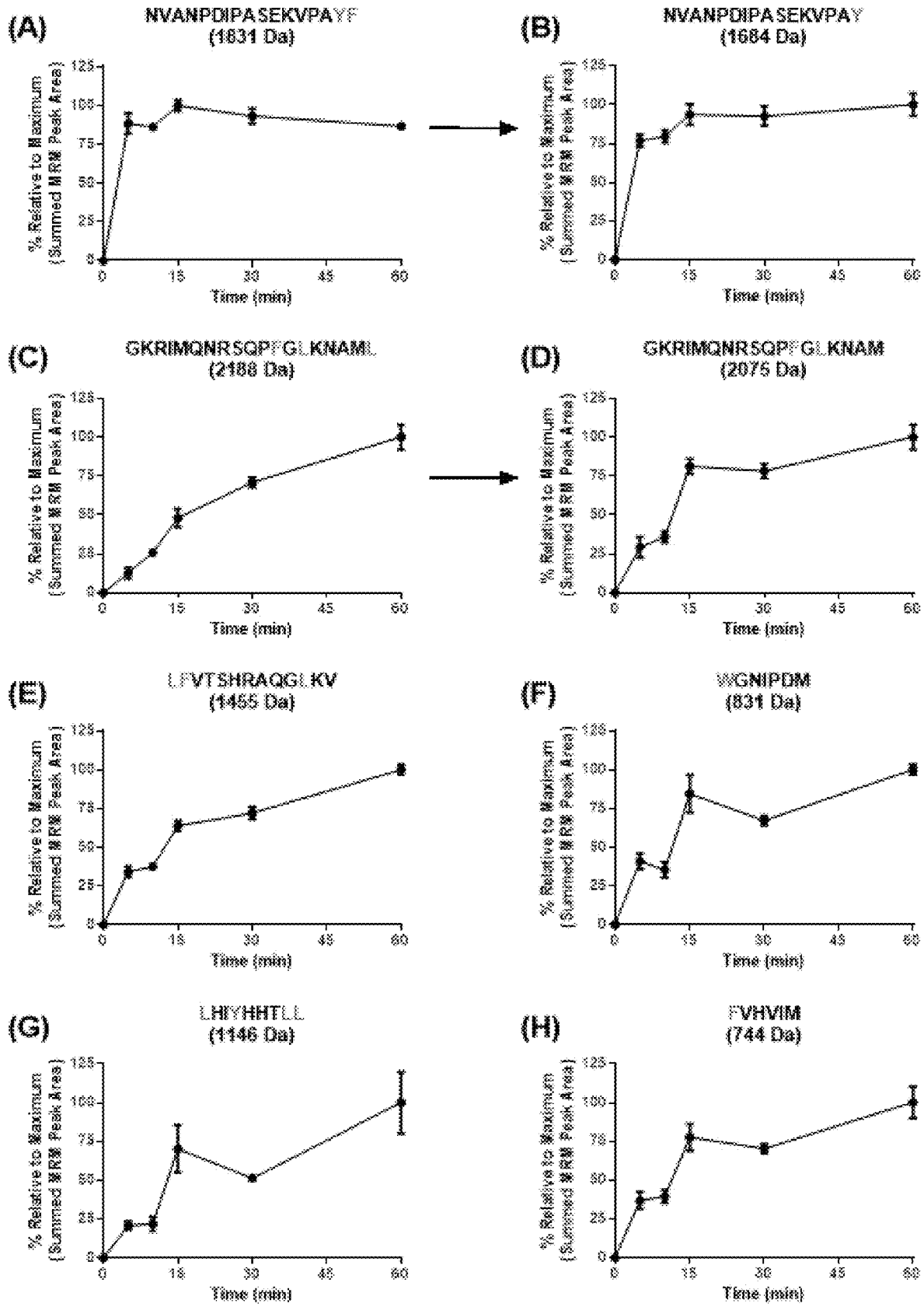
FIG. 35 Panels (A) to (H) are graphs showing LC-MRM-MS analysis of His-Pyrco-Δ5E pepsin proteolytic fragments. The response in the LC-MS system (measured as peak area) was converted to a percentage relative to the maximum peak area observed during pepsin digestion. Experimental control: time 0, no pepsin. The peptides are graphed in order from protein N- to C-termini. The peptide sequence (and calculated molecular weight) are denoted above each graph. Arrows indicate a subsequent cleavage to yield a secondary cleavage variant. The potential sites for secondary pepsin cleavage within the sequence, per Panel, are (A): YF; (B): Y; (C): F, L, and L; (D): F and L; (E): LF and L; (F): W; (G): L and Y; (H): F (expected cleavage); or Panel (G): LL (potentially hindered). Error bars: SD.

In the case of the His-Pyrco-Δ5E protein, only a single tryptic product could be detected owing to the small-scale (6.7 μg load) digest and also due to the distribution of trypsin sites within the protein sequence resulting in few peptides amenable to LC-MS. The single peptide monitored, SQPF↓GL↓K (residues 66-72 of SEQ ID NO: 6), contained two pepsin cleavage sites (as indicated by the arrows) and it was expected that pepsin would cleave this peptide resulting in a decrease in peptide abundance over the time course of the pepsin digestion. After 5 min, the peptide peak area was noted to increase 3-fold, however, and remain relatively constant over the next 5 min before declining slowly over the next 50 min (FIG. 36). A similar phenomenon was observed previously for a peptide derived from Δ4D wherein a 2-fold increase in the peak area of a tryptic peptide (WEGEPISK) (residues 274-281 of SEQ ID NO: 7) was noted after 5 min incubation of the protein with pepsin. Both scenarios are postulated to arise from the peptides monitored residing within the core of the molecule which in its native conformation is partially protected from trypsin digestion. After a short incubation with pepsin (5 min), the tertiary structure of the protein (Pyrco-Δ5E) is destroyed allowing full access to the tryptic sites and hence liberation of the tryptic peptide (SQPFGLK) (aa 66-72 of SEQ ID NO: 6) at its maximal level (FIG. 36). The absence of detectable tryptic peptides derived from the Pyrco-Δ5E protein precluded the determination of the final percentage (Table B) degradation as determined for Δ4-Desaturase and ω3-Desaturase herein, however the appearance of peptic products (FIG. 35) demonstrated that the Pyrco-Δ5E protein is digested by pepsin over the time course of the experiment with >75% cleavage of the N-terminal region achieved in <5 min (FIG. 35A-B).

TABLE 3

Percentage of each tryptic peptide remaining during pepsin time course

| | Time (min) | | | | |
|---|---|---|---|---|---|
| Peptide Sequence | 5 | 10 | 15 | 30 | 60 |
| SQPFGLK[1] | 100.0 | 97.6 | 69.6 | 65.1 | 48.0 |

[1]SQPFGLK is aa 66-72 of SEQ ID NO: 6.

Pyrco-Δ5E is an integral membrane protein. Currently there is no functional antibody for western blot analysis available to quantify the transgenic protein content in ω3LCPUFA canola, or detect the stability of Pyrco-Δ5E as native protein. The commercially raised poly- and monoclonal antibodies by GenScript (Piscataway, N.J., US) failed to generate a specific signal towards Pyrco-Δ5E. The antibodies were raised against the synthetic peptides predicted as potential epitopes for antigens (FIG. 37).

Although Pyrco-Δ5E, expressed as the His-tag fusion protein, may be analyzed by western blot using the anti-His-tag antibody, such analysis could monitor only the fusion region, rather than whole protein, which remains problematic once the His-tag is cleaved off, for example, during SGF digestion. In addition, the anti-His-tag antibody is not suitable for quantification of the native Pyrco-Δ5E (unfused) protein in ω3LCPUFA canola. Thus, an alternative approach using LC-MRM-MS analysis was developed as described herein, which can be applied both to the quantification of target protein expressed and to the target protein stability assay. These results demonstrate that the LC-MS approach is suitable for such an application. This method is as sensitive as traditional western blot, which can normally detect proteins on a ng to μg scale. In contrast, the LC-MRM-MS approach used demonstrated detected Pyrco-Δ5E levels as low as 7.80 femtomoles (injected on-column), which equates to 2.44 μg protein. In addition, western blot using antibodies might only detect a limited number of epitopes (one or two) from the target protein. In contrast, the methods described herein targeted eight peptides, spanning the intact protein, provides an understanding of the kinetics of digestion and the susceptibility of specific regions of the protein to proteolysis. Technical difficulty involved in the filtration and washing steps after pepsin digestion with four replicates, allowed an earliest practical time point was 5 min. Nevertheless, the results have shown the successful application of LC-MRM-MS for protein digestibility analysis.

The Pyrco-Δ5E protein belongs to the subfamily of microalgae fatty acid elongases that introduce a carbon to the carboxyl end of fatty acids. The Pyrco-Δ5E protein presented in this Example for digestion analysis is a representative of the two microalgae fatty acid elongases, both recalcitrant, membrane-associated proteins, engineered into ω3LCPUFA canola. The microalgae fatty acid elongases include Δ5-, Δ6- and Δ9-elongases, existing in a wide range of organisms including algae, diatoms, fungi, mosses, and bacteria. Desaturase activity has been assayed in crude extracts when the required substrates are added (Jackson et al., 252 Eur. J. Biochem. 513-19 (1998) but with DHA canola it is far more difficult because there are multiple desaturases and elongases expressed in the canola seed and the levels of the transgenic proteins in seed were very low. For example, Pyrco-Δ5E was expressed at 409 ng per mg total protein in mature seed with as little as 2.78 mg of total protein extracted from 1 g of seed.

The results of this Example demonstrated that the His-Pyrco-Δ5E protein was rapidly digested over the time course of the experiment, with >75% cleavage of the N-terminal region achieved in <5 min. Within 60 min of pepsin incubation, a suite of pepsin products <3,000 Da were produced that spanned the entire peptide sequence. In addition to rapid digestion of the full-length His-Pyrco-Δ5E protein in SGF, Pyrco-Δ5E protein represented a negligible portion of the total protein present in ω3LCPUFA canola mature seed. Rapid digestion and low expression levels are two of many factors that indicate the protein safety of Pyrco-Δ5E protein.

Example 6. In Vitro Stability of *Pichia Pastoris* ω3-/Δ15-Desaturase (Picpa-ω3D) Protein This particular Example focuses on the representative yeast acyl-CoA type fatty acid desaturase of the pathway, *P. pastoria* ω3-/Δ15-desaturase (Picpa-ω3D) protein, which was used in the engineering of ω3LCPUFA canola, to catalyze the desaturation of linoleic acid LA into α-linoleic acid ALA ($18:2^{\Delta,9,12} \rightarrow 18:3^{\Delta9,12,15}$).

This Example assesses the in vitro stability of the *Pichia pastoris* ω3-/Δ15-desaturase (Picpa-ω3D) protein in SGF comprising the proteolytic enzyme, pepsin, in combination with a novel pepsin-trypsin assay employing state-of-the-art mass spectrometric approaches to monitor the precise degradation products. The extent of protein digestion was evaluated by the appearance of peptic products and the disappearance of tryptic peptide products (as a proxy for intact protein). The Example shows that >80% digested within 5 min and 97% of the full-length Picpa-ω3D protein was digested within 60 min of incubation in pepsin, as determined using LC-MS/MS; or 98.7% of the full-length Picpa-ω3D protein was digested within 5 min and 99.5% of the full-length Picpa-ω3D protein was digested within 60 min of incubation in pepsin, as analyzed using LC-MS/MS; and shows that the integral membrane protein Picpa-ω3D was readily digestible in pepsin or trypsin.

The ω3-/Δ15-desaturase gene used in DHA canola was cloned from alga *P. pastoria* (see, e.g., WO 2010/057246).

The Picpa-ω3D protein was expressed in *E. coli* C41 strain as a fusion protein with green fluorescent protein (GFP) followed by eight histidine residues (8× His) at the N-terminus of the protein (His-GFP-Picpa-ω3D) and then purified. The vector contained coding sequence encoding a His-tag (His) and a PreScission protease (GE Healthcare) cleavage site (SLEVLFQ↓GP) (SEQ ID NO: 12) fused to the codon optimized Picpa-ω3D gene.

For protein extraction, the ω3D protein-transformed *E. coli* C41 cells were grown to $OD_{600}$ of 0.8, and protein expression induced with 0.5 mM IPTG at 37° C. for 4 hr. Cells were then spun down and resuspended in lysis buffer (150 mL per 60 g cell paste) containing 20 mM Hepes pH 7.6, 150 mM NaCl, 10% glycerol, 2 mM $MgCl_2$, three Ultra complete protease inhibitor tablets per 150 mL (Roche), 1 mM PMSF, 1 mM DTT, and 1200 units of Benzonase (Merck Millipore). Cells were lysed using EmulsiFlexC5 cell homogenizer (Avestin) by three passes at 15,000 psi. After lysis, cellular debris was removed by centrifugation, then the supernatant was further centrifuged at 00,000×g for 90 min at 4° C. to isolate the membrane fraction. The membrane pellet was resuspended in 50 mL of HNG buffer (20 mM Hepes, 150 mM NaCl, 10% glycerol, pH 7.6). To solubilize His-GFP-Picpa-ω3D from the membrane fraction 1% (w/v) FosCholine-16 (Glycon Biochemicals GmbH) was added and the mixture incubated for 3 hr at 4° C. The mixture was then centrifuged for 45 min at 200,000×g at 4° C. and the supernatant loaded on a 5 mL HisTrap FF column (GE Healthcare, AU) in the presence of 10 mM imidazole and 1 mM DTT. The protein was eluted with an imidazole gradient. Fractions were analyzed by SDS-PAGE with western blotting. Fractions containing His-GFP-Picpa-ω3D fusion protein were pooled and concentrated to 2.5 mL using 100 kDa MWCO concentrators (Millipore). Concentrated sample was injected onto a Superdex 200 16/60 µg gel filtration column (GE Healthcare) equilibrated in HNG buffer in the presence of 0.01% FosCholine-16 and 1 mM DTT. Fractions containing purified His-GFP-Picpa-ω3D protein were pooled, concentrated to 1.3 mg/mL, flash frozen in liquid nitrogen and stored at −80° C. Concentrated protein was analyzed by SDS-PAGE and western blotting using an anti-His HRP conjugated antibody (A7058, Sigma-Aldrich) (see FIG. 38). The estimated purity was ~90%.

For LC-MS/MS following pepsin digestion, His-GFP-Picpa-ω3D protein was diluted in LA buffer (8 M urea, 0.1 M Tris-HCl, pH 8.5) to ~0.125 µg/µL. An aliquot of the protein extract (equivalent to ~25 µg) was subjected to FASP. Wisniewski et al., 2009. The protein extract was applied to a 10 kDa MWCO filter (Millipore), washed with two 200 µL volumes of UA buffer with centrifugation (20,800×g, 15 min). The filter-held protein was reduced with DTT (50 mM, 200 µL) by incubation at room temp for 50 min with shaking. The filter was washed twice with 200 µL UA buffer with centrifugation (20,800×g, 15 min). Cysteine residues were then alkylated with IAM (50 mM, 100 µL) with incubation for 40 min at room temp in the dark. The filter was washed twice with 200 µL UA buffer and centrifugation (20,800×g, 15 min). Buffer exchange used 50 mM $(NH_4)HCO_3$ (pH 8.0) and two consecutive wash/centrifugation steps. Sequencing grade porcine trypsin at a concentration of 0.01 µg/µL (2 µg in 200 µL of 50 mM $(NH_4)HCO_3$ with 1 mM $CaCl_2$)) was added to the protein on the 10 kDa filters and incubated for 16 hr at 37° C. in a wet chamber. The filter was transferred to a fresh centrifuge tubes and the filtrate (digested peptides) was collected following centrifugation (20,800×g, 10 min). The filters were washed with 200 µL of 100 mM $(NH_4)HCO_3$ and the filtrates were combined and lyophilized. The tryptic peptides were resuspended in 50 μL of 1% formic acid and 10 μL was injected on the LC-MS/MS system.

Further regarding LC-MS/MS, proteolytically digested (either pepsin or trypsin) protein were analyzed as described previously with chromatographic separation (2%/min linear gradient from 2%-40% acetonitrile) using a nano HPLC system (Shimadzu Scientific, Rydalmere, Australia) directly coupled to a TripleTOF 5600 MS (AB SCIEX, Redwood City, Calif, US). ProteinPilot™ 4.0 software (AB SCIEX) with the Paragon Algorithm was used for protein identification. Shilov et al., 2007. Tandem mass spectrometry data was searched against in silico tryptic digests of a custom-built database. The database (57,652 sequences) comprised the *E. coli* proteins of the Uniprot-KB database (version 2016/02) appended with the transgenic proteins and additionally with a database of contaminant proteins (known as the common repository of adventitious proteins). The search parameters were defined as: (a) no modification to cysteine and pepsin as the digestion enzyme; or (b) iodoacetamide modified for cysteine alkylation and trypsin as the digestion enzyme. Additional modifications and cleavages were defined previously. The database search results were manually curated to yield the protein identifications using a 1% global false discovery rate (FDR) determined by the in-built FDR tool within ProteinPilot software. Tang et al., 2008.

For the tryptic data, peptide summaries generated by ProteinPilot were used to select peptides that yielded intense peaks and were fully tryptic, i.e. no unusual or missed cleavages. For the pepsin data, peptide summaries generated by ProteinPilot were used to select peptides that yielded intense peaks after 120 min incubation with pepsin. As pepsin is non-specific, many of these peptide products were overlapping or contained missed cleavages. MRM transitions (Tables 23-24) were determined for each peptide where the precursor ion (Q1) m/z and the fragment ion (Q3) m/z values were determined from the data collected in the discovery experiments. Three transitions were used per peptide (with eleven peptic and eight tryptic peptides from His-GFP-Picpa-ω3D), and the peak area of the three MRM transitions summed.

Two test systems, pepsin digestion (representing simulated gastric fluid, SGF) and a combined pepsin-trypsin digestion, were utilized independently to test the stability of the His-GFP-Picpa-ω3D protein. SGF contained the proteolytic enzyme pepsin in a buffer adjusted to an acidic pH 1.2, using a highly purified form of pepsin. The SGF was formulated so that an enzyme:protein ratio of 3:1 would be present in the digestion reactions. The digestion of the Picpa-ω3) protein was monitored by LC-MS/MS (as described herein).

By using LC-MS/MS analysis, the peptide products resulting from both pepsin and trypsin digestions could first be determined qualitatively and then subsequently a quantitative LC-MS/MS for the detection of these peptide fragments was developed. LC-MS analysis is capable of simultaneously monitoring peptides spanning the entire protein sequence that are generated by proteolytic digestion. The approach to analyze digestibility in this Example may mimic the typical mammalian digestive system that exposes food proteins to both pepsin (stomach) and trypsin (intestine) enzymes in transit through the gut.

For pepsin digestion, 25 μg of protein (58.4 μL, n=30 comprising five replicate digestions and six time-points) were applied to a 10 kDa molecular weight cut-off filter (Millipore, Australia), washed twice with 200 μL volumes of UA buffer with centrifugation (20,800×g, 15 min). The buffer was exchanged using 50 mM $(NH_4)HCO_3$ (pH 8.0) by two consecutive wash/centrifugation steps. The pH was adjusted by further washing with acidified 50 mM $(NH_4)HCO_3$ (pH 1.2) by two consecutive wash/centrifugation steps. A number of acids may be used to bring the pH of the digestion buffer to pH 1.5-pH 2.5, such as HCl, acetic acid, or citric acid. The 10 kDa filters were transferred to fresh centrifuge tubes and 84 μg pepsin (150 μL, 0.562 μg/mL in acidified 50 mM $(NH_4)HCO_3$ (pH 1.2) was added to obtain an enzyme to protein ratio of 3:1. The replicate tubes were incubated at 37° C. for five time-points (5, 10, 15, 30, 60 min). Pepsin was not applied to the 0 time-point, which served as an experimental control for acid hydrolysis. The digestion was stopped by the addition of 200 μL of 50 mM $(NH_4)HCO_3$ (pH 8.0), which irreversibly inactivated the enzyme. The 10 kDa filters were immediately centrifuged (20,800×g, 15 min) and the filtrate containing digested peptides were collected. The filters were washed twice with 200 μL of 50 mM $(NH_4)HCO_3$, pH 8.0, and the filtrates were combined and lyophilized and stored in a −80° C. freezer until further analysis. For C-MS, the peptic peptides were resuspended in 50 μL of 1% formic acid, and a 3 μL aliquot run on a QTRAP 6500+ LC-MS system and quantified.

For trypsin digestion, the 10 kDa filters were transferred to fresh centrifuge tubes and the residual protein reduced with 200 μL of 50 mM DTT, 50 mM $(NH_4)HCO_3$ (pH 8.5) on mixer at 600 rpm for 45 min prior to centrifugation (20,800×g, 15 min). The protein was alkylated with 200 μL of 50 mM iodoacetamide (IAM), 50 mM $(NH_4)HCO_3$, at pH 8.5, in the dark for 20 min prior to centrifugation (20,800×g, 15 min). The 10 kDa filters were transferred to fresh centrifuge tubes and 2 μg trypsin (200 μL, 0.01 μg/mL in 50 mM $(NH_4)HCO_3$, pH 8.5, and 1 mM $CaCl_2$)) was added to obtain an enzyme:protein ratio of 1:15. Replicate tubes were incubated at 37° C. for 16 hr. The filters were centrifuged (20,800×g, 15 min) and the filtrates containing digested peptides collected. The filters were washed twice with 200 μL of 50 mM $(NH_4)HCO_3$, pH 8.5, and the filtrates combined and lyophilized and stored in a −80° C. freezer until further analysis. For LC-MS, the tryptic peptides were resuspended in 50 μL of 16% formic acid, and a 3 μL aliquot run on a QTRAP 6500+ LC-MS system and quantified.

For LC-MS/MS quantification of the digestion products, either 3 μL of native peptic peptides (Table 23) or reduced and alkylated tryptic peptides (Table 24) were chromatographically separated on a Nexera UHPLC (Shimadzu) and analyzed on a QTRAP 6500+ mass spectrometer (AB SCIEX). Quantification was achieved using scheduled MRM scanning experiments using a 60 sec-detection window for each MRM transition and a 0.3 sec cycle time. Peaks were integrated using MultiQuant v3.0 (AB SCIEX), in which three transitions were required to co-elute at the same retention time (RT, min) with a signal-to-noise (S/N)>3 for detection and a S/N>5 for quantification. The graphs showing digestibility of the Picpa-ω3D protein were generated using GraphPad Prism v6 software.

Pepsin is a protease produced in the stomach and is efficient at cleaving the peptide bonds adjacent to aromatic and hydrophobic amino acids phenylalanine, tyrosine, tryptophan, and leucine (FIG. 27B). Histidine, lysine, and arginine at the P3 position act to hinder proteolysis, while proline at P3 or P4 positions promotes proteolysis. Upon digestion with pepsin alone, there are a number of scenarios that may occur (see FIG. 28A). The simplest is when the protein is rapidly digested to produce fully peptic fragments wherein the response rapidly increases reaching a maximum and creating a plateau (filled circle). The second involves the slow digestion that does not reach a plateau within the experimental duration (filled triangles). This scenario is difficult to judge for completeness as LC-MS monitors the peptide response (peptide peak intensity or area). The third involves a rapid, but incomplete digestion that may appear to be complete as judged by the plateau in peptide response (empty circles). Lastly, slow and incomplete digestion may be observed (empty triangles). For these reasons, examining pepsin proteolytic fragments may allow the digestion of a protein to be monitored, but determining whether degradation has reached completion may be difficult.

By employing trypsin post-pepsin (see FIG. 28B), it is possible to judge the completeness of the digestion by comparison with an experimental control (time 0, no pepsin added) wherein the tryptic peptides liberated appear at the maximum value (in this instance as the MRM peak area). Trypsin is a serine protease that is found in the digestive system. Trypsin cleaves polypeptide chains at the carboxyl side of the basic amino acids lysine or arginine, but its cleavage is hindered by the presence of proline as the preceding amino acid (P1' position, FIG. 27A). If the protein is not digested, then no decrease in peptide response is observed (circles, dashed line). If the protein is partially digested, a partial decrease in the peptide response is observed (squares, dotted line). If the protein is completely digested, the peptide response drops to zero within the experiment duration (triangles, solid line).

Therefore, for this digestibility assay, two enzymes were used pepsin and trypsin. Tryptic peptide products were used as a proxy for intact protein, whereby in the absence of pepsin the amount of tryptic peptide present was equated to 100% of protein being present. In the presence of pepsin (at varying time points during digestion), the level of tryptic peptides would be expected to decrease for peptides that contained a pepsin cleavage site. In this way the complete degradation of the protein was monitored.

SGF was represented by the proteolytic enzyme pepsin in a buffer adjusted to acidic pH 1.2. The digestion was performed for 5, 10, 15, 30, and 60 min, with 0 min (no pepsin added) as the control, each with five replicates. Due to the difficulty involved in filtering and washing with five replicates, an early practical time point was 5 min from the addition of pepsin. The increased abundance of targeted peptic peptides was used as indicator of the protein digestibility. The SGF digestion was further extended by pepsin digestion at the same time points as above, followed by a 16 hr digestion with trypsin, designated as "combined pepsin-trypsin digestion." The relative abundance of pepsin-trypsin tryptic peptides, compared with the abundance of same peptides in no-pepsin digestion (0 min, no pepsin) followed by trypsin digestion, was used as indicator of the protein digestibility.

The His-GFP-Picpa-ω3D fusion protein ran, during electrophoresis, as a doublet with apparent molecular weights of 50 kDa and 60 kDa as determined by SDS-PAGE and western blotting. The predicted molecular weight of the His-GFP-Picpa-ω3D fusion construct is 76.4 kDa, however, a lower than predicted apparent molecular weight on SDS-PAGE is a common and well-documented phenomenon for membrane proteins caused by the presence and binding of detergent to the hydrophobic regions. Rath et al., 2009. In addition, the presence of two separate bands (FIG. 38, His-GFP-Picpa-ω3D) may be due to a population where the GFP in the fusion remains (partially) folded, causing it to migrate faster (lower band) than the population where the GFP is completely denatured (upper band). Geertsma et al., 105 PNAS 5722 (2008). Partial proteolysis of the C-terminus of the His-GFP-Picpa-ω3D could provide another explanation for the observed doublet, however it is clear from the Coomassie-stained gel that if this is the case, this lower potentially cleaved band is only a minor contaminant. The total protein extracted was estimated to be ~1.3 mg/mL.

The protein was also identified/characterized by LC-MS/MS analysis after proteolytic digestion using both trypsin and pepsin. Because of the difficulty of expressing membrane proteins in general in prokaryotic or eukaryotic systems, the strategy was to express the Picpa-ω3D as a. GFP fusion in $E. coli$ with a His-tag added to aid in purification. GFP is widely used as a fusion partner for soluble expression and allowing tracking of protein expression by monitoring its fluorescence. The presence of the fusion partner (His-GFP) is unlikely to affect the proteolysis and LC-MS characterization of the His-GFP-Picpa-ω3D protein, nor is the presence of contaminating proteins in the mixture.

As noted above, pepsin is a relatively non-specific enzyme and its use results in cleavage at Phe (F), Tyr (Y), Trp (W) and Leu (L), resulting in hundreds of possible peptide fragments wherein missed cleavages are commonly observed. In silico analysis of the native Picpa-ω3D protein with pepsin digestion suggested the theoretical pepsin cleavage map shown in FIG. 39A. In this Example, the peptide fragments of Picpa-ω3D persisting after pepsin digestion for 120 min were characterized by untargeted LC-MS/MS, as shown in FIG. 39B.

In contrast, trypsin is a relatively specific enzyme and its use results in cleavage at Lys (K) and Arg (R) resulting in thirty-six possible peptide fragments (FIG. 39C), of which twenty were in the mass range suited to LC-MS/MS analysis. In this Example, the peptide fragments present after trypsin digestion for 16 hr were characterized by untargeted LC-MS/MS, as shown in FIG. 39D.

To assess the digestibility of the Picpa-ω3D protein, a targeted LC-MS/MS method based on the use of multiple reaction monitoring (MRM) (Lange et al., 2008) mass spectrometry (MS) was developed. The appearance and the increase of the peptic peptides during the time course of pepsin digestion were used as the evidence of the protein digestibility. Moreover, the rapid decline of the tryptic peptides subsequent to pepsin digestion served as confirmation of the protein digestibility.

In order to select peptides to quantify in this method, the digestion products resulting from both pepsin and trypsin digestion were first characterized. Peptides that were identified with 95% confidence and that yielded intense signals in the MIS were selected for relative quantification. Eleven peptides were selected from the digestion of the H-is-GFP-Picpa-ω3D protein with pepsin and eight peptides for trypsin digestion are summarized in Tables 23-24. The selected peptides spanned the length of the protein.

TABLE 23

Peptide MRM transitions for Picpa-ω3D pepsin products

| Peptide | RT | Q1 m/z | z | Q3 m/z | Fragment | CE |
|---|---|---|---|---|---|---|
| FKVPDYTIKDIL (aa 42-53, SEQ ID NO: 1) | 6.66 | 484.610 | 3+ | 601.392<br>702.440<br>587.319 | y5+<br>y6+<br>b5+ | 21.3<br>21.3<br>21.3 |
| FKVPDY (aa 42-47, SEQ ID NO: 1) | 4.42 | 384.702 | 2+ | 394.161<br>621.324<br>587.319 | y3+<br>y5+<br>b5+ | 17.9<br>17.9<br>17.9 |
| TIKDIL (aa 48-53, SEQ ID NO: 1) | 4.60 | 351.723 | 2+ | 488.308<br>601.392<br>571.345 | y4+<br>y5+<br>b5+ | 16.2<br>16.2<br>16.2 |
| TYIPLLPNEF (aa 88-97, SEQ ID NO: 1) | 8.07 | 603.824 | 3+ | 619.309<br>829.445<br>701.423 | y5+<br>y7+<br>b6+ | 27.0<br>27.0<br>27.0 |
| TYIPLLPNE (aa 88-96, SEQ ID NO: 1) | 6.75 | 530.290 | 3+ | 682.377<br>588.339<br>701.423 | y6+<br>b5+<br>b6+ | 23.5<br>23.5<br>23.5 |
| TYIPLL (aa 88-93, SEQ ID NO: 1) | 7.34 | 360.221 | 2+ | 378.202<br>475.255<br>588.339 | b3+<br>b4+<br>b5+ | 16.7<br>16.7<br>16.7 |
| IPLLPNEF (aa 90-97, SEQ ID NO: 1) | 7.36 | 471.768 | 2+ | 437.312<br>648.408<br>777.451 | b4+<br>b6+<br>b7+ | 22.1<br>22.1<br>22.1 |
| IPLLPNE (aa 90-96, SEQ ID NO: 1) | 5.74 | 398.234 | 2+ | 324.228<br>437.312<br>648.408 | b3+<br>b4+<br>b6+ | 18.5<br>18.5<br>18.5 |
| NATGQPYPGVSKF (aa 221-233, SEQ ID NO: 1) | 4.32 | 683.344 | 3+ | 894.472<br>1079.552<br>1180.600 | y8+<br>y9+<br>y10+ | 30.8<br>30.8<br>30.8 |
| FKSHYWPSSPVF (aa 234-245, SEQ ID NO: 1) | 5.69 | 494.579 | 3+ | 560.764<br>609.291<br>658.825 | b9++<br>b10++<br>b11++ | 21.7<br>21.7<br>21.7 |
| TAYKVFGF (aa 269-276, SEQ ID NO: 1) | 5.89 | 466.748 | 2+ | 597.340<br>760.403<br>831.440 | y5+<br>y6+<br>y7+ | 21.9<br>21.9<br>21.9 |

Picpa-ω3D sequence[b]:

(SEQ ID NO: 1)
MSKVTVSGSEILEGSTKTVRRSGNVASFKQQKTAIDTFGNVFKVPDYTIKDILDAIPKHCYERSLVKS
MSYVVRDIVAISAIAYVGLTYIPLLPNEFLRFAAWSAYVESISCFGFGIWILGHECGHSAFSNYGWVN
DTVGWVLHSLVMVPYFSWKFSHAKHHKATGHMTRDMVFVPYTAEEFKEKHQVTSLHDIAEETPIYSVF
ALLFQQLGGISLYLATNATGQPYPGVSKFFKSHYWPSSPVFDKKDYWYIVLSDLGILATLTSVYTAYK
VFGFWPTFITWFCPWILVNHWLVFVTFLQHTDSSMPHYDAQEWTFAKGAAATIDREFGILGIIFHDII
ETHVLHHYVSRIPFYHAREATECIKKVMGEHYRHTDENMWVSLWKTWRSCQFVENHDGVYMERNCNNV
GVKPKDT

RT, retention time (min); Q1 m/z, precursor ion mass-to-charge ratio (m/z); z, charge state; Q3 m/z, fragment ion m/z; CE, collision energy in V.
[b]Picpa-ω3D sequence with mapped peptic peptides (bold, underlined). For pepsin, different cleavage variants were observed owing to the incomplete digestion and these peptides have been differentiated by single, double or waved underline.

TABLE 24

Peptide MRM transitions for Picpa-ω3D trypsin products

| Peptide | RT | Q1 m/z | z | Q3 m/z | Fragment | CE |
|---|---|---|---|---|---|---|
| VTVSGSEILEGSTK (aa 4-17, SEQ ID NO: 1) | 4.40 | 703.870 | 2+ | 1020.250<br>1107.550<br>1206.620 | y10+<br>y11+<br>y12+ | 33.5<br>33.5<br>33.5 |
| SGNVASFK (aa 22-29, SEQ ID NO: 1) | 2.41 | 405.210 | 2+ | 452.250<br>665.360<br>551.320 | y4+<br>y6+<br>y5+ | 18.9<br>18.9<br>18.9 |

TABLE 24-continued

Peptide MRM transitions for Picpa-ω3D trypsin products

| Peptide | RT | Q1 m/z | z | Q3 m/z | Fragment | CE |
|---|---|---|---|---|---|---|
| TAIDTFGNVFK<br>(aa 33-43, SEQ ID NO: 1) | 5.90 | 606.820 | 2+ | 927.460<br>1040.540<br>812.430 | y8+<br>y9+<br>y7+ | 28.7<br>28.7<br>28.7 |
| VPDYTIK<br>(aa 44-50, SEQ ID NO: 1) | 3.42 | 418.230 | 2+ | 736.390<br>368.690<br>639.330 | y6+<br>y6++<br>y5+ | 19.5<br>19.5<br>19.5 |
| DILDAIPK<br>(aa 51-58, SEQ ID NO: 1) | 3.42 | 442.760 | 2+ | 656.400<br>543.310<br>244.170 | y6+<br>y5+<br>y2+ | 20.7<br>20.7<br>20.7 |
| EATEC[CAM]IK<br>(SEQ ID NO: 9) | 1.43 | 425.700 | 2+ | 549.240<br>650.290<br>325.650 | y4+<br>y5+<br>y5++ | 19.9<br>19.9<br>19.9 |
| HTDENMWVSLWK<br>(aa 374-385, SEQ ID NO: 1) | 6.45 | 515.910 | 3+ | 533.300<br>632.380<br>818.450 | y4+<br>y5+<br>y6+ | 24.3<br>24.3<br>24.3 |
| SC[CAM]QFVENHDGV<br>YMFR<br>(SEQ ID NO: 10) | 5.07 | 630.260 | 3+ | 772.380<br>887.410<br>1024.470 | y6+<br>y7+<br>y8+ | 29.9<br>29.9<br>29.9 |

Picpa-ω3D sequence:[b]

(SEQ ID NO: 1)
MSKVTVSGSEILEGSTKTVRRSGNVASFKQQKTAIDTFGNVFK<u>VPDYTIK</u>DILDAIPKHCYERSLVKSMSYV
VRD<u>IVAISAIAYVGLTYIPLL</u>PNEFLRFAAWSAYVFSISCFGFGIWILGHECGHSAFSNYGWVNDTVGWVLH
SLVMVPYFSWKFSHAKHHKATGHMTRDMVFVPYTAEEFKEKHQVTSLHDIAEETPIYSVFALLFQQLGGLSL
YLATNATGQPYPGVSKFFKSHYWPSSPVFDKKDYWYIVLSDLGILATLTSVYTAYKVFGFWPTFITWFCPWI
LVNHWLVFVTFLQHTDSSMPHYDAQEWTFAKGAAATIDREFGILGIIFHDIIETHVLHHYVSRIPFYHARE<u>A
TECIKK</u>VMGEHYRHTDENMWVSLWKTWRSCQFVENHDGVYMFRNCNNVGVKPKDT

RT, retention time (min); Q1 m/z, precursor ion mass-to-charge ratio (m/z); z, charge state;
Q3 m/z, fragment ion m/z; CE, collision energy in V.
[b]Picpa-ω3D sequence with mapped tryptic peptides (bold, underlined). For trypsin, all peptides
selected were fully tryptic, i.e., contained no missed cleavages. As some of the peptides were
adjacent in the sequence, these have been differentiated by single or double underline.

Digestibility of the His-GFP-Picpa-ω3D in SGF was assessed by LC-MRM-MS method as described herein. Characterization and quantification of the targeted peptic peptides showed the rapid degradation of the His-GFP-Picpa-ω3D protein. The pepsin digestion data has been presented in FIG. 40 as the mean of five replicate digests relative percentage of the maximum detected MRM peak area (sum of three transitions) per peptide across the time points (0, 5, 10, 15, 30, 60 min).

Figure 40:
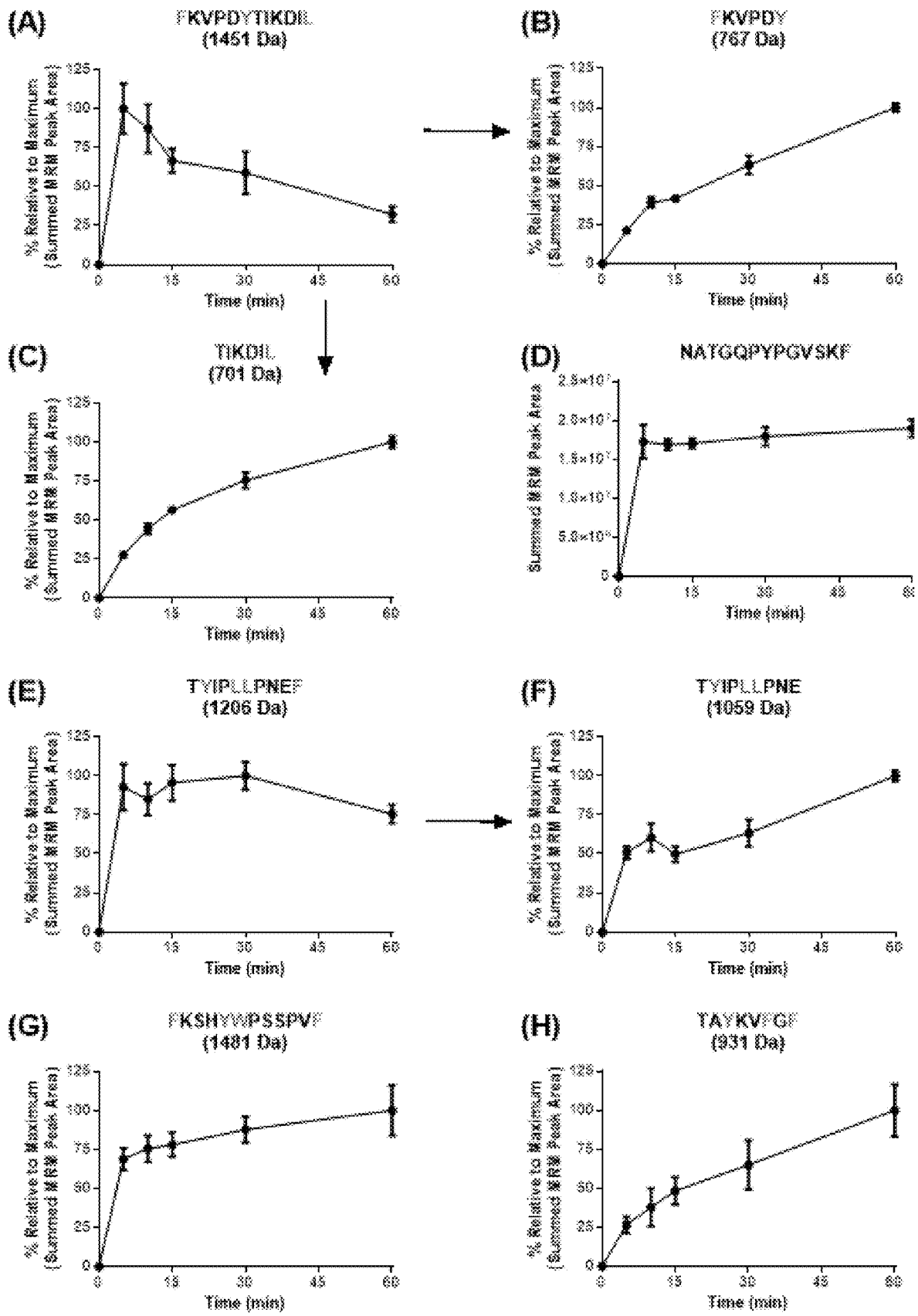
FIG. 40 shows chromatographs presenting quantification of His-GFP-Picpa-ω3D peptides of after pepsin digestion and LC-MRM-MS analysis of pepsin proteolytic fragments. The response in the LC-MS system (measured as peak area) was converted to a percentage relative to the maximum peak area observed during pepsin digestion. The peptides are graphed in order from protein N- to C-termini. The peptide sequence (and calculated molecular weight) is denoted above each graph. Arrows indicate a subsequent cleavage to yield a secondary cleavage variant. Potential sites for secondary pepsin cleavage within the sequence are Panel (A): F, Y, L; (B): F, Y; (C): L; (E): Y, LL, F; (F): Y, LL; (G): F, YW, F; (H): Y, F, F. Experimental control: time 0 with no pepsin; error bars: SD.
Figure 41:
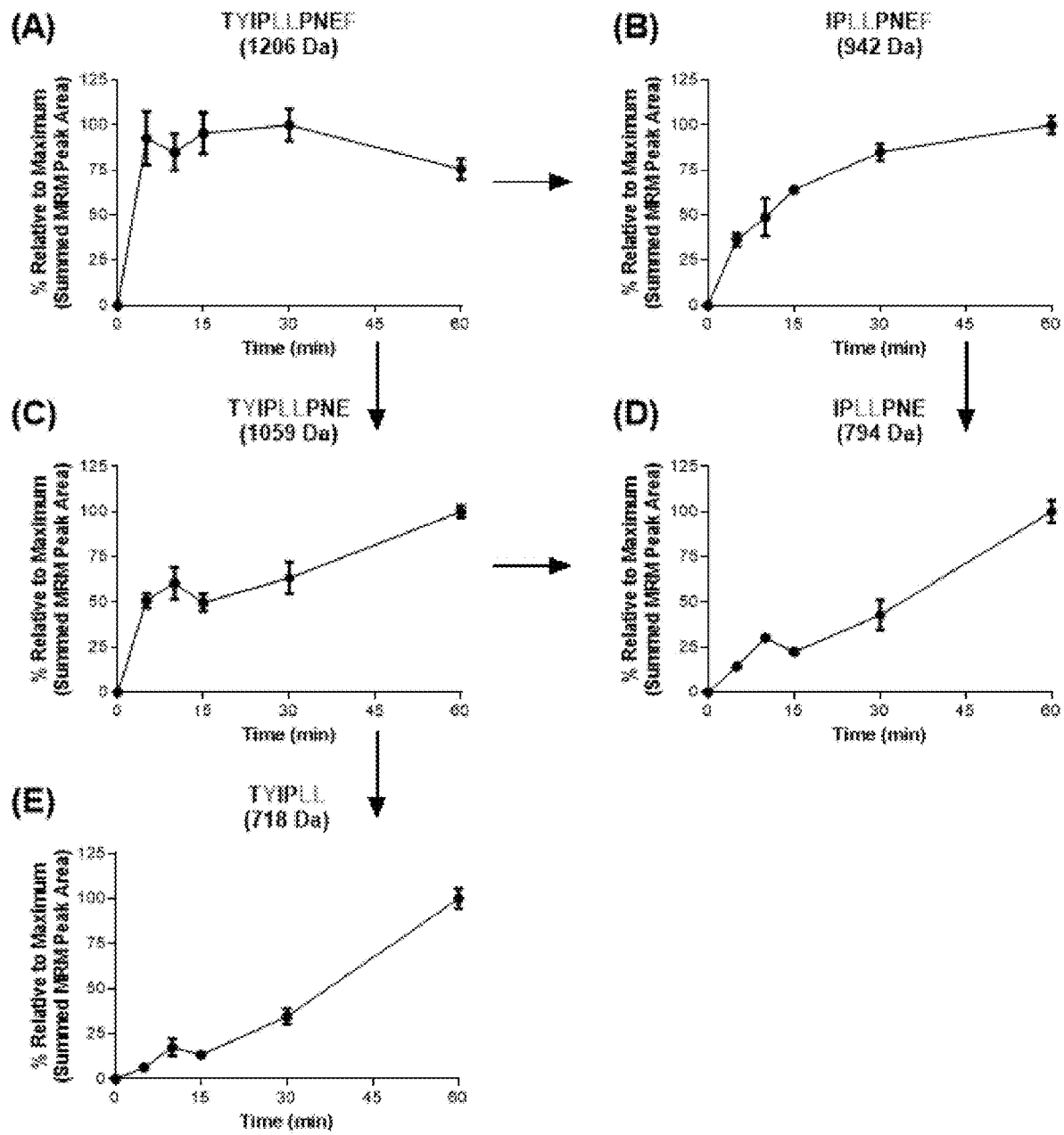
FIG. 41 shows chromatographs presenting LC-MRM-MS analysis of pepsin proteolytic fragments of His-GFP-Picpa-ω3D cleavage variants produced after pepsin digestion. The response in the LC-MS system (measured as peak area) was converted to a percentage relative to the maximum peak area observed during pepsin digestion. The peptides are graphed in order from protein N- to C-termini. The peptide sequence (and calculated molecular weight) is denoted above each graph. Arrows indicate a subsequent cleavage to yield a secondary cleavage variant. The potential sites for secondary pepsin cleavage are: Panel (A): Y, LL, F; (B) LL, F; (C): Y, LL; (D): LL; (E): Y, LL. Control: time 0, no pepsin.
Figure 42:
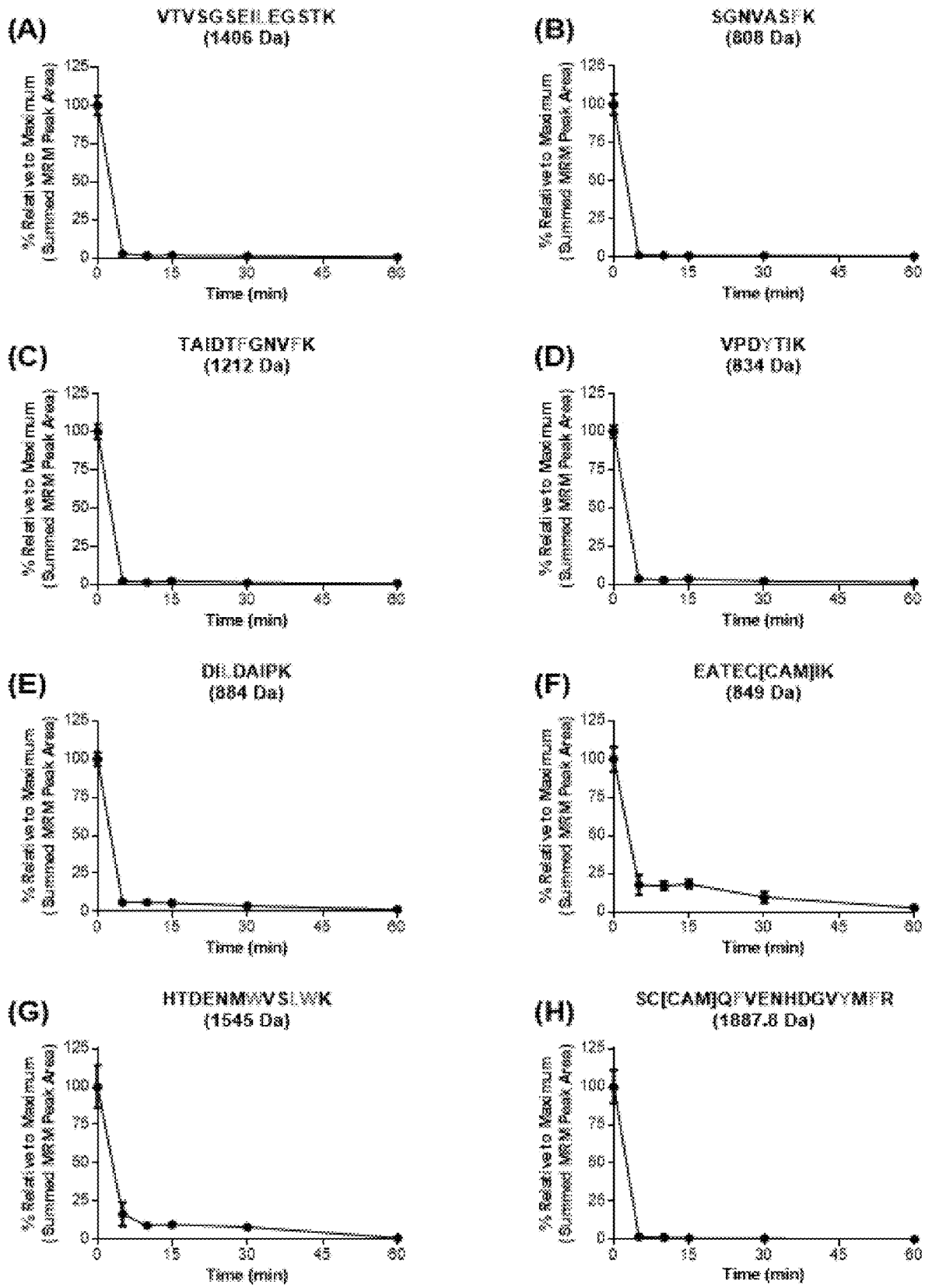
FIG. 42 shows chromatographs presenting quantification of the tryptic peptides of His-GFP-Picpa-ω3D after combined pepsin-trypsin digestion. The trypsin data has been presented as the mean percentage (n=5 replicate digests) reduction relative to the experimental control at 0 min (no pepsin, measured as MRM peak area, sum of three transitions) per peptide across the time points (0, 5, 10, 15, 30, 60 min). The peptides are graphed in order from protein N- to C-termini. The peptide sequence (and calculated molecular weight) is denoted above each graph. The potential sites for pepsin cleavage of these peptide sequences are Panel (A): L; (B): F; (C): F, F; (D): Y; (G): W, W; (H): F, Y, F (expected cleavage) or (E): L (potentially hindered) font. Error bars denote standard deviation (SD).

Five of the peptides characterized and quantified after pepsin digestion were cleavage variants (FIG. 40 Panels (A)-(C), (E)-(F)). The black arrows in FIG. 40 indicate that the peptide in the upper left panel is cleaved further by pepsin to yield the peptide in the upper right and panel immediately beneath. All peptic peptides monitored were produced rapidly (<15 min). The peptide NATGQPYPGV-SKF (aa 221-233, SEQ ID NO: 1) (FIG. 40 Panel (D)) reached equilibrium over this time frame and notably was the only peptide that was fully peptic, i.e., could not undergo further hydrolysis by pepsin. The majority of the peptic peptides monitored did not represent the fully cleaved final product as pepsin is relatively non-specific. In some cases, a decrease in peptide level is noted over time, for example, TYIPLLPNEF (aa 88-97, SEQ ID NO: 1) (FIG. 40 Panel (E)) decreases slowly from ~5 min and its product TYIPLLPNE (aa 88-96, SEQ ID NO: 1) (FIG. 40 Panel (F)) increases in concentration from 10-60 min. Several other examples of pepsin proteolysis products containing missed cleavages, susceptible to further degradation, were monitored (FIG. 40 Panels (A)-(B), (E)-(H)). In fact, only NATGQPYPGVSKF (aa 221-233, SEQ ID NO: 1) (FIG. 40 Panel (D)) contains no predicted cleavage sites. The appearance of these peptides in the digest is taken as evidence of the degradation and therefore digestibility of the Picpa-ω3D protein. Three of the eight peptides monitored reached a peak at 5 min. To further illustrate the low specificity of pepsin and the generation of multiple related cleavage products, five cleavage variants of TYIPLLPNEF (aa 88-97, SEQ ID NO: 1) were monitored (FIG. 41). The larger fragments were noted to plateau, whereas the smaller peptide fragments were still increasing in concentration at the conclusion of the 60 min-digestion period.

The tryptic peptides monitored after the pepsin digest show a rapid decline in the first 5 min and then a further decline over the remainder of the experiment (60 min duration). It is estimated that >97% of the protein is cleaved after 60 min on the basis of the disappearance of these eight tryptic peptides. The peptides containing multiple pepsin cleavage sites: TAIDTF↓GNVF↓K (aa 33-43, SEQ ID NO: 1), HTDENMW↓VSL↓W↓K (aa 374-385 of SEQ ID NO: 1), SC[CAM]QF↓VENHDGVY↓MF↓R (SEQ ID NO: 10) (where X↓X represent pepsin cleavage site) are reduced to 0.9, 1.1 and 0.3% of the undigested control (no pepsin digest) respectively. This is supported by analysis of the digested peptides on the TripleTOF 5600 LC-MS/MS, which shows that these peptides are more frequently fragmented to yield smaller fragments after 30-60 min. The tryptic peptides containing fewer sites: VTVSGSEIL↓EG-STK (aa 4-17, SEQ ID NO: 1), SGNVASF↓K (aa 22-29, SEQ ID NO: 1) and VPDY↓TIK (aa 44-50, SEQ ID NO: 1) (with a single site) or DIL↓DAIPK (aa 51-58, SEQ ID NO: 1) (where the lysine in position P3 is known to hinder pepsin cleavage) were reduced to 0.7, 0.5, 1.3 and 1.4% respectively. The higher percentage of EATECIK (SEQ ID NO: 9) observed (17.5% at 5 min and 2.7% at 60 min) can be explained by the absence of peptic digestion sites within this peptide sequence. Overall, it was observed that the peptides from the termini (both N- and extreme C-termini) of the protein were liberated rapidly with <6% remaining after 5 min (Table 25). Within as short as 5 min, only 1.3% of the tryptic peptide SGNVASFK (aa 22-29, SEQ ID NO: 1) remained (Table 25), indicating that 98.7% of the intact protein was degraded. The existence of some tryptic peptides at low levels after 60 min solely suggested that the intact protein was degraded into small peptides by pepsin, and these peptides were detectable. The tryptic peptide SGNVASFK (aa 22-29, SEQ ID NO: 1) was reduced to 0.56% after 60 min, indicating that essentially there was no intact protein remained beyond this pepsin digestion time.

TABLE 25

Percentage of each tryptic peptide remaining during pepsin time course

| Peptide Sequence | Incubation time (min) | | | | |
| --- | --- | --- | --- | --- | --- |
|  | 5 | 10 | 15 | 30 | 60 |
| VTVSGSEILEGSTK[1] | 2.8 | 1.5 | 1.8 | 1.3 | 0.7 |
| SGNVASFK[2] | 1.3 | 1.1 | 1.0 | 1.0 | 0.5 |
| TAIDTFGNVFK[3] | 2.5 | 1.7 | 2.6 | 1.4 | 0.9 |
| VPDYTIK[4] | 3.8 | 2.7 | 3.6 | 2.3 | 1.3 |
| DILDAIPK[5] | 6.0 | 6.1 | 5.5 | 3.7 | 1.4 |
| EATEC[CAM]IK[6] | 17.5 | 17.1 | 18.1 | 9.4 | 2.7 |
| HTDENMWVSLWK[7] | 16.5 | 9.2 | 9.9 | 8.2 | 1.1 |
| SC[CAM]QFVENHDGVYMFR[8] | 2.0 | 1.3 | 1.1 | 0.9 | 0.3 |

[1] residues (aa) 4-17 of SEQ ID NO: 1;
[2] aa 22-29 of SEQ ID NO: 1;
[3] aa 33-43 of SEQ ID NO: 1;
[4] aa 44-50 of SEQ ID NO: 1;
[5] aa 51-58 of SEQ ID NO: 1;
[6] SEQ ID NO:9;
[7] aa 374-385 of SEQ ID NO: 1;
[8] SEQ ID NO: 10.

Picpa-ω3D is an integral membrane protein. Until recently, there is no functional antibody for western blot analysis available to quantify the transgenic protein content in transgenic canola, or detect the stability of Picpa-ω3D as a native protein. The commercially raised polyclonal and monoclonal antibodies (GenScript, Piscataway, NJ, US) failed to generate a specific signal towards Picpa-ω3D. The antibodies were raised against the synthetic peptides predicted as potential epitopes for antigens (FIG. 43).

Although Picpa-ω3D expressed as the His-GFP fusion protein could be analyzed by western blot against the anti-His-tag antibody, such a western blot analysis could only monitor the fusion region, rather than whole protein, when the His-tag is cleaved off, for example after SGF digestion. In addition, the anti-His-tag antibody is not suitable for quantification of the native Picpa-ω3D (unfused) protein in transgenic ω3LCPUFA canola. Thus, an alternative approach using LC-MRM-MS analysis was developed here, which can be applied both for the quantification of protein expressed in canola and for the stability assays. The results shown here clearly demonstrated that the IC-MS approach is suitable for such an application. This method is as sensitive as traditional western blot, which can normally detect ng to μg of protein. The LC-MRM-MS approach described herein detected as little as 7.86 fmol (injected on-column) which equates to ~372 μg. In addition, western blot using antibodies might only detect a limited number of epitopes (one or two) from the protein. Here, eleven (peptic) and eight (tryptic) peptides were targeted, along with the intact protein, which provides an understanding of the kinetics of digestion and the susceptibility of specific regions of the protein to proteolysis. Due to the technical difficulty that was involved in filtering and washing steps after pepsin digestion with five replicates, the earliest practical time point was 5 min. Nevertheless, the results show the successful application of LC-MRM-MS for target protein digestibility analysis. For example, Picpa-ω3D) was expressed at 352 ng per mg of total protein in mature seed with as little as 2.78 mg of total protein extracted from 1 g of seed.

The Picpa-ω3D protein belongs to the subfamily of yeast acyl-CoA type fatty acid desaturases that introduce a double bond between the Δ15-position from the carboxyl end of fatty acids. The yeast acyl-CoA type fatty acid desaturases include Δ12- and ω3-/Δ15-desaturases. Some of these yeast acyl-CoA type fatty acid desaturases are also common in food, animal feeds or in food production. The Picpa-ω3D protein was used as the representative of two yeast acyl-CoA type fatty acid desaturases (Picpa-ω3D and Lack1-Δ12 desaturase) engineered into ω3LCPUFA canola.

The results of this Example demonstrate that the combined pepsin-trypsin assay showed a rapid decline in the tryptic peptides that were used as a proxy for the presence of intact protein. 98.7% of the full-length Picpa-ω3D protein was digested within 5 min, and 99.5% was digested within 60 min of incubation in pepsin. In addition to rapid digestion of Picpa-ω3D protein in SGF, Picpa-ω3D protein represents a negligible portion of the total protein present in the transgenic ω3LCPUFA Example 7. LC-MS/MS Analysis of Pavlova Salina Δ5-Desaturase Protein Stability assess the in vitro stability of the Pavlova salina Δ5-desaturase (Pavsa-Δ5D) protein in simulated gastric fluid (SGF) comprising the proteolytic enzyme, pepsin, and in combination with a novel pepsin-trypsin assay and LC-MS/MS to monitor the precise degradation products. The extent of protein digestion was evaluated by the appearance of peptic products and the disappearance of tryptic peptide products (as a proxy for intact protein). The method in this Example demonstrated that 99.9% of the full-length Pavsa-Δ5D protein was digested within 5 min, and six out of twelve peptides were present <0.2% after 60 min of incubation in pepsin.

The Δ5-desaturase gene used in DHA canola was previously cloned from alga P. salina. The Pavsa-Δ5D protein was expressed as a His-tag fusion in Sf9 insect cell line infected with recombinant baculovirus constructed using pFastBac vector (Invitrogen, DE) and then purified. The vector contained coding sequences encoding a His-tag (His10) and a PreScission protease cleavage site (SLEVLFQ↓GP) fused to the codon optimized Pavsa-Δ5D gene produce fusion protein His10::Pavsa-Δ5D. The main band identified in the gel and Western Blot was excised and subjected to proteolytic digestion with trypsin. The band was identified with >99% confidence as containing His10::Pavsa-Δ5D (with or without minor contaminating proteins). The other minor bands are likely to be insect cell proteins. The recombinant protein was also analyzed by LC-MS/MS. Protein extraction, digestions, LC-MS characterization of the protein post-trypsin digestion and post-pepsin digestion, peptide summaries, and general assays were conducted as described above. Three transitions were used per peptide (with 11 peptides from Pavsa-Δ5D), wherein the peak area of the three MRM transitions were summed.

Two test systems, pepsin digestion (representing simulated gastric fluid, SGF) and a combined pepsin-trypsin digestion, were utilized independently to test the stability of the His10::Pavsa-Δ5D protein. SGF contained the proteolytic enzyme pepsin in a buffer adjusted to an acidic pH 1.2, using a highly purified form of pepsin. The SGF was formulated so that an enzyme:protein ratio of 3:1 would be present in the digestion reactions. The digestion of the Pavsa-Δ5D protein was monitored by LC-MS/MS.

In this study, the peptide fragments of His10::Pavsa-Δ5D persisting after pepsin digestion for 120 min were characterized by untargeted LC-MS/MS. Protein sequence coverage obtained after pepsin digestion is depicted below, in which bold indicates peptides identified with >95%0 confidence; italics indicates peptides identified with 50-95% confidence; underline indicates peptides identified with <50% confidence; normal means residues were not detected; the wave underline is the N-terminal His-tag and protease cleavage site followed by methionine of native Pavsa-Δ5D in the fusion protein:

(SEQ ID NO: 17)
MHHHHHHHHHHSLEVLFQGPMPP*RDSYS*YAAPPSAQLHEVDTPQEHDKK

ELVIGDRAY*DVTNF*VKRHPGGKIIAY*QV*GTDATDAYKQFHVRSAKADKM

LKSLPSRPVHKGYSPRRADLI*ADFQEFTKQLEAEGMFEPSLPHVAYRLA*

EVIAMHVAGAALIWHGYTF*AGIA*MLGVVQGRCGWLMHEGGHYSLIGNIA

FDRAIQVACYGLGCGMSGAWWRNQHNKHHATPQKLQHDVDLDTLPLVAF

HERIAAKVKSPAMKA*WL*SMQAKLFAPVTTLL**VALGWQLYLHPRHMLRTK

HYDELAMLGIRYGLVGYLAANYGAGY*VLACYLLYVQLGAMYIFCN*FAVS

HTHLPVVEPNEHATW<u>VEYAANHTTNCSPSWWCDWWMSY</u>LNYQIEHHLYP

SMPQFRHPKIAPRVKOLFEKHGLHYDVRGYFEAMADTFANLDNVAHAPE

KKMQ

Protein sequence coverage obtained after trypsin digestion was characterized by LC-MS/MS and is depicted below, in which bold indicates peptides identified with >95% confidence; italics indicates peptides identified with 50-95% confidence; underline indicates peptides identified with <50% confidence; normal means residues were not detected; the wave underline is the N-terminal His-tag and protease cleavage site followed by methionine of native Pavsa-Δ5D in the fusion protein:

(SEQ ID NO: 17)
MHHHHHHHHHHSLEVLFQGPMPPRDSYSYAAPPSAQLHEVDTPQEHDKK

ELVIGDRAYDVTNFVKRHPGGKIIAYQVGTDATDAYKQFHVRSAKAD*KM*

LKSLPSRPVHKGYSPRRADLIADFQEFTKQLEAEGMFEPSLPHVAYRLA

EVIAMHVAGAALIWHGYTFAGIAMLGVVQGRCGWLMHEGGHYSLTGNIA

FDRAIQVACYGLGCGMSGAWWRNQHNKHHATPQKLQHDVDLDTLPLVAF

HERI*AAK*VKSPAMKAWLSMQAKLFAPVTTLLVALGWQLYLHPRHMLRTK

HYDELAMLGIRYGLVGYLAANYGAGYVLACYLLYVQLGAMYIFCNFAVS

HTHLPVVEPNEHATWVEYAANHTTNCSPSWWCDWWMSYLNYQIEHHLYP

SMPQFRHPKIAPRVKOLFEKHGLHYDVRGYFEAMADTFANLDNVAHAPE

KKMQ

Peptides that were identified with 95% confidence and that yielded intense signals in the MS were selected for relative quantification. The 11 pepsin-derived and 12 trypsin-derived peptides that were selected from the digestion of the His10::Pavsa-Δ5D protein are summarized in Tables 1-2. The selected peptides spanned the length of the protein. Details are shown in Tables 26 and 27

TABLE 26

Peptide MRM transitions for Pavsa-Δ5D pepsin products

| Peptide | RT | Q1 m/z | z | Q3 m/z | Fragment | CE |
|---|---|---|---|---|---|---|
| SYAAPPSAQL | 4.52 | 502.756 | 2+ | 745.351 | b8+ | 23.6 |
|  |  |  |  | 612.335 | y6+ |  |
|  |  |  |  | 683.372 | y7+ |  |
| YAAPPSAQL | 4.42 | 459.240 | 2+ | 786.378 | b8+ | 21.5 |
|  |  |  |  | 612.335 | y6+ |  |
|  |  |  |  | 658.319 | b7+ |  |
| FVKRHPGGKIIA | 2.13 | 661.900 | 2+ | 1120.673 | b10+ | 31.4 |
|  |  |  |  | 879.494 | b8+ |  |
|  |  |  |  | 1007.589 | b9+ |  |
| VKRHPGGKIIA | 1.03 | 588.372 | 2+ | 860.521 | b8+ | 27.8 |
|  |  |  |  | 655.413 | y7+ |  |
|  |  |  |  | 948.573 | y9+ |  |
| LKSLPSRPVHKGYSPRRADL | 2.69 | 456.260 | 5+ | 581.820 | y10++ | 20.8 |
|  |  |  |  | 650.349 | y11++ |  |
|  |  |  |  | 517.770 | y9++ |  |
| QEFTKQ | 1.12 | 390.698 | 2+ | 634.319 | b5+ | 18.1 |
|  |  |  |  | 523.287 | y4+ |  |
|  |  |  |  | 652.330 | y5+ |  |
| FAPVTTL | 5.85 | 374.715 | 2+ | 516.281 | b5+ | 17.4 |
|  |  |  |  | 617.329 | b6+ |  |
|  |  |  |  | 530.318 | y5+ |  |

TABLE 26-continued

Peptide MRM transitions for Pavsa-Δ5D pepsin products

| Peptide | RT | Q1 m/z | z | Q3 m/z | Fragment | CE |
|---|---|---|---|---|---|---|
| YLHPRHMLRTKHYDEL | 3.00 | 528.025 | 4+ | 721.864 | y11++ | 24.4 |
|  |  |  |  | 848.440 | y13++ |  |
|  |  |  |  | 676.293 | y5+ |  |
| DVRGYF | 4.30 | 378.687 | 2+ | 428.225 | b4+ | 17.6 |
|  |  |  |  | 591.288 | b5+ |  |
|  |  |  |  | 542.272 | y4+ |  |
| DVRGY | 1.65 | 305.150 | 2+ | 371.203 | b3+ | 14.0 |
|  |  |  |  | 395.203 | y3+ |  |
|  |  |  |  | 494.272 | y4+ |  |
| DNVAHAPEKKMQ | 1.22 | 684.340 | 2+ | 760.402 | y6+ | 32.5 |
|  |  |  |  | 831.439 | y7+ |  |
|  |  |  |  | 968.498 | y8+ |  |
| DNVAHAPEKKM*Q | 0.66 | 692.340 | 2+ | 776.402 | y6+ | 32.9 |
|  |  |  |  | 847.439 | y7+ |  |
|  |  |  |  | 984.498 | y8+ |  |

Pavsa-Δ5D sequence:[b]

(SEQ ID NO: 5)

MPPRDSYSYAAPPSAQLHEVDTPQEHDKKELVIGDRAYDVTNFVKRHPGGKIIAYQVGTDATDAYKQFHVR
SAKADKM<u>LKSLPSRPVHKGYSPRRADL</u>IADFQEFTKQLEAEGMFEPSLPHVAYRLAEVIAMHVAGAALIWH
GYTFAGIAMLGVVQGRCGWLMHEGGHYSLTGNIAFDRAIQVACYGLGCGMSGAWWRNQHNKHHATPQKLQH
DVDLDTLPLVAFHERIAAKVKSPAMKAWLSMQAKLFAPVTTLLVALGWQLYLHPRHMLRTKHYDELAMLGI
RYGLVGYLAANYGAGYVLACYLLYVQLGAMYIFCNFAVSHTHLPVVEPNEHATWVEYAANHTINCSPSWWC
DWWMSYLNYQIEHHLYPSMPQFRHPKIAPRVKQLFEKHGLHYDVRGYFEAMADTFANLDNVAHAPEKKMQ

RT, retention time (min); Q1 m/z, precursor ion mass-to-charge ratio (m/z); z, charge state; Q3 m/z, fragment ion m/z; CE, collision energy in V. The amino acid marked with * represents modified form: oxidation (Met).
[b]The mature Pavsa-Δ5D sequence with mapped peptic peptides (bold, underlined). For pepsin, different cleavage variants were observed owing to the incomplete digestion and these peptides have been differentiated by single or double underline.

TABLE 27

Peptide MRM transitions for Pavsa-Δ5D trypsin products

| Peptide | RT | Q1 m/z | z | Q3 m/z | Fragment | CE |
|---|---|---|---|---|---|---|
| DSYSYAAPPSAQLHEVDTPQEHDK | 4.29 | 672.058 | 4+ | 915.935 | y16++ | 31.6 |
|  |  |  |  | 964.461 | y17++ |  |
|  |  |  |  | 753.353 | y6+ |  |
| ELVIGDR | 3.62 | 401.227 | 2+ | 559.320 | y5+ | 18.7 |
|  |  |  |  | 460.251 | y4+ |  |
|  |  |  |  | 243.130 | b2+ |  |
| AYDVTNFVK | 4.85 | 528.772 | 2+ | 822.436 | y7+ | 24.9 |
|  |  |  |  | 707.409 | y6+ |  |
|  |  |  |  | 608.340 | y5+ |  |
| IIAYQVGTDATDAYK | 4.80 | 814.912 | 2+ | 1040.489 | y10+ | 38.9 |
|  |  |  |  | 941.421 | y9+ |  |
|  |  |  |  | 884.400 | y8+ |  |
| SLPSRPVHK | 1.44 | 510.801 | 2+ | 820.479 | y7+ | 24.0 |
|  |  |  |  | 723.426 | y6+ |  |
|  |  |  |  | 636.394 | y5+ |  |
| ADLIADFQEFTK | 7.11 | 699.351 | 2+ | 1211.631 | y10+ | 33.3 |
|  |  |  |  | 985.463 | y8+ |  |
|  |  |  |  | 799.398 | y6+ |  |
| QLEAEGMFEPSLPHVAYR | 6.37 | 692.000 | 3+ | 742.400 | y6+ | 31.2 |
|  |  |  |  | 1039.569 | y9+ |  |
|  |  |  |  | 1168.612 | y10+ |  |

TABLE 27-continued

Peptide MRM transitions for Pavsa-Δ5D trypsin products

| Peptide | RT | Q1 m/z | z | Q3 m/z | Fragment | CE |
|---|---|---|---|---|---|---|
| LQHDVDLDTLPLVAFHER | 6.83 | 706.704 | 3+ | 968.531 | y8+ | 31.9 |
| | | | | 871.478 | y7+ | |
| | | | | 758.394 | y6+ | |
| AWLSMQAK | 4.60 | 467.744 | 2+ | 677.365 | y6+ | 21.9 |
| | | | | 564.281 | y5+ | |
| | | | | 477.249 | y4+ | |
| HYDELAMLGIR | 6.04 | 439.890 | 3+ | 458.309 | y4+ | 19.1 |
| | | | | 589.340 | y5+ | |
| | | | | 660.380 | y6+ | |
| HGLHYDVR | 2.21 | 498.754 | 2+ | 859.442 | y7+ | 23.4 |
| | | | | 802.421 | y6+ | |
| | | | | 689.337 | y5+ | |
| GYFEAMADTFANLDNVAHAPEK | 7.58 | 804.370 | 3+ | 865.453 | y8+ | 36.6 |
| | | | | 980.480 | y9+ | |
| | | | | 1207.600 | y11+ | |

Pavsa-Δ5D sequence:
(SEQ ID NO: 5)
MPPRDSYSYAAPPSAQLHEVDTPQEHDKKELVIGDRAYDVTNFVKRHPGGKIIAYQVGTDATDAYKQFH
VRSAKADKMLKSLPSRPVHKGYSPRRADLIADFQEFTKQLEAEGMFEPSLPHVAYRLAEVIAMHVAGAA
LIWHGYTFAGIAMLGVVQGRCGWLMHEGGHYSLTGNIAFDRAIQVACYGLGCGMSGAWWRNQHNKHHAT
PQKLQHDVDLDTLPLVAFHERIAAKVKSPAMKAWLSMQAKLFAPVTTLLVALGWQLYLHPRHMLRTKHY
DELAMLGIRYGLVGYLAANYGAGYVLACYLLYVQLGAMYIFCNFAVSHTHLPVVEPNEHATWVEYAANH
TTNCSPSWWCDWWMSYLNYQIEHHLYPSMPQFRHPKIAPRVKQLFEKHGLHYDVRGYFEAMADTFANLD
NVAHAPEKKMQ The mature Pavsa-Δ5D sequence with mapped tryptic peptides (bold, underlined). For trypsin, all peptides selected were fully tryptic, i.e. contained no missed cleavages. As some of the peptides were adjacent in the sequence, these have been differentiated by single or double underline.
RT, retention time (min); Q1 m/z, precursor ion mass-to-charge ratio (m/z); z, charge state; Q3 m/z, fragment ion m/z; CE, collision energy in V.

The digestibility of His10::Pavsa-Δ5D in SGF was assessed by LC-MRM-MS method as described above. Characterization and quantification of the targeted peptic peptides showed the rapid degradation of His10::Pavsa-Δ5D. The pepsin digestion data has been presented in FIG. 44 as the mean (n=5) relative percentage of the maximum detected MRM peak area (sum of three transitions) per peptide across the time points (0, 5, 10, 15, 30, 60 min).

Figure 44:
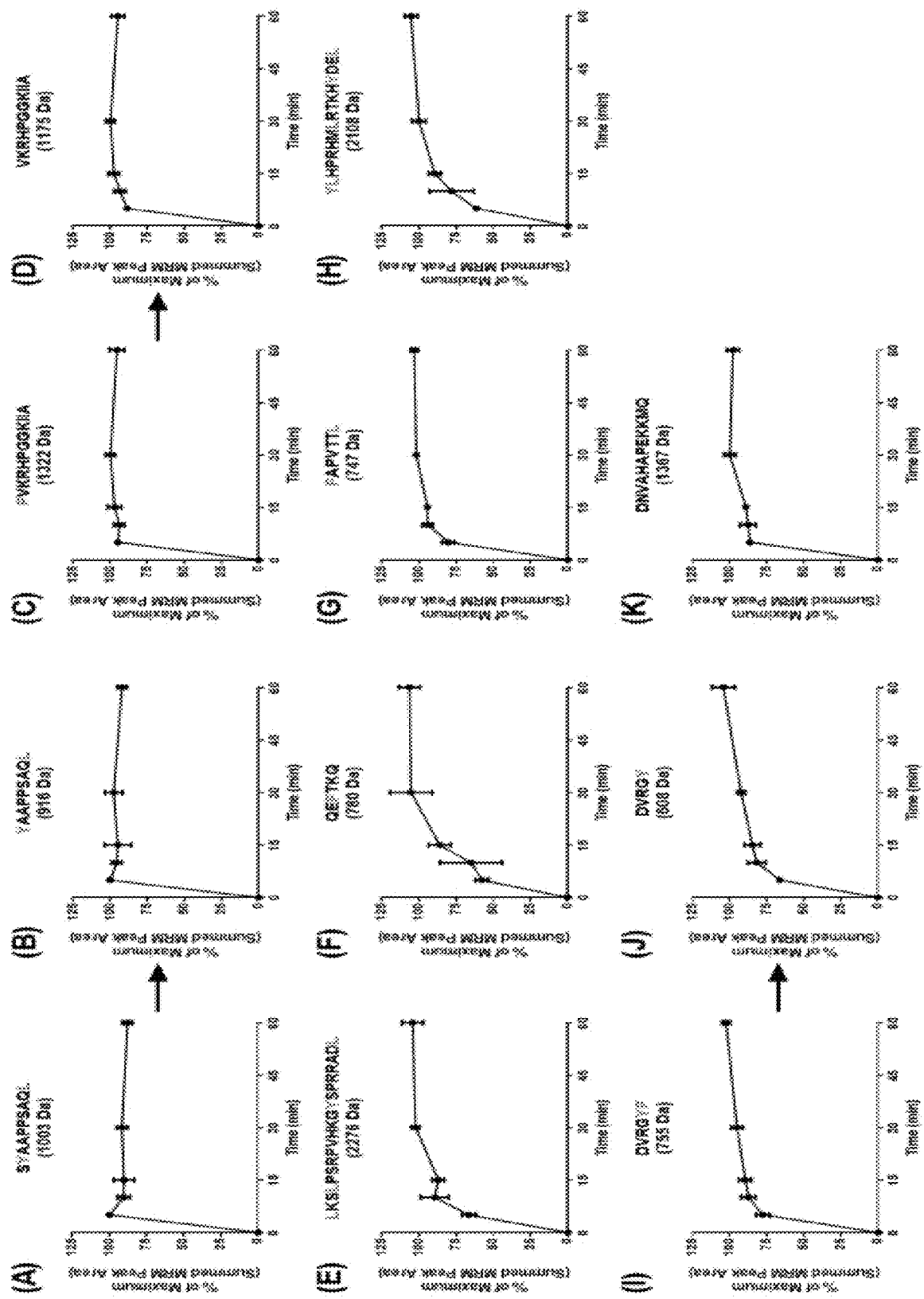
FIG. 44 presents data from quantification of the peptide products of His10::Pavsa-Δ5D after pepsin digestion. LC-MRM-MS analysis of pepsin proteolytic fragments. The response in the LC-MS system (measured as peak area) was converted to a percentage relative to the maximum peak area observed during pepsin digestion. The experimental control was time 0 with no pepsin addition. The peptides are graphed in order from protein N- to C-terminus. The peptide sequence (and calculated molecular weight) are denoted above each graph. Arrows indicate a subsequent cleavage to yield a secondary cleavage variant. The potential sites for pepsin cleavage of these peptide sequences are Panels (A): Y, L; (B): Y, L; (C): F; (F): F; (G): L; (H): YL, L (expected cleavage) or (E): L, L, Y; (G): F; (H): L, Y; (I): YF; (J): Y (potentially hindered). The error bars denote SD.

Eleven peptides were monitored by LC-MRM-MS spanning the length of the protein. A number of the peptides characterized and quantified after pepsin digestion were cleavage variants (FIGS. 44(A)-(B), (C)-(D) and (I)-(J)). The black arrows in FIG. 44 indicate that the peptide in the left panel is cleaved further by pepsin to yield the peptide in the right panel. All peptic peptides monitored were produced rapidly (<15 min) and many reached an equilibrium over this time frame. The peptic peptides monitored may not represent the fully cleaved final product as pepsin is relatively non-specific. Several examples of pepsin proteolysis products contained missed cleavages, indicated by red font (expected cleavage sites) or orange font (potentially hindered sites) in the peptide sequences. These peptides are susceptible to further degradation, exemplified in FIG. 44 Panels (B), (D) and (J). In fact, only peptides VKRHPGG-KIIA (44-54 of SEQ ID NO: 5) and DNVAHAPEKKMQ (414-425 of SEQ ID NO: 5) contain no predicted secondary cleavage sites. The appearance of these peptides in the digest is taken as evidence of the degradation and therefore digestibility of the Pavsa-Δ5D protein. Seven of the eleven peptides monitored reached >756% of the maximum value at 5 min. The remaining five peptides had reached 55% of maximum peptide liberation by 5 min and all eleven had reached a plateau by 60 min in the pepsin time course (FIG. 44).

TABLE 28

Percentage of each tryptic peptide remaining during pepsin time course

| | Time (min) | | | | |
|---|---|---|---|---|---|
| Peptide Sequence | 5 | 10 | 15 | 30 | 60 |
| DSYSYAAPPSAQLHEVDTPQEHDK | 0.1 | 0.0 | 0.1 | 0.0 | 0.1 |
| ELVIGDR | 0.9 | 0.5 | 0.5 | 0.3 | 0.2 |
| AYDVTNFVK | 0.4 | 0.2 | 0.2 | 0.1 | 0.1 |
| IIAYQVGTDATDAYK | 0.5 | 0.3 | 0.3 | 0.2 | 0.2 |
| SLPSRPVHK | 21.6 | 6.6 | 8.1 | 6.4 | 3.7 |
| ADLIADFQEFTK | 19.4 | 6.9 | 7.6 | 6.0 | 2.7 |
| QLEAEGMFEPSLPHVAYR | 100.0 | 57.3 | 64.2 | 51.4 | 30.7 |
| LQHDVDLDTLPLVAFHER | 0.2 | 0.1 | 0.1 | 0.1 | 0.1 |
| AWLSMQAK | 31.6 | 9.1 | 12.9 | 10.8 | 5.7 |
| HYDELAMLGIR | 100.0 | 43.2 | 49.2 | 38.6 | 21.4 |
| HGLHYDVR | 43.3 | 29.2 | 32.6 | 28.4 | 18.8 |
| GYFEAMADTFANLDNVAHAPEK | 0.9 | 0.5 | 0.6 | 0.3 | 0.2 |

All peptides contained in SEQ ID NO: 5

Figure 45:
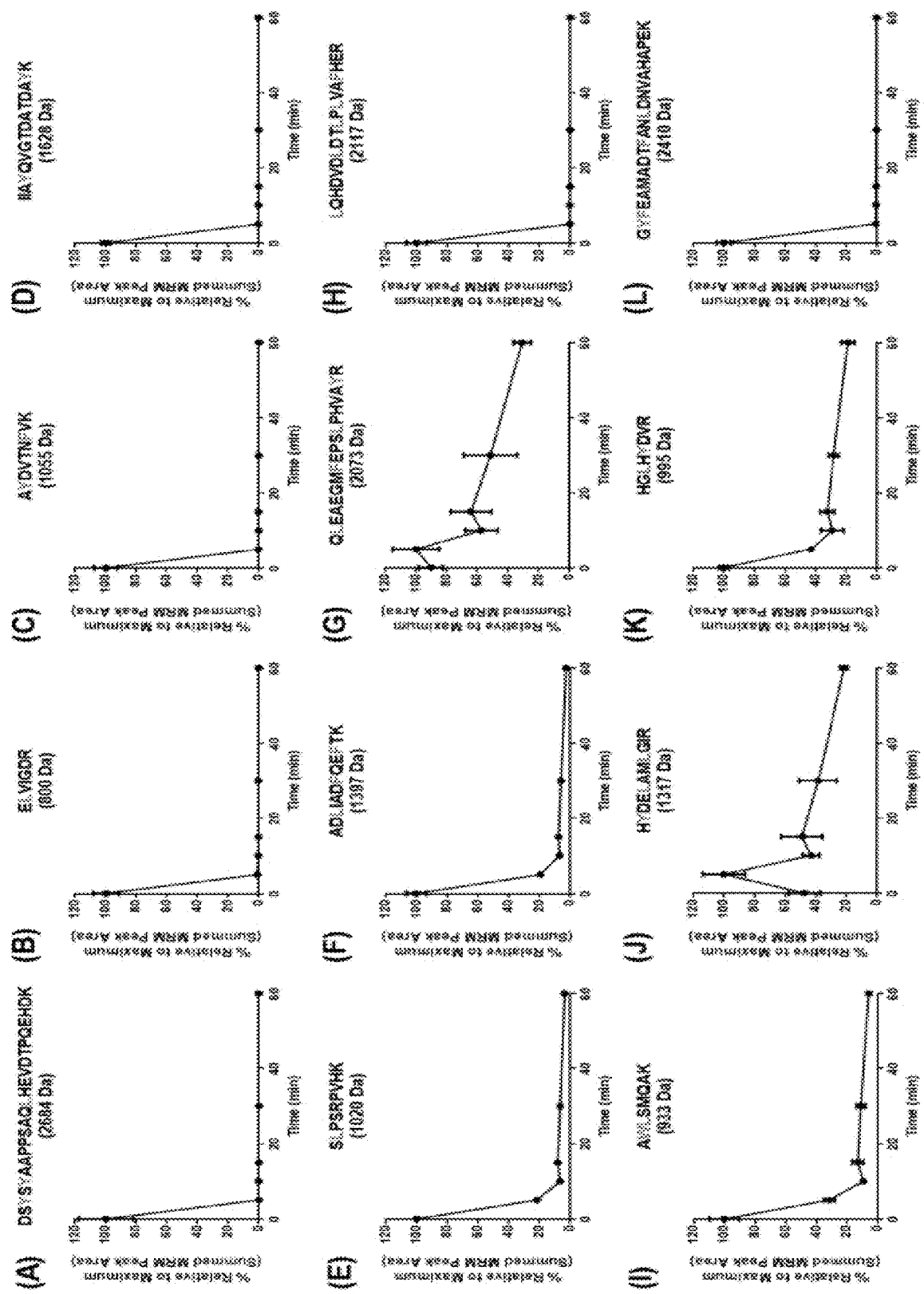
FIG. 45 presents data from quantification of the tryptic peptide products of $His_{10}$::Pavsa-Δ5D after combined pepsin-trypsin digestion. The trypsin data has been presented as the mean percentage (n=5 replicate digests) reduction relative to the experimental control at 0 min (no pepsin addition, measured as MRM peak area, sum of three transitions) per peptide across the time points (0, 5, 10, 15, 30, 60 min). The peptides are graphed in order from protein N- to C-terminus. The peptide sequence (and calculated molecular weight) are denoted above each graph. The potential sites for pepsin cleavage of these peptide sequences are: Panels (A): Y, Y, L; (C): F; (F): F, F; (G): F, L; (H): L, L, L, F; (J): L, L; (K): L, Y; (L): F, L (expected cleavage) or (B): Y: (C): Y; (D): Y, Y; (E) L; (F): L; (G): Y; (I): WL; (J): Y; and (L): YF (potentially hindered). Error bars denote standard deviation (SD).

The rapid degradation of the $His_{10}$::Pavsa-Δ5D protein demonstrated by the rapid increase of peptic peptides was further demonstrated by rapid decline of tryptic peptides in trypsin digestion after pepsin digestion (combined pepsin-trypsin digestion). The majority (9/12) of the tryptic peptides monitored after the pepsin digest show a rapid decline in the first 5-10 min and then a further decline over the remainder of the 60 min duration experiment (FIG. 45). The summed MRM peak area of the tryptic peptides without pepsin digestion (0 min) was used as the undigested control. The summed MRM peak area of the tryptic peptides after digestion of pepsin for 5, 10, 15, 30, 45 and 60 min followed by trypsin were calculated as the percentage relative to the undigested control, as the indicator of the protein cleavage.

It is estimated that >93% of the protein (taken as the average of all peptides) is cleaved after 60 min on the basis of the disappearance of these twelve tryptic peptides. Six of the twelve peptides were reduced rapidly to <1% of the undigested control (no pepsin digest) after only 5 min. By 10 min, nine peptides were decreased to <10%. Only three of the twelve peptides monitored showed a slower degradation, wherein two peptides (FIG. 45, Panels (G), (J)) increased after 5 min of pepsin digestion implying that they were located in a partially protected region of the protein. Once pepsin had partially degraded the protein, these tryptic peptides were liberated and then decreased but at a slower rate than the other nine peptides monitored. Overall, it was observed that the peptides from the N-terminus through to middle region of the protein were liberated rapidly with <10% remaining after 5 min (Table 3). The C-terminal region of the protein also revealed degradation but at a lower rate with ~70-80% degraded after 10 min.

Additionally, 99.9% of the full-length Pavsa-Δ5D protein was digested within min and six out of 12 peptides remained less than 0.2% after 60 min of incubation in pepsin. The combined pepsin-trypsin assay showed a rapid decline in the tryptic peptides that were used as a proxy for the presence of intact protein. This LC-MRM-MS approach, using twelve peptides that spanned the intact protein, provided an understanding of the kinetics of digestion and the susceptibility of specific regions of the protein to proteolysis, and detected Pavsa-Δ5D amounts as low as 7.80 femtomoles (injected on-column) which equates to ~376 μg on a protein scale.

Example 8. LC-MS/MS Analysis of *Pyramimonas Cordata* Δ6-Elongase Protein Stability This Example assess the in vitro stability of the *Pyramimonas cordata* Δ6-elongase (Pyrco-Δ6E) protein in simulated gastric fluid (SGF) comprising the proteolytic enzyme, pepsin, and in combination with a novel pepsin-trypsin assay employing state-of-the-art mass spectrometric approaches to monitor the precise degradation products. The extent of protein digestion was evaluated by the appearance of peptic products and the disappearance of tryptic peptide products (as a proxy for intact protein). This Example shows that this integral membrane protein, when analyzed by LC-MS/MS, was readily digestible in pepsin and/or trypsin: >95% of the N-terminal and C-terminal regions of Pyrco-Δ6E protein digested within 5 min and full-length protein was rapidly digested within 60 min of incubation in pepsin producing a suite of pepsin products <2,000 Da that spanned the entire peptide sequence.

This Δ6-elongase gene was previously cloned from alga *P. cordata*. The Pyrco-Δ6E protein was expressed as a $His_{10}$:: tag fusion in insect cell lines (Sf) infected with recombinant baculovirus constructed using pFastBac vector (Invitrogen, DE) and then purified. The vector contained coding sequences encoding a His-tag ($His_{10}$) and a PreScission protease cleavage site (SLEVLFQ↓GP) fused to the codon optimized Pyrco-Δ6E gene to produce fusion protein $His_{10}$:: Pyrco-Δ6E.

The peptide fragments of $His_{10}$::Pyrco-Δ6E persisting after pepsin digestion for 120 min were characterized by untargeted LC-MS/MS, and shown in bold (wave underline shows the N-terminal $His_{10}$::tag and protease cleavage site followed by methionine of native Pyrco-Δ6E in the fusion protein):

(SEQ ID NO: 18)
MHHHHHHHHHHSLEVLFQGPMEFAQPLVAMAQEQYAAIDAVVAPAIFSA

TDSIGWGLKPISSATKDLPLVESPTPLILSLLAYFAIVGSGLVYRKVFP

RTVKGQDPFLLKALMLAHNVFLIGLSLYMCLKLVYEAYVNKYSFWGNAY

NPAQTEMAKVIWIFYVSKIYEFMDTFIMLLKGNVNQVSFLHVYHHGSIS

GIWWMITYAAPGGDAYFSAALNSWVHVCMYTYYFMAAVLPKDEKTKRKY

LWWGRYLTQMQMFQFFMNLLQAVYLLYSSSPYPKFIAQLLVVYMVILLM

LFGNFYYMKHHASK

The peptide fragments present after trypsin digestion (for 16 h) were characterized by untargeted LC-MS/MS as shown below, in which bold indicates peptides identified with >9500' confidence, italics shows peptides identified with 50-95% confidence, and underlined indicates peptides identified with <50% confidence:

(SEQ ID NO: 18)
MHHHHHHHHHHSLEVLFQGPMEFAQPLVAMAQEQYAAIDAVVAPAIFSA

TDSIGWGLKPISSATKDLPLVESPTPLILSLLAYFAIVGSGLVYRKVFP

R*TV*KGQDPFLLKALMLAHNVFLIGLSLYMCLKLVYEAYVNKYSFWGNAY

NPAQTEMAKVIWIFYVSKIYEFMDTFIMLLKGNVNQVSFLHVYHHGSIS

GIWWMITYAAPGGDAYFSAALNSWVHVCMYTYYFMAAVLPKDEKTKRKY

LWWGRYLTQMOMFQFFMNLLQAVYLLYSSSPYPKFIAQLLVVYMVTLLM

LFGNFYYMKHHASK

Pepsin-derived peptides that were identified with 95% c confidence and that yielded intense signals in the MS were selected for relative quantification. Twelve peptides were selected from the pepsin digestion of the $His_{10}$::Pyrco-Δ6E: protein, and four tryptic peptides, are summarized in Tables 29-30. The selected pepsin-derived peptides spanned the length of the protein.

TABLE 29

| Peptide MRM transitions for Pyrco-Δ6E pepsin products | | | | | | |
| --- | --- | --- | --- | --- | --- | --- |
| Peptide | RT | Q1 m/z | z | Q3 m/z | Fragment | CE |
| FAQPLVA | 5.16 | 373.220 | 2+ | 444.220 | b4+ | 17.3 |
|  |  |  |  | 557.300 | b5+ |  |
|  |  |  |  | 656.370 | b6+ |  |
| MAQEQY | 2.16 | 385.160 | 2+ | 460.180 | b4+ | 17.9 |
|  |  |  |  | 588.240 | b5+ |  |
|  |  |  |  | 439.180 | y3+ |  |

TABLE 29-continued

Peptide MRM transitions for Pyrco-Δ6E pepsin products

| Peptide | RT | Q1 m/z | z | Q3 m/z | Fragment | CE |
|---|---|---|---|---|---|---|
| SATDSIGWGLKPISS | 6.06 | 759.890 | 2+ | 1057.600 | y10+ | 36.2 |
|  |  |  |  | 887.500 | y8+ |  |
|  |  |  |  | 944.520 | y9+ |  |
| WGLKPISS | 4.92 | 444.250 | 2+ | 531.310 | y5+ | 20.8 |
|  |  |  |  | 644.400 | y6+ |  |
|  |  |  |  | 701.420 | y7+ |  |
| VESPTPLIL | 7.16 | 484.790 | 2+ | 611.300 | b6+ | 22.8 |
|  |  |  |  | 724.390 | b7+ |  |
|  |  |  |  | 837.470 | b8+ |  |
| FAIVGSGL | 6.48 | 382.220 | 2+ | 431.270 | b4+ | 17.7 |
|  |  |  |  | 575.320 | b6+ |  |
|  |  |  |  | 632.340 | b7+ |  |
| LAHNVF | 3.68 | 350.690 | 2+ | 436.230 | b4+ | 16.2 |
|  |  |  |  | 535.300 | b5+ |  |
|  |  |  |  | 587.290 | y5+ |  |
| YVSKIYE | 3.13 | 451.240 | 2+ | 754.410 | b6+ | 21.1 |
|  |  |  |  | 639.330 | y5+ |  |
|  |  |  |  | 738.400 | y6+ |  |
| VSKIYE | 2.30 | 369.700 | 2+ | 591.350 | b5+ | 17.1 |
|  |  |  |  | 552.300 | y4+ |  |
|  |  |  |  | 639.330 | y5+ |  |
| YAAPGGDAY | 3.30 | 442.690 | 2+ | 632.260 | b7+ | 20.7 |
|  |  |  |  | 703.300 | b8+ |  |
|  |  |  |  | 579.240 | y6+ |  |
| YSSSPYPKF | 4.43 | 538.260 | 2+ | 651.350 | y5+ | 25.4 |
|  |  |  |  | 825.410 | y7+ |  |
|  |  |  |  | 912.450 | y8+ |  |
| YYMKHHASK | 0.65 | 582.780 | 2+ | 707.390 | y6+ | 27.6 |
|  |  |  |  | 838.440 | y7+ |  |
|  |  |  |  | 1001.500 | y8+ |  |

Pyrco-Δ6E sequence:[b]

(SEQ ID NO: 4)

MEFAQPLVAMAQEQYAAIDAVVAPAIFSATDSIGWGLKPISSATKDLPLVESPTPLILSLLAYFAIVGSGL
VYRKVFPRTVKGQDPFLLKALM<u>LAHNVF</u>LIGLSLYMCLKLVYEAYVNKYSFWGNAYNPAQTEMAKVIWIF<u>Y</u>
<u>VSKIYE</u>FMDTFIMLLKGNVQVSFLHVYHHGSISGIWWMITYAAPGGDAYFSAALNSWVHVCMYTYYFMAA
VLPKDEKTKRKYLWWGRYLTQMQMFQFFMNLLQAVYLLYSSSPYPKFIAQLLVVYMVTLLMLFGNFYYMKH
HASK

[b]Pyrco-Δ6E sequence with mapped peptic peptides (bold, underlined). For pepsin, different cleavage variants were observed owing to the incomplete digestion and these peptides have been differentiated by single or double underline.
RT, retention time (min); Q1 m/z, precursor ion mass-to-charge ratio (m/z); z, charge state; Q3 m/z, fragment ion m/z; CE, collision energy in V.

TABLE 30

Peptide MRM transitions for Pyrco-Δ6E trypsin products

| Peptide | RT | Q1 m/z | z | Q3 m/z | Fragment | CE |
|---|---|---|---|---|---|---|
| GQDPFLLK | 5.12 | 459.258 | 2+ | 732.429 | y6+ | 21.5 |
|  |  |  |  | 617.402 | y5+ |  |
|  |  |  |  | 260.190 | y2+ |  |
| LVYEAYVNK | 4.14 | 549.780 | 2+ | 886.430 | y7+ | 25.9 |
|  |  |  |  | 594.320 | y5+ |  |
|  |  |  |  | 723.360 | y6+ |  |
| YSFWGNAYNPAQTEMAK | 6.07 | 989.440 | 2+ | 1152.530 | y10+ | 47.5 |
|  |  |  |  | 1394.600 | y13+ |  |
|  |  |  |  | 875.430 | y8+ |  |

TABLE 30-continued

Peptide MRM transitions for Pyrco-Δ6E trypsin products

| Peptide | RT | Q1 m/z | z | Q3 m/z | Fragment | CE |
|---|---|---|---|---|---|---|
| YSFWGNAYNPAQTEM*AK | 5.64 | 997.440 | 2+ | 1168.530 | y10+ | 47.9 |
|  |  |  |  | 1410.630 | y13+ |  |
|  |  |  |  | 891.430 | y8+ |  |
| VIWIFYVSK | 7.80 | 577.830 | 2+ | 942.510 | y7+ | 27.3 |
|  |  |  |  | 756.430 | y6+ |  |
|  |  |  |  | 643.340 | y5+ |  |

Pyrco-Δ6E sequence:[b]

(SEQ ID NO: 4)
MEFAQPLVAMAQEQYAAIDAVVAPAIFSATDSIGWGLKPISSATKDLPLVESPTPLILSLLAYFAIV
GSGLVYRKVFPRTVKGQDPFLLKALMLAHNVELIGLSLYMCLKLVYEAYVNKYSEWGNAYNPAQTEM
AKVIWIFYVSKIYEFMDTFIMLLKGNVNQVSFLHVYHHGSISGIWWMITYAAPGGDAYFSAALNSWV
HVCMYTYYFMAAVLPKDEKTKRKYLWWGRYLTQMQMFQFFMNLLQAVYLLYSSSPYPKFIAQLLVVY
MVTLLMLFGNFYYMKHHASK

RT, retention time (min); Q1 m/z, precursor ion mass-to-charge ratio (m/z); z, charge state; Q3 m/z, fragment ion m/z; CE, collision energy in V. The amino acid marked with * represents modified form: oxidation (Met).

Figure 46:
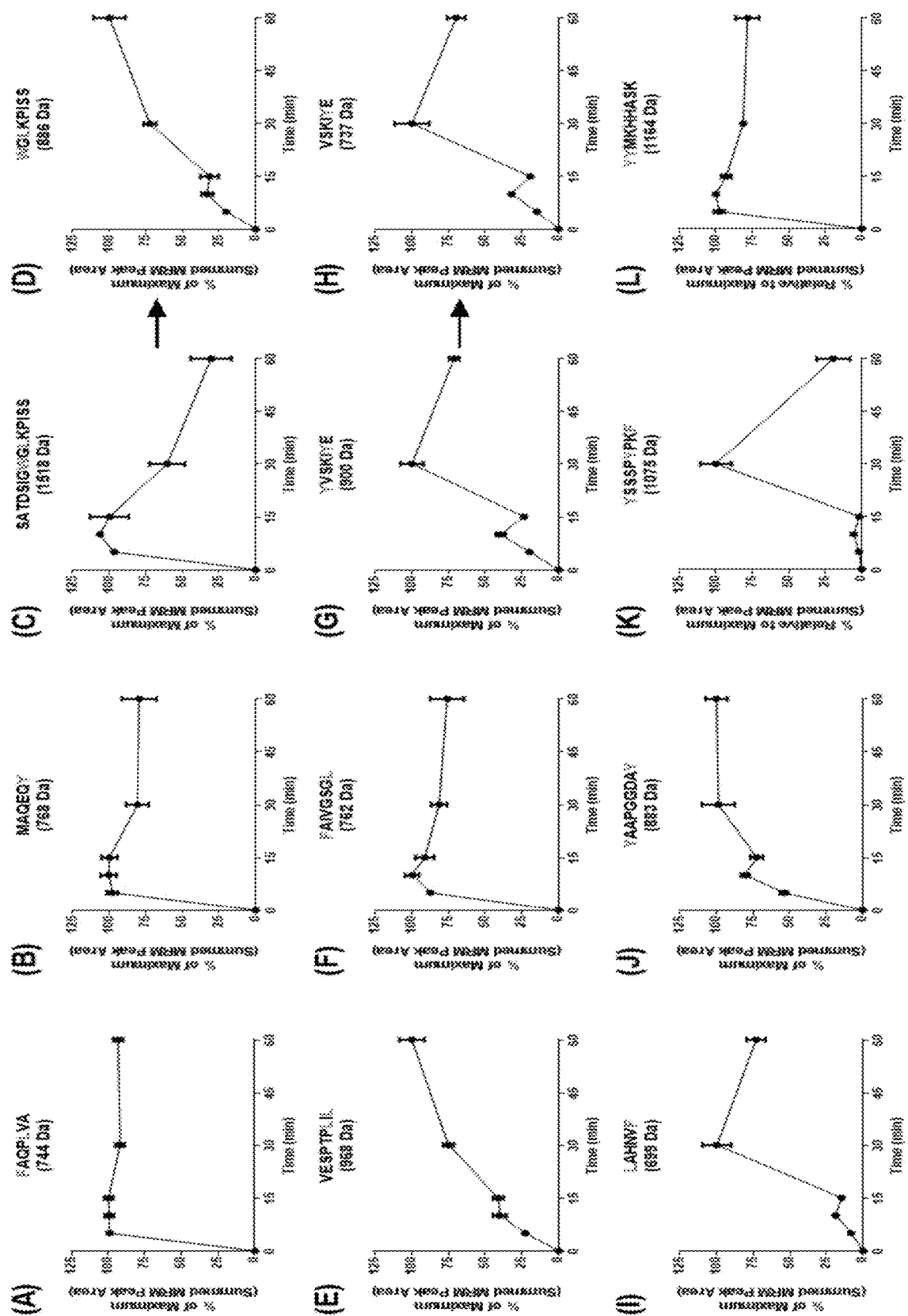
FIG. 46 shows quantification of the peptide products of His10::Pyrco-Δ6E after pepsin digestion. LC-MRM-MS analysis of pepsin proteolytic fragments. The response in the LC-MS system (measured as peak area) was converted to a percentage relative to the maximum peak area observed during pepsin digestion. The experimental control was time 0 with no pepsin addition. The peptides are graphed in order from protein N- to C-terminus. The peptide sequence (and calculated molecular weight) are denoted above each graph. Arrows indicate a subsequent cleavage to yield a secondary cleavage variant. The potential sites for secondary pepsin cleavage are Panels (A): F, L; (B): Y; (C): W, L: (D): W, L; (E): L, L; (F): F, L; (G): Y; (I): L; (J): Y, Y; (K): Y, Y, F; (L): YY (expected cleavage), or (G): Y; (I): F (potentially hindered) font within the sequence; error bars denote SD.

Digestibility of $His_{10}$::Pyrco-Δ6E in SGF was assessed by LC-MRM-MS method as described above. Characterization and quantification of the targeted peptic peptides showed the rapid degradation of $His_{10}$::Pyrco-Δ6E. The pepsin digestion data has been presented in FIG. 46 as the mean of four replicate digests relative percentage of the maximum detected MRM peak area (sum of three transitions) per peptide across the time points (0, 5, 10, 15, 30, 60 min).

The rapid degradation of the $His_{10}$::Pyrco-Δ6E protein demonstrated by the rapid liberation of peptic peptides was further confirmed by the decline of the single tryptic peptide after trypsin digestion (in the combined pepsin-trypsin digestion). Four of the peptides characterized and quantified after pepsin digestion were cleavage variants (FIG. 46 Panels (C)-(D), (G)-(H)). The black arrows in FIG. 46 indicate that the peptide in the left panel is cleaved further by pepsin to yield the peptide in the right panel. The N-terminal peptic peptides monitored were produced rapidly (<5 min, FIG. 46 Panels (A)-(C)) and reached an equilibrium over the experimental duration. The peptic peptides monitored may not represent the fully cleaved final product as pepsin is relatively non-specific. All of the displayed pepsin proteolysis products in FIG. 46 contained missed cleavages and are therefore susceptible to further degradation. In the case of the N-terminal peptide SATDSIGWGLKPISS (SEQ ID NO: 4) (FIG. 46 Panel (C)), this cleavage variant is produced rapidly reaching 97% after 5 min and then is rapidly cleaved to a range of products including WGLKPISS (SEQ ID NO: 4) (FIG. 46 Panel (D)) which shows a steady increase over the experimental duration. The only peptide that might be considered a final product of pepsin digestion is VSKIYE (SEQ ID NO: 4) wherein the lysine (K) located in the P3 position is likely to hinder further cleavage before Y (FIG. 46 Panel (II)). This peptide reaches a maximum level by 30 min before decreasing by ~30% and the pepsin digestion profile directly mimicked its intermediate product YVSKIYE (SEQ ID NO: 4) (FIG. 46 Panel (G)). The appearance of these peptides spanning the entire length of the protein in the pepsin digest is taken as evidence of the degradation and therefore digestibility of the $His_{10}$::Pyrco-Δ6E protein.

TABLE 31

Percentage of each tryptic peptide remaining during pepsin time course

| | Time (min) | | | | |
|---|---|---|---|---|---|
| Peptide Sequence | 5 | 10 | 15 | 30 | 60 |
| GQDPFLLK | 100.0 | 88.0 | 93.0 | 55.8 | 69.5 |
| LVYEAYVNK | 9.8 | 14.5 | 11.0 | 100.0 | 29.1 |
| VIWIFYVSK | 100.0 | 90.1 | 95.8 | 30.3 | 77.8 |
| YSFWGNAYNPAQTEMAK | 100.0 | 66.0 | 77.9 | 18.5 | 36.0 |

See SEQ ID NO: 4

Figure 47:
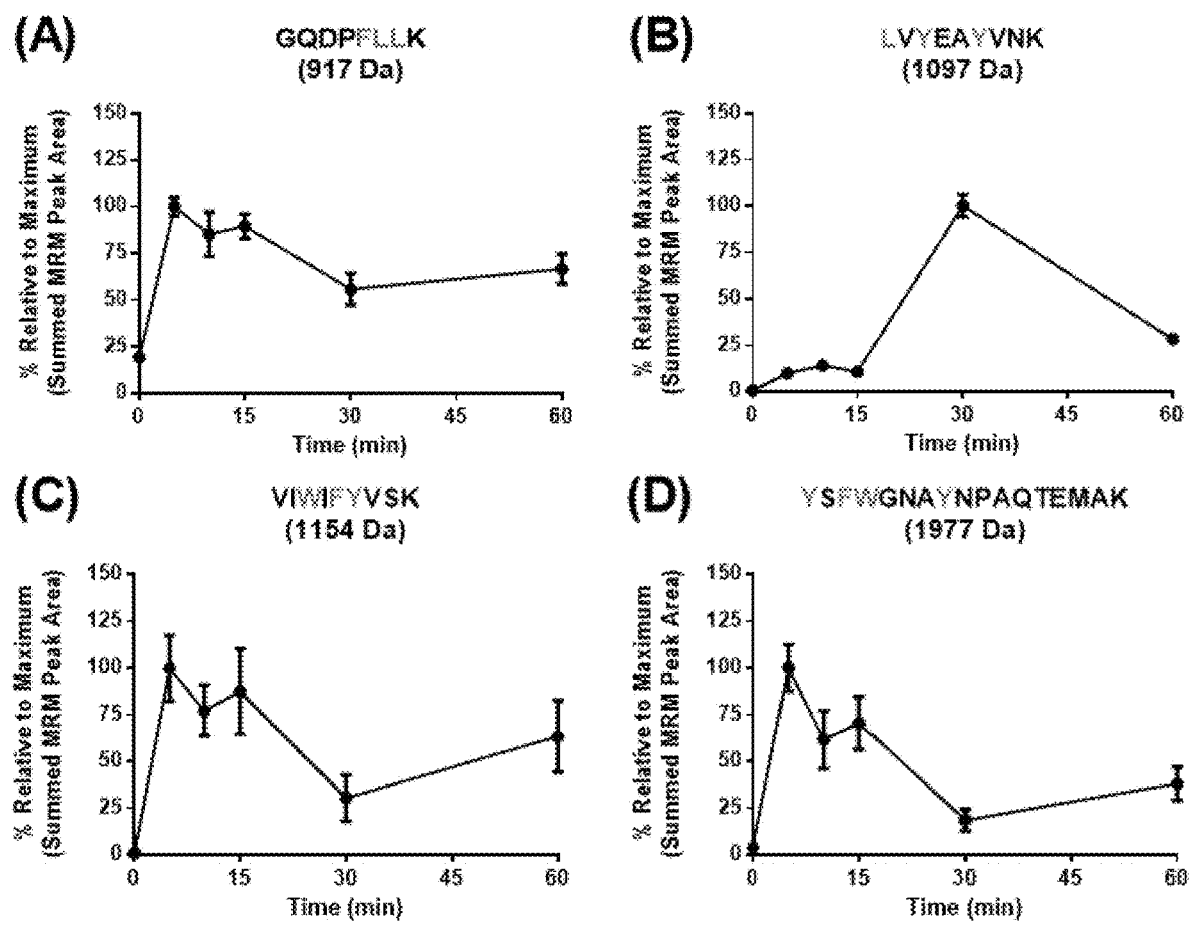
FIG. 47 shows quantification of the tryptic peptide products of $His_{10}$::Pyrco-Δ6E after combined pepsin-trypsin digestion. The trypsin data has been presented as the mean percentage (n=5 replicate digests) reduction relative to the experimental control at 0 min (no pepsin addition, measured as MRM peak area, sum of three transitions) per peptide across the time points (0, 5, 10, 15, 30, 60 min). The peptides are graphed in order from protein N- to C-terminus. The peptide sequence (and calculated molecular weight) are denoted above each graph. The potential sites for pepsin cleavage of these peptide sequences are: Panels (A): FLL; (B): L, Y; (C): FY; (D): Y, W, Y (expected cleavage) or (B): Y; (C): W; (D): F (potentially hindered) font; error bars denote SD.

In the case of the $His_{10}$::Pyrco-Δ6E protein, fewer tryptic products were confidently identified and hence available for protein digestion monitoring. This was due to the decreased frequency and distribution of trypsin sites within the protein sequence resulting in few peptides amenable to LC-MS which were confined to the middle region of the protein. The first peptide monitored, GQDPF↓L↓L↓K (SEQ ID NO: 4), contained three potential pepsin cleavage sites (as indicated by the arrows) and it was expected that pepsin would cleave this peptide resulting in a decrease in peptide abundance over the time course of the pepsin digestion. After 5 min, however, the peptide peak area was noted to increase 4-fold, remain relatively constant over the next 10 min before proceeding to decline slowly over the next 45 min (FIG. 47 Panel (A)). A similar phenomenon was observed previously for a peptide derived from Pyrco-Δ5E wherein a 3-fold increase in the peak area of a tryptic peptide (SQPFGLK) (SEQ ID NO: 6) was noted after 5 min incubation of the protein with pepsin. Both scenarios are postulated to arise from the peptides monitored residing within the core of the molecule, which in its native conformation is partially protected from trypsin digestion. After a short incubation with pepsin (5 min), the tertiary structure of the protein (Pyrco-Δ6E) is destroyed allowing full access to the tryptic sites and hence liberation of the tryptic peptide (GQDPFLLK) (SEQ ID NO: 4) at its maximal level (FIG. 46(A)). A similar profile was observed for the peptides VIW↓I-F↓Y↓VSK and Y↓SF↓W↓GNAY↓NPAQTEMAK (FIG. 47(C)-(D)). In the case of LVY↓EAY↓VNK (FIG. 47(B)), the maximum level was detected at 30 min decreasing by >70% at 60 min. The absence of detectable tryptic peptides derived from the N- and C-termini of the Pyrco-Δ6E protein precluded the determination of the final percentage degradation as determined for Picpa-ω3D and Pavsa-Δ4D, the appearance of peptic products (FIG. 46) demonstrated that the Pyrco-Δ6E protein is digested by pepsin over the time course of the experiment with >95% cleavage of the N-terminal and C-terminal regions achieved in <5 min (FIG. 46 Panels (A)-(C), (L)).

Sequence Listing information:

SEQ ID NO: 1, Picpa-ω3D
MSKVTVSGSEILEGSTKTVRRSGNVASFKQQKTAIDTFGNVFKVPDYTI
KDILDAIPKHCYERSLVKSMSYVVRDIVAISAIAYVGLTYIPLLPNEFL
RFAAWSAYVESISCFGFGIWILGHECGHSAFSNYGWVNDTVGWVLHSLV
MVPYFSWKFSHAKHHKATGHMTRDMVFVPYTAEEFKEKHQVTSLHDIAE
ETPIYSVFALLFQQLGGLSLYLATNATGQPYPGVSKFFKSHYWPSSPVE
DKKDYWYIVLSDIGILATLTSVYTAYKVFGFWPTFITWFCPWILVNHWL
VFVTFLQHTDSSMPHYDAQEWTFAKGAAATIDREFGILGIIFHDIIETH
VLHHYVSRIPFYHAREATECIKKVMGEHYRHTDENMWVSLWKTWRSCQF
VENHDGVYMERNCNNVGVKPKDT SEQ ID NO: 2, Lackl-Δ12D
MSAVTVTGSDPKNRGSSSNTEQEVPKVAIDINGNVFSVPDFTIKDILGA
IPHECYERRLATSLYYVERDIFCMLTTGYLTHKILYPLLISYTSNSIIK
FTFWALYTYVQGLFGTGIWVLAHECGHQAFSDYGIVNDFVGWTLHSYLM
VPYFSWKYSHGKHHKATGHMTRDMVFVPATKEEFKKSRNFFGNLAEYSE
DSPLRTLYELLVQQLGGWIAYLEVNVTGQPYPDVPSWKWNHEWLTSPLF
EQRDALYIFLSDLGILTQGIVLTLWYKKFGGWSLFINWFVPYIWVNHWL
VFITFLQHTDPTMPHYNAEEWTFAKGAAATIDRKFGFIGPHIFHDIIET
HVLHHYCSRIPFYNARPASEAIKKVMGKHYRSSDENMWKSLWKSFRSCQ
YVDGDNGVLMERNINNCGVGAAEK SEQ ID NO: 3, Micpu-Δ6D
MCPPKTDGRSSPRSPLTRSKSSAEALDAKDASTAPVDLKTLEPHELAAT
FETRWVRVEDVEYDVTNEKHPGGSVIFYMLANTGADATEAFKEFHMRSL
KAWKMLRALPSRPAEIKRSESEDAPMLEDFARWRAELERDGFEKPSITH
VAYRLLELLATFALGTALMYAGYPIIASVVYGAFFGARCGWVQHEGGHN
SLTGSVYVDKRLQAMTCGFGLSTSGEMWNQMHNKHHATPQKVRHDMDLD
TTPAVAFFNTAVEDNRPRGFSRAWARLQAWTFVPVTSGLLVQAFWIYVL
HPRQVLRKKNYEEASWMLVSHVVRTAVIKLATGYSWPVAYWWFTEGNWI
AYMYLFAHESTSHTHLPVVPSDKHLSWVNYAVDHTVDIDPSRGYVNWLM
GYLNCQVIHHLEPDMPQFRQPEVSRREVPEAKKWGLNYKVLSYYGAWKA
TESNLDKVGQHYYVNGKAEKAH SEQ ID NO: 4, Pyrco-Δ6E
MEFAQPLVAMAQEQYAAIDAVVAPAIFSATDSIGWGLKPISSATKDLPL
VESPTPLILSLLAYFAIVGSGLVYRKVFPRTVKGQDPFLLKALMLAHNV
FLIGLSLYMCLKLVYEAYVNKYSFWGNAYNPAQTEMAKVIWIFYVSKIY
EFMDTFIMLLKGNVNQVSFLHVYHHGSISGIWWMITYAAPGGDAYFSAA
LNSWVHVCMYTYYFMAAVLPKDEKTKRKYLWWGRYLTQMQMFQFFMNLL
QAVYLLYSSSPYPKFIAQLLVVYMVTLLMLFGNFYYMKHHASK SEQ ID NO: 5, Pavsa-Δ5D
MPPRDSYSYAAPPSAQLHEVDTPQEHDKKELVIGDRAYDVTNFVKRHPG
GKIIAYQVGTDATDAYKQFHVRSAKADKMLKSLPSRPVHKGYSPRRADL
IADFQEFTKQLEAEGMFEPSLPHVAYRLAEVIAMHVAGAALIWHGYTEA
GIAMLGVVQGRCGWLMHEGGHYSLTGNIAFDRAIQVACYGLGCGMSGAW
WRNQHNKHHATPQKLQHDVDLDTLPLVAFHERIAAKVKSPAMKAWLSMQ
AKLFAPVTTLLVALGWQLYLHPRHMLRTKHYDELAMLGIRYGLVGYLAA
NYGAGYVLACYLLYVQLGAMYIFCNFAVSHTHLPVVEPNEHATWVEYAA
NHTTNCSPSWWCDWWMSYLNYQIEHHLYPSMPQFRHPKIAPRVKQLFEK
HGLHYDVRGYFEAMADTFANLDNVAHAPEKKMQ SEQ ID NO: 6, Pyrco-Δ5E
MASIAIPAALAGTLGYVTYNVANPDIPASEKVPAYFMQVEYWGPTIGTI
GYLLFIYFGKRIMQNRSQPFGLKNAMLVYNFYQTFENSYCIYLFVTSHR
AQGLKVWGNIPDMTANSWGISQVIWLHYNNKYVELLDTFEMVMRKKEDQ
LSFLHIYHHTLLIWSWFVVMKLEPVGDCYFGSSVNTFVHVIMYSYYGLA
ALGVNCFWKKYITQIQMLQFCICASHSIYTAYVQNTAFWLPYLQLWVMV
NMFVLFANFYRKRYKSKGAKKQ SEQ ID NO: 7, Pavsa-Δ4D
MPPSAAKQMGASTGVHAGVTDSSAFTRKDVADRPDLTIVGDSVYDAKAF
RSEHPGGAHFVSLFGGRDATEAFMEYHRRAWPKSRMSRFHVGSLASTEE
PVAADEGYLQLCARIAKMVPSVSSGFAPASYWVKAGLILGSAIALEAYM
LYAGKRLLPSIVLGWLFALIGLNIQHDANHGALSKSASVNLALGLCQDW
IGGSMILWLQEHVVMHHLHTNDVDKDPDQKAHGALRLKPTDAWSPMHWL
QHLYLLPGETMYAFKLLFLDISELVMWRWEGEPISKLAGYLFMPSLLLK
LTFWARFVALPLYLAPSVHTAVCIAATVMTGSFYLAFFFFISHNFEGVA
SVGPDGSITSMTRGASELKRQAETSSNVGGPLLATLNGGLNYQIEHHLF
PRVHHGFYPRLAPLVKAELEARGIEYKHYPTIWSNLASTLRHMYALGRR
PRSKAE

SEQ ID NO: 8
TEPQTPQEWIDDLER

SEQ ID NO: 9
EATECIK

SEQ ID NO: 10
SCCAMQFVENHDGVYMER

SEQ ID NO: 11
FHVGSLASTEEPVAADEGYLQLCAR

SEQ ID NO: 12
SLEVLFQGP

SEQ ID NO: 13
SVVAVIGLPNDPSVR

SEQ ID NO: 14, His-tagged Picpa-ω3D
HHHHHHHHSKGEELFTGVVPILVELDGDVNGHKFSVRGEGEGDATNGKL
TLKFICTTGKLPVPWPTLVTTLTYGVQCFSRYPDHMKRHDFFKSAMPEG

YVQERTISFKDDGTYKTRAEVKFEGDTLVNRIELKGIDFKEDGNILGHK

LEYNENSHNVYITADKQKNGIKANFKIRHNVEDGSVQLADHYQQNTPIG

DGPVLLPDNHYLSTQSVLSKDPNEKRDHMVLLEFVTAAGITHGMDELYK

ENLYFQGGSSKVTVSGSEILEGSTKTVRRSGNVASFKQQKTAIDTFGNV

FKVPDYTIKDILDAIPKHCYERSLVKSMSYVVRDIVAISAIAYVGLTYI

PLLPNEFLRFAAWSAYVESISCFGFGIWILGHECGHSAFSNYGWVNDTV

GWVLHSLVMVPYFSWKESHAKHHKATGHMTRDMVFVPYTAEEFKEKHQV

TSLHDIAEETPIYSVFALLFQQLGGLSLYLATNATGQPYPGVSKFFKSH

YWPSSPVEDKKDYWYIVLSDLGILATLTSVYTAYKVFGFWPTFITWFCP

WILVNHWLVFVTFLQHTDSSMPHYDAQEWTFAKGAAATIDREFGILGII

FHDIIETHVLHHYVSRIPFYHAREATECIKKVMGEHYRHTDENMWVSLW

KTWRSCQFVENHDGVYMERNCNNVGVKPKDT

SEQ ID NO: 15, His-tagged Pyrco-Δ5E
MHHHHHHHHHHSLEVLFQGPMASIAIPAALAGTLGYVTYNVANPDIPAS

EKVPAYFMQVEYWGPTIGTIGYLLFIYFGKRIMQNRSQPFGLKNAMLVY

NFYQTFFNSYCIYLEVTSHRAQGLKVWGNIPDMTANSWGISQVIWLHYN

NKYVELLDTFFMVMRKKEDQLSFLHIYHHTLLIWSWFVVMKLEPVGDCY

FGSSVNTFVHVIMYSYYGLAALGVNCFWKKYITQIQMLQFCICASHSIY

TAYVQNTAFWLPYLQLWVMVNMEVLFANFYRKRYKSKGAKKQ

SEQ ID NO: 16, His-tagged Pavsa-Δ4D
MHHHHHHHHHHSLEVLFQGPMPPSAAKQMGASTGVHAGVIDSSAFTRKD

VADRPDLTIVGDSVYDAKAFRSEHPGGAHFVSLFGGRDATEAFMEYHRR

AWPKSRMSRFHVGSLASTEEPVAADEGYLQLCARIAKMVPSVSSGFAPA

SYWVKAGLILGSAIALEAYMLYAGKRLLPSIVLGWLFALIGLNIQHDAN

HGALSKSASVNLALGLCQDWIGGSMILWLQEHVVMHHLHTNDVDKDPDQ

KAHGALRLKPTDAWSPMHWLQHLYLLPGETMYAFKLLFLDISELVMWRW

EGEPISKLAGYLFMPSLLLKLTFWARFVALPLYLAPSVHTAVCIAATVM

TGSFYLAFFFFISHNFEGVASVGPDGSITSMTRGASFLKRQAETSSNVG

GPLLATLNGGLNYQIEHHLFPRVHHGFYPRLAPLVKAELEARGIEYKHY

PTIWSNLASTLRHMYALGRRPRSKAE

SEQ ID NO: 17, His-tagged Pavsa-Δ5D
MHHHHHHHHHHSLEVLFQGPMPPRDSYSYAAPPSAQLHEVDTPQEHDKK

ELVIGDRAYDVTNFVKRHPGGKIIAYQVGTDATDAYKQFHVRSAKADKM

LKSLPSRPVHKGYSPRRADLIADEQEFTKQLEAEGMFEPSLPHVAYRIA

EVIAMHVAGAALIWHGYTFAGIAMLGVVQGRCGWLMHEGGHYSLTGNIA

FDRAIQVACYGLGCGMSGAWWRNQHNKHHATPQKLQHDVDLDTLPLVAF

HERIAAKVKSPAMKAWLSMQAKLFAPVTTLLVALGWQLYLHPRHMLRTK

HYDELAMLGIRYGLVGYLAANYGAGYVLACYLLYVQLGAMYIFCNFAVS

HTHLPVVEPNEHATWVEYAANHTTNCSPSWWCDWWMSYLNYQIEHHLYP

SMPQFRHPKIAPRVKQLFEKHGLHYDVRGYFEAMADTFANLDNVAHAPE

KKMQ

SEQ ID NO: 18, His-tagged Pyrco-Δ6E
MHHHHHHHHHHSLEVLFQGPMEFAQPLVAMAQEQYAAIDAVVAPAIFSA

TDSIGWGLKPISSATKDLPLVESPTPLILSLLAYFAIVGSGLVYRKVFP

RTVKGQDPFLLKALMLAHNVFLIGLSLYMCLKLVYEAYVNKYSFWGNAY

NPAQTEMAKVIWIFYVSKIYEFMDTFIMLLKGNVNQVSFLHVYHHGSIS

GIWWMITYAAPGGDAYFSAALNSWVHVCMYTYYFMAAVLPKDEKTKRKY

LWWGRYLTQMQMFQFFMNLLQAVYLLYSSSPYPKFIAQLLVVYMVILLM

LFGNFYYMKHHASK

We claim:

1. A method for characterizing the stability of a target protein in a simulated digestion assay, comprising the steps of:
   (a) subjecting a target protein to pepsin digestion;
   (b) obtaining a plurality of samples of peptides resulting from pepsin digestion at a plurality of time points and collecting LC-MS/MS data directly for each of the plurality of pepsin digestion samples at each of the plurality of time points without first enriching for membrane or microsomal fractions or separating the target protein by electrophoresis;
   (c) subjecting the plurality of samples of pepsin digestion samples to complete trypsin digestion and collecting LC-MS/MS data directly for each of the plurality of pepsin-trypsin digestion samples after trypsin digestion is completed for each of the plurality of time points without first enriching for membrane or microsomal fractions or separating the target protein by electrophoresis; and (d) determining from the LC-MS/MS data the kinetics of target protein digestion and the susceptibility to proteolysis of specific regions of the target protein by comparing the data from each of the plurality of time points of the pepsin digestion with the data from the corresponding dual pepsin-trypsin digestion, wherein the decline of tryptic peptides obtained from the dual pepsin-trypsin digestion is used as a proxy for intact target protein, and the appearance and disappearance of peptic peptides is used to indicate the in vitro digestibility of the target protein.

2. The method of claim 1, wherein the target protein is a recombinant protein.

3. The method of claim 1, wherein the target protein is a recalcitrant or membrane-bound protein.

4. The method of claim 1, wherein the target protein is obtained from tissues or seeds of a transgenic plant.

5. The method of claim 1, wherein the target protein is obtained from transgenic *Brassica*.

6. The method of claim 1, wherein peptides liberated from said dual pepsin-trypsin digestion are assessed using protein extracts from a source selected from total protein extracts from canola or from recombinant proteins expressed in yeast, bacterial, or baculovirus expression systems.

7. The method of claim 1, wherein said dual pepsin-trypsin digestion is used to assess the allergenic potential of the target protein.

* * * * *

SEQUENCE LISTING

<160> NUMBER OF SEQ IDS NOS: 18

<210> SEQ ID NO 1
<211> LENGTH: 415
<212> TYPE: PRT
<213> ORGANISM: Pichia pastoris

<400> SEQUENCE: 1

Met Ser Lys Val Thr Val Ser Gly Ser Glu Ile Leu Glu Gly Ser Thr
1               5                   10                  15

Lys Thr Val Arg Arg Ser Gly Asn Val Ala Ser Phe Lys Gln Gln Lys
            20                  25                  30

Thr Ala Ile Asp Thr Phe Gly Asn Val Phe Lys Val Pro Asp Tyr Thr
        35                  40                  45

Ile Lys Asp Ile Leu Asp Ala Ile Pro Lys His Cys Tyr Glu Arg Ser
    50                  55                  60

Leu Val Lys Ser Met Ser Tyr Val Val Arg Asp Ile Val Ala Ile Ser
65                  70                  75                  80

Ala Ile Ala Tyr Val Gly Leu Thr Tyr Ile Pro Leu Leu Pro Asn Glu
                85                  90                  95

-continued

Phe Leu Arg Phe Ala Ala Trp Ser Ala Tyr Val Phe Ser Ile Ser Cys
            100                 105                 110

Phe Gly Phe Gly Ile Trp Ile Leu Gly His Glu Cys Gly His Ser Ala
        115                 120                 125

Phe Ser Asn Tyr Gly Trp Val Asn Asp Thr Val Gly Trp Val Leu His
    130                 135                 140

Ser Leu Val Met Val Pro Tyr Phe Ser Trp Lys Phe Ser His Ala Lys
145                 150                 155                 160

His His Lys Ala Thr Gly His Met Thr Arg Asp Met Val Phe Val Pro
                165                 170                 175

Tyr Thr Ala Glu Glu Phe Lys Glu Lys His Gln Val Thr Ser Leu His
            180                 185                 190

Asp Ile Ala Glu Glu Thr Pro Ile Tyr Ser Val Phe Ala Leu Leu Phe
        195                 200                 205

Gln Gln Leu Gly Gly Leu Ser Leu Tyr Leu Ala Thr Asn Ala Thr Gly
    210                 215                 220

Gln Pro Tyr Pro Gly Val Ser Lys Phe Lys Ser His Tyr Trp Pro
225                 230                 235                 240

Ser Ser Pro Val Phe Asp Lys Lys Asp Tyr Trp Tyr Ile Val Leu Ser
                245                 250                 255

Asp Leu Gly Ile Leu Ala Thr Leu Thr Ser Val Tyr Thr Ala Tyr Lys
            260                 265                 270

Val Phe Gly Phe Trp Pro Thr Phe Ile Thr Trp Phe Cys Pro Trp Ile
        275                 280                 285

Leu Val Asn His Trp Leu Val Phe Val Thr Phe Leu Gln His Thr Asp
    290                 295                 300

Ser Ser Met Pro His Tyr Asp Ala Gln Glu Trp Thr Phe Ala Lys Gly
305                 310                 315                 320

Ala Ala Ala Thr Ile Asp Arg Glu Phe Gly Ile Leu Gly Ile Ile Phe
                325                 330                 335

His Asp Ile Ile Glu Thr His Val Leu His His Tyr Val Ser Arg Ile
            340                 345                 350

Pro Phe Tyr His Ala Arg Glu Ala Thr Glu Cys Ile Lys Lys Val Met
        355                 360                 365

Gly Glu His Tyr Arg His Thr Asp Glu Asn Met Trp Val Ser Leu Trp
    370                 375                 380

Lys Thr Trp Arg Ser Cys Gln Phe Val Glu Asn His Asp Gly Val Tyr
385                 390                 395                 400

Met Phe Arg Asn Cys Asn Asn Val Gly Val Lys Pro Lys Asp Thr
                405                 410                 415

<210> SEQ ID NO 2
<211> LENGTH: 416
<212> TYPE: PRT
<213> ORGANISM: Saccharomyces kluyveri

<400> SEQUENCE: 2

Met Ser Ala Val Thr Val Thr Gly Ser Asp Pro Lys Asn Arg Gly Ser
1               5                   10                  15

Ser Ser Asn Thr Glu Gln Glu Val Pro Lys Val Ala Ile Asp Thr Asn
            20                  25                  30

Gly Asn Val Phe Ser Val Pro Asp Phe Thr Ile Lys Asp Ile Leu Gly
        35                  40                  45

Ala Ile Pro His Glu Cys Tyr Glu Arg Arg Leu Ala Thr Ser Leu Tyr
    50                  55                  60

Tyr Val Phe Arg Asp Ile Phe Cys Met Leu Thr Gly Tyr Leu Thr
65                  70                  75                  80

His Lys Ile Leu Tyr Pro Leu Leu Ile Ser Tyr Thr Asn Ser Ile
                85                  90                  95

Ile Lys Phe Thr Phe Trp Ala Leu Tyr Thr Val Gln Gly Leu Phe
            100                 105                 110

Gly Thr Gly Ile Trp Val Leu Ala His Glu Cys Gly His Gln Ala Phe
            115                 120                 125

Ser Asp Tyr Gly Ile Val Asn Asp Phe Val Gly Trp Thr Leu His Ser
            130                 135                 140

Tyr Leu Met Val Pro Tyr Phe Ser Trp Lys Tyr Ser His Gly Lys His
145                 150                 155                 160

His Lys Ala Thr Gly His Met Thr Arg Asp Met Val Phe Val Pro Ala
                165                 170                 175

Thr Lys Glu Glu Phe Lys Lys Ser Arg Asn Phe Phe Gly Asn Leu Ala
            180                 185                 190

Glu Tyr Ser Glu Asp Ser Pro Leu Arg Thr Leu Tyr Glu Leu Leu Val
        195                 200                 205

Gln Gln Leu Gly Gly Trp Ile Ala Tyr Leu Phe Val Asn Val Thr Gly
210                 215                 220

Gln Pro Tyr Pro Asp Val Pro Ser Trp Lys Trp Asn His Phe Trp Leu
225                 230                 235                 240

Thr Ser Pro Leu Phe Glu Gln Arg Asp Ala Leu Tyr Ile Phe Leu Ser
                245                 250                 255

Asp Leu Gly Ile Leu Thr Gln Gly Ile Val Leu Thr Leu Trp Tyr Lys
            260                 265                 270

Lys Phe Gly Gly Trp Ser Leu Phe Ile Asn Trp Phe Val Pro Tyr Ile
            275                 280                 285

Trp Val Asn His Trp Leu Val Phe Ile Thr Phe Leu Gln His Thr Asp
290                 295                 300

Pro Thr Met Pro His Tyr Asn Ala Glu Glu Trp Thr Phe Ala Lys Gly
305                 310                 315                 320

Ala Ala Ala Thr Ile Asp Arg Lys Phe Gly Phe Ile Gly Pro His Ile
                325                 330                 335

Phe His Asp Ile Ile Glu Thr His Val Leu His His Tyr Cys Ser Arg
            340                 345                 350

Ile Pro Phe Tyr Asn Ala Arg Pro Ala Ser Glu Ala Ile Lys Lys Val
            355                 360                 365

Met Gly Lys His Tyr Arg Ser Ser Asp Glu Asn Met Trp Lys Ser Leu
        370                 375                 380

Trp Lys Ser Phe Arg Ser Cys Gln Tyr Val Asp Gly Asp Asn Gly Val
385                 390                 395                 400

Leu Met Phe Arg Asn Ile Asn Asn Cys Gly Val Gly Ala Ala Glu Lys
                405                 410                 415

<210> SEQ ID NO 3
<211> LENGTH: 463
<212> TYPE: PRT
<213> ORGANISM: Micromonas pusilla

<400> SEQUENCE: 3

Met Cys Pro Pro Lys Thr Asp Gly Arg Ser Pro Arg Ser Pro Leu
1               5                   10                  15

Thr Arg Ser Lys Ser Ser Ala Glu Ala Leu Asp Ala Lys Asp Ala Ser

```
                20                  25                  30
Thr Ala Pro Val Asp Leu Lys Thr Leu Glu Pro His Glu Leu Ala Ala
                35                  40                  45
Thr Phe Glu Thr Arg Trp Val Arg Val Glu Asp Val Glu Tyr Asp Val
                50                  55                  60
Thr Asn Phe Lys His Pro Gly Gly Ser Val Ile Phe Tyr Met Leu Ala
65                  70                  75                  80
Asn Thr Gly Ala Asp Ala Thr Glu Ala Phe Lys Glu Phe His Met Arg
                85                  90                  95
Ser Leu Lys Ala Trp Lys Met Leu Arg Ala Leu Pro Ser Arg Pro Ala
                100                 105                 110
Glu Ile Lys Arg Ser Glu Ser Glu Asp Ala Pro Met Leu Glu Asp Phe
                115                 120                 125
Ala Arg Trp Arg Ala Glu Leu Glu Arg Asp Gly Phe Phe Lys Pro Ser
                130                 135                 140
Ile Thr His Val Ala Tyr Arg Leu Leu Glu Leu Leu Ala Thr Phe Ala
145                 150                 155                 160
Leu Gly Thr Ala Leu Met Tyr Ala Gly Tyr Pro Ile Ile Ala Ser Val
                165                 170                 175
Val Tyr Gly Ala Phe Phe Gly Ala Arg Cys Gly Trp Val Gln His Glu
                180                 185                 190
Gly Gly His Asn Ser Leu Thr Gly Ser Val Tyr Val Asp Lys Arg Leu
                195                 200                 205
Gln Ala Met Thr Cys Gly Phe Gly Leu Ser Thr Ser Gly Glu Met Trp
                210                 215                 220
Asn Gln Met His Asn Lys His His Ala Thr Pro Gln Lys Val Arg His
225                 230                 235                 240
Asp Met Asp Leu Asp Thr Thr Pro Ala Val Ala Phe Phe Asn Thr Ala
                245                 250                 255
Val Glu Asp Asn Arg Pro Arg Gly Phe Ser Arg Ala Trp Ala Arg Leu
                260                 265                 270
Gln Ala Trp Thr Phe Val Pro Val Thr Ser Gly Leu Leu Val Gln Ala
                275                 280                 285
Phe Trp Ile Tyr Val Leu His Pro Arg Gln Val Leu Arg Lys Lys Asn
                290                 295                 300
Tyr Glu Glu Ala Ser Trp Met Leu Val Ser His Val Val Arg Thr Ala
305                 310                 315                 320
Val Ile Lys Leu Ala Thr Gly Tyr Ser Trp Pro Val Ala Tyr Trp Trp
                325                 330                 335
Phe Thr Phe Gly Asn Trp Ile Ala Tyr Met Tyr Leu Phe Ala His Phe
                340                 345                 350
Ser Thr Ser His Thr His Leu Pro Val Val Pro Ser Asp Lys His Leu
                355                 360                 365
Ser Trp Val Asn Tyr Ala Val Asp His Thr Val Asp Ile Asp Pro Ser
                370                 375                 380
Arg Gly Tyr Val Asn Trp Leu Met Gly Tyr Leu Asn Cys Gln Val Ile
385                 390                 395                 400
His His Leu Phe Pro Asp Met Pro Gln Phe Arg Gln Pro Glu Val Ser
                405                 410                 415
Arg Arg Phe Val Pro Phe Ala Lys Lys Trp Gly Leu Asn Tyr Lys Val
                420                 425                 430
Leu Ser Tyr Tyr Gly Ala Trp Lys Ala Thr Phe Ser Asn Leu Asp Lys
                435                 440                 445
```

```
Val Gly Gln His Tyr Tyr Val Asn Gly Lys Ala Glu Lys Ala His
    450                 455                 460

<210> SEQ ID NO 4
<211> LENGTH: 288
<212> TYPE: PRT
<213> ORGANISM: Pyramimonas cordata

<400> SEQUENCE: 4

Met Glu Phe Ala Gln Pro Leu Val Ala Met Ala Gln Glu Gln Tyr Ala
1               5                   10                  15

Ala Ile Asp Ala Val Val Ala Pro Ala Ile Phe Ser Thr Ala Thr Asp Ser
            20                  25                  30

Ile Gly Trp Gly Leu Lys Pro Ile Ser Ser Ala Thr Lys Asp Leu Pro
        35                  40                  45

Leu Val Glu Ser Pro Thr Pro Leu Ile Leu Ser Leu Leu Ala Tyr Phe
    50                  55                  60

Ala Ile Val Gly Ser Gly Leu Val Tyr Arg Lys Val Phe Pro Arg Thr
65                  70                  75                  80

Val Lys Gly Gln Asp Pro Phe Leu Leu Lys Ala Leu Met Leu Ala His
                85                  90                  95

Asn Val Phe Leu Ile Gly Leu Ser Leu Tyr Met Cys Leu Lys Leu Val
                100                 105                 110

Tyr Glu Ala Tyr Val Asn Lys Tyr Ser Phe Trp Gly Asn Ala Tyr Asn
            115                 120                 125

Pro Ala Gln Thr Glu Met Ala Lys Val Ile Trp Ile Phe Tyr Val Ser
130                 135                 140

Lys Ile Tyr Glu Phe Met Asp Thr Phe Ile Met Leu Leu Lys Gly Asn
145                 150                 155                 160

Val Asn Gln Val Ser Phe Leu His Val Tyr His Gly Ser Ile Ser
                165                 170                 175

Gly Ile Trp Trp Met Ile Thr Tyr Ala Ala Pro Gly Gly Asp Ala Tyr
            180                 185                 190

Phe Ser Ala Ala Leu Asn Ser Trp Val His Val Cys Met Tyr Thr Tyr
        195                 200                 205

Tyr Phe Met Ala Ala Val Leu Pro Lys Asp Glu Lys Thr Lys Arg Lys
    210                 215                 220

Tyr Leu Trp Trp Gly Arg Tyr Leu Thr Gln Met Gln Met Phe Gln Phe
225                 230                 235                 240

Phe Met Asn Leu Leu Gln Ala Val Tyr Leu Tyr Ser Ser Ser Pro
                245                 250                 255

Tyr Pro Lys Phe Ile Ala Gln Leu Leu Val Val Tyr Met Val Thr Leu
            260                 265                 270

Leu Met Leu Phe Gly Asn Phe Tyr Tyr Met Lys His His Ala Ser Lys
        275                 280                 285

<210> SEQ ID NO 5
<211> LENGTH: 425
<212> TYPE: PRT
<213> ORGANISM: Pavlova salina

<400> SEQUENCE: 5

Met Pro Pro Arg Asp Ser Tyr Ser Tyr Ala Ala Pro Pro Ser Ala Gln
1               5                   10                  15

Leu His Glu Val Asp Thr Pro Gln Glu His Asp Lys Lys Glu Leu Val
            20                  25                  30
```

Ile Gly Asp Arg Ala Tyr Asp Val Thr Asn Phe Val Lys Arg His Pro
                35                  40                  45

Gly Gly Lys Ile Ile Ala Tyr Gln Val Gly Thr Asp Ala Thr Asp Ala
    50                  55                  60

Tyr Lys Gln Phe His Val Arg Ser Ala Lys Ala Asp Lys Met Leu Lys
65                  70                  75                  80

Ser Leu Pro Ser Arg Pro Val His Lys Gly Tyr Ser Pro Arg Arg Ala
                85                  90                  95

Asp Leu Ile Ala Asp Phe Gln Glu Phe Thr Lys Gln Leu Glu Ala Glu
                100                 105                 110

Gly Met Phe Glu Pro Ser Leu Pro His Val Ala Tyr Arg Leu Ala Glu
                115                 120                 125

Val Ile Ala Met His Val Ala Gly Ala Ala Leu Ile Trp His Gly Tyr
130                 135                 140

Thr Phe Ala Gly Ile Ala Met Leu Gly Val Val Gln Gly Arg Cys Gly
145                 150                 155                 160

Trp Leu Met His Glu Gly Gly His Tyr Ser Leu Thr Gly Asn Ile Ala
                165                 170                 175

Phe Asp Arg Ala Ile Gln Val Ala Cys Tyr Gly Leu Gly Cys Gly Met
                180                 185                 190

Ser Gly Ala Trp Trp Arg Asn Gln His Asn Lys His His Ala Thr Pro
                195                 200                 205

Gln Lys Leu Gln His Asp Val Asp Leu Asp Thr Leu Pro Leu Val Ala
                210                 215                 220

Phe His Glu Arg Ile Ala Ala Lys Val Lys Ser Pro Ala Met Lys Ala
225                 230                 235                 240

Trp Leu Ser Met Gln Ala Lys Leu Phe Ala Pro Val Thr Thr Leu Leu
                245                 250                 255

Val Ala Leu Gly Trp Gln Leu Tyr Leu His Pro Arg His Met Leu Arg
                260                 265                 270

Thr Lys His Tyr Asp Glu Leu Ala Met Leu Gly Ile Arg Tyr Gly Leu
                275                 280                 285

Val Gly Tyr Leu Ala Ala Asn Tyr Gly Ala Gly Tyr Val Leu Ala Cys
                290                 295                 300

Tyr Leu Leu Tyr Val Gln Leu Gly Ala Met Tyr Ile Phe Cys Asn Phe
305                 310                 315                 320

Ala Val Ser His Thr His Leu Pro Val Val Glu Pro Asn Glu His Ala
                325                 330                 335

Thr Trp Val Glu Tyr Ala Ala Asn His Thr Thr Asn Cys Ser Pro Ser
                340                 345                 350

Trp Trp Cys Asp Trp Trp Met Ser Tyr Leu Asn Tyr Gln Ile Glu His
                355                 360                 365

His Leu Tyr Pro Ser Met Pro Gln Phe Arg His Pro Lys Ile Ala Pro
                370                 375                 380

Arg Val Lys Gln Leu Phe Glu Lys His Gly Leu His Tyr Asp Val Arg
385                 390                 395                 400

Gly Tyr Phe Glu Ala Met Ala Asp Thr Phe Ala Asn Leu Asp Asn Val
                405                 410                 415

Ala His Ala Pro Glu Lys Lys Met Gln
                420                 425

<210> SEQ ID NO 6
<211> LENGTH: 267

<212> TYPE: PRT
<213> ORGANISM: Pyramimonas cordata

<400> SEQUENCE: 6

Met Ala Ser Ile Ala Ile Pro Ala Ala Leu Ala Gly Thr Leu Gly Tyr
1               5                   10                  15

Val Thr Tyr Asn Val Ala Asn Pro Asp Ile Pro Ala Ser Glu Lys Val
            20                  25                  30

Pro Ala Tyr Phe Met Gln Val Glu Tyr Trp Gly Pro Thr Ile Gly Thr
        35                  40                  45

Ile Gly Tyr Leu Leu Phe Ile Tyr Phe Gly Lys Arg Ile Met Gln Asn
    50                  55                  60

Arg Ser Gln Pro Phe Gly Leu Lys Asn Ala Met Leu Val Tyr Asn Phe
65                  70                  75                  80

Tyr Gln Thr Phe Phe Asn Ser Tyr Cys Ile Tyr Leu Phe Val Thr Ser
                85                  90                  95

His Arg Ala Gln Gly Leu Lys Val Trp Gly Asn Ile Pro Asp Met Thr
            100                 105                 110

Ala Asn Ser Trp Gly Ile Ser Gln Val Ile Trp Leu His Tyr Asn Asn
        115                 120                 125

Lys Tyr Val Glu Leu Leu Asp Thr Phe Phe Met Val Met Arg Lys Lys
    130                 135                 140

Phe Asp Gln Leu Ser Phe Leu His Ile Tyr His His Thr Leu Leu Ile
145                 150                 155                 160

Trp Ser Trp Phe Val Val Met Lys Leu Glu Pro Val Gly Asp Cys Tyr
                165                 170                 175

Phe Gly Ser Ser Val Asn Thr Phe Val His Val Ile Met Tyr Ser Tyr
            180                 185                 190

Tyr Gly Leu Ala Ala Leu Gly Val Asn Cys Phe Trp Lys Lys Tyr Ile
        195                 200                 205

Thr Gln Ile Gln Met Leu Gln Phe Cys Ile Cys Ala Ser His Ser Ile
    210                 215                 220

Tyr Thr Ala Tyr Val Gln Asn Thr Ala Phe Trp Leu Pro Tyr Leu Gln
225                 230                 235                 240

Leu Trp Val Met Val Asn Met Phe Val Leu Phe Ala Asn Phe Tyr Arg
                245                 250                 255

Lys Arg Tyr Lys Ser Lys Gly Ala Lys Lys Gln
            260                 265

<210> SEQ ID NO 7
<211> LENGTH: 447
<212> TYPE: PRT
<213> ORGANISM: Pavlova salina

<400> SEQUENCE: 7

Met Pro Pro Ser Ala Ala Lys Gln Met Gly Ala Ser Thr Gly Val His
1               5                   10                  15

Ala Gly Val Thr Asp Ser Ser Ala Phe Thr Arg Lys Asp Val Ala Asp
            20                  25                  30

Arg Pro Asp Leu Thr Ile Val Gly Asp Ser Val Tyr Asp Ala Lys Ala
        35                  40                  45

Phe Arg Ser Glu His Pro Gly Gly Ala His Phe Val Ser Leu Phe Gly
    50                  55                  60

Gly Arg Asp Ala Thr Glu Ala Phe Met Glu Tyr His Arg Arg Ala Trp
65                  70                  75                  80

```
Pro Lys Ser Arg Met Ser Arg Phe His Val Gly Ser Leu Ala Ser Thr
                85                  90                  95
Glu Glu Pro Val Ala Ala Asp Glu Gly Tyr Leu Gln Leu Cys Ala Arg
            100                 105                 110
Ile Ala Lys Met Val Pro Ser Val Ser Gly Phe Ala Pro Ala Ser
        115                 120                 125
Tyr Trp Val Lys Ala Gly Leu Ile Leu Gly Ser Ala Ile Ala Leu Glu
    130                 135                 140
Ala Tyr Met Leu Tyr Ala Gly Lys Arg Leu Leu Pro Ser Ile Val Leu
145                 150                 155                 160
Gly Trp Leu Phe Ala Leu Ile Gly Leu Asn Ile Gln His Asp Ala Asn
                165                 170                 175
His Gly Ala Leu Ser Lys Ser Ala Ser Val Asn Leu Ala Leu Gly Leu
            180                 185                 190
Cys Gln Asp Trp Ile Gly Gly Ser Met Ile Leu Trp Leu Gln Glu His
        195                 200                 205
Val Val Met His His Leu His Thr Asn Asp Val Asp Lys Asp Pro Asp
    210                 215                 220
Gln Lys Ala His Gly Ala Leu Arg Leu Lys Pro Thr Asp Ala Trp Ser
225                 230                 235                 240
Pro Met His Trp Leu Gln His Leu Tyr Leu Leu Pro Gly Glu Thr Met
                245                 250                 255
Tyr Ala Phe Lys Leu Leu Phe Leu Asp Ile Ser Glu Leu Val Met Trp
            260                 265                 270
Arg Trp Glu Gly Glu Pro Ile Ser Lys Leu Ala Gly Tyr Leu Phe Met
        275                 280                 285
Pro Ser Leu Leu Leu Lys Leu Thr Phe Trp Ala Arg Phe Val Ala Leu
    290                 295                 300
Pro Leu Tyr Leu Ala Pro Ser Val His Thr Ala Val Cys Ile Ala Ala
305                 310                 315                 320
Thr Val Met Thr Gly Ser Phe Tyr Leu Ala Phe Phe Phe Ile Ser
                325                 330                 335
His Asn Phe Glu Gly Val Ala Ser Val Gly Pro Asp Gly Ser Ile Thr
            340                 345                 350
Ser Met Thr Arg Gly Ala Ser Phe Leu Lys Arg Gln Ala Glu Thr Ser
        355                 360                 365
Ser Asn Val Gly Gly Pro Leu Leu Ala Thr Leu Asn Gly Gly Leu Asn
    370                 375                 380
Tyr Gln Ile Glu His His Leu Phe Pro Arg Val His His Gly Phe Tyr
385                 390                 395                 400
Pro Arg Leu Ala Pro Leu Val Lys Ala Glu Leu Glu Ala Arg Gly Ile
                405                 410                 415
Glu Tyr Lys His Tyr Pro Thr Ile Trp Ser Asn Leu Ala Ser Thr Leu
            420                 425                 430
Arg His Met Tyr Ala Leu Gly Arg Pro Arg Ser Lys Ala Glu
        435                 440                 445

<210> SEQ ID NO 8
<211> LENGTH: 15
<212> TYPE: PRT
<213> ORGANISM: Artificial Sequence
<220> FEATURE:
<223> OTHER INFORMATION: tryptic peptide 1 of marker protein R

<400> SEQUENCE: 8
```

-continued

```
Thr Glu Pro Gln Thr Pro Gln Glu Trp Ile Asp Asp Leu Glu Arg
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: tryptic peptide of Pichia pastoris
      omega3-/delta15-desaturase

<400> SEQUENCE: 9

Glu Ala Thr Glu Cys Ile Lys
1               5

<210> SEQ ID NO 10
<211> LENGTH: 15
<212> TYPE: PRT
<213> ORGANISM: Artificial Sequence
<220> FEATURE:
<223> OTHER INFORMATION: tryptic peptide 2 of P. pastoris
      omega3-/delta15-desaturase

<400> SEQUENCE: 10

Ser Cys Gln Phe Val Glu Asn His Asp Gly Val Tyr Met Phe Arg
1               5                   10                  15

<210> SEQ ID NO 11
<211> LENGTH: 25
<212> TYPE: PRT
<213> ORGANISM: Artificial Sequence
<220> FEATURE:
<223> OTHER INFORMATION: tryptic peptide of P. salina delta4-desaturase

<400> SEQUENCE: 11

Phe His Val Gly Ser Leu Ala Ser Thr Glu Glu Pro Val Ala Ala Asp
1               5                   10                  15

Glu Gly Tyr Leu Gln Leu Cys Ala Arg
            20                  25

<210> SEQ ID NO 12
<211> LENGTH: 9
<212> TYPE: PRT
<213> ORGANISM: Artificial Sequence
<220> FEATURE:
<223> OTHER INFORMATION: Peptide containing PreScission protease
      cleavage site

<400> SEQUENCE: 12

Ser Leu Glu Val Leu Phe Gln Gly Pro
1               5

<210> SEQ ID NO 13
<211> LENGTH: 15
<212> TYPE: PRT
<213> ORGANISM: Artificial Sequence
<220> FEATURE:
<223> OTHER INFORMATION: artificial peptide 2 of marker protein R

<400> SEQUENCE: 13

Ser Val Val Ala Val Ile Gly Leu Pro Asn Asp Pro Ser Val Arg
1               5                   10                  15

<210> SEQ ID NO 14
<211> LENGTH: 668
<212> TYPE: PRT
<213> ORGANISM: Artificial Sequence
```

<220> FEATURE:
<223> OTHER INFORMATION: His-tagged P. pastoris omega3-/delta15-
    desaturase

<400> SEQUENCE: 14

```
His His His His His His His Ser Lys Gly Glu Glu Leu Phe Thr
1               5                   10                  15

Gly Val Val Pro Ile Leu Val Glu Leu Asp Gly Asp Val Asn Gly His
            20                  25                  30

Lys Phe Ser Val Arg Gly Glu Gly Glu Gly Asp Ala Thr Asn Gly Lys
        35                  40                  45

Leu Thr Leu Lys Phe Ile Cys Thr Thr Gly Lys Leu Pro Val Pro Trp
    50                  55                  60

Pro Thr Leu Val Thr Thr Leu Thr Tyr Gly Val Gln Cys Phe Ser Arg
65                  70                  75                  80

Tyr Pro Asp His Met Lys Arg His Asp Phe Phe Lys Ser Ala Met Pro
                85                  90                  95

Glu Gly Tyr Val Gln Glu Arg Thr Ile Ser Phe Lys Asp Asp Gly Thr
            100                 105                 110

Tyr Lys Thr Arg Ala Glu Val Lys Phe Glu Gly Asp Thr Leu Val Asn
        115                 120                 125

Arg Ile Glu Leu Lys Gly Ile Asp Phe Lys Glu Asp Gly Asn Ile Leu
    130                 135                 140

Gly His Lys Leu Glu Tyr Asn Phe Asn Ser His Asn Val Tyr Ile Thr
145                 150                 155                 160

Ala Asp Lys Gln Lys Asn Gly Ile Lys Ala Asn Phe Lys Ile Arg His
                165                 170                 175

Asn Val Glu Asp Gly Ser Val Gln Leu Ala Asp His Tyr Gln Gln Asn
            180                 185                 190

Thr Pro Ile Gly Asp Gly Pro Val Leu Leu Pro Asp Asn His Tyr Leu
        195                 200                 205

Ser Thr Gln Ser Val Leu Ser Lys Asp Pro Asn Glu Lys Arg Asp His
    210                 215                 220

Met Val Leu Leu Glu Phe Val Thr Ala Ala Gly Ile Thr His Gly Met
225                 230                 235                 240

Asp Glu Leu Tyr Lys Glu Asn Leu Tyr Phe Gln Gly Gly Ser Ser Lys
                245                 250                 255

Val Thr Val Ser Gly Ser Glu Ile Leu Glu Gly Ser Thr Lys Thr Val
            260                 265                 270

Arg Arg Ser Gly Asn Val Ala Ser Phe Lys Gln Gln Lys Thr Ala Ile
        275                 280                 285

Asp Thr Phe Gly Asn Val Phe Lys Val Pro Asp Tyr Thr Ile Lys Asp
    290                 295                 300

Ile Leu Asp Ala Ile Pro Lys His Cys Tyr Glu Arg Ser Leu Val Lys
305                 310                 315                 320

Ser Met Ser Tyr Val Val Arg Asp Ile Val Ala Ile Ser Ala Ile Ala
                325                 330                 335

Tyr Val Gly Leu Thr Tyr Ile Pro Leu Leu Pro Asn Glu Phe Leu Arg
            340                 345                 350

Phe Ala Ala Trp Ser Ala Tyr Val Phe Ser Ile Ser Cys Phe Gly Phe
        355                 360                 365

Gly Ile Trp Ile Leu Gly His Glu Cys Gly His Ser Ala Phe Ser Asn
    370                 375                 380

Tyr Gly Trp Val Asn Asp Thr Val Gly Trp Val Leu His Ser Leu Val
```

```
            385                 390                 395                 400
Met Val Pro Tyr Phe Ser Trp Lys Phe Ser His Ala Lys His His Lys
                    405                 410                 415

Ala Thr Gly His Met Thr Arg Asp Met Val Phe Val Pro Tyr Thr Ala
                    420                 425                 430

Glu Glu Phe Lys Glu Lys His Gln Val Thr Ser Leu His Asp Ile Ala
                    435                 440                 445

Glu Glu Thr Pro Ile Tyr Ser Val Phe Ala Leu Leu Phe Gln Gln Leu
            450                 455                 460

Gly Gly Leu Ser Leu Tyr Leu Ala Thr Asn Ala Thr Gly Gln Pro Tyr
465                 470                 475                 480

Pro Gly Val Ser Lys Phe Lys Ser His Tyr Trp Pro Ser Ser Pro
                    485                 490                 495

Val Phe Asp Lys Lys Asp Tyr Trp Tyr Ile Val Leu Ser Asp Leu Gly
                    500                 505                 510

Ile Leu Ala Thr Leu Thr Ser Val Tyr Thr Ala Tyr Lys Val Phe Gly
                    515                 520                 525

Phe Trp Pro Thr Phe Ile Thr Trp Phe Cys Pro Trp Ile Leu Val Asn
            530                 535                 540

His Trp Leu Val Phe Val Thr Phe Leu Gln His Thr Asp Ser Ser Met
545                 550                 555                 560

Pro His Tyr Asp Ala Gln Glu Trp Thr Phe Ala Lys Gly Ala Ala Ala
                    565                 570                 575

Thr Ile Asp Arg Glu Phe Gly Ile Leu Gly Ile Ile Phe His Asp Ile
                    580                 585                 590

Ile Glu Thr His Val Leu His His Tyr Val Ser Arg Ile Pro Phe Tyr
                    595                 600                 605

His Ala Arg Glu Ala Thr Glu Cys Ile Lys Lys Val Met Gly Glu His
                    610                 615                 620

Tyr Arg His Thr Asp Glu Asn Met Trp Val Ser Leu Trp Lys Thr Trp
625                 630                 635                 640

Arg Ser Cys Gln Phe Val Glu Asn His Asp Gly Val Tyr Met Phe Arg
                    645                 650                 655

Asn Cys Asn Asn Val Gly Val Lys Pro Lys Asp Thr
                    660                 665

<210> SEQ ID NO 15
<211> LENGTH: 287
<212> TYPE: PRT
<213> ORGANISM: Artificial Sequence
<220> FEATURE:
<223> OTHER INFORMATION: His-tagged P. cordata delta5-elongase

<400> SEQUENCE: 15

Met His His His His His His His His Ser Leu Glu Val Leu
1               5                   10                  15

Phe Gln Gly Pro Met Ala Ser Ile Ala Ile Pro Ala Ala Leu Ala Gly
                    20                  25                  30

Thr Leu Gly Tyr Val Thr Tyr Asn Val Ala Asn Pro Asp Ile Pro Ala
            35                  40                  45

Ser Glu Lys Val Pro Ala Tyr Phe Met Gln Val Glu Tyr Trp Gly Pro
        50                  55                  60

Thr Ile Gly Thr Ile Gly Tyr Leu Leu Phe Ile Tyr Phe Gly Lys Arg
65                  70                  75                  80

Ile Met Gln Asn Arg Ser Gln Pro Phe Gly Leu Lys Asn Ala Met Leu
```

```
                    85                  90                  95
Val Tyr Asn Phe Tyr Gln Thr Phe Phe Asn Ser Tyr Cys Ile Tyr Leu
                100                 105                 110

Phe Val Thr Ser His Arg Ala Gln Gly Leu Lys Val Trp Gly Asn Ile
                115                 120                 125

Pro Asp Met Thr Ala Asn Ser Trp Gly Ile Ser Gln Val Ile Trp Leu
            130                 135                 140

His Tyr Asn Asn Lys Tyr Val Glu Leu Leu Asp Thr Phe Phe Met Val
145                 150                 155                 160

Met Arg Lys Lys Phe Asp Gln Leu Ser Phe Leu His Ile Tyr His His
                165                 170                 175

Thr Leu Leu Ile Trp Ser Trp Phe Val Val Met Lys Leu Glu Pro Val
                180                 185                 190

Gly Asp Cys Tyr Phe Gly Ser Ser Val Asn Thr Phe Val His Val Ile
                195                 200                 205

Met Tyr Ser Tyr Tyr Gly Leu Ala Ala Leu Gly Val Asn Cys Phe Trp
            210                 215                 220

Lys Lys Tyr Ile Thr Gln Ile Gln Met Leu Gln Phe Cys Ile Cys Ala
225                 230                 235                 240

Ser His Ser Ile Tyr Thr Ala Tyr Val Gln Asn Thr Ala Phe Trp Leu
                245                 250                 255

Pro Tyr Leu Gln Leu Trp Val Met Val Asn Met Phe Val Leu Phe Ala
                260                 265                 270

Asn Phe Tyr Arg Lys Arg Tyr Lys Ser Lys Gly Ala Lys Lys Gln
                275                 280                 285

<210> SEQ ID NO 16
<211> LENGTH: 467
<212> TYPE: PRT
<213> ORGANISM: Artificial Sequence
<220> FEATURE:
<223> OTHER INFORMATION: His-tagged P. salina delta4-desaturase

<400> SEQUENCE: 16

Met His His His His His His His His His Ser Leu Glu Val Leu
1               5                   10                  15

Phe Gln Gly Pro Met Pro Pro Ser Ala Ala Lys Gln Met Gly Ala Ser
                20                  25                  30

Thr Gly Val His Ala Gly Val Thr Asp Ser Ser Ala Phe Thr Arg Lys
            35                  40                  45

Asp Val Ala Asp Arg Pro Asp Leu Thr Ile Val Gly Asp Ser Val Tyr
50                  55                  60

Asp Ala Lys Ala Phe Arg Ser Glu His Pro Gly Gly Ala His Phe Val
65                  70                  75                  80

Ser Leu Phe Gly Gly Arg Asp Ala Thr Glu Ala Phe Met Glu Tyr His
                85                  90                  95

Arg Arg Ala Trp Pro Lys Ser Arg Met Ser Arg Phe His Val Gly Ser
                100                 105                 110

Leu Ala Ser Thr Glu Glu Pro Val Ala Ala Asp Glu Gly Tyr Leu Gln
            115                 120                 125

Leu Cys Ala Arg Ile Ala Lys Met Val Pro Ser Val Ser Ser Gly Phe
        130                 135                 140

Ala Pro Ala Ser Tyr Trp Val Lys Ala Gly Leu Ile Leu Gly Ser Ala
145                 150                 155                 160

Ile Ala Leu Glu Ala Tyr Met Leu Tyr Ala Gly Lys Arg Leu Leu Pro
```

```
            165                 170                 175
Ser Ile Val Leu Gly Trp Leu Phe Ala Leu Ile Gly Leu Asn Ile Gln
            180                 185                 190

His Asp Ala Asn His Gly Ala Leu Ser Lys Ser Ala Ser Val Asn Leu
        195                 200                 205

Ala Leu Gly Leu Cys Gln Asp Trp Ile Gly Gly Ser Met Ile Leu Trp
    210                 215                 220

Leu Gln Glu His Val Val Met His His Leu His Thr Asn Asp Val Asp
225                 230                 235                 240

Lys Asp Pro Asp Gln Lys Ala His Gly Ala Leu Arg Leu Lys Pro Thr
                245                 250                 255

Asp Ala Trp Ser Pro Met His Trp Leu Gln His Leu Tyr Leu Leu Pro
            260                 265                 270

Gly Glu Thr Met Tyr Ala Phe Lys Leu Leu Phe Leu Asp Ile Ser Glu
        275                 280                 285

Leu Val Met Trp Arg Trp Glu Gly Glu Pro Ile Ser Lys Leu Ala Gly
    290                 295                 300

Tyr Leu Phe Met Pro Ser Leu Leu Lys Leu Thr Phe Trp Ala Arg
305                 310                 315                 320

Phe Val Ala Leu Pro Leu Tyr Leu Ala Pro Ser Val His Thr Ala Val
                325                 330                 335

Cys Ile Ala Ala Thr Val Met Thr Gly Ser Phe Tyr Leu Ala Phe Phe
            340                 345                 350

Phe Phe Ile Ser His Asn Phe Glu Gly Val Ala Ser Val Gly Pro Asp
        355                 360                 365

Gly Ser Ile Thr Ser Met Thr Arg Gly Ala Ser Phe Leu Lys Arg Gln
    370                 375                 380

Ala Glu Thr Ser Ser Asn Val Gly Gly Pro Leu Leu Ala Thr Leu Asn
385                 390                 395                 400

Gly Gly Leu Asn Tyr Gln Ile Glu His His Leu Phe Pro Arg Val His
                405                 410                 415

His Gly Phe Tyr Pro Arg Leu Ala Pro Leu Val Lys Ala Glu Leu Glu
            420                 425                 430

Ala Arg Gly Ile Glu Tyr Lys His Tyr Pro Thr Ile Trp Ser Asn Leu
        435                 440                 445

Ala Ser Thr Leu Arg His Met Tyr Ala Leu Gly Arg Arg Pro Arg Ser
    450                 455                 460

Lys Ala Glu
465

<210> SEQ ID NO 17
<211> LENGTH: 445
<212> TYPE: PRT
<213> ORGANISM: Artificial Sequence
<220> FEATURE:
<223> OTHER INFORMATION: His-tagged P. salina delta5-desaturase

<400> SEQUENCE: 17

Met His His His His His His His His His Ser Leu Glu Val Leu
1               5                   10                  15

Phe Gln Gly Pro Met Pro Pro Arg Asp Ser Tyr Ser Tyr Ala Ala Pro
            20                  25                  30

Pro Ser Ala Gln Leu His Glu Val Asp Thr Pro Gln Glu His Asp Lys
        35                  40                  45

Lys Glu Leu Val Ile Gly Asp Arg Ala Tyr Asp Val Thr Asn Phe Val
```

```
            50                  55                  60
Lys Arg His Pro Gly Gly Lys Ile Ile Ala Tyr Gln Val Gly Thr Asp
 65                  70                  75                  80

Ala Thr Asp Ala Tyr Lys Gln Phe His Val Arg Ser Ala Lys Ala Asp
                 85                  90                  95

Lys Met Leu Lys Ser Leu Pro Ser Arg Pro Val His Lys Gly Tyr Ser
            100                 105                 110

Pro Arg Arg Ala Asp Leu Ile Ala Asp Phe Gln Glu Phe Thr Lys Gln
            115                 120                 125

Leu Glu Ala Glu Gly Met Phe Glu Pro Ser Leu Pro His Val Ala Tyr
130                 135                 140

Arg Leu Ala Glu Val Ile Ala Met His Val Ala Gly Ala Ala Leu Ile
145                 150                 155                 160

Trp His Gly Tyr Thr Phe Ala Gly Ile Ala Met Leu Gly Val Val Gln
                165                 170                 175

Gly Arg Cys Gly Trp Leu Met His Glu Gly Gly His Tyr Ser Leu Thr
            180                 185                 190

Gly Asn Ile Ala Phe Asp Arg Ala Ile Gln Val Ala Cys Tyr Gly Leu
            195                 200                 205

Gly Cys Gly Met Ser Gly Ala Trp Trp Arg Asn Gln His Asn Lys His
            210                 215                 220

His Ala Thr Pro Gln Lys Leu Gln His Asp Val Asp Leu Asp Thr Leu
225                 230                 235                 240

Pro Leu Val Ala Phe His Glu Arg Ile Ala Ala Lys Val Lys Ser Pro
                245                 250                 255

Ala Met Lys Ala Trp Leu Ser Met Gln Ala Lys Leu Phe Ala Pro Val
            260                 265                 270

Thr Thr Leu Leu Val Ala Leu Gly Trp Gln Leu Tyr Leu His Pro Arg
            275                 280                 285

His Met Leu Arg Thr Lys His Tyr Asp Glu Leu Ala Met Leu Gly Ile
            290                 295                 300

Arg Tyr Gly Leu Val Gly Tyr Leu Ala Ala Asn Tyr Gly Ala Gly Tyr
305                 310                 315                 320

Val Leu Ala Cys Tyr Leu Leu Tyr Val Gln Leu Gly Ala Met Tyr Ile
                325                 330                 335

Phe Cys Asn Phe Ala Val Ser His Thr His Leu Pro Val Val Glu Pro
            340                 345                 350

Asn Glu His Ala Thr Trp Val Glu Tyr Ala Ala Asn His Thr Thr Asn
            355                 360                 365

Cys Ser Pro Ser Trp Trp Cys Asp Trp Trp Met Ser Tyr Leu Asn Tyr
            370                 375                 380

Gln Ile Glu His His Leu Tyr Pro Ser Met Pro Gln Phe Arg His Pro
385                 390                 395                 400

Lys Ile Ala Pro Arg Val Lys Gln Leu Phe Glu Lys His Gly Leu His
                405                 410                 415

Tyr Asp Val Arg Gly Tyr Phe Glu Ala Met Ala Asp Thr Phe Ala Asn
            420                 425                 430

Leu Asp Asn Val Ala His Ala Pro Glu Lys Lys Met Gln
            435                 440                 445

<210> SEQ ID NO 18
<211> LENGTH: 308
<212> TYPE: PRT
<213> ORGANISM: Artificial Sequence
```

-continued

```
<220> FEATURE:
<223> OTHER INFORMATION: His-tagged P. cordata delta6-elongase

<400> SEQUENCE: 18

Met His His His His His His His His His Ser Leu Glu Val Leu
1               5                   10                  15

Phe Gln Gly Pro Met Glu Phe Ala Gln Pro Leu Val Ala Met Ala Gln
            20                  25                  30

Glu Gln Tyr Ala Ala Ile Asp Ala Val Val Ala Pro Ala Ile Phe Ser
            35                  40                  45

Ala Thr Asp Ser Ile Gly Trp Gly Leu Lys Pro Ile Ser Ser Ala Thr
        50                  55                  60

Lys Asp Leu Pro Leu Val Glu Ser Pro Thr Pro Leu Ile Leu Ser Leu
65                  70                  75                  80

Leu Ala Tyr Phe Ala Ile Val Gly Ser Gly Leu Val Tyr Arg Lys Val
                85                  90                  95

Phe Pro Arg Thr Val Lys Gly Gln Asp Pro Phe Leu Leu Lys Ala Leu
            100                 105                 110

Met Leu Ala His Asn Val Phe Leu Ile Gly Leu Ser Leu Tyr Met Cys
            115                 120                 125

Leu Lys Leu Val Tyr Glu Ala Tyr Val Asn Lys Tyr Ser Phe Trp Gly
        130                 135                 140

Asn Ala Tyr Asn Pro Ala Gln Thr Glu Met Ala Lys Val Ile Trp Ile
145                 150                 155                 160

Phe Tyr Val Ser Lys Ile Tyr Glu Phe Met Asp Thr Phe Ile Met Leu
                165                 170                 175

Leu Lys Gly Asn Val Asn Gln Val Ser Phe Leu His Val Tyr His His
            180                 185                 190

Gly Ser Ile Ser Gly Ile Trp Trp Met Ile Thr Tyr Ala Ala Pro Gly
            195                 200                 205

Gly Asp Ala Tyr Phe Ser Ala Ala Leu Asn Ser Trp Val His Val Cys
    210                 215                 220

Met Tyr Thr Tyr Tyr Phe Met Ala Ala Val Leu Pro Lys Asp Glu Lys
225                 230                 235                 240

Thr Lys Arg Lys Tyr Leu Trp Trp Gly Arg Tyr Leu Thr Gln Met Gln
                245                 250                 255

Met Phe Gln Phe Phe Met Asn Leu Leu Gln Ala Val Tyr Leu Leu Tyr
            260                 265                 270

Ser Ser Ser Pro Tyr Pro Lys Phe Ile Ala Gln Leu Leu Val Val Tyr
            275                 280                 285

Met Val Thr Leu Leu Met Leu Phe Gly Asn Phe Tyr Tyr Met Lys His
    290                 295                 300

His Ala Ser Lys
305
```